(12) United States Patent
Pagratis et al.

(10) Patent No.: US 6,855,496 B2
(45) Date of Patent: Feb. 15, 2005

(54) TRUNCATION SELEX METHOD

(75) Inventors: Nikos Pagratis, Boulder, CO (US);
Larry Gold, Boulder, CO (US); Timur Shtatland, Boulder, CO (US); Brenda Javornik, Boulder, CO (US)

(73) Assignee: Gilead Sciences, Inc., Foster City, CA (US)

( * ) Notice: Subject to any disclaimer, the term of this patent is extended or adjusted under 35 U.S.C. 154(b) by 106 days.

(21) Appl. No.: 09/907,111

(22) Filed: Jul. 17, 2001

(65) Prior Publication Data

US 2003/0003461 A1 Jan. 2, 2003

Related U.S. Application Data

(63) Continuation of application No. 09/275,850, filed on Mar. 24, 1999, now Pat. No. 6,261,774.

(51) Int. Cl.[7] .......................... C12Q 1/68; C12P 19/34; C07H 21/02; C07H 21/04
(52) U.S. Cl. ..................... 435/6; 435/91.1; 435/91.2; 536/23.1; 536/24.3
(58) Field of Search ......................... 435/6, 91.2, 91.1; 536/23.1, 24.3

(56) References Cited

U.S. PATENT DOCUMENTS

| | | | | |
|---|---|---|---|---|
| 4,717,670 A | * | 1/1988 | Beck ....................... | 435/320.1 |
| 5,308,751 A | * | 5/1994 | Ohkawa et al. ............ | 435/6 |
| 5,475,096 A | | 12/1995 | Gold et al. | |
| 5,496,938 A | | 3/1996 | Gold et al. | |
| 5,683,867 A | | 11/1997 | Biesecker et al. | |
| 5,723,323 A | | 3/1998 | Kauffman et al. | |
| 6,203,984 B1 | * | 3/2001 | Hu et al. ................... | 435/6 |

FOREIGN PATENT DOCUMENTS

| | | |
|---|---|---|
| GB | 2 183 661 A | 6/1987 |
| WO | WO 89/06694 | 7/1989 |
| WO | WO 91/19813 | 12/1991 |
| WO | WO 92/14843 | 9/1992 |

OTHER PUBLICATIONS

Frohman et al., PNAS (USA) 85:8998–9002, Dec. 1988.*
Gold et al., SCIENCE 249:505–510, Aug. 3, 1990.*
Joyce (1989) Gene 82:83–87.
Joyce & Inoue (1989) Nucleic Acids Research 17:711–722.
Ellington & Szostak (1990) Abstracts of papers presented at the 1990 meeting on RNA Processing, Cold Spring Harbor Laboratory, Cold Spring Harbor, NY, p. 84.
Kinzler & Vogelstein (1989) Nucleic Acids Research 17:3645–3653.
Kramer et al. (1974) J. Mol. Biol. 89:719–736.
Levisohn & Spiegelman (1969) Proc. Natl. Acad. Sci. USA 63:805–811.
Levisohn & Spiegelman (1968) Proc. Natl. Acad. Sci. USA 60:866–872.
Oliphant et al. (1989) Mol. Cell. Biol. 9:2944–2949.
Oliphant & Struhl (1988) Nucleic Acids Research 16:7673–7683.
Oliphant & Struhl (1987) Methods in Enzymology 155:568–582.
Oliphant et al. (1986) Gene 44:177–183.
Robertson & Joyce (1990) Nature 344:467–468.
Thiesen & Bach (1990) Nucleic Acids Research 18:3203–3208.
Szostak (1988) (S.A. Benner ed.) Springer–Verlag Berlin Heidelberg, pp. 87–113.

* cited by examiner

*Primary Examiner*—B J Forman
(74) *Attorney, Agent, or Firm*—Swanson & Bratschun, LLC

(57) ABSTRACT

This invention is directed to a method for identifying nucleic acid ligands by the SELEX method wherein the participation of fixed sequences is eliminated or minimized.

9 Claims, 44 Drawing Sheets

(SEQ ID NO:323)

(SEQ ID NO:324)

(SEQ ID NO:325)

(SEQ ID NO:326)

(SEQ ID NO:327)

ATTCACTGAGCATCAGCCCAGACTGTGTCATGCATCTGGCAGCCGAAAGCCATGTTGACCGTTCTATTGAC
(SEQ ID NO:328)

Figure 5A

3'-nnnnnnnngtctgctgctcgccct-5' (SEQ ID NO:329)
ATTCACTGAGCATCAGCCCAGACTGTGTCATGCATCTGGCAGCCGAA-AGCCATGTTGACCGTTCTATTGAC
(SEQ ID NO:330)

Figure 5B

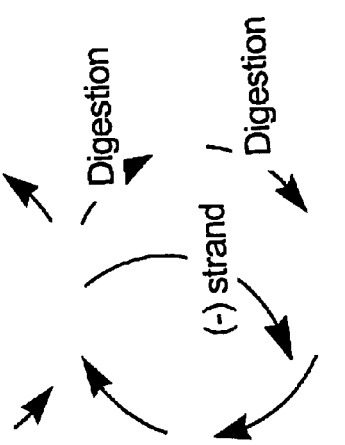
FIGURE 6C HybSELEX
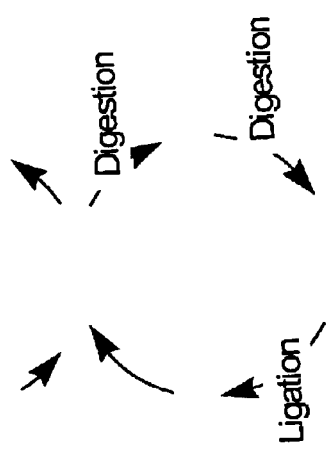
FIGURE 6B LigSELEX
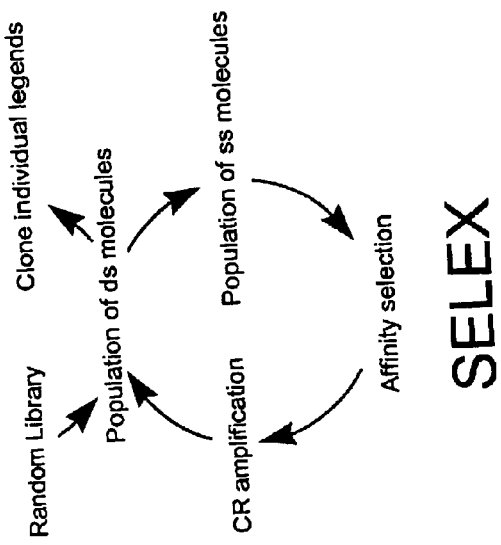
FIGURE 6A SELEX

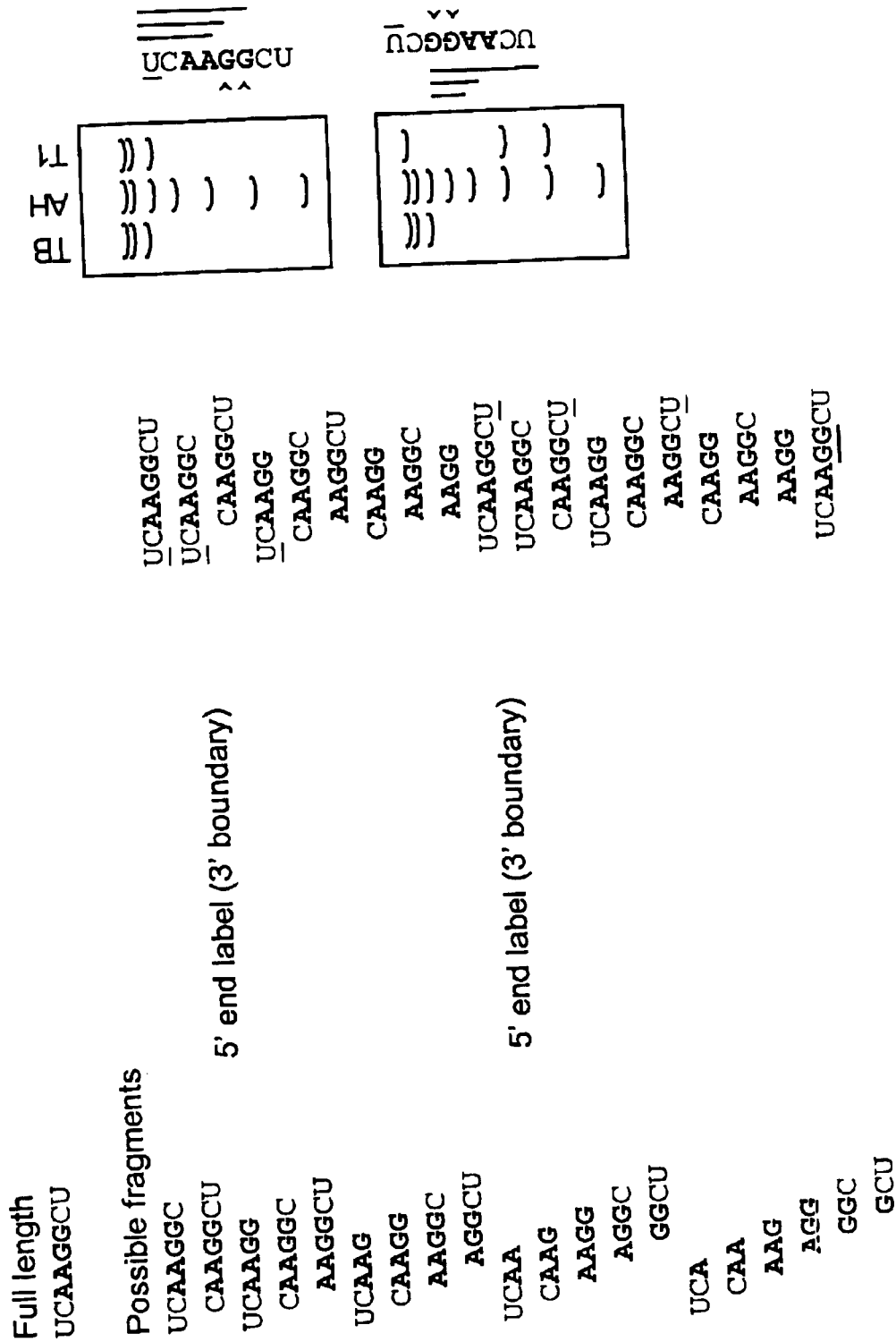
FIGURE 11 (Page 1)

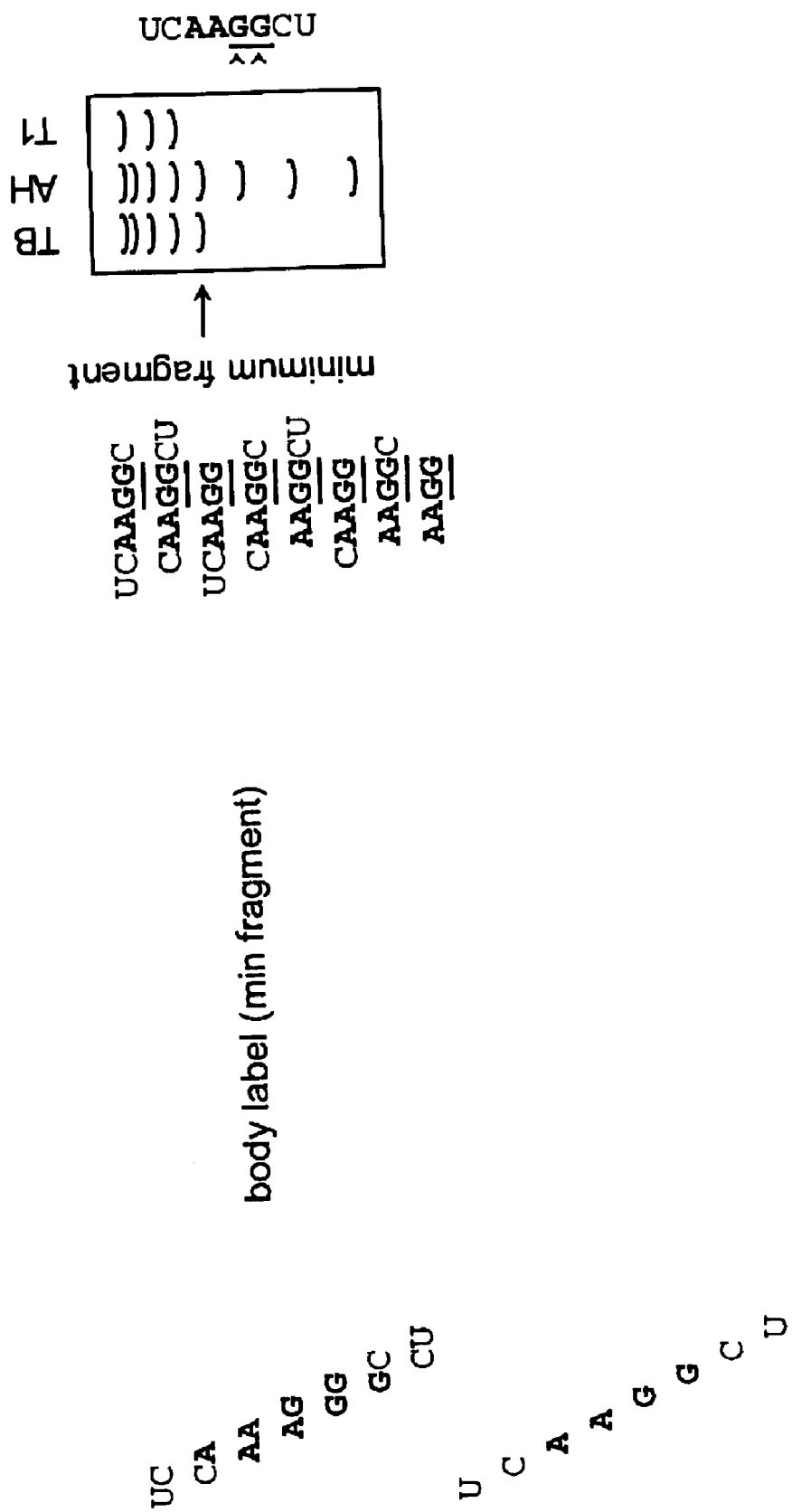
FIGURE 11 (Page 2)

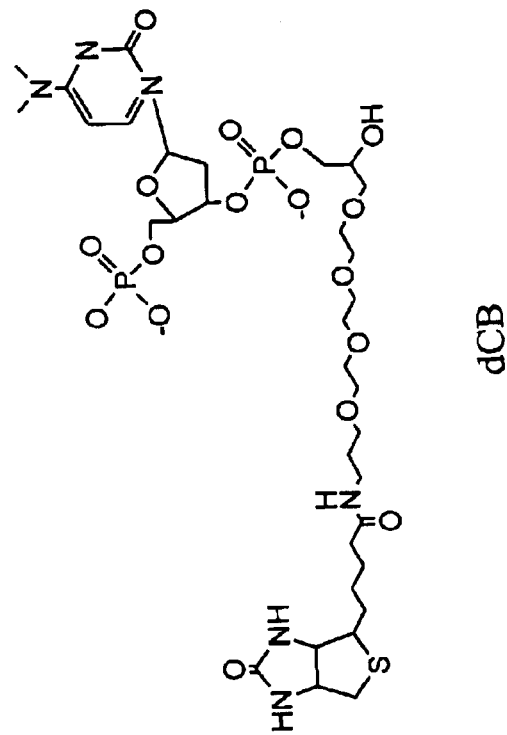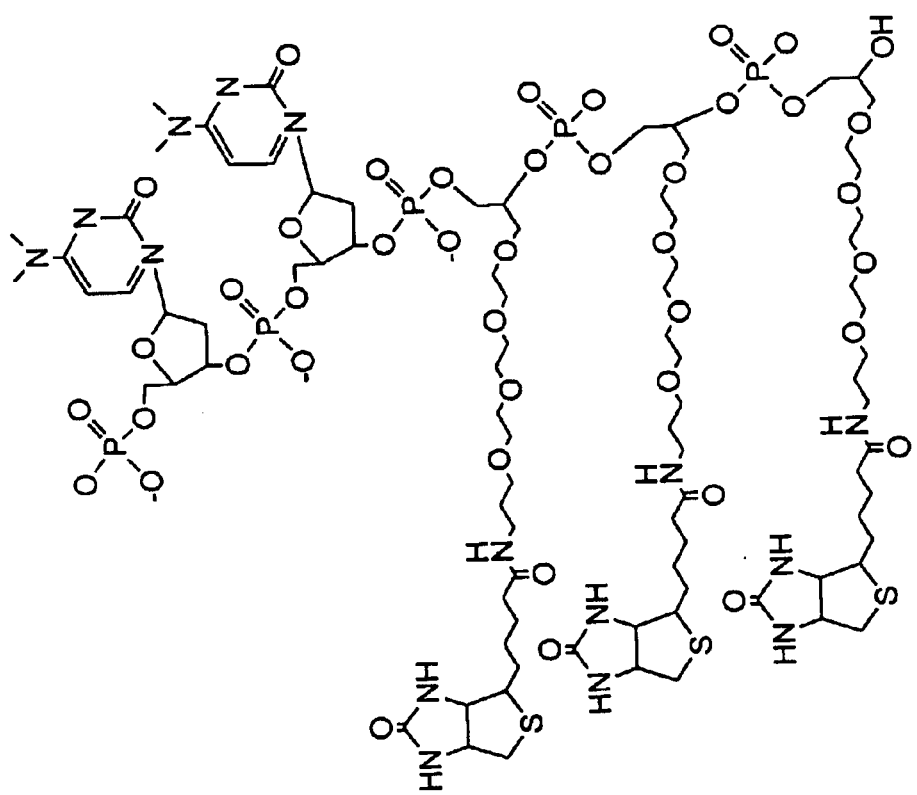
FIGURE 15

Biotinylated RNA   + - + - + - + - + -
PCR cycles         3   6   9   12  15

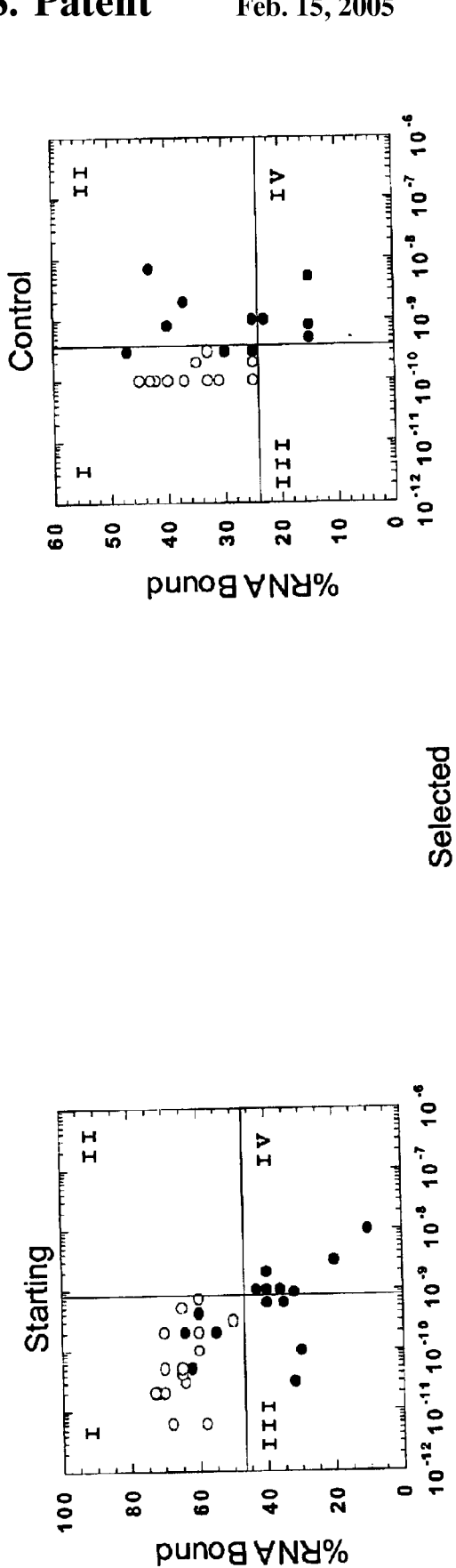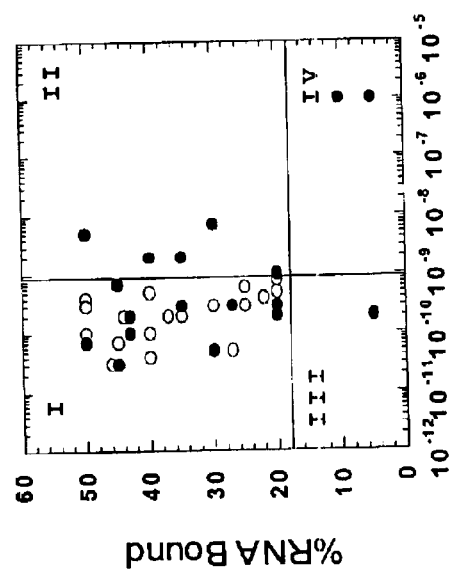
FIGURE 26A
FIGURE 26B
FIGURE 26C

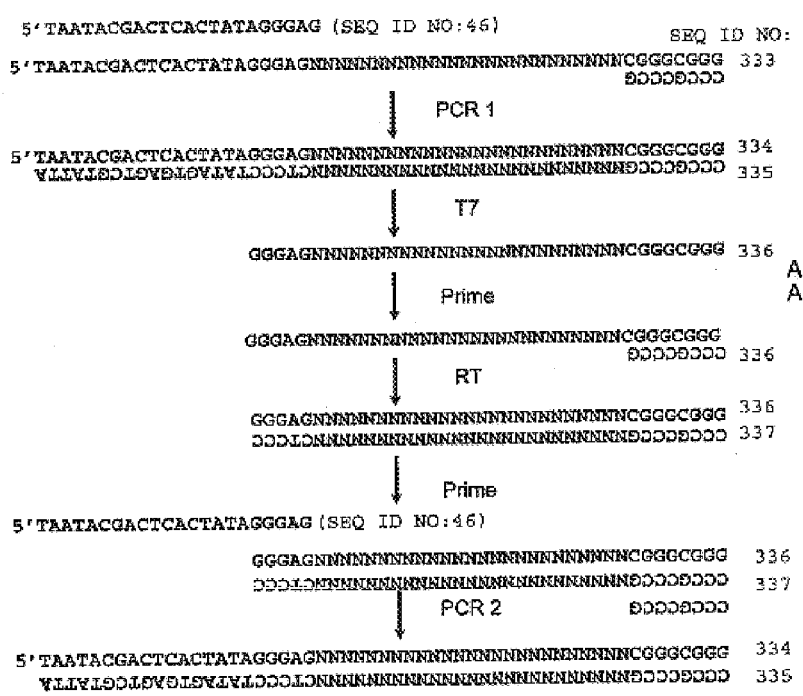
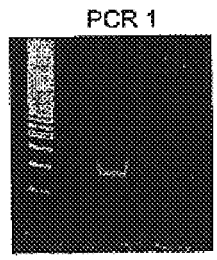
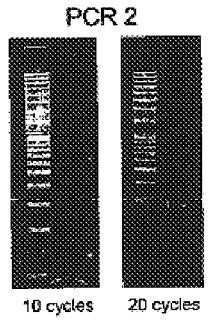
FIGURE 29A
FIGURE 29B
FIGURE 29C

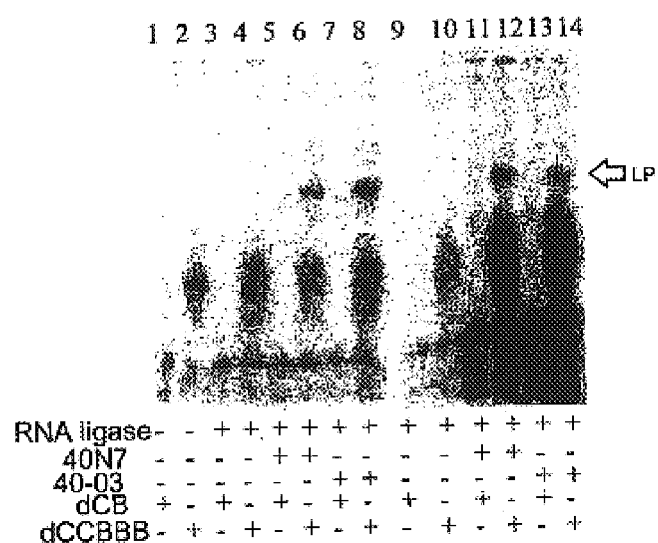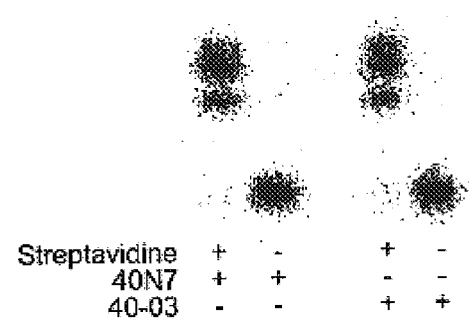
FIGURE 33A
FIGURE 33B

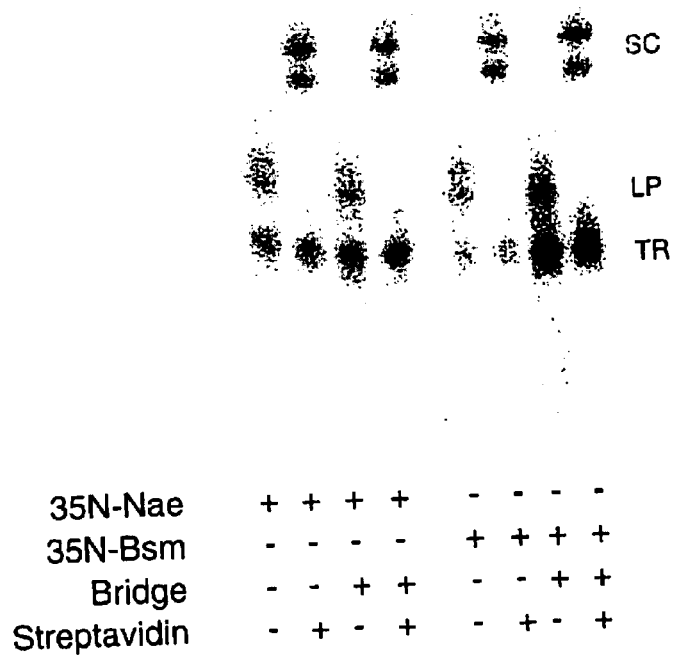

|             |   |   |   |   |   |   |   |   |
|-------------|---|---|---|---|---|---|---|---|
| 35N-Nae     | + | + | + | + | − | − | − | − |
| 35N-Bsm     | − | − | − | − | + | + | + | + |
| Bridge      | − | − | + | + | − | − | + | + |
| Streptavidin| − | + | − | + | − | + | − | + |

Figure 34A (SEQ ID NO:338)
TAATACGACTCACTATAGGGA [NNNNNNN]₅GGCCGGCCTCCCTTTAGTGAGGGTTAATT
ATTAATGGGAGTCACTCCCGGAGGCCGG ₅[NNNNNNN] AGGGATATCACTCAGCATAAT
(SEQ ID NO:339)

GGGA[NNNNNNN]₅GGCC    35N-Nae (SEQ ID NO:338)
TAATACGACTCACTATAGGGA [NNNNNNN]₅GCATTCTCCCTTTAGTGAGGGTTAATT
ATTAATGGGAGTCACTCCCGGAGGCCGG ₅[NNNNNNN] AGGGATATCACTCAGCATAAT
(SEQ ID NO:339)

(SEQ ID NO:340) GGGA[NNNNNNN]₅    35N-Bsm

Figure 34B

```
35N Bam RNA 5'pGGGANNNNNNN...   SEQ ID NO:351
                        +
5G7NOT7 5'GGAGGACGATGCGG         SEQ ID NO:341
        CICCTACGCCCCCTNNNNNNN ,5 CRCS  SEQ ID NO:342
                        ↓
                        ^
5G7NOT7 5'GGAGGACGATGCGGGGGANNNNNNN... SEQ ID NO:343
        CICCTACGCCCCCTNNNNNN ,5 CRCS
                                  SEQ ID NO:342
```

FIGURE 35A

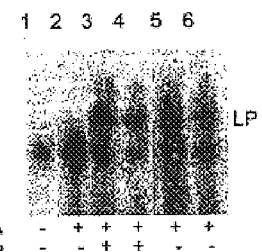

Kinased RNA     − + + + + +
BMB Ligase      − − + + − −
NEB Ligase      − − − − + +
[RNA], nM           50 25 50 25

FIGURE 35B

```
VT30Rd12 cDNA 5'...NNNTCCC
                           +
        SEQ ID NO:34    pTATAGTGAGTCGTATTA 5G7RC Linker
        SEQ ID NO:35    ATTATGCACTCAGCATAAT TN ,S
                        or
        SEQ ID NO:36    pCTCCCTATAGTGAGTCGTATTA 5N7 Linker
        SEQ ID NO:37    NNNNNATTATGCACTCAGCATAAT eBpTIB NS
                        ↓
                        ^
VT30Rd12 cDNA 5'...NNNTCCCTATAGTGAGTCGTATTA 5G7RC Linker
        SEQ ID NO:35       ATTATGCACTCAGCATAAT TN ,S
                        or
VT30Rd12 cDNA 5'...NNNTCCCCTCCCTATAGTGAGTCGTATTA 5N7 Linker
        SEQ ID NO:37    NNNNNATTATGCACTCAGCATAAT eBpTIB NS
```

FIGURE 35C

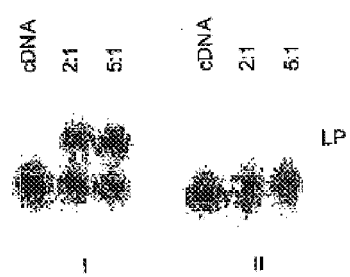

FIGURE 35D

SEQUENCE LISTING

<160> NUMBER OF SEQ ID NOS: 351

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(32)
<223> OTHER INFORMATION: N at position 16 is A, C, G or T.

<400> SEQUENCE: 1
gggaggacga ugcggncaga cgacgagcgg ga 32

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 2
ccgcatcgtc ctccc 15

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 3
tcccgctcgt cgtctg 16

<210> SEQ ID NO 4
<211> LENGTH: 36
<212> TYPE: RNA
<213> ORGANISM: Artificial Sequence
<220> FEATURE:
<223> OTHER INFORMATION: Description of Artificial Sequence: Synthetic
      Sequence

<400> SEQUENCE: 4
ggcacgcgua uucacugagc aucagccaga cugugu 36

<210> SEQ ID NO 5
<211> LENGTH: 39
<212> TYPE: RNA
<213> ORGANISM: Artificial Sequence
<220> FEATURE:
<223> OTHER INFORMATION: Description of Artificial Sequence: Synthetic
      Sequence

<400> SEQUENCE: 5
cuucgcuuca guaccgucga gcagcaccag cguuucgcc 39

<210> SEQ ID NO 6
<211> LENGTH: 38
<212> TYPE: RNA
<213> ORGANISM: Artificial Sequence
<220> FEATURE:
<223> OTHER INFORMATION: Description of Artificial Sequence: Synthetic
      Sequence

<400> SEQUENCE: 6
aauguuccac cagcagggga aaugauguug uucuggcu 38

<210> SEQ ID NO 7
<211> LENGTH: 44
<212> TYPE: RNA
<213> ORGANISM: Artificial Sequence
<220> FEATURE:
<223> OTHER INFORMATION: Description of Artificial Sequence: Synthetic
      Sequence

<400> SEQUENCE: 7
uaggagagcg uuaacaacag caucagcguu gaagugacgg aggu                44

<210> SEQ ID NO 8
<211> LENGTH: 45
<212> TYPE: RNA
<213> ORGANISM: Artificial Sequence
<220> FEATURE:
<223> OTHER INFORMATION: Description of Artificial Sequence: Synthetic
      Sequence

<400> SEQUENCE: 8
ugauuugcag caacagcgca augaggaaag agagccagau uaccc               45

<210> SEQ ID NO 9
<211> LENGTH: 32
<212> TYPE: RNA
<213> ORGANISM: Artificial Sequence
<220> FEATURE:
<223> OTHER INFORMATION: Description of Artificial Sequence: Synthetic
      Sequence

<400> SEQUENCE: 9
ugacuggaca ucaucagagu uugcacuuga gc                             32

<210> SEQ ID NO 10
<211> LENGTH: 43
<212> TYPE: RNA
<213> ORGANISM: Artificial Sequence
<220> FEATURE:
<223> OTHER INFORMATION: Description of Artificial Sequence: Synthetic
      Sequence

<400> SEQUENCE: 10
aguaauuacg ccaugaacac aggcauaaag aaguacauau ggu                 43

<210> SEQ ID NO 11
<211> LENGTH: 44
<212> TYPE: RNA
<213> ORGANISM: Artificial Sequence
<220> FEATURE:
<223> OTHER INFORMATION: Description of Artificial Sequence: Synthetic
      Sequence

<400> SEQUENCE: 11
uauucuggcu aucuacagcu accagcaugg agaucaacga uccu                44

<210> SEQ ID NO 12
<211> LENGTH: 42
<212> TYPE: RNA
<213> ORGANISM: E. coli

<400> SEQUENCE: 12
ugagugccga agaucgugag cagaggaaca cccugauuau cc                  42

<210> SEQ ID NO 13
<211> LENGTH: 15
<212> TYPE: RNA
<213> ORGANISM: E. coli

<400> SEQUENCE: 13
ccgacgacca cgcgg                                                15

<210> SEQ ID NO 14
<211> LENGTH: 15
<212> TYPE: RNA
<213> ORGANISM: E. coli

-continued

<400> SEQUENCE: 14
acgaccauca ggcgu                                                          15

<210> SEQ ID NO 15
<211> LENGTH: 15
<212> TYPE: RNA
<213> ORGANISM: E. coli
<220> FEATURE:
<223> OTHER INFORMATION: Description of Artificial Sequence: Synthetic
      Sequence

<400> SEQUENCE: 15
cugacgagca cgcag                                                          15

<210> SEQ ID NO 16
<211> LENGTH: 15
<212> TYPE: RNA
<213> ORGANISM: E. coli

<400> SEQUENCE: 16
accagcacca gcggu                                                          15

<210> SEQ ID NO 17
<211> LENGTH: 15
<212> TYPE: RNA
<213> ORGANISM: E. coli

<400> SEQUENCE: 17
gccagcaaca gcggc                                                          15

<210> SEQ ID NO 18
<211> LENGTH: 15
<212> TYPE: RNA
<213> ORGANISM: E. coli

<400> SEQUENCE: 18
ugcagcagca gcgca                                                          15

<210> SEQ ID NO 19
<211> LENGTH: 15
<212> TYPE: RNA
<213> ORGANISM: E. coli

<400> SEQUENCE: 19
cccagcaaca gcggg                                                          15

<210> SEQ ID NO 20
<211> LENGTH: 15
<212> TYPE: RNA
<213> ORGANISM: E. coli

<400> SEQUENCE: 20
cacagcauca gcgug                                                          15

<210> SEQ ID NO 21
<211> LENGTH: 15
<212> TYPE: RNA
<213> ORGANISM: E. coli

<400> SEQUENCE: 21
ugcagcaaca gcgca                                                          15

-continued

```
<210> SEQ ID NO 22
<211> LENGTH: 15
<212> TYPE: RNA
<213> ORGANISM: E. coli

<400> SEQUENCE: 22
cugagcauca gccag                                                      15

<210> SEQ ID NO 23
<211> LENGTH: 14
<212> TYPE: RNA
<213> ORGANISM: E. coli

<400> SEQUENCE: 23
gccagcaaca gcgg                                                       14

<210> SEQ ID NO 24
<211> LENGTH: 15
<212> TYPE: RNA
<213> ORGANISM: E. coli

<400> SEQUENCE: 24
gugaccaaca ggcac                                                      15

<210> SEQ ID NO 25
<211> LENGTH: 15
<212> TYPE: RNA
<213> ORGANISM: E. coli

<400> SEQUENCE: 25
gccagcagca gcggc                                                      15

<210> SEQ ID NO 26
<211> LENGTH: 15
<212> TYPE: RNA
<213> ORGANISM: E. coli

<400> SEQUENCE: 26
ugcaccauca gggca                                                      15

<210> SEQ ID NO 27
<211> LENGTH: 15
<212> TYPE: RNA
<213> ORGANISM: E. coli

<400> SEQUENCE: 27
uccagcacca gcgga                                                      15

<210> SEQ ID NO 28
<211> LENGTH: 15
<212> TYPE: RNA
<213> ORGANISM: E. coli

<400> SEQUENCE: 28
accagcauca gcggu                                                      15

<210> SEQ ID NO 29
<211> LENGTH: 15
<212> TYPE: RNA
<213> ORGANISM: E. coli

<400> SEQUENCE: 29
ggcaggaaca ccgcc                                                      15
```

```
<210> SEQ ID NO 30
<211> LENGTH: 15
<212> TYPE: RNA
<213> ORGANISM: E. coli

<400> SEQUENCE: 30
ucgaccacca ggcga                                              15

<210> SEQ ID NO 31
<211> LENGTH: 15
<212> TYPE: RNA
<213> ORGANISM: E. coli

<400> SEQUENCE: 31
uccaccagca gggga                                              15

<210> SEQ ID NO 32
<211> LENGTH: 15
<212> TYPE: RNA
<213> ORGANISM: E. coli

<400> SEQUENCE: 32
gccagcauca gcggc                                              15

<210> SEQ ID NO 33
<211> LENGTH: 15
<212> TYPE: RNA
<213> ORGANISM: E. coli

<400> SEQUENCE: 33
ggcagcauca gcgcc                                              15

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 34
tatagtgagt cgtatta                                            17

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 35
taatacgact cactataggg a                                       21

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 36
ctccctatag tgagtcgtat ta                                      22
```

```
<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(27)
<223> OTHER INFORMATION: N's at positions 23-27 are A, C G or T.

<400> SEQUENCE: 37
taatacgact cactataggg agnnnnn                                          27

<210> SEQ ID NO 38
<211> LENGTH: 71
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: N's at positions 16-55 are A, C, G or T.

<400> SEQUENCE: 38
gggaggacga tgcggnnnnn nnnnnnnnnn nnnnnnnnnn nnnnnnnnnn nnnnncagac     60
gactcgcccg a                                                          71

<210> SEQ ID NO 39
<211> LENGTH: 61
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: N's at positions 16-45 are A, C, G or T.

<400> SEQUENCE: 39
gggaggacga tgcggnnnnn nnnnnnnnnn nnnnnnnnnn nnnnncagac gactcgcccg     60
a                                                                     61

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 40
taatacgact cactataggg aggacgatgc gg                                   32

<210> SEQ ID NO 41
<211> LENGTH: 16
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 41
tcgggcgagt cgtctg                                                     16
```

<210> SEQ ID NO 42
<211> LENGTH: 15
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (5)..(15)
<223> OTHER INFORMATION: Bases at positions 5-15 are 2'-OMe

<400> SEQUENCE: 42
ccgcaucguc cuccc                                                           15

<210> SEQ ID NO 43
<211> LENGTH: 16
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(12)
<223> OTHER INFORMATION: Bases at positions 1-12 are 2'-OMe

<400> SEQUENCE: 43
ucgggcgagu cgtctg                                                          16

<210> SEQ ID NO 44
<211> LENGTH: 43
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(43)
<223> OTHER INFORMATION: N's at positions 6-35 are A, C, G or T.

<400> SEQUENCE: 44
gggagnnnnn nnnnnnnnnn nnnnnnnnnn nnnnncgggc ggg                            43

<210> SEQ ID NO 45
<211> LENGTH: 40
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(40)
<223> OTHER INFORMATION: N's at positions 6-32 are A, C, G or T.

<400> SEQUENCE: 45
gggagnnnnn nnnnnnnnnn nnnnnnnnnn nncgggcggg                                40

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 46
taatacgact cactataggg ag                                                   22

<210> SEQ ID NO 47
<211> LENGTH: 8

```
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 47 cccgcccg                                                              8

<210> SEQ ID NO 48
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 48
gggaggacga ugcgguugaa gaauugggcg cauguucucc guccucagac gacucgcccg    60
a                                                                    61

<210> SEQ ID NO 49
<211> LENGTH: 62
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(62)
<223> OTHER INFORMATION: All pyrimidines are 2'-F

<400> SEQUENCE: 49
gggaggacga ugcggaaacg gaaguauugg auacauaagc accccucaga cgacucgccc    60
ga                                                                   62

<210> SEQ ID NO 50
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 50
gggaggacga ugcggcagga uuuuggaaga auuggauauu ggccucagac gacucgcccg    60
a                                                                    61

<210> SEQ ID NO 51
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 51
gggaggacga ugcggcuuaa guuuuggaag aauugaauac ugggucagac gacucgcccg    60
a                                                                    61

<210> SEQ ID NO 52
<211> LENGTH: 61
```

<210> SEQ ID NO 64
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 64
gggaggacga ugcgguacua ggugaaugcc gauaaucuua uccgucagac gacucgcccg    60
a                                                                    61

<210> SEQ ID NO 65
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 65
gggaggacga ugcggaugga aguauugagc cgauugucau cuccccagac gacucgcccg    60
a                                                                    61

<210> SEQ ID NO 66
<211> LENGTH: 60
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(60)
<223> OTHER INFORMATION: All pyrimidines are 2'-F

<400> SEQUENCE: 66
gggaggacga ugcggucuuu ggguuuuugc caacgguuuu cgcccagacg acucgcccga    60

<210> SEQ ID NO 67
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 67
gggaggacga ugcggucgau cgcuuauuuu cucggucauc uccccagac gacucgcccg     60 a                                                                    61

<210> SEQ ID NO 68
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)

-continued

<223> OTHER INFORMATION: All pyrimidines are 2'-F

<400> SEQUENCE: 68
gggaggacga ugcggaaacg gaacuucuug gauacaucug cucgucagac gacucgcccg    60
a                                                                   61

<210> SEQ ID NO 69
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 69
gggaggacga ugcgguugaa uauuucucgg ucgugauucc cgccucagac gacucgcccg    60
a                                                                   61

<210> SEQ ID NO 70
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 70
gggaggacga ugcggauuug gaugcauguc aaggcguuuu gcccucagac gacucgcccg    60
a                                                                   61

<210> SEQ ID NO 71
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 71
gggaggacga ugcgguguug aucgagauuu aaucuauuuc cacgucagac gacucgcccg    60
a                                                                   61

<210> SEQ ID NO 72
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 72
gggaggacga ugcggugauc gauuuccugg ucuguucucc cuccucagac gacucgcccg    60
a                                                                   61

<210> SEQ ID NO 73
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 73
gggaggacga ugcggaucag uauuggcugc uucuauuccu cuggucagac gacucgcccg    60
a                                                                   61

<210> SEQ ID NO 74
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 74
gggaggacga ugcggaaggc gacuuguaug ugauucagua uuggucagac gacucgcccg    60
a                                                                   61

<210> SEQ ID NO 75
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 75
gggaggacga ugcggauuug gaagaauugg auuuagcacg ucccucagac gacucgcccg    60
a                                                                   61

<210> SEQ ID NO 76
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 76
gggaggacga ugcgggaacg gaagaauugg auacgcuagc auggucagac gacucgcccg    60
a                                                                   61

<210> SEQ ID NO 77
<211> LENGTH: 59
<212> TYPE: RNA
<213> ORGANISM: Artificial Sequence
<220> FEATURE:

<223> OTHER INFORMATION: Description of Artificial Sequence: Synthetic
      Sequence
<221> NAME/KEY: modified_base
<222> LOCATION: (1)..(59)
<223> OTHER INFORMATION: All pyrimidines are 2'-F

<400> SEQUENCE: 77
gggaggacga ugcgguaaac ggaagaauug gaacauugcu cgucagacga cucgcccga      59

<210> SEQ ID NO 78
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 78
gggaggacga ugcggaaacc agugaaugcu uaucggaucc guugucagac gacucgcccg      60
a                                                                    61

<210> SEQ ID NO 79
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 79
gggaggacga ugcggaaauc agugaaugcu uauaguuucu cgcgucagac gacucgcccg      60
a                                                                    61

<210> SEQ ID NO 80
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 80
gggaggacga ugcggaauca gugaaugcuu agaaauccac accgucagac gacucgcccg      60
a                                                                    61

<210> SEQ ID NO 81
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 81
gggaggacga ugcggaucag ugaaugcuua caaaccgugu guccucagac gacucgcccg      60
a                                                              61

<210> SEQ ID NO 82
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 82
gggaggacga ugcggaauca gugaaugcuu agaaauccac accgucagac gacucgcccg    60
a                                                              61

<210> SEQ ID NO 83
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: misc_structure
<222> LOCATION: (1)..(61)
<223> OTHER INFORMATION: All pyrimidines are 2'-F

<400> SEQUENCE: 83
gggaggacga ugcggggaaa ucagugaaug cuuauaccuu cgccucagac gacucgcccg    60
a                                                              61

<210> SEQ ID NO 84
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 84
gggaggacga ugcggauaac agaauuuuug gagaacaagu gucgucagac gacucgcccg    60
a                                                              61

<210> SEQ ID NO 85
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 85
gggaggacga ugcggaaauu gacuaguuuc ggucuucuac ccccucagac gacucgcccg    60
a                                                              61

<210> SEQ ID NO 86
<211> LENGTH: 61
<212> TYPE: RNA

<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 86
gggaggacga ugcgguugaa auuucucggu cuuucucucc cuccucagac gacucgcccg      60
a                                                                    61

<210> SEQ ID NO 87
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 87
gggaggacga ugcgguguag agguuuugac uuuucccuuu uccgucagac gacucgcccg      60
a                                                                    61

<210> SEQ ID NO 88
<211> LENGTH: 60
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(60)
<223> OTHER INFORMATION: All pyrimidines are 2'-F

<400> SEQUENCE: 88
gggaggacga ugcgguugac acuucucgau uguucuccug uccucagacg acucgcccga     60

<210> SEQ ID NO 89
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 89
gggaggacga ugcgguugau cggacguuag ucauuucccg aucgucagac gacucgcccg      60
a                                                                    61

<210> SEQ ID NO 90
<211> LENGTH: 60
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(60)
<223> OTHER INFORMATION: All pyrimidines are 2'-F

<400> SEQUENCE: 90
gggaggacga ugcgguugau cgacuuuccu gaucuucucc uccucagacg acucgcccga    60

<210> SEQ ID NO 91
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 91
gggaggacga ugcgggauca cgaacauuuu gacgauuuuc cucccagac gacucgcccg    60 a                                                                  61

<210> SEQ ID NO 92
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 92
gggaggacga ugcggacacu gguuccgaag uauugucuuu guccucagac gacucgcccg    60
a                                                                  61

<210> SEQ ID NO 93
<211> LENGTH: 63
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(63)
<223> OTHER INFORMATION: All pyrimidines are 2'-F

<400> SEQUENCE: 93
gggaggacga ugcggggguu auugggcguc aacauucuuu ucacguccag acgacucgcc    60
cga                                                                63

<210> SEQ ID NO 94
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 94
gggaggacga ugcggggugc cuguagucuu ugcaucuuau aaaugcaauc ugccccagac    60
gacucgcccg a                                                       71

<210> SEQ ID NO 95
<211> LENGTH: 71
<212> TYPE: RNA

<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 95
gggaggacga ugcggggugc cuuuagucuu ugcaucuuau aaaugcaauc ugccccagac      60
gacucgcccg a                                                          71

<210> SEQ ID NO 96
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 96
gggaggacga ugcgguagug augaauuuuu gcuggaucug guuugaacc gucccagac       60 gacucgcccg a                                                          71

<210> SEQ ID NO 97
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 97
gggaggacga ugcgguagug acgaauuuuu gcuggaucug guuugaacc gucccagac       60 gacucgcccg a                                                          71

<210> SEQ ID NO 98
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 98
gggaggacga ugcgguagug augaacuuuu gcuggaucug guuugagcc gucccagac       60 gacucgcccg a                                                          71

<210> SEQ ID NO 99
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F

```
<400> SEQUENCE: 99
gggaggacga ugcgguagug augaacuuuu gcuggauugg uuuugaaccg uccccagacg     60
acucgcccga                                                           70

<210> SEQ ID NO 100
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F

<400> SEQUENCE: 100
gggaggacga ugcggaucug aauuuauucg ucuacaguua cgcugggccu uccgcagacg     60
acucgcccga                                                           70

<210> SEQ ID NO 101
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 101
gggaggacga ugcggaucug aauuuauucg ucuacaguua cggcugggcc uuccgcagac     60
gacucgcccg a                                                         71

<210> SEQ ID NO 102
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 102
gggaggacga ugcggaucug aauuuauucg ucuacaguua cagcugggcc uuccgcagac     60
gacucgcccg a                                                         71

<210> SEQ ID NO 103
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 103
gggaggacga ugcggaugcc uuuugccuuc agggugugau uccuugaucu guccgcagac     60
gacucgcccg a                                                         71
```

<210> SEQ ID NO 104
<211> LENGTH: 69
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(69)
<223> OTHER INFORMATION: All pyrimidines are 2'-F

<400> SEQUENCE: 104
gggaggacga ugcgggugcc uuuugccuag guugugauuu guaaccuucu gcccagacga    60
cucgcccga                                                            69

<210> SEQ ID NO 105
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F

<400> SEQUENCE: 105
gggaggacga ugcgguuagu ucgggcucaa caccgcuaau auucuucguu ccccagacg     60 acucgcccga                                                           70

<210> SEQ ID NO 106
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F

<400> SEQUENCE: 106
gggaggacga ugcgguuagu ucgggcucaa caccgcuaag auucuucguu ccccagacg     60 acucgcccga                                                           70

<210> SEQ ID NO 107
<211> LENGTH: 72
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(72)
<223> OTHER INFORMATION: All pyrimidines are 2'-F

<400> SEQUENCE: 107
gggaggacga ugcgguuagg ucgggcucaa caccgcuaaa aaauucuucg uuccccaga     60 cgacucgccc ga                                                        72

<210> SEQ ID NO 108
<211> LENGTH: 67
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(67)
<223> OTHER INFORMATION: All pyrimidines are 2'-F

<400> SEQUENCE: 108
gggaggacga ugcggugccu uuagucugaa ucuuaccaug auucucugcc gcagacgacu    60
cgcccga                                                              67

<210> SEQ ID NO 109
<211> LENGTH: 69
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(69)
<223> OTHER INFORMATION: All pyrimidines are 2'-F

<400> SEQUENCE: 109
gggaggacga ugcggugccu uagcaugaau auacugaugu auauucucug ccccagacga    60
cucgcccga                                                            69

<210> SEQ ID NO 110
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 110
gggaggacga ugcggugccu uuagccugau augcguuucg uguauaucuc ugccgcagac    60
gacucgcccg a                                                         71

<210> SEQ ID NO 111
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 111
gggaggacga ugcgggacgu agcgggaugc uuuaacuuug aucguccauc augugcagac    60
gacucgcccg a                                                         71

<210> SEQ ID NO 112
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 112
gggaggacga ugcgggaugu agcgggaugc uuuaacuuug aucguccacc augugcagac    60
gacucgcccg a    71

<210> SEQ ID NO 113
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F

<400> SEQUENCE: 113
gggaggacga ugcggaguuu caggauaugu uguggucg uucuuuucc uccccagacg    60 acucgcccga    70

<210> SEQ ID NO 114
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F

<400> SEQUENCE: 114
gggaggacga ugcggaucug ggugaccucu guguacguuu auuuuaccg accccagacg    60 acucgcccga    70

<210> SEQ ID NO 115
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 115
gggaggacga ugcggaaggc aagaagcuuu augugucgcg uaacacaacu guccgcagac    60
gacucgcccg a    71

<210> SEQ ID NO 116
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 116
gggaggacga ugcggaguuu ugggaucgcc acagaucuua cugugagcua cugugcagac    60
gacucgcccg a    71

<210> SEQ ID NO 117
<211> LENGTH: 68

```
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(68)
<223> OTHER INFORMATION: All pyrimidines are 2'-F

<400> SEQUENCE: 117
gggaggacga ugcggucuuu cgaacuggga auuuuggug uagccguaug cccagacgac    60
ucgcccga                                                            68

<210> SEQ ID NO 118
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 118
gggaggacga ugcggaagac cguuccgagu gguacaagua aaccccugug uuccgcagac    60
gacucgcccg a                                                        71

<210> SEQ ID NO 119
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F

<400> SEQUENCE: 119
gggaggacga ugcggguuuc ucuuucacau uuuuuuuuu uuuuucacu uccccagacg     60 acucgcccga                                                          70

<210> SEQ ID NO 120
<211> LENGTH: 69
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(69)
<223> OTHER INFORMATION: All pyrimidines are 2'-F

<400> SEQUENCE: 120
gggaggacga ugcgggauag guuuuuuuc uagguuuuuu uuuucagugu ccccagacga    60
cucgcccga                                                           69

<210> SEQ ID NO 121
<211> LENGTH: 68
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(68)
```

<223> OTHER INFORMATION: All pyrimidines are 2'-F

<400> SEQUENCE: 121
gggaggacga ugcggcguug uuuuuucuuu auuuuuuguu cuuuugguug gccagacgac    60
ucgcccga    68

<210> SEQ ID NO 122
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F

<400> SEQUENCE: 122
gggaggacga ugcggugacc acauuuauuu uuucuucuua ccuccuuugg uccccagacg    60
acucgcccga    70

<210> SEQ ID NO 123
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F

<400> SEQUENCE: 123
gggaggacga ugcggucuuc aucuguguuu uuaucucucu cuucucacgc ucccagacg    60 acucgcccga    70

<210> SEQ ID NO 124
<211> LENGTH: 73
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(73)
<223> OTHER INFORMATION: All pyrimidines are 2'-F

<400> SEQUENCE: 124
gggaggacga ugcggccuaa gcuuccuuuu auuuuuucu ucuuuaauuu ccugggccag    60
acgacucgcc cga    73

<210> SEQ ID NO 125
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F

<400> SEQUENCE: 125
gggaggacga ugcggcucuu uucuuuaugu uuuuuucuuu uuucuuguc cccccagacg    60 acucgcccga    70

<210> SEQ ID NO 126
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F

<400> SEQUENCE: 126
gggaggacga ugcgguccca ucauccaagc gugauacuuu uuuuucccc uccccagacg    60 acucgcccga                                                          70

<210> SEQ ID NO 127
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F

<400> SEQUENCE: 127
gggaggacga ugcgggaccu uuuuucuug cuuucuuuu ugccuuuccg uccccagacg    60
acucgcccga                                                          70

<210> SEQ ID NO 128
<211> LENGTH: 68
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(68)
<223> OTHER INFORMATION: All pyrimidines are 2'-F

<400> SEQUENCE: 128
gggaggacga ugcgguuucg uuucuuuau cuuuuucuc guuuuugcc cccagacgac    60 ucgcccga                                                            68

<210> SEQ ID NO 129
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 129
gggaggacga ugcgguuaau uucauauuuu uuuuuucuu uuucccuaac guggccagac    60
gacucgcccg a                                                        71

<210> SEQ ID NO 130
<211> LENGTH: 71
<212> TYPE: RNA
<213> ORGANISM: Artificial Sequence
<220> FEATURE:

<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 130
gggaggacga ugcgguccccu aucacaacuu uguuucuuu uauuuucuc uucgccagac    60 gacucgcccg a                                                       71

<210> SEQ ID NO 131
<211> LENGTH: 65
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: All pyrimidines are 2'-F; N's at positions
      17-18, 27, 33 and 43 are A, C, G or U.

<400> SEQUENCE: 131
gggaggacga ugcgggnncu ggguucnacu uuncauauuu gunuuuuuc agacgacucg    60 cccga                                                              65

<210> SEQ ID NO 132
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 132
gggaggacga ugcgggacgu uguguuuacu gauuucuuuu ucuuuuucc gccugcagac    60 gacucgcccg a                                                       71

<210> SEQ ID NO 133
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 133
gggaggacga ugcggcacua gucauuuucu aucuuucuuu uucucccuug ugccccagac    60
gacucgcccg a                                                       71

<210> SEQ ID NO 134
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

```
<400> SEQUENCE: 134
gggaggacga ugcggacugg guuuauucuu cuuuuucuu guuccuacca cccccagac      60 gacucgcccg a                                                        71

<210> SEQ ID NO 135
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F

<400> SEQUENCE: 135
gggaggacga ugcggauccu cuugucauag aucguuuguu uuguuuugu accgcagacg    60 acucgcccga                                                          70

<210> SEQ ID NO 136
<211> LENGTH: 69
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(69)
<223> OTHER INFORMATION: All pyrimidines are 2'-F

<400> SEQUENCE: 136
gggaggacga ugcggucuuu ucucuguuuc cuuuuguuuu ucccuguacu ccccagacga    60
cucgcccga                                                           69

<210> SEQ ID NO 137
<211> LENGTH: 72
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(72)
<223> OTHER INFORMATION: All pyrimidines are 2'-F

<400> SEQUENCE: 137
gggaggacga ugcgguccuu ugguuuuagu uguuauuguu uuuccuuuug ugucgccaga    60
cgacucgccc ga                                                       72

<210> SEQ ID NO 138
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 138
gggaggacga ugcggcgacc auuuauuucu cuuaucauuc uuuucucccu aucgccagac    60
gacucgcccg a                                                        71
```

<210> SEQ ID NO 139
<211> LENGTH: 70
<212> TYPE: RNA
<213> ORGANISM: Artificial Sequence
<220> FEATURE:
<223> OTHER INFORMATION: Description of Artificial Sequence: Synthetic
    Sequence
<221> NAME/KEY: modified_base
<222> LOCATION: (1)..(70)
<223> OTHER INFORMATION: All pyrimidines are 2'-F

<400> SEQUENCE: 139
gggaggacga ugcggucguc ggauucucua uguuuuguuu ucauuucuuc cccccagacg    60
acucgcccga                                                          70

<210> SEQ ID NO 140
<211> LENGTH: 71
<212> TYPE: RNA
<213> ORGANISM: Artificial Sequence
<220> FEATURE:
<223> OTHER INFORMATION: Description of Artificial Sequence: Synthetic
    Sequence
<221> NAME/KEY: modified_base
<222> LOCATION: (1)..(71)
<223> OTHER INFORMATION: All pyrimidines are 2'-F

<400> SEQUENCE: 140
gggaggacga ugcggucgaa cuauuacucu uuuauuauuc cuuaauuuuu gccgccagac    60
gacucgcccg a                                                        71

<210> SEQ ID NO 141
<211> LENGTH: 71
<212> TYPE: RNA
<213> ORGANISM: Artificial Sequence
<220> FEATURE:
<223> OTHER INFORMATION: Description of Artificial Sequence: Synthetic
    Sequence
<221> NAME/KEY: modified_base
<222> LOCATION: (1)..(71)
<223> OTHER INFORMATION: All pyrimidines are 2'-F

<400> SEQUENCE: 141
gggaggacga ugcggauuga gggutucuuu uucgucuuuu uccuuucccu cucccagac    60 gacucgcccg a                                                        71

<210> SEQ ID NO 142
<211> LENGTH: 70
<212> TYPE: RNA
<213> ORGANISM: Artificial Sequence
<220> FEATURE:
<223> OTHER INFORMATION: Description of Artificial Sequence: Synthetic
    Sequence
<221> NAME/KEY: modified_base
<222> LOCATION: (1)..(70)
<223> OTHER INFORMATION: All pyrimidines are 2'-F

<400> SEQUENCE: 142
gggaggacga ugcgguuccg gucuuucuu guguuuaugu uucuuucugu ugcccagacg    60
acucgcccga                                                          70

<210> SEQ ID NO 143
<211> LENGTH: 71
<212> TYPE: RNA
<213> ORGANISM: Artificial Sequence
<220> FEATURE:
<223> OTHER INFORMATION: Description of Artificial Sequence: Synthetic
    Sequence <221> NAME/KEY: modified_base
<222> LOCATION: (1)..(71)
<223> OTHER INFORMATION: All pyrimidines are 2'-F

<400> SEQUENCE: 143
gggaggacga ugcggggaca uauuucuuc uucuuccucu gcuuuuguu gucccccagac    60 gacucgcccg a    71

<210> SEQ ID NO 144
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F

<400> SEQUENCE: 144
gggaggacga ugcggguacu ugcuucucua cuauuucuc cucauccccc ugugcagacg    60
acucgcccga    70

<210> SEQ ID NO 145
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 145
gggaggacga ugcgguucuu cguuucuucu cucucuucua gccguccuuc gcccccagac    60
gacucgcccg a    71

<210> SEQ ID NO 146
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 146
gggaggacga ugcggcucag uuuauaugac acuucacuuu cuuucguuu uaccgcagac    60 gacucgcccg a    71

<210> SEQ ID NO 147
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F

<400> SEQUENCE: 147
gggaggacga ugcggugcga cauuauuuaa uuuucuccuu ccuuucaucg ugcccagacg    60

```
acucgcccga                                                              70

<210> SEQ ID NO 148
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 148
gggaggacga ugcggcagcu cacuuauauu uccguccaau uccuucuuua cugcccagac      60
gacucgcccg a                                                           71

<210> SEQ ID NO 149
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F

<400> SEQUENCE: 149
gggaggacga ugcgguqucu uuagccuaca guugacuguu caauuguucu gccgcagacg      60
acucgcccga                                                              70

<210> SEQ ID NO 150
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 150
gggaggacga ugcgguguuu gugcuacgac cuacauucgu uggaauguuc ugccgcagac      60
gacucgcccg a                                                           71

<210> SEQ ID NO 151
<211> LENGTH: 69
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(69)
<223> OTHER INFORMATION: All pyrimidines are 2'-F

<400> SEQUENCE: 151
gggaggacga ugcggaucac uaggcucauu ugugagccgu uauuccuuga cuccagacga      60
cucgcccga                                                              69

<210> SEQ ID NO 152
<211> LENGTH: 70
<212> TYPE: RNA
```

<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F

<400> SEQUENCE: 152
gggaggacga ugcggaguga auugcauccu ucgauuaccu acucuuuugu gccccagacg    60
acucgcccga                                                          70

<210> SEQ ID NO 153
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F

<400> SEQUENCE: 153
gggaggacga ugcggggagg gaaaugaaau gacaagaacg agacuaagau gggacagacg    60
acucgcccga                                                          70

<210> SEQ ID NO 154
<211> LENGTH: 40
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(40)
<223> OTHER INFORMATION: All pyrimidines are 2'-F

<400> SEQUENCE: 154
ygggaggacg augcgguugu uccgcagacg acucgcccga                         40

<210> SEQ ID NO 155
<211> LENGTH: 53
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(53)
<223> OTHER INFORMATION: All pyrimidines are 2'-F; N's at positions 16,
      21, 29 and 31 are A, C, G or U.

<400> SEQUENCE: 155
gggaggacga ugcggnucuu nuucccucna nuguccccag acgacucgcc cga          53

<210> SEQ ID NO 156
<211> LENGTH: 36
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(36)
<223> OTHER INFORMATION: All pyrimidines are 2'-F; N at position 17 is
      A, C, G or U.

<400> SEQUENCE: 156
gggaggacga ugcggcnuaa cagacgacuc gcccga       36

<210> SEQ ID NO 157
<211> LENGTH: 40
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(40)
<223> OTHER INFORMATION: All pyrimidines are 2'-F; N at position 21 is
      A, C, G or U.

<400> SEQUENCE: 157
gggaggacga ugcggggugu nuuucagacg acucgcccga       40

<210> SEQ ID NO 158
<211> LENGTH: 62
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(62)
<223> OTHER INFORMATION: All pyrimidines are 2'-F; N's at positions
      17-46 are A, C, G or U.

<400> SEQUENCE: 158
ygggaggacg augcggnnnn nnnnnnnnnn nnnnnnnnnn nnnnnncaga cgacucgccc       60
ga       62

<210> SEQ ID NO 159
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(30)
<223> OTHER INFORMATION: All pyrimidines are 2'-F

<400> SEQUENCE: 159
aaacggaaga auuggauacc gcuacguguu       30

<210> SEQ ID NO 160
<211> LENGTH: 29
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(29)
<223> OTHER INFORMATION: All pyrimidines are 2'-F

<400> SEQUENCE: 160
uaaccagugg aagaauuggc ugcuauccu       29

<210> SEQ ID NO 161
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence

```
<221> NAME/KEY: modified_base
<222> LOCATION: (1)..(30)
<223> OTHER INFORMATION: All pyrimidines are 2'-F

<400> SEQUENCE: 161
cuuaaguuuu ggaagaauug aauacugggu                                    30

<210> SEQ ID NO 162
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(30)
<223> OTHER INFORMATION: All pyrimidines are 2'-F

<400> SEQUENCE: 162
agcuaacgga agaauuggaa acaaccgcgu                                    30

<210> SEQ ID NO 163
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(30)
<223> OTHER INFORMATION: All pyrimidines are 2'-F

<400> SEQUENCE: 163
ucaaccgguu gaauauuugg ucgcugaccu                                    30

<210> SEQ ID NO 164
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(30)
<223> OTHER INFORMATION: All pyrimidines are 2'-F

<400> SEQUENCE: 164
aacuagugaa ugcuuauacg accguguugu                                    30

<210> SEQ ID NO 165
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(30)
<223> OTHER INFORMATION: All pyrimidines are 2'-F

<400> SEQUENCE: 165
aucagugaau gcuuauagac cguauugcgu                                    30

<210> SEQ ID NO 166
<211> LENGTH: 30
<212> TYPE: RNA
<213> ORGANISM: Artificial Sequence
<220> FEATURE:
<223> OTHER INFORMATION: Description of Artificial Sequence: Synthetic
```

```
        Sequence
<221> NAME/KEY: modified_base
<222> LOCATION: (1)..(30)
<223> OTHER INFORMATION: All pyrimidines are 2'-F

<400> SEQUENCE: 166
agaaucagug aaugcuuaua aaucucgugu                                       30

<210> SEQ ID NO 167
<211> LENGTH: 33
<212> TYPE: RNA
<213> ORGANISM: Artificial Sequence
<220> FEATURE:
<223> OTHER INFORMATION: Description of Artificial Sequence: Synthetic
        Sequence
<221> NAME/KEY: modified_base
<222> LOCATION: (1)..(33)
<223> OTHER INFORMATION: All pyrimidines are 2'-F

<400> SEQUENCE: 167
cggaaucagu gaaugcuuau acauccgcuc ggu                                   33

<210> SEQ ID NO 168
<211> LENGTH: 29
<212> TYPE: RNA
<213> ORGANISM: Artificial Sequence
<220> FEATURE:
<223> OTHER INFORMATION: Description of Artificial Sequence: Synthetic
        Sequence
<221> NAME/KEY: modified_base
<222> LOCATION: (1)..(29)
<223> OTHER INFORMATION: All pyrimidines are 2'-F

<400> SEQUENCE: 168
aaccagugaa ugcuuauaag acugcucgu                                        29

<210> SEQ ID NO 169
<211> LENGTH: 30
<212> TYPE: RNA
<213> ORGANISM: Artificial Sequence
<220> FEATURE:
<223> OTHER INFORMATION: Description of Artificial Sequence: Synthetic
        Sequence
<221> NAME/KEY: modified_base
<222> LOCATION: (1)..(30)
<223> OTHER INFORMATION: All pyrimidines are 2'-F

<400> SEQUENCE: 169
aaucagugaa ugcuuauagc uccgcguggu                                       30

<210> SEQ ID NO 170
<211> LENGTH: 30
<212> TYPE: RNA
<213> ORGANISM: Artificial Sequence
<220> FEATURE:
<223> OTHER INFORMATION: Description of Artificial Sequence: Synthetic
        Sequence
<221> NAME/KEY: modified_base
<222> LOCATION: (1)..(30)
<223> OTHER INFORMATION: All pyrimidines are 2'-F

<400> SEQUENCE: 170
accagugaau gcuuauaagc ccaucgaccu                                       30

<210> SEQ ID NO 171
<211> LENGTH: 30
<212> TYPE: RNA
<213> ORGANISM: Artificial Sequence
<220> FEATURE:
```

```
<223> OTHER INFORMATION: Description of Artificial Sequence: Synthetic
      Sequence
<221> NAME/KEY: modified_base
<222> LOCATION: (1)..(30)
<223> OTHER INFORMATION: All pyrimidines are 2'-F; N at position 25 is
      A, C, G or U.

<400> SEQUENCE: 171
aaucagugaa ugcuuauagc uccgnguccu                                    30

<210> SEQ ID NO 172
<211> LENGTH: 29
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(29)
<223> OTHER INFORMATION: All pyrimidines are 2'-F

<400> SEQUENCE: 172 ucuuugggu uuugccaacg guuuucgcu                                      29

<210> SEQ ID NO 173
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(30)
<223> OTHER INFORMATION: All pyrimidines are 2'-F

<400> SEQUENCE: 173
auuuggaugc augucaaggc guuuugcccu                                    30

<210> SEQ ID NO 174
<211> LENGTH: 16
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 174
cagacgactc gcccga                                                   16

<210> SEQ ID NO 175
<211> LENGTH: 14
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 175
gacgactcgc ccga                                                     14

<210> SEQ ID NO 176
<211> LENGTH: 22
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(22)
```

<223> OTHER INFORMATION: N's at positions 17-22 are A, C, G or T.

<400> SEQUENCE: 176
tcgggcgagt cgtctgnnnn nn                                          22

<210> SEQ ID NO 177
<211> LENGTH: 15
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 177
cgcattctcc cttta                                                  15

<210> SEQ ID NO 178
<211> LENGTH: 16
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(16)
<223> OTHER INFORMATION: N's at positions 11-16 are A, C, G or T.

<400> SEQUENCE: 178
ggagaatgcg nnnnnn                                                 16

<210> SEQ ID NO 179
<211> LENGTH: 51
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(51)
<223> OTHER INFORMATION: All pyrimidines are 2'-F; N's at positions 6-35
      are A, C, G or U.

<400> SEQUENCE: 179
gggagnnnnn nnnnnnnnnn nnnnnnnnnn nnnnncagac gacucgcccg a          51

<210> SEQ ID NO 180
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'-F

<400> SEQUENCE: 180
gggaguguga aacggaagaa uuggaaacau ugcucgucac agacgacucg cccga       55

<210> SEQ ID NO 181
<211> LENGTH: 57
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(57)
<223> OTHER INFORMATION: All pyrimidines are 2'-F

```
<400> SEQUENCE: 181
gggagcuggc uuaaguuuug gaagaauuga auacugggtuc acagacgacu cgcccga        57

<210> SEQ ID NO 182
<211> LENGTH: 56
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(56)
<223> OTHER INFORMATION: All pyrimidines are 2'-F

<400> SEQUENCE: 182
gggaguggaa gaauuggaua uaucguucgu uuuccgguca cagacgacuc gcccga         56

<210> SEQ ID NO 183
<211> LENGTH: 58
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(58)
<223> OTHER INFORMATION: All pyrimidines are 2'-F

<400> SEQUENCE: 183
gggaguugga agaauugaua cgaucgucca ucuacucuuc agcagacgac ucgcccga       58

<210> SEQ ID NO 184
<211> LENGTH: 44
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(44)
<223> OTHER INFORMATION: All pyrimidines are 2'-F

<400> SEQUENCE: 184
gggaggaaga auuggaaaca uugcucguca gacgacucgc ccga                     44

<210> SEQ ID NO 185
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'-F

<400> SEQUENCE: 185
gggagugguc aaccgguuga auauuugguc gcugaccuac agacgacucg cccga          55

<210> SEQ ID NO 186
<211> LENGTH: 56
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(56)
```

<223> OTHER INFORMATION: All pyrimidines are 2'-F

<400> SEQUENCE: 186
gggagcggaa auuagugaau gcuuauaacu uccacgguca cagacgacuc gcccga        56

<210> SEQ ID NO 187
<211> LENGTH: 53
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(53)
<223> OTHER INFORMATION: All pyrimidines are 2'-F

<400> SEQUENCE: 187
gggagggacu aggugaaugc cguuauucuu ccugucacag acgacucgcc cga        53

<210> SEQ ID NO 188
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'-F

<400> SEQUENCE: 188
gggagggggA cuaggugaau gccaauauuc uucuccguce agacgacucg cccga        55

<210> SEQ ID NO 189
<211> LENGTH: 56
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(56)
<223> OTHER INFORMATION: All pyrimidines are 2'-F

<400> SEQUENCE: 189
gggagggggA cuaggugaau gccaauauuc uucuccguca cagacgacuc gcccga        56

<210> SEQ ID NO 190
<211> LENGTH: 58
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(58)
<223> OTHER INFORMATION: All pyrimidines are 2'-F

<400> SEQUENCE: 190
gggagcuagg gacuagguga augccaauau ucuucuccgu cacagacgac ucgcccga        58

<210> SEQ ID NO 191
<211> LENGTH: 59
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base

```
<222> LOCATION: (1)..(59)
<223> OTHER INFORMATION: All pyrimidines are 2'-F

<400> SEQUENCE: 191
gggagcggac gaccuggnga augccaauau acuuucgcg ucacagacga cucgcccga      59

<210> SEQ ID NO 192
<211> LENGTH: 59
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(59)
<223> OTHER INFORMATION: All pyrimidines are 2'-F

<400> SEQUENCE: 192
gggaggcccu cagguacucg gugaaugcca uuaugcuugc ccucagacga cucgcccga      59

<210> SEQ ID NO 193
<211> LENGTH: 56
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(56)
<223> OTHER INFORMATION: All pyrimidines are 2'-F

<400> SEQUENCE: 193
gggagggggg gggagugaau gcuuauuaga ucugccguca cagacgacuc gcccga      56

<210> SEQ ID NO 194
<211> LENGTH: 54
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(54)
<223> OTHER INFORMATION: All pyrimidines are 2'-F

<400> SEQUENCE: 194
gggaggguga augccaacga uuuuaucgcc uaucgucaca gacgacucgc ccga      54

<210> SEQ ID NO 195
<211> LENGTH: 54
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(54)
<223> OTHER INFORMATION: All pyrimidines are 2'-F

<400> SEQUENCE: 195
gggagcuggu gaaugccaac gauuuuaucg ccuaucguca gacgacucgc ccga      54

<210> SEQ ID NO 196
<211> LENGTH: 53
<212> TYPE: RNA
<213> ORGANISM: Artificial Sequence
<220> FEATURE:
<223> OTHER INFORMATION: Description of Artificial Sequence: Synthetic
      Sequence
```

```
<221> NAME/KEY: modified_base
<222> LOCATION: (1)..(53)
<223> OTHER INFORMATION: All pyrimidines are 2'-F

<400> SEQUENCE: 196
gggagcagac gacucgcccg acagaccacu cgcccgacag acgacucgcc cga         53

<210> SEQ ID NO 197
<211> LENGTH: 49
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(49)
<223> OTHER INFORMATION: All pyrimidines are 2'-F

<400> SEQUENCE: 197
gggagcagac gacucgcccg aggaggaggg gggcagacga cucgcccga              49

<210> SEQ ID NO 198
<211> LENGTH: 58
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(58)
<223> OTHER INFORMATION: All pyrimidines are 2'-F

<400> SEQUENCE: 198
gggagaccac cagacgacuc gcccgaacgc uuauccucug gucagacgac ucgcccga    58

<210> SEQ ID NO 199
<211> LENGTH: 56
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(56)
<223> OTHER INFORMATION: All pyrimidines are 2'-F

<400> SEQUENCE: 199
gggaggcaga cgacucgccc gaggauacac aucguguggu cagacgacuc gcccga      56

<210> SEQ ID NO 200
<211> LENGTH: 57
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(57)
<223> OTHER INFORMATION: All pyrimidines are 2'-F

<400> SEQUENCE: 200
gggagauagg cagacgacuc gcccgaggaa acauugcucg ucagacgacu cgcccga     57

<210> SEQ ID NO 201
<211> LENGTH: 51
<212> TYPE: RNA
<213> ORGANISM: Artificial Sequence
<220> FEATURE:
<223> OTHER INFORMATION: Description of Artificial Sequence: Synthetic
```

```
            Sequence
<221> NAME/KEY: modified_base
<222> LOCATION: (1)..(51)
<223> OTHER INFORMATION: All pyrimidines are 2'-F

<400> SEQUENCE: 201
gggagcagac gacucgcccg acagacaacu cgccccagac gacucgcccg a          51

<210> SEQ ID NO 202
<211> LENGTH: 54
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(54)
<223> OTHER INFORMATION: All pyrimidines are 2'-F

<400> SEQUENCE: 202
gggaggcaga cgacucgccc gauugaauuu guccguguca gacgacucgc ccga       54

<210> SEQ ID NO 203
<211> LENGTH: 47
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(47)
<223> OTHER INFORMATION: All pyrimidines are 2'-F

<400> SEQUENCE: 203
gggagcagac gacucgcccg acagacgacu ccagacgacu cgcccga              47

<210> SEQ ID NO 204
<211> LENGTH: 56
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(56)
<223> OTHER INFORMATION: All pyrimidines are 2'-F

<400> SEQUENCE: 204
gggagugcau cagacgacuc gcccgacaac acucgcccga cagacgacuc gcccga    56

<210> SEQ ID NO 205
<211> LENGTH: 52
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(52)
<223> OTHER INFORMATION: All pyrimidines are 2'-F

<400> SEQUENCE: 205 gggaggggc cagacgacuc gcccgacaga cgacuccaga cgacucgccc ga          52

<210> SEQ ID NO 206
<211> LENGTH: 57
<212> TYPE: RNA
<213> ORGANISM: Artificial Sequence
<220> FEATURE:
```

-continued

<223> OTHER INFORMATION: Description of Artificial Sequence: Synthetic
      Sequence
<221> NAME/KEY: modified_base
<222> LOCATION: (1)..(57)
<223> OTHER INFORMATION: All pyrimidines are 2'-F; N at position 6 is A,
      C, G or U.

<400> SEQUENCE: 206
gggagngcag cagacgacuc gcccgacaga cgaucgcccg acagacgacu cgcccga         57

<210> SEQ ID NO 207
<211> LENGTH: 52
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(52)
<223> OTHER INFORMATION: All pyrimidines are 2'-F

<400> SEQUENCE: 207
gggaggucuu cgaaucagua aaugcuuagc gcucgucaga cgacucgccc ga              52

<210> SEQ ID NO 208
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'-F

<400> SEQUENCE: 208
gggagagagg uuucaguauu ggcaucgcgu uuguccucac agacgacucg cccga           55

<210> SEQ ID NO 209
<211> LENGTH: 57
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(57)
<223> OTHER INFORMATION: All pyrimidines are 2'-F

<400> SEQUENCE: 209
gggagcuagu ugaucgauuu ccugaugucc uuuccuccuc acagacgacu cgcccga         57

<210> SEQ ID NO 210
<211> LENGTH: 52
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(52)
<223> OTHER INFORMATION: All pyrimidines are 2'-F

<400> SEQUENCE: 210
gggaggaauu ggauacucgc ugugguucuu cccccucaga cgacucgccc ga              52

<210> SEQ ID NO 211
<211> LENGTH: 52
<212> TYPE: RNA

<210> SEQ ID NO 211
<211> LENGTH: 52
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(52)
<223> OTHER INFORMATION: All pyrimidines are 2'-F

<400> SEQUENCE: 211
gggaggcauu gacuaggcua ggcuucucuu uccccacaga cgacucgccc ga     52

<210> SEQ ID NO 212
<211> LENGTH: 55
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(55)
<223> OTHER INFORMATION: All pyrimidines are 2'-F

<400> SEQUENCE: 212
gggagugauc aaaaguggau ucuucguuuu ucccccccac agacgacucg cccga     55

<210> SEQ ID NO 213
<211> LENGTH: 56
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(56)
<223> OTHER INFORMATION: All pyrimidines are 2'-F

<400> SEQUENCE: 213
gggaguaguu gacuuuuccc gauuauccuc ucgugccuca cagacgacuc gcccga     56

<210> SEQ ID NO 214
<211> LENGTH: 55
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(55)
<223> OTHER INFORMATION: All pyrimidines are 2'-F

<400> SEQUENCE: 214
gggaggugga cacugguucc gaaguauugu cuuugccuc agacgacucg cccga     55

<210> SEQ ID NO 215
<211> LENGTH: 53
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(53)
<223> OTHER INFORMATION: All pyrimidines are 2'-F

<400> SEQUENCE: 215
gggagcguga cauuucucga ucguaauacc uccccccucag acgacucgcc cga     53

<210> SEQ ID NO 216
<211> LENGTH: 49

```
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(49)
<223> OTHER INFORMATION: All pyrimidines are 2'-F

<400> SEQUENCE: 216
gggaguuccg guuuggcauu cuucgucucc ucacagacga cucgcccga                    49

<210> SEQ ID NO 217
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'-F

<400> SEQUENCE: 217
gggagugguu ggcacuucuc gauuguucuc cuguccucac agacgacucg cccga             55

<210> SEQ ID NO 218
<211> LENGTH: 42
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(42)
<223> OTHER INFORMATION: All pyrimidines are 2'-F; N at position 13 is
      A, C, G or U.

<400> SEQUENCE: 218
gggagcaggu gungcacaug gugcugcaga cgacucgccc ga                           42

<210> SEQ ID NO 219
<211> LENGTH: 36
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(36)
<223> OTHER INFORMATION: All pyrimidines are 2'-F

<400> SEQUENCE: 219 gggagggga ggacgaugcg cagacgacuc gcccga                                   36

<210> SEQ ID NO 220
<211> LENGTH: 26
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(26)
<223> OTHER INFORMATION: All pyrimidines are 2'-F

<400> SEQUENCE: 220
gggaggucuc cagacgacuc gcccga                                             26
```

<210> SEQ ID NO 221
<211> LENGTH: 26
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(26)
<223> OTHER INFORMATION: All pyrimidines are 2'-F

<400> SEQUENCE: 221
gggagcgcug cagacgacuc gcccga                                        26

<210> SEQ ID NO 222
<211> LENGTH: 59
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(59)
<223> OTHER INFORMATION: All pyrimidines are 2'-F

<400> SEQUENCE: 222
gggagcugga aacggaagua uuggauacau aagcaucccc acacagacga cucgcccga    59

<210> SEQ ID NO 223
<211> LENGTH: 57
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(57)
<223> OTHER INFORMATION: All pyrimidines are 2'-F

<400> SEQUENCE: 223
gggagggaga cuuuggaaga auugaauuug uccgugucac acagacgacu cgcccga      57

<210> SEQ ID NO 224
<211> LENGTH: 49
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(49)
<223> OTHER INFORMATION: All pyrimidines are 2'-F

<400> SEQUENCE: 224
gggaggaaac ggaagaauug gaaacacccc guccagacga cucgcccga               49

<210> SEQ ID NO 225
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'-F

<400> SEQUENCE: 225
gggagggaga cuuuggaaga auugaauuug uccgcgucac agacgacucg cccga        55

<210> SEQ ID NO 226
<211> LENGTH: 58
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(58)
<223> OTHER INFORMATION: All pyrimidines are 2'-F

<400> SEQUENCE: 226
gggaggggag gaaacggaag aauuggaaaa cacccgucag cacagacgac ucgcccga        58

<210> SEQ ID NO 227
<211> LENGTH: 57
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(57)
<223> OTHER INFORMATION: All pyrimidines are 2'-F

<400> SEQUENCE: 227
gggaggguga ugcaguggaa gaauugguug cagccgucac acagacgacu cgcccga         57

<210> SEQ ID NO 228
<211> LENGTH: 57
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(57)
<223> OTHER INFORMATION: All pyrimidines are 2'-F

<400> SEQUENCE: 228
gggaguggug aaacggaaga auuggaaaca uugcucgucc acagacgacu cgcccga         57

<210> SEQ ID NO 229
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'-F

<400> SEQUENCE: 229
gggagggcua guaggaagaa uuguaagcug ccucgugcac agacgacucg cccga           55

<210> SEQ ID NO 230
<211> LENGTH: 58
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(58)
<223> OTHER INFORMATION: All pyrimidines are 2'-F

<400> SEQUENCE: 230
gggagcgggg auaacagaau ucuuggugaa caaccgguca cacagacgac ucgcccga        58

<210> SEQ ID NO 231
<211> LENGTH: 56
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(56)
<223> OTHER INFORMATION: All pyrimidines are 2'-F

<400> SEQUENCE: 231
gggagugguc aaccgguuga auauuugguc gcugaccuca cagacgacuc gcccga       56

<210> SEQ ID NO 232
<211> LENGTH: 52
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(52)
<223> OTHER INFORMATION: All pyrimidines are 2'-F

<400> SEQUENCE: 232
gggagugguc aaccgguuga auauuugguc gcagaccaga cgacucgccc ga           52

<210> SEQ ID NO 233
<211> LENGTH: 58
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(58)
<223> OTHER INFORMATION: All pyrimidines are 2'-F

<400> SEQUENCE: 233
gggagggguc aaccgguuga auauuugguc gcugaccuca cacagacgac ucgcccga     58

<210> SEQ ID NO 234
<211> LENGTH: 57
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(57)
<223> OTHER INFORMATION: All pyrimidines are 2'-F

<400> SEQUENCE: 234
gggagggcga aucagugaau gcuuaaugcu cgucggucac acagacgacu cgcccga      57

<210> SEQ ID NO 235
<211> LENGTH: 58
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(58)
<223> OTHER INFORMATION: All pyrimidines are 2'-F

<400> SEQUENCE: 235

-continued gggagucugg agaaucagug aaugcuuaua aaucuguguc cacagacgac ucgcccga    58

<210> SEQ ID NO 236
<211> LENGTH: 57
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(57)
<223> OTHER INFORMATION: All pyrimidines are 2'-F

<400> SEQUENCE: 236
gggaggggac cgggugaaug ccaauguacu uuucgcgucc acagacgacu cgcccga    57

<210> SEQ ID NO 237
<211> LENGTH: 57
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(57)
<223> OTHER INFORMATION: All pyrimidines are 2'-F

<400> SEQUENCE: 237
gggaggguac cuaggugaau gccguuauuc uguugcccac acagacgacu cgcccga    57

<210> SEQ ID NO 238
<211> LENGTH: 58
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(58)
<223> OTHER INFORMATION: All pyrimidines are 2'-F

<400> SEQUENCE: 238
gggagaggag aaucagugaa ugcuuauaaa ucucguguca cacagacgac ucgcccga    58

<210> SEQ ID NO 239
<211> LENGTH: 58
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(58)
<223> OTHER INFORMATION: All pyrimidines are 2'-F

<400> SEQUENCE: 239
gggaguggaa aucagugaau gcuuauaguu ucucgcguca cacagacgac ucgcccga    58

<210> SEQ ID NO 240
<211> LENGTH: 56
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(56)
<223> OTHER INFORMATION: All pyrimidines are 2'-F

<400> SEQUENCE: 240
gggagggacu gaaugaaugu ugacgguuac gcuucccca cagacgacuc gcccga    56

<210> SEQ ID NO 241
<211> LENGTH: 58
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(58)
<223> OTHER INFORMATION: All pyrimidines are 2'-F

<400> SEQUENCE: 241
gggagggaca cugguuccga aguauugucu uuguccucac agcagacgac ucgcccga    58

<210> SEQ ID NO 242
<211> LENGTH: 58
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(58)
<223> OTHER INFORMATION: All pyrimidines are 2'-F

<400> SEQUENCE: 242
gggaggggac acugguuccg aaguauuguc uuuguccuca cacagacgac ucgcccga    58

<210> SEQ ID NO 243
<211> LENGTH: 57
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(57)
<223> OTHER INFORMATION: All pyrimidines are 2'-F

<400> SEQUENCE: 243
gggagggaca cugguuccga aguauugucu uuguccucac acagacgacu cgcccga    57

<210> SEQ ID NO 244
<211> LENGTH: 58
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(58)
<223> OTHER INFORMATION: All pyrimidines are 2'-F

<400> SEQUENCE: 244
gggaggguuu ggaacggaag aauuggauac gcaccucaca cacagacgac ucgcccga    58

<210> SEQ ID NO 245
<211> LENGTH: 56
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(56)
<223> OTHER INFORMATION: All pyrimidines are 2'-F

```
<400> SEQUENCE: 245
gggagaggau guaggaagaa uuggaagauc cgugugcgua cagacgacuc gcccga        56

<210> SEQ ID NO 246
<211> LENGTH: 56
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(56)
<223> OTHER INFORMATION: All pyrimidines are 2'-F

<400> SEQUENCE: 246
gggaguggca ggauuuugga agaauuggau auuggccuca cagacgacuc gcccga        56

<210> SEQ ID NO 247
<211> LENGTH: 59
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(59)
<223> OTHER INFORMATION: All pyrimidines are 2'-F

<400> SEQUENCE: 247
gggagggacc uuuuggaagu uauuggauag gccgugucac gcacagacga cucgcccga    59

<210> SEQ ID NO 248
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'-F

<400> SEQUENCE: 248
gggagggaca uguaggaaga auuggaagau gcgccacagc agacgacucg cccga         55

<210> SEQ ID NO 249
<211> LENGTH: 53
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(53)
<223> OTHER INFORMATION: All pyrimidines are 2'-F

<400> SEQUENCE: 249
gggaggguaa ccgguugaag uuauuggucg cuaugcucag acgacucgcc cga           53

<210> SEQ ID NO 250
<211> LENGTH: 62
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(62)
<223> OTHER INFORMATION: All pyrimidines are 2'-F
```

```
<400> SEQUENCE: 250
gggagggagg ucaaccgguu gaauauuugg ucgcugaccu cacacacaga cgacucgccc      60
ga                                                                    62

<210> SEQ ID NO 251
<211> LENGTH: 60
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(60)
<223> OTHER INFORMATION: All pyrimidines are 2'-F

<400> SEQUENCE: 251
gggaggguca accgguugaa uauuuggucg cugaucucgc cacacagacg acucgcccga      60

<210> SEQ ID NO 252
<211> LENGTH: 58
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(58)
<223> OTHER INFORMATION: All pyrimidines are 2'-F

<400> SEQUENCE: 252
gggagugguc aaccgguuga auauuugguc gcugaccuca cacagacgac ucgcccga        58

<210> SEQ ID NO 253
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'-F

<400> SEQUENCE: 253
gggagagcgu aaccgucaac auucauucag uccccucccc agacgacucg cccga           55

<210> SEQ ID NO 254
<211> LENGTH: 59
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(59)
<223> OTHER INFORMATION: All pyrimidines are 2'-F

<400> SEQUENCE: 254
gggagggaga aaucagugaa ugcuuauugc uucucgucac acacagacga cucgcccga       59

<210> SEQ ID NO 255
<211> LENGTH: 59
<212> TYPE: RNA
<213> ORGANISM: Artificial Sequence
<220> FEATURE:
<223> OTHER INFORMATION: Description of Artificial Sequence: Synthetic
      Sequence
```

<221> NAME/KEY: modified_base
<222> LOCATION: (1)..(59)
<223> OTHER INFORMATION: All pyrimidines are 2'-F

<400> SEQUENCE: 255
gggagggcac uaggugaaug ccguuauucu ugcugcucuc ucucagacga cucgcccga    59

<210> SEQ ID NO 256
<211> LENGTH: 60
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(60)
<223> OTHER INFORMATION: All pyrimidines are 2'-F

<400> SEQUENCE: 256 gggagggag aaaucaguga augcuuaucg uuucucguca cacacagacg acucgcccga    60

<210> SEQ ID NO 257
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 257
gggaggggga cuaggugaau gccaauauuc uucuccguca ccacacagac gacucgcccg    60
a                                                                  61

<210> SEQ ID NO 258
<211> LENGTH: 56
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(56)
<223> OTHER INFORMATION: All pyrimidines are 2'-F

<400> SEQUENCE: 258
gggagggcgg aucagugaau gcuuacaaac cgugugaccc cagacgacuc gcccga    56

<210> SEQ ID NO 259
<211> LENGTH: 57
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(57)
<223> OTHER INFORMATION: All pyrimidines are 2'-F

<400> SEQUENCE: 259
gggaggcaaa aucagugaau gcuuauugcu uuggcucacc acagacgacu cgcccga    57

<210> SEQ ID NO 260
<211> LENGTH: 60
<212> TYPE: RNA
<213> ORGANISM: Artificial Sequence

```
<220> FEATURE:
<223> OTHER INFORMATION: Description of Artificial Sequence: Synthetic
      Sequence
<221> NAME/KEY: modified_base
<222> LOCATION: (1)..(60)
<223> OTHER INFORMATION: All pyrimidines are 2'-F

<400> SEQUENCE: 260
gggagggcgg aacuagugaa ugcuuauacg accguguugu cacacagacg acucgcccga       60

<210> SEQ ID NO 261
<211> LENGTH: 57
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(57)
<223> OTHER INFORMATION: All pyrimidines are 2'-F

<400> SEQUENCE: 261
gggaguuagg aaucagugaa ugcuuauaca uccgcucggu ccagacgacu cgcccga          57

<210> SEQ ID NO 262
<211> LENGTH: 76
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(76)
<223> OTHER INFORMATION: All pyrimidines are 2'-F

<400> SEQUENCE: 262
gggaguggac acugguuccg aaguaacguu gaaguaaaau ucguucucuc ggcguuuggc       60
cagacgacuc gcccga                                                      76

<210> SEQ ID NO 263
<211> LENGTH: 58
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(58)
<223> OTHER INFORMATION: All pyrimidines are 2'-F

<400> SEQUENCE: 263
gggagggaca cuaggugcau gccaaaauuc uugccucag cacagacgac ucgccga           58

<210> SEQ ID NO 264
<211> LENGTH: 60
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(60)
<223> OTHER INFORMATION: All pyrimidines are 2'-F

<400> SEQUENCE: 264
gggaggggac auugguuccg aaguauugac uuugcccuca cacacagacg acucgcccga       60

<210> SEQ ID NO 265
```

-continued

<211> LENGTH: 53
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(53)
<223> OTHER INFORMATION: All pyrimidines are 2'-F

<400> SEQUENCE: 265
gggaggguua accguuaaga cggcgucauu uugucccag acgacucgcc cga         53

<210> SEQ ID NO 266
<211> LENGTH: 53
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(53)
<223> OTHER INFORMATION: All pyrimidines are 2'-F

<400> SEQUENCE: 266
gggaggguua accguuaaga cggcuucauu uugucccag acgacucgcc cga         53

<210> SEQ ID NO 267
<211> LENGTH: 53
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(53)
<223> OTHER INFORMATION: All pyrimidines are 2'-F

<400> SEQUENCE: 267
gggaggguua accguuaaga cggcguuauu uugucccag acgacucgcc cga         53

<210> SEQ ID NO 268
<211> LENGTH: 53
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(53)
<223> OTHER INFORMATION: All pyrimidines are 2'-F; N at position 25 is
      A, C, G or U.

<400> SEQUENCE: 268
gggaggguua accguuaaga cggcnucauu uugucccag acgacucgcc cga         53

<210> SEQ ID NO 269
<211> LENGTH: 53
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(53)
<223> OTHER INFORMATION: All pyrimidines are 2'-F

<400> SEQUENCE: 269
gggaggguua accguuaaga cggcuuuauu uugucccag acgacucgcc cga         53

<210> SEQ ID NO 270
<211> LENGTH: 53
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(53)
<223> OTHER INFORMATION: All pyrimidines are 2'-F; N at position 27 is
      A, C, G or U.

<400> SEQUENCE: 270
gggaggguua accguuaaga cggcgunauu ugucCccag acgacucgcc cga         53

<210> SEQ ID NO 271
<211> LENGTH: 53
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(53)
<223> OTHER INFORMATION: All pyrimidines are 2'-F

<400> SEQUENCE: 271
gggaggguua accguaaaga cggcauuaug uagucCccag acgacucgcc cga         53

<210> SEQ ID NO 272
<211> LENGTH: 51
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(51)
<223> OTHER INFORMATION: All pyrimidines are 2'-F

<400> SEQUENCE: 272
gggaggggaa uuuuugguaa agccguaugc cucgccagac gacucgcccg a           51

<210> SEQ ID NO 273
<211> LENGTH: 53
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(53)
<223> OTHER INFORMATION: All pyrimidines are 2'-F

<400> SEQUENCE: 273
gggaggggaa uuuuugguaa agccauaugc cucgccacag acgacucgcc cga         53

<210> SEQ ID NO 274
<211> LENGTH: 54
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(54)
<223> OTHER INFORMATION: All pyrimidines are 2'-F

<400> SEQUENCE: 274

```
gggagcggga auuuuuggua aagccguaug ccucgccaca gacgacucgc ccga          54

<210> SEQ ID NO 275
<211> LENGTH: 52
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(52)
<223> OTHER INFORMATION: All pyrimidines are 2'-F

<400> SEQUENCE: 275
gggaguggga auuuuuggua aagccguaug ccucgccaga cgacucgccc ga            52

<210> SEQ ID NO 276
<211> LENGTH: 53
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(53)
<223> OTHER INFORMATION: All pyrimidines are 2'-F

<400> SEQUENCE: 276
gggagcgggg aauuuuuggu aaagccguau gccucgccag acgacucgcc cga           53

<210> SEQ ID NO 277
<211> LENGTH: 60
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(60)
<223> OTHER INFORMATION: All pyrimidines are 2'-F

<400> SEQUENCE: 277
gggaggguuu cauggaauuu uugguaaagc cguaugccuc gccacagacg acucgcccga    60

<210> SEQ ID NO 278
<211> LENGTH: 35
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(35)
<223> OTHER INFORMATION: All pyrimidines are 2'-F

<400> SEQUENCE: 278
gggagauuuu ugguaaagcc agacgacucg cccga                              35

<210> SEQ ID NO 279
<211> LENGTH: 53
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(53)
<223> OTHER INFORMATION: All pyrimidines are 2'-F

<400> SEQUENCE: 279
```
gggagggaau uuuugauuua gucguacgcc gcaucccag acgacucgcc cga         53

<210> SEQ ID NO 280
<211> LENGTH: 53
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(53)
<223> OTHER INFORMATION: All pyrimidines are 2'-F

<400> SEQUENCE: 280 gggagggguuu cauggaauuu uugguuuagc cguaugccag acgacucgcc cga         53

<210> SEQ ID NO 281
<211> LENGTH: 51
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(51)
<223> OTHER INFORMATION: All pyrimidines are 2'-F

<400> SEQUENCE: 281 gggagggguuc uggaauuuuu gguuuagccg uacgccagac gacucgcccg a           51

<210> SEQ ID NO 282
<211> LENGTH: 53
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(53)
<223> OTHER INFORMATION: All pyrimidines are 2'-F

<400> SEQUENCE: 282
gggagaggga ucuggaauuu uugguuuagc cguacgccag acgacucgcc cga         53

<210> SEQ ID NO 283
<211> LENGTH: 50
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(50)
<223> OTHER INFORMATION: All pyrimidines are 2'-F; N at positions 7, 25,
      and 32 are A, C, G or U.

<400> SEQUENCE: 283
gggagancug guaauuuugg uuuanccgua uncccagacg acucgcccga              50

<210> SEQ ID NO 284
<211> LENGTH: 53
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(53)
<223> OTHER INFORMATION: All pyrimidines are 2'-F; N at position 25 is A, C, G or U.

<400> SEQUENCE: 284
gggagagggg ucuggaauuu uuggnuuacc cguacgccag acgacucgcc cga                53

<210> SEQ ID NO 285
<211> LENGTH: 52
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(52)
<223> OTHER INFORMATION: All pyrimidines are 2'-F

<400> SEQUENCE: 285
gggagggaau uuuuguguag acguaugccc uuugcccaga cgacucgccc ga                 52

<210> SEQ ID NO 286
<211> LENGTH: 54
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(54)
<223> OTHER INFORMATION: All pyrimidines are 2'-F; N at position 37 is
      A, C, G or U.

<400> SEQUENCE: 286
gggagcggaa uuuuugugua gacguaugcc gcuuugncca gacgacucgc ccga               54

<210> SEQ ID NO 287
<211> LENGTH: 53
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(53)
<223> OTHER INFORMATION: All pyrimidines are 2'-F

<400> SEQUENCE: 287
gggaggggcu caacuuuucu cuucuucuuu uccgcccag acgacucgcc cga                 53

<210> SEQ ID NO 288
<211> LENGTH: 54
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(54)
<223> OTHER INFORMATION: All pyrimidines are 2'-F

<400> SEQUENCE: 288
gggagggccc cauucuuuuu uauuucuuuu uugccccaca gacgacucgc ccga               54

<210> SEQ ID NO 289
<211> LENGTH: 53
<212> TYPE: RNA
<213> ORGANISM: Artificial Sequence
<220> FEATURE:
<223> OTHER INFORMATION: Description of Artificial Sequence: Synthetic
      Sequence

```
<221> NAME/KEY: modified_base
<222> LOCATION: (1)..(53)
<223> OTHER INFORMATION: All pyrimidines are 2'-F

<400> SEQUENCE: 289
gggagggccc gguuuucuu uuucuuuucu uuuccccag acgacucgcc cga           53

<210> SEQ ID NO 290
<211> LENGTH: 54
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(54)
<223> OTHER INFORMATION: All pyrimidines are 2'-F

<400> SEQUENCE: 290
gggagggccu ucuuucuuuc uuucuuuuu uccgucccca gacgacucgc ccga         54

<210> SEQ ID NO 291
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F; N's at positions 6-45
      are A, C, G or U.

<400> SEQUENCE: 291
gggagnnnnn nnnnnnnnnn nnnnnnnnnn nnnnnnnnnn nnnnncagac gacucgcccg  60
a                                                                 61

<210> SEQ ID NO 292
<211> LENGTH: 65
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: All pyrimidines are 2'-F; N at position 49 is
      A, C, G or U.

<400> SEQUENCE: 292
gggaggggac agacgacucg cccgauaaua cgacucacua uagggaggnc agacgacucg  60
cccga                                                             65

<210> SEQ ID NO 293
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 293
gggaggggag ggcagacgac ucgcccgaua auacgacuca cuauacagac gacucgcccg  60
a                                                                 61
```

<210> SEQ ID NO 294
<211> LENGTH: 67
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(67)
<223> OTHER INFORMATION: All pyrimidines are 2'-F; N at position 46 is
      A, C, G or U.

<400> SEQUENCE: 294
gggaggggac acgacgacuc gcccgauaau acgacucacu auaggnaguu gcagacgacu      60
cgcccga                                                               67

<210> SEQ ID NO 295
<211> LENGTH: 74
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(74)
<223> OTHER INFORMATION: All pyrimidines are 2'-F

<400> SEQUENCE: 295
gggaggggac ucacuauaca gacgacucgc ccgaccgcua uuacaaucuu cgccucccca      60
gacgacucgc ccga                                                       74

<210> SEQ ID NO 296
<211> LENGTH: 67
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(67)
<223> OTHER INFORMATION: All pyrimidines are 2'-F

<400> SEQUENCE: 296
gggaggggac cagacgacuc gcccgaggga acguucuccc accuccugc ccagacgacu      60 cgcccga                                                               67

<210> SEQ ID NO 297
<211> LENGTH: 69
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(69)
<223> OTHER INFORMATION: All pyrimidines are 2'-F

<400> SEQUENCE: 297
gggaggggac agacgacucg cccgagggau uuuacguucg ucucgcgucu ccccagacga      60
cucgcccga                                                             69

<210> SEQ ID NO 298
<211> LENGTH: 71
<212> TYPE: RNA
<213> ORGANISM: Artificial Sequence

```
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 298
gggaggggag cagacgacuc gcccgaacug ggaauuuuug guugagccgu augcccagac    60
gacucgcccg a                                                        71

<210> SEQ ID NO 299
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F

<400> SEQUENCE: 299
gggaggggag cagacgacuc gcccgagcug ggaauuuuug gcugagccgu augcccagac    60
gacucgcccg a                                                        71

<210> SEQ ID NO 300
<211> LENGTH: 74
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(74)
<223> OTHER INFORMATION: All pyrimidines are 2'-F

<400> SEQUENCE: 300
gggaggggag gguccagacg acucgcccga gggggaauuu uugguugagc cguaugccca    60
gacgacucgc ccga                                                     74

<210> SEQ ID NO 301
<211> LENGTH: 69
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(69)
<223> OTHER INFORMATION: All pyrimidines are 2'-F

<400> SEQUENCE: 301
gggaggggag cagacgacuc gcccgagggg aauuuuggu ugagccguau gcccagacga    60
cucgcccga                                                           69

<210> SEQ ID NO 302
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'-F
```

<400> SEQUENCE: 302
gggaggggac agacgacucg cccgagacug ggaauuuuug guugagccgu augcccagac      60
gacucgcccg a      71

<210> SEQ ID NO 303
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F; N at position 47 is
      A, C, G or U.

<400> SEQUENCE: 303
gggaggggac agacgaacuc gcccgaacug ggaauuuugg uugagcngua ugcccagacg      60
acucgcccga      70

<210> SEQ ID NO 304
<211> LENGTH: 65
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: All pyrimidines are 2'-F

<400> SEQUENCE: 304
gggaggggag gguguuucga acugggaauu uugguuuag ccguaugccc agacgacucg      60
cccga      65

<210> SEQ ID NO 305
<211> LENGTH: 65
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: All pyrimidines are 2'-F

<400> SEQUENCE: 305
gggaggggag gguguuucga acugggaauu uugguugag ccguaugccc agacgacucg      60
cccga      65

<210> SEQ ID NO 306
<211> LENGTH: 65
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: All pyrimidines are 2'-F

<400> SEQUENCE: 306
gggaggggag gguguuucga acugggaauu uugguugag ccguauccccc agacgacucg      60 cccga      65

<210> SEQ ID NO 307
<211> LENGTH: 66
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(66)
<223> OTHER INFORMATION: All pyrimidines are 2'-F

<400> SEQUENCE: 307
gggaggggag ggauucugcc gaguuaauuu cggugucugu agcuuauccc cagacgacuc    60
gcccga                                                              66

<210> SEQ ID NO 308
<211> LENGTH: 66
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(66)
<223> OTHER INFORMATION: All pyrimidines are 2'-F

<400> SEQUENCE: 308
gggaggggag ggauucugcc gaguuaacgu cggugucugu agcuuauccc cagacgacuc    60
gcccga                                                              66

<210> SEQ ID NO 309
<211> LENGTH: 75
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(75)
<223> OTHER INFORMATION: All pyrimidines are 2'-F; N at position 32 is
      A, C, G or U.

<400> SEQUENCE: 309
gggaggggag gacgaugcgg ggguuauugg gngucaacau ccccgauucu uuucacgucc    60
agacgacucg cccga                                                    75

<210> SEQ ID NO 310
<211> LENGTH: 75
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(75)
<223> OTHER INFORMATION: All pyrimidines are 2'-F

<400> SEQUENCE: 310
gggaggggag gacgaugcgg ggguuauugg gcgucaacau ccccgauucu uuucacgucc    60
agacgacucg cccga                                                    75

<210> SEQ ID NO 311
<211> LENGTH: 75
<212> TYPE: RNA
<213> ORGANISM: Artificial Sequence
<220> FEATURE:

-continued

<223> OTHER INFORMATION: Description of Artificial Sequence: Synthetic
      Sequence
<221> NAME/KEY: modified_base
<222> LOCATION: (1)..(75)
<223> OTHER INFORMATION: All pyrimidines are 2'-F

<400> SEQUENCE: 311
gggaggggag gacgaugcgg ggguuauugg gcgucaacau ccccgauucu uuucaccucc      60
agacgacucg cccga                                                      75

<210> SEQ ID NO 312
<211> LENGTH: 66
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(66)
<223> OTHER INFORMATION: All pyrimidines are 2'-F

<400> SEQUENCE: 312
gggaggggag gacgaugcgg agcggauuaa uuagucugac uucuuguccc cagacgacuc      60
gcccga                                                                66

<210> SEQ ID NO 313
<211> LENGTH: 66
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(66)
<223> OTHER INFORMATION: All pyrimidines are 2'-F

<400> SEQUENCE: 313
gggaggggag gacgaugcgg uaaaguagca uuauccucua acauccugcc cagacgacuc      60
gcccga                                                                66

<210> SEQ ID NO 314
<211> LENGTH: 67
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(67)
<223> OTHER INFORMATION: All pyrimidines are 2'-F

<400> SEQUENCE: 314
gggaggggag gggugccuuu agcuuggucu guuuaguaca uuccucugcc ccagacgacu      60
cgcccga                                                               67

<210> SEQ ID NO 315
<211> LENGTH: 67
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(67)
<223> OTHER INFORMATION: All pyrimidines are 2'-F

<400> SEQUENCE: 315
gggaggggag gggugccugu agucuuugca ucuuauaaau gcaaucugcc ccagacgacu    60
cgcccga    67

<210> SEQ ID NO 316
<211> LENGTH: 27
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(27)
<223> OTHER INFORMATION: All pyrimidines are 2'-F

<400> SEQUENCE: 316
gggaggggag gcagacgacu cgcccga    27

<210> SEQ ID NO 317
<211> LENGTH: 65
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: All pyrimidines are 2'-F

<400> SEQUENCE: 317
gggaggggag gguguuacga gcgucggacc cuguuuccaa cauccucccc agacgacucg    60
cccga    65

<210> SEQ ID NO 318
<211> LENGTH: 63
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(63)
<223> OTHER INFORMATION: All pyrimidines are 2'-F

<400> SEQUENCE: 318
gggaggggac uuccuccggc uaucauuuuc uucucuuucu cucucccag acgacucgcc    60 cga    63

<210> SEQ ID NO 319
<211> LENGTH: 67
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(67)
<223> OTHER INFORMATION: All pyrimidines are 2'-F

<400> SEQUENCE: 319
gggaggggag ggaguggucg accaugauuc uuuuuauuuc uccuuccucc ccagacgacu    60
cgcccga    67

<210> SEQ ID NO 320
<211> LENGTH: 68
<212> TYPE: RNA

```
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(68)
<223> OTHER INFORMATION: All pyrimidines are 2'-F

<400> SEQUENCE: 320
gggaggggag ggaccuuucu acuucaucau uuuucuucac ucucuccguc cccagacgac    60
ucgcccga                                                             68

<210> SEQ ID NO 321
<211> LENGTH: 67
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(67)
<223> OTHER INFORMATION: All pyrimidines are 2'-F; N at position 27 is
      A, C, G or U.

<400> SEQUENCE: 321 gggagggguag ggagguuucu gacucunagc uuuccuuucc uccugccucc ccagacgacu   60
cgcccga                                                              67

<210> SEQ ID NO 322
<211> LENGTH: 49
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(49)
<223> OTHER INFORMATION: All pyrimidines are 2'-F; N at position 19 is
      A, C, G or U.

<400> SEQUENCE: 322
gggaggggac agacgacung cccgacguau gcccagacga cucgcccga                49

<210> SEQ ID NO 323
<211> LENGTH: 15
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(15)
<223> OTHER INFORMATION: All pyrimidines are 2'-F; N at positions 1-3,
      5-6, 8 and 11-15 are A, C, G or U.

<400> SEQUENCE: 323
nnnrnnrnya nnnnn                                                     15

<210> SEQ ID NO 324
<211> LENGTH: 15
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(15)
<223> OTHER INFORMATION: All pyrimidines are 2'-F
```

-continued

```
<400> SEQUENCE: 324
cugagcauca gccag                                                  15

<210> SEQ ID NO 325
<211> LENGTH: 15
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(15)
<223> OTHER INFORMATION: All pyrimidines are 2'-F

<400> SEQUENCE: 325
cugagcauca cgaaa                                                  15

<210> SEQ ID NO 326
<211> LENGTH: 67
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(67)
<223> OTHER INFORMATION: All pyrimidines are 2'-F

<400> SEQUENCE: 326
gggaaagccc acgccggcac gcguauucac ugagcaucag ccagacugug uaccgaacug     60
ccgcacc                                                               67

<210> SEQ ID NO 327
<211> LENGTH: 15
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(15)
<223> OTHER INFORMATION: All pyrimidines are 2'-F;  N's at positions
      1-2, 8, and 14-15 are A, C, G or U.

<400> SEQUENCE: 327
nnsassanca sssnn                                                  15

<210> SEQ ID NO 328
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F

<400> SEQUENCE: 328
auucacugag caucagccag acugugucau gcaucuggca gccgaaagcc auguugaccg     60
uucuauugac                                                            70

<210> SEQ ID NO 329
<211> LENGTH: 25
<212> TYPE: RNA
<213> ORGANISM: Artificial Sequence
<220> FEATURE:
```

<223> OTHER INFORMATION: Description of Artificial Sequence: Synthetic
      Sequence
<221> NAME/KEY: modified_base
<222> LOCATION: (1)..(25)
<223> OTHER INFORMATION: All pyrimidines are 2'-F; N's at positions
      17-25 are A, C, G or U.

<400> SEQUENCE: 329
ucccgcucgu cgucugnnnn nnnnn                                          25

<210> SEQ ID NO 330
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'-F

<400> SEQUENCE: 330
auucacugag caucagccag acugugucau gcaucuggca gccgaaagcc auguugaccg    60
uucuauugac                                                          70

<210> SEQ ID NO 331
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 331
gggaggacga ugcggaauca gugaaugcuu auacauccgc ucggucagac gacucgcccg    60
a                                                                   61

<210> SEQ ID NO 332
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F

<400> SEQUENCE: 332
gggaggacga ugcggguaac caguggaaga auuggcugcu auccucagac gacucgcccg    60
a                                                                   61

<210> SEQ ID NO 333
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'-F; N's at positions
      23-47 are A, C, G or U.

<400> SEQUENCE: 333

```
uaauacgacu cacuauaggg agnnnnnnnn nnnnnnnnnn nnnnnnncgg gcggg          55

<210> SEQ ID NO 334
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'-F; N's at positions
      23-47 are A, C, G or U.

<400> SEQUENCE: 334
uaauacgacu cacuauaggg agnnnnnnnn nnnnnnnnnn nnnnnnncgg gcggg          55

<210> SEQ ID NO 335
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'-F; N's at positions 9-33
      are A, C, G or U.

<400> SEQUENCE: 335
cccgcccgnn nnnnnnnnnn nnnnnnnnnn nnncucccua uagugagucg uauua          55

<210> SEQ ID NO 336
<211> LENGTH: 38
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(38)
<223> OTHER INFORMATION: All pyrimidines are 2'-F; N's at positions 6-30
      are A, C, G or U.

<400> SEQUENCE: 336
gggagnnnnn nnnnnnnnnn nnnnnnnnnn cgggcggg                            38

<210> SEQ ID NO 337
<211> LENGTH: 38
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(38)
<223> OTHER INFORMATION: All pyrimidines are 2'-F; N's at positions 9-33
      are A, C, G or U.

<400> SEQUENCE: 337
cccgcccgnn nnnnnnnnnn nnnnnnnnnn nnncuccc                            38

<210> SEQ ID NO 338
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
```

<221> NAME/KEY: modified_base
<222> LOCATION: (1)..(85)
<223> OTHER INFORMATION: All pyrimidines are 2'-F; N's at positions
      22-56 are A, C, G or U.

<400> SEQUENCE: 338
uaauacgacu cacuauaggg annnnnnnnn nnnnnnnnnn nnnnnnnnnn nnnnnnggcc    60
ggccucccuu uagugagggu uaauu                                         85

<210> SEQ ID NO 339
<211> LENGTH: 85
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(85)
<223> OTHER INFORMATION: All pyrimidines are 2'-F; N's at positions
      29-64 are A, C, G or U.

<400> SEQUENCE: 339
aauuaacccu cacuaaaggg aggccggccn nnnnnnnnn nnnnnnnnnn nnnnnnnnnn    60
nnnnucccua uagugagucg uauua                                         85

<210> SEQ ID NO 340
<211> LENGTH: 39
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(39)
<223> OTHER INFORMATION: All pyrimidines are 2'-F; N's at positions 5-40
      are A, C, G or U.

<400> SEQUENCE: 340
gggannnnnn nnnnnnnnnn nnnnnnnnnn nnnnnnnn                           39

<210> SEQ ID NO 341
<211> LENGTH: 14
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(14)
<223> OTHER INFORMATION: All pyrimidines are 2'-F

<400> SEQUENCE: 341
ggaggacgau gcgg                                                     14

<210> SEQ ID NO 342
<211> LENGTH: 20
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(20)
<223> OTHER INFORMATION: All pyrimidines are 2'-F; N's at positions 1-6
      are A, C, G or U.

<400> SEQUENCE: 342
nnnnnnuccc ccgcaucguc                                               20

<210> SEQ ID NO 343
<211> LENGTH: 25
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(25)
<223> OTHER INFORMATION: All pyrimidines are 2'-F; N's at positions
      19-25 are A, C, G or U.

<400> SEQUENCE: 343
ggaggacgau gcgggggann nnnnn                                           25

<210> SEQ ID NO 344
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F; N's at positions
      16-45 are A, C, G or U.

<400> SEQUENCE: 344
gggaggacgg aauucnnnnn nnnnnnnnnn nnnnnnnnnn nnnnncugca gacucgcccg     60
a                                                                    61

<210> SEQ ID NO 345
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'-F; N's at positions17-46
      are A, C, G or U.

<400> SEQUENCE: 345
ucgggcgagu cugcagnnnn nnnnnnnnnn nnnnnnnnnn nnnnnngaau uccguccucc     60
c                                                                    61

<210> SEQ ID NO 346
<211> LENGTH: 16
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(16)
<223> OTHER INFORMATION: All pyrimidines are 2'-F; N at position 1 is A,
      C, G or U.

<400> SEQUENCE: 346
ngaauuccgu ccuccc                                                    16

<210> SEQ ID NO 347
<211> LENGTH: 17
<212> TYPE: RNA
<213> ORGANISM: Artificial Sequence
<220> FEATURE:

```
<223> OTHER INFORMATION: Description of Artificial Sequence: Synthetic
      Sequence
<221> NAME/KEY: modified_base
<222> LOCATION: (1)..(17)
<223> OTHER INFORMATION: All pyrimidines are 2'-F; N at position 17 is
      A, C, G or U.

<400> SEQUENCE: 347
ucgggcgagu cugcagn                                                      17

<210> SEQ ID NO 348
<211> LENGTH: 40
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(40)
<223> OTHER INFORMATION: All pyrimidines are 2'-F; N's at positions 6-35
      are A, C, G or U.

<400> SEQUENCE: 348
aauucnnnnn nnnnnnnnnn nnnnnnnnnn nnnnncugca                             40

<210> SEQ ID NO 349
<211> LENGTH: 15
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(15)
<223> OTHER INFORMATION: All pyrimidines are 2'-F

<400> SEQUENCE: 349
gggaggacgg aauuc                                                        15

<210> SEQ ID NO 350
<211> LENGTH: 16
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(16)
<223> OTHER INFORMATION: All pyrimidines are 2'-F

<400> SEQUENCE: 350
acucgggcga gucugc                                                       16

<210> SEQ ID NO 351
<211> LENGTH: 11
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(11)
<223> OTHER INFORMATION: All pyrimidines are 2'-F; N's at positions 5-11
      are A, C, G or U.

<400> SEQUENCE: 351
gggannnnnn n                                                            11
```

TRUNCATION SELEX METHOD

RELATED APPLICATIONS

This application is a continuation of U.S. patent application Ser. No. 09/275,850, filed Mar. 24, 1999, now U.S. Pat. No. 6,261,774.

FIELD OF THE INVENTION

The present invention is directed to methods for identifying oligonucleotide sequences which specifically bind to target molecules. More particularly, this invention is directed to methods for identifying oligonucleotide sequences in which the participation of fixed sequences is eliminated or minimized.

BACKGROUND OF THE INVENTION

The dogma for many years was that nucleic acids had primarily an informational role. Through a method known as Systematic Evolution of Ligands by Exponential enrichment, termed SELEX, it has become clear that nucleic acids have three dimensional structural diversity not unlike proteins. SELEX is a method for the in vitro evolution of nucleic acid molecules with highly specific binding to target molecules and is described in U.S. patent application Ser. No. 07/536,428, filed Jun. 11, 1990, entitled "Systematic Evolution of Ligands by Exponential Enrichment," now abandoned, U.S. patent application Ser. No. 07/714,131, filed Jun. 10, 1991, entitled "Nucleic Acid Ligands," now U.S. Pat. No. 5,475,096 and U.S. patent application Ser. No. 07/931,473, filed Aug. 17, 1992, entitled "Methods for Identifying Nucleic Acid Ligands," now U.S. Pat. No. 5,270,163 (see also WO 91/19813), each of which is specifically incorporated by reference herein. Each of these applications, collectively referred to herein as the SELEX Patent Applications, describes a fundamentally novel method for making a Nucleic Acid Ligand to any desired target molecule. The SELEX process provides a class of products which are referred to as Nucleic Acid Ligands, each ligand having a unique sequence, and which has the property of binding specifically to a desired target compound or molecule. Each SELEX-identified Nucleic Acid Ligand is a specific ligand of a given target compound or molecule. SELEX is based on the unique insight that Nucleic Acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of Nucleic Acids, preferably comprising a segment of randomized sequence, the SELEX method includes steps of contacting the mixture with the target under conditions favorable for binding, partitioning unbound Nucleic Acids from those Nucleic Acids which have bound specifically to target molecules, dissociating the Nucleic Acid-target complexes, amplifying the Nucleic Acids dissociated from the Nucleic Acid-target complexes to yield a ligand-enriched mixture of Nucleic Acids, then reiterating the steps of binding, partitioning, dissociating and amplifying through as many cycles as desired to yield highly specific high affinity Nucleic Acid Ligands to the target molecule.

It has been recognized by the present inventors that the SELEX method demonstrates that Nucleic Acids as chemical compounds can form a wide array of shapes, sizes and configurations, and are capable of a far broader repertoire of binding and other functions than those displayed by Nucleic Acids in biological systems.

The present inventors have recognized that SELEX or SELEX-like processes could be used to identify Nucleic Acids which can facilitate any chosen reaction in a manner similar to that in which Nucleic Acid Ligands can be identified for any given target. In theory, within a Candidate Mixture of approximately $10^{13}$ to $10^{18}$ Nucleic Acids, the present inventors postulate that at least one Nucleic Acid exists with the appropriate shape to facilitate each of a broad variety of physical and chemical interactions.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," now abandoned (see U.S. Pat. No. 5,707,796), describes the use of SELEX in conjunction with gel electrophoresis to select Nucleic Acid molecules with specific structural characteristics, such as bent DNA. U.S. patent application Ser. No. 08/123,935, filed Sep. 17, 1993, entitled "Photoselection of Nucleic Acid Ligands," now abandoned (see U.S. Pat. No. 5,763,177), describes a SELEX based method for selecting Nucleic Acid Ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," now U.S. Pat. No. 5,580,737, describes a method for identifying highly specific Nucleic Acid Ligands able to discriminate between closely related molecules, which can be non-peptidic, termed Counter-SELEX. U.S. patent application Ser. No. 08/143,564, filed Oct. 25, 1993, entitled "Systematic Evolution of Ligands by Exponential Enrichment: Solution SELEX," now U.S. Pat. No. 5,567,588, describes a SELEX-based method which achieves highly efficient partitioning between oligonucleotides having high and low affinity for a target molecule.

The SELEX method encompasses the identification of high-affinity Nucleic Acid Ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified Nucleic Acid Ligands containing modified nucleotides are described in U.S. patent application Ser. No. 08/117,991, filed Sep. 8, 1993, entitled "High Affinity Nucleic Acid Ligands Containing Modified Nucleotides," now U.S. Pat. No. 5,660,985, that describes oligonucleotides containing nucleotide derivatives chemically modified at the 5- and 2'-positions of pyrimidines. U.S. patent application Ser. No. 08/134,028, supra, describes highly specific Nucleic Acid Ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2'-Modified Nucleosides by Intramolecular Nucleophilic Displacement," now abandoned, describes oligonucleotides containing various 2'-modified pyrimidines.

The SELEX method encompasses combining selected oligonucleotides with other selected oligonucleotides and non-oligonucleotide functional units as described in U.S.

patent application Ser. No. 08/284,063, filed Aug. 2, 1994, entitled "Systematic Evolution of Ligands by Exponential Enrichment: Chimeric SELEX," now U.S. Pat. No. 5,637,459, and U.S. patent application Ser. No. 08/234,997, filed Apr. 28, 1994, entitled "Systematic Evolution of Ligands by Exponential Enrichment: Blended SELEX," now U.S. Pat. No. 5,683,867, respectively. These applications allow the combination of the broad array of shapes and other properties, and the efficient amplification and replication properties, of oligonucleotides with the desirable properties of other molecules.

The SELEX method further encompasses combining selected nucleic acid ligands with lipophilic compounds or non-immunogenic, high molecular weight compounds in a diagnostic or therapeutic complex as described in U.S. patent application Ser. No. 08/434,465, filed May 4, 1995, entitled "Nucleic Acid Ligand Complexes." VEGF Nucleic Acid Ligands that are associated with a Lipophilic Compound, such as diacyl glycerol or dialkyl glycerol, in a diagnostic or therapeutic complex are described in U.S. patent application Ser. No. 08/739,109, filed Oct. 25, 1996, entitled "Vascular Endothelial Growth Factor (VEGF) Nucleic Acid Ligand Complexes," now U.S. Pat. No. 5,859,228. VEGF Nucleic Acid Ligands that are associated with a Lipophilic Compound, such as a glycerol lipid, or a Non-Immunogenic, High Molecular Weight Compound, such as polyethylene glycol, are further described in U.S. patent application Ser. No. 08/897,351, filed Jul. 21, 1997, entitled "Vascular Endothelial Growth Factor (VEGF) Nucleic Acid Ligand Complexes." VEGF Nucleic Acid Ligands that are associated with a non-immunogenic, high molecular weight compound or lipophilic compound are also further described in WO 98/18480, published May 7, 1998, entitled "Vascular Endothelial Growth Factor (VEGF) Nucleic Acid Ligand Complexes." Each of the above described patent applications that describe modifications of the basic SELEX procedure are specifically incorporated by reference herein in their entirety.

In the SELEX process, generally the candidate mixture includes regions of fixed sequences (i.e., each of the members of the candidate mixture contains the same sequences in the same location) and regions of randomized sequence. The fixed sequences are usually selected for: a) assisting in the amplification steps; b) mimicking a sequence known to bind to the target; or c) enhancing the concentration of a given structural arrangement of the nucleic acids in the candidate mixture. The fixed region(s) (or part of the fixed region) in the SELEX-identified Nucleic Acid Ligand may participate in binding to the target. Additionally, the fixed region(s) (or part of the fixed region) could form a structure(s) or contribute to a structure that binds to or facilitates binding to the target. Although in some circumstances this is a desirable attribute, in other circumstances the fixed region(s) may limit the possible structural variation and number of different nucleic acid ligands resulting from the SELEX process. The development of a method for generating nucleic acid ligands in which the participation of fixed sequences in binding to the target is minimized or eliminated is desirable.

Toole et al. (WO 92/14843) discloses a method for identifying oligonucleotide sequences which specifically bind biomolecules. In one embodiment, the method includes identifying and amplifying oligonucleotides without attached flanking regions or structural constraints, but which nevertheless are capable of specific binding to desired targets. This method provides the ability to engineer appropriate means for amplifying the desired oligonucleotides. In this method, a pool of oligonucleotides is generated in which the sequences are unknown. These sequences are incubated with the target under conditions wherein some of the oligonucleotides complex with the target. The oligonucleotides that complex with the target are recovered and known sequences are added to at least one end of the oligonucleotide. These known sequences are then used in amplifying the nucleic acid ligands. Once the nucleic acid ligands have been amplified, the known nucleotide sequence is removed. The process may be repeated for the desired number of rounds until an optimal nucleic acid ligand population may be identified.

SUMMARY OF THE INVENTION

The present invention describes methods for generating nucleic acid ligands in which the participation of fixed sequences in binding to the target is minimized or eliminated.

In one embodiment of the method of this invention, a method for generating nucleic acid ligands without the participation of fixed sequences is described, comprising:

a) preparing a candidate mixture of single-stranded nucleic acids wherein each nucleic acid member of said candidate mixture comprises a fixed region;

b) annealing oligonucleotides to the fixed sequences that are complementary to said fixed sequences;

c) contacting said candidate mixture with said target molecule;

d) partitioning the nucleic acids having an increased affinity to the target molecule relative to the candidate mixture from the remainder of the candidate mixture; and e) amplifying the increased affinity nucleic acids, in vitro, to yield a ligand-enriched mixture of nucleic acids whereby nucleic acid ligands of the target molecule are identified.

In another embodiment of the method of this invention, a method for generating nucleic acid ligands without the participation of fixed sequences is described, comprising a) preparing a candidate mixture of single-stranded nucleic acids wherein each nucleic acid member of said candidate mixture comprises one or more regions of fixed sequences;

b) contacting said candidate mixture with said target molecule;

c) partitioning the nucleic acids having an increased affinity to the target molecule relative to the candidate mixture from the remainder of the candidate mixture;

d) amplifying the increased affinity nucleic acids, in vitro, to yield a ligand-enriched mixture of nucleic acids;

f) replacing said one or more regions of fixed sequences with a different one or more regions of fixed sequences; and g) repeating steps b)–d), whereby nucleic acid ligands of the target molecule are identified.

In yet another embodiment of the invention, a method for generating nucleic acid ligands without the participation of fixed sequences is described as follows:

a) contacting a candidate mixture with a target molecule;

b) partitioning the nucleic acids having an increased affinity to the target molecule relative to the candidate mixture from the remainder of the candidate mixture;

c) hybridizing the nucleic acids partitioned in step b) with a library of single stranded nucleic acids that are complementary to the single stranded nucleic acids of the candidate mixture, wherein each nucleic acid member of the complementary library has a fixed region;

d) amplifying the nucleic acids that hybridized to a nucleic acid in the complementary library whereby increased affinity nucleic acid ligands of the target molecule having fixed regions are produced; and e) cleaving said fixed regions of the increased affinity nucleic acids whereby nucleic acid ligands of the target molecule are identified.

BRIEF DESCRIPTION OF THE FIGURES

FIG. 2A shows the consensus binding site of MS2 CP. NN' is any base pair, R is either A or G, Y is either U or C. FIG. 2B shows a frequent selection artifact. The fixed sequence is shown in lowercase, the genomic insert in uppercase, the tail is underlined. FIG. 2C shows the actual genomic sequence (from GenBank) that corresponds to the artifact shown in FIG. 2B. It is shown "folded" only for comparison with FIG. 2A and FIG. 2B, and is not predicted to bind MS2 CP. FIG. 2D shows the predicted structure of the major isolate (rffG) from SELEX with changing the fixed sequences. The genomic insert nucleotides are in uppercase, fixed sequence (starting with ggg at the 5' end) in lowercase. The consensus binding site is shown in boldface. FIG. 2E shows the SELEX consensus binding site of MS2 CP. SS' is either GC or CG base pair. The first 2 NN' base pairs must have at least one SS'.

FIGS. 5A and B show the genomic sequence of rffG in the vicinity of the MS2 CP binding site. FIG. 5A shows the distribution of library 3' end-points in the sequence of rffG. I designates an end-point, which is the terminal nucleotide of the genomic insert, right next to the library fixed sequence. The number of I's above a position is equal to the number of sequenced isolates (out of 19 total) with the end-point at this position. The MS2 CP consensus binding site is underlined. Asterisks (*'s) designate the predicted range of end-points, given the size of the genomic inserts of the library (65 nucleotides), and allowing room for binding both of the rffG genomic primers during the isolation of these molecules from the starting library. The double-underlined sequence designates end-points that correspond to the majority (93%) of the rffG isolates in SELEX. The positions of these end-points were inferred from the isolates' sequences and from the FokI cutting specificity (9–13 nucleotides away from the FokI recognition site). The majority of the library end-points (I's) fall in the same region as the majority of end-points of the rffG SELEX isolates. FIG. 5B shows a hypothetical event during library construction that may have caused the observed clustering of end-points. The rffG genomic sequence (shown in FIG. 5A) is predicted to anneal weakly in its single-stranded form to the primer used in library construction. The primer has 9 randomized nucleotides at the 3' end, and a fixed 5' end sequence. This fixed sequence anneals to some genomic sites, such as the one shown, better than to others, and thus may cause an over-representation of the corresponding DNA in the library.

FIGS. 6A–C show the comparison of the truncation SELEX protocols to regular SELEX.

FIG. 11 shows the schematic of the process of determining the 5', 3' or minimum binding fragment of a given Nucleic Acid Ligand. A hypothetical sequence of an octamer is shown as full length and all possible fragments resulting from partial digestion at each position. The fragments that will be visible on a sequencing gel along with the expected gel pattern are as shown at each labeling scheme. The pattern of the T1 partial digestion (at G positions as shown by arrowheads (>)) is also shown at the right side of each gel pattern. The body labeled fragment is assumed to be labeled at A positions. Symbols TB, AH, T1, represent target bound fragments, partial alkaline hydrolysis ladder, and partial RNaseT1 digestion ladder, respectively. The expected tetramer minimum fragment is shown by arrow.

FIG. 15 shows compounds used to biotinylate RNA at its 3' end using T4 RNA ligase.

In FIG. 24A selected truncate RNA from the first VEGF round of the truncation SELEX by hybridization was hybridized to fall length complementary strands as described and the hybridization products were treated (+SA) or not (−SA) and then electrophoresed on native 10% polyacrylamide TBE gel. The streptavidin/hybrid complex (SA Hyb-C) from both the +SA and −SA lane were excised and recovered as described. FIG. 24B shows PCR amplification products at the indicated number of cycles using the eluted material from the +SA and −SA gel slices. FIG. 24C shows selected truncate RNA from the second VEGF round of the truncation SELEX by hybridization was hybridized to full length complementary strands as described and the hybridization products were partitioned as above. For the second round both the template generated by the +SA (designated Rd1) and the −SA (designated Rd1-ct) material were used as shown.

FIG. 26 shows the effect of removal of fixed sequences on the affinities of ligands from the starting, selected, and control libraries obtained in the VEGF truncation SELEX by hybridization experiment. Full length and truncated RNA transcripts from individual ligands were used to determine Kd and plateau values using nitrocellulose filter binding curves. Each graph point is defined by the Kd and plateau for an RNA. Open circles are affinity values obtained with full length RNA while closed circles are affinity values from truncated RNA (lacking both 5' and 3' fixed sequences). The plots were separated into four quadrants by placing all the full length points in quadrant I.

FIGS. 29A–C show PCR using short primers. The sequence of the template, primers, and expected reaction products are as shown in FIG. 29A. PCR1 indicates (FIG. 29B) the gel results with PCR reactions at two temperatures in the presence (+) or absence (−) of 10% DMSO using the template and primers shown in the top. PCR2 indicates (FIG. 29C) the gel results for RT/PCR reactions starting with 0.5 pmole of RNA transcript generated using the template from PCR1. The RT/PCR product was analyzed following 10 or 20 PCR cycles. The gels were calibrated using 20 base-pair marker.

FIGS. 33A and B show biotinylation of 2'F pyrimidine modified RNA with T4 RNA ligase. In FIG. 33A RNA ligase reactions were set that included the critical components as shown under each lane. dCB and dCCBBB were kinased in the presence of α-$^{32}$P-ATP prior to use. Reactions shown in lanes 1–8 were done at 4° C. in the presence of 2-fold excess of dCB or dCCBBB over RNA. Reactions in lanes 9–14 were done at 0° C. in the presence of 20-fold excess of dCB or dCCBBB over RNA. LP, and 40-03 designate ligated products and the use of TGFβ1 Nucleic Acid Ligand 40-03 described in U.S. application Ser. No. 09/046,247, filed Mar. 23, 1998 (which is incorporated herein in its entirety), respectively. FIG. 33B shows streptavidin gel shifts of gel purified ligated products from the gel depicted in FIG. 33A. Purified ligated products and the use of streptavidin is as shown under each lane.

FIGS. 34A and B show the ligation of the 3' fixed sequence at the 3' end of 2'F pyrimidine modified RNA. FIG. 34A depicts ligation products from reactions containing body labeled RNA transcripts from the indicated templates and the critical components as shown were analyzed on a 10% acrylamide, 8 M urea gel. Symbols SC, LP and TR indicate streptavidin complexes, ligated products, and unligated transcript, respectively. FIG. 34B depicts the sequence of the two templates used to generate RNA transcripts for this experiment. Arrowheads indicated the site of cleavage of restriction sites as follows: The 35N-Nae template contains downstream of the random region the site 5'GGCCG- GCC which is digested symmetrically by the restriction enzyme FseI between the second and third base from the 3' end. The FseI site contains the restriction site for NaeI (5'GCCGGC) which is digested by NaeI symmetrically between the third and fourth base from the 5' end. The 35N-Bsm template contains downstream of the random region the site 5'GCATTC which is digested asymmetrically by the restriction enzyme BsmI as shown. The RNA transcripts derived from restriction digested templates are as shown.

FIGS. 35A–D show the ligation of the 5' fixed sequence. FIGS. 35A and B show at the 5' end of 2'F pyrimidine modified RNA. Schematic of the reaction reactants and products are shown in FIG. 35A. Results from the ligation reaction at the 5' end of RNA is shown in FIG. 35B. The critical components of the reaction are as shown. FIGS. 35C and D show ligation of the 5' fixed sequence at the 3' end of cDNA. The schematic of the reaction reactants and products are shown in FIG. 35C. Two sets of ligation oligo/bridge oligo were used as shown. The results from the ligation reaction at the 3' end of cDNA is shown in FIG. 35D. (I) Results with the 5G7RC Linker/5'N7 oligonucleotides. (II) Results with the 5N7 Linker/5N7 Bridge oligonucleotides. The ratio of linker oligonucleotide to cDNA is shown above each lane. Symbol LC indicates ligated products.

FIG. 36A depicts the size of the PCR products from the starting round 12 VT30 pool, starting 5' truncated pool (LTR0), truncation SELEX round 1 (LTR1) and truncation SELEX round 2 (LTR2). The size of molecular weight markers is as shown.

FIG. 41A shows the schematic addition of the fixed sequences by ligation using appropriately designed stem-loop structures.

DETAILED DESCRIPTION OF THE INVENTION

Definitions

Figure 1:
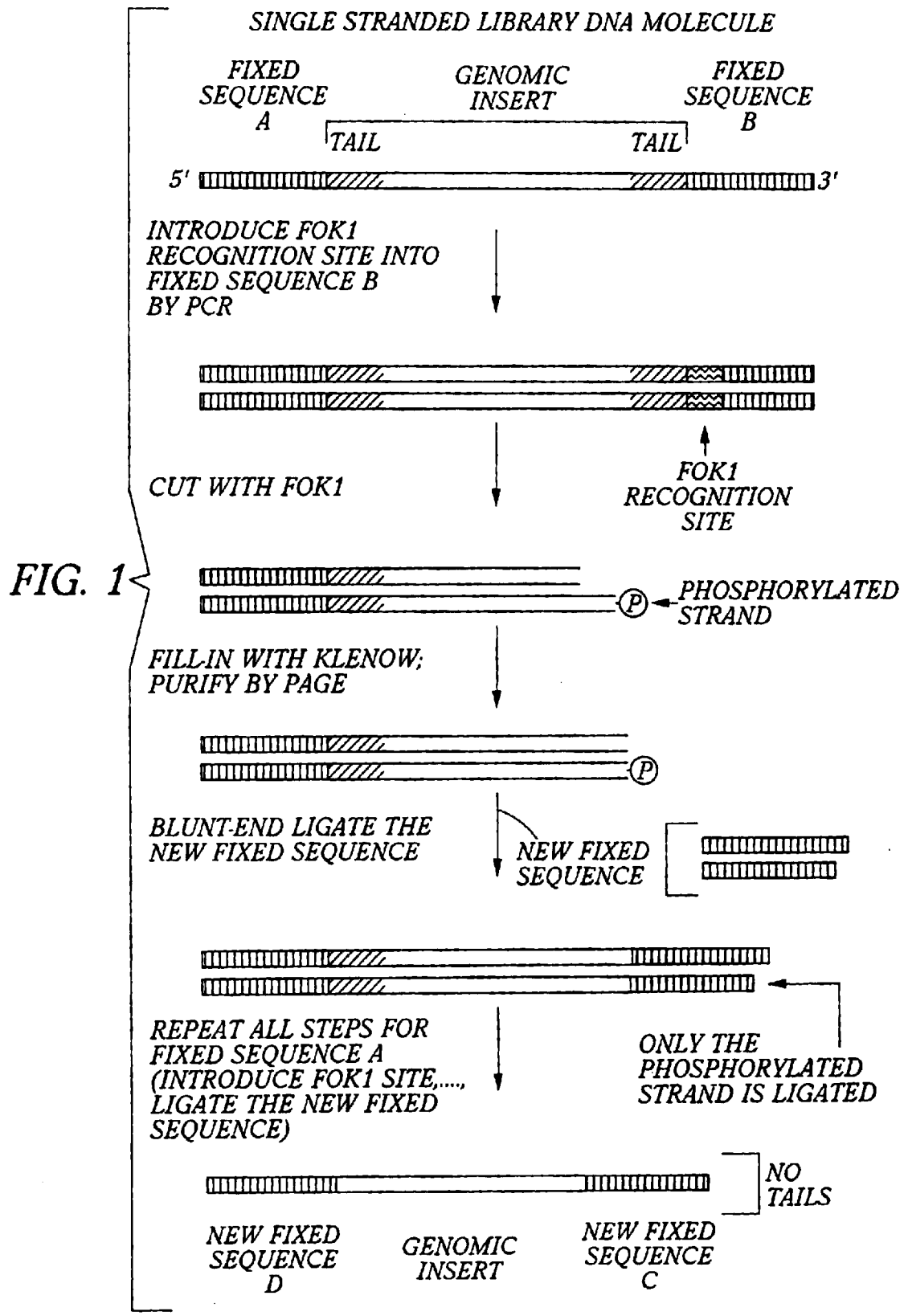
FIG. 1 shows the strategy of changing the fixed sequences. See Example 1 for detailed explanation.

"Nucleic Acid Ligand" or "Aptamer" as used herein is a non-naturally occurring Nucleic Acid having a desirable action on a Target. A desirable action includes, but is not limited to, binding of the Target, catalytically changing the Target, reacting with the Target in a way which modifies/alters the Target or the functional activity of the Target, covalently attaching to the Target as in a suicide inhibitor, facilitating the reaction between the Target and another molecule. In the preferred embodiment, the action is specific binding affinity for a Target molecule, such Target molecule being a three dimensional chemical structure other than a polynucleotide that binds to the Nucleic Acid Ligand through a mechanism which predominantly depends on Watson/Crick base pairing or triple helix binding, wherein the Nucleic Acid Ligand is not a Nucleic Acid having the known physiological function of being bound by the Target molecule.

"Candidate Mixture" is a mixture of Nucleic Acids of differing sequence from which to select a desired ligand. The source of a Candidate Mixture can be from naturally occurring Nucleic Acids or fragments thereof, chemically synthesized Nucleic Acids, enzymatically synthesized Nucleic Acids or Nucleic Acids made by a combination of the foregoing techniques. In a preferred embodiment, each Nucleic Acid has fixed sequences surrounding a randomized region to facilitate the amplification process.

"Nucleic Acid" means either DNA, RNA, single-stranded or double-stranded and any chemical modifications thereof. Modifications include, but are not limited to, those that provide other chemical groups that incorporate additional charge, polarizability, hydrogen bonding, electrostatic interaction, and fluxionality to the Nucleic Acid Ligand bases or to the Nucleic Acid Ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications such as internucleoside phosphorothioate linkages, methylations, unusual base-pairing combinations such as the isobases isocytidine and isoguanidine and the like. Modifications can also include 3' and 5' modifications such as capping.

"SELEX" methodology involves the combination of selection of Nucleic Acid Ligands that interact with a Target in a desirable manner, for example binding to a protein, with amplification of those selected Nucleic Acids. Iterative cycling of the selection/amplification steps allows selection of one or a small number of Nucleic Acids that interact most strongly with the Target from a pool which contains a very large number of Nucleic Acids. Cycling of the selection/amplification procedure is continued until a selected goal is achieved. The SELEX methodology is described in the SELEX Patent Applications. The SELEX methodology is sometimes referred to herein as Conventional SELEX.

"Genomic SELEX" is a variation on the SELEX methodology in which the nucleic acids in the randomized region of the candidate mixture are replaced by genomic sequences (or inserts) derived from an organism. Genomic SELEX is also sometimes referred to herein as Conventional (or Regular) Genomic SELEX when the method is performed without changing the fixed sequences or annealing of oligonucleotides. It will be understood from the context of the specification whether Genomic SELEX is being performed with or without changing the fixed sequences or annealing of oligonucleotides.

"Truncation SELEX" is a variation on the SELEX methodology in which the participation of fixed sequences in the binding to the Target is minimized or eliminated.

Figure 7:
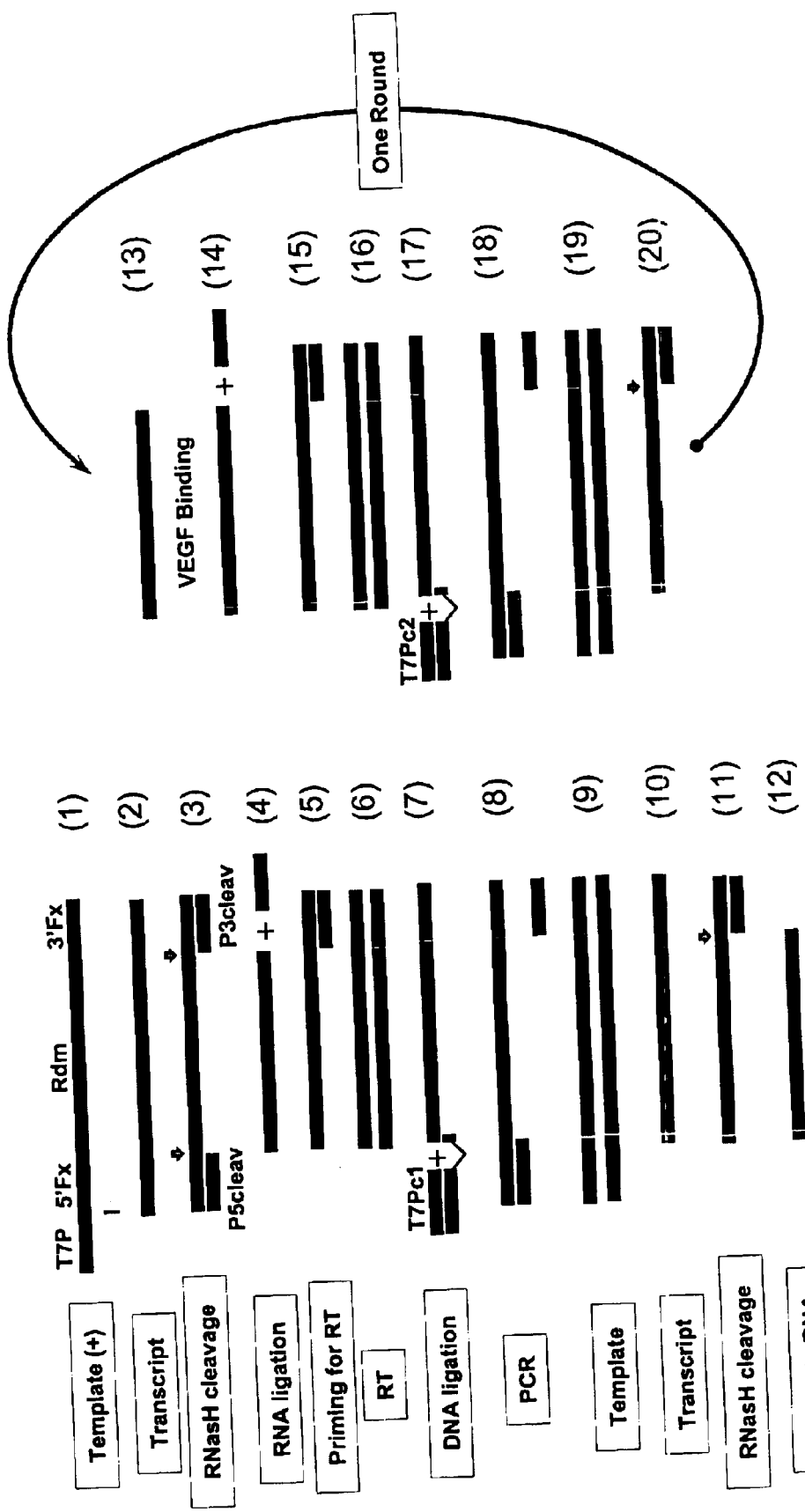
FIG. 7 shows the truncation SELEX by ligation process. Symbols are as follows: T7P, T7 promoter sequence; 5'Fx, 5' fixed sequence for 5' primer binding; 3'Fx, 3' fixed sequence for 3' primer binding; Rdm, random region; P5 cleav, chimeric oligonucleotide used for site directed cleavage at the 5' fixed sequence by RNaseH; P3cleav, chimeric oligonucleotide used for site directed cleavage at the 3' fixed sequence by RNaseH; T7Pc1, DNA oligonucleotide complementary to T7 promoter-initiation sequence, annealed to a complementary DNA oligonucleotide extended by 5 random nucleotides; T7Pc2, DNA oligonucleotide complementary to T7 promoter sequence, annealed to a complementary DNA oligonucleotide extended by the initiator sequence 5'GGGA.

"Truncation SELEX by Ligation" is a variation on the Truncation SELEX Method whereby amplifiable molecules are created by introducing fixed regions with a ligation reaction after interaction with the target (i.e., the nucleic acid does not contain fixed sequences when it interacts with the target). An example of Truncation SELEX by Ligation is illustrated in FIG. 7. Other examples of the method are also contemplated.

Figure 9:
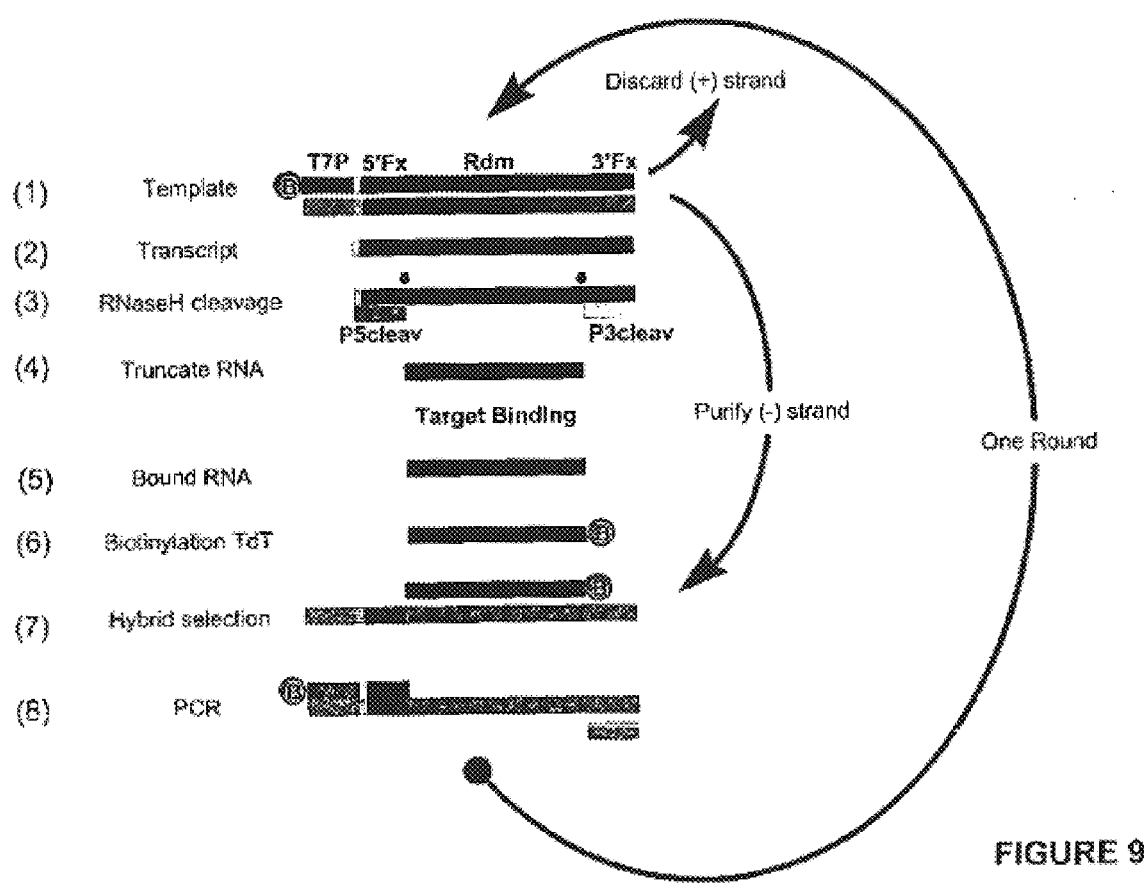
FIG. 9 shows truncation SELEX by hybrid selection process. Symbols are as follows: T7P, T7 promoter sequence; 5'Fx, 5' fixed sequence for 5' primer binding; 3'Fx, 3' fixed sequence for 3' primer binding; Rdm, random region; P5 cleav, chimeric oligonucleotide used for site directed cleavage at the 5' fixed sequence by RNaseH; P3cleav, chimeric oligonucleotide used for site directed cleavage at the 3' fixed sequence by RNaseH; B, biotin.
Figure 10:
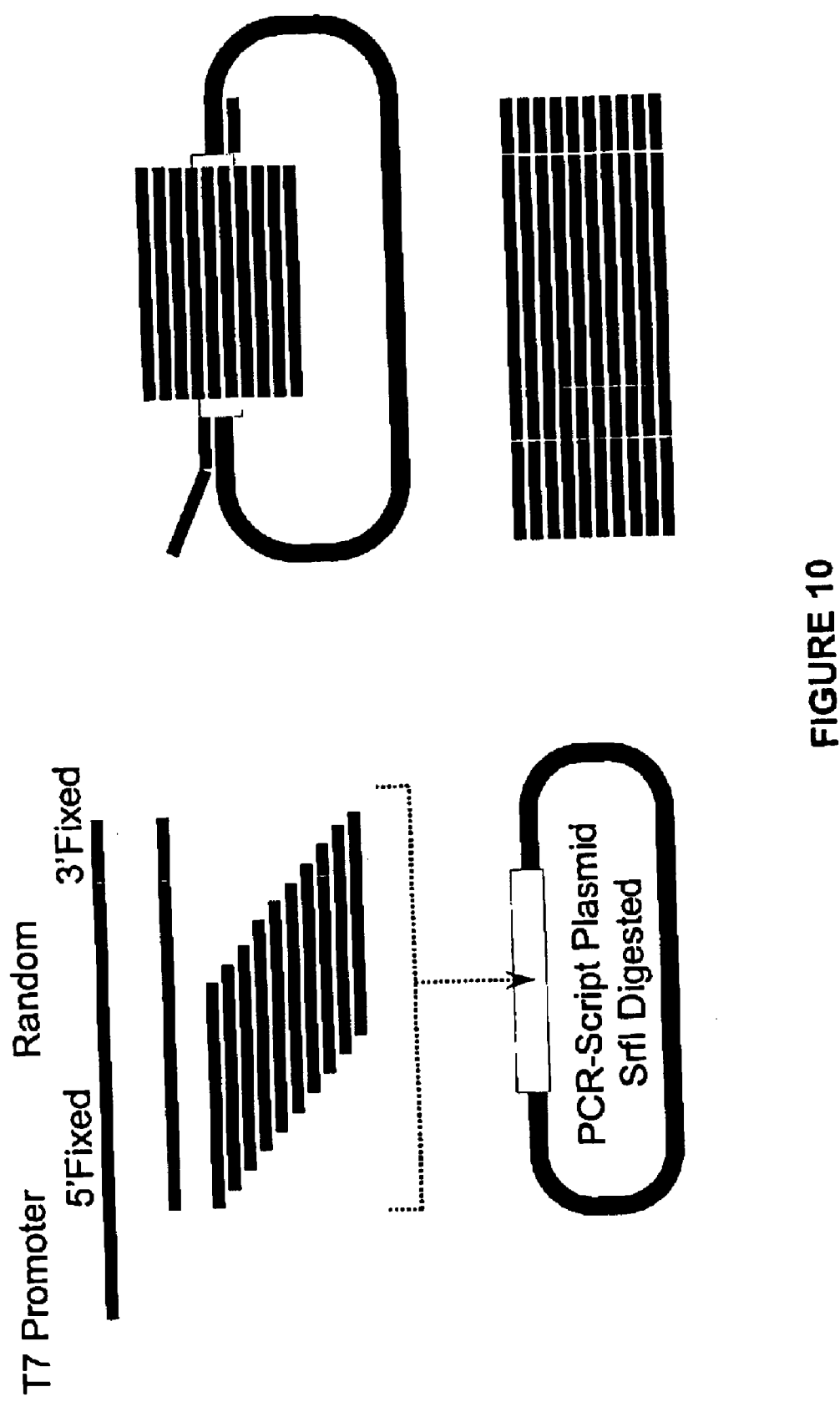
FIG. 10 shows truncation SELEX by size selection at the DNA level. An advanced SELEX pool is PCR amplified using primers lacking the T7 promoter sequence. The PCR products are partially digested with DNaseI and size fractionated by gel electrophoresis. Size fractionated partial digestion products are ligated to a plasmid digested by blunt end restriction enzyme. Ligation products are then PCR amplified using a set of primers binding to plasmid sequences flanking the digestion site. One of the primers contains the sequence for the T7 promoter which may or may not be part of the plasmid sequence. Such ligation reaction will create circular molecules having both possible orientations for each insert. To eliminate the molecules with the wrong orientation with respect to the T7 promoter, transcripts from the final PCR library are hybridized with excess biotinylated transcripts from the starting library and the hybrids are removed by streptavidin capture. Remaining unhybridized RNAs are then PCR amplified to generate the starting pool for truncation SELEX by size selection.

"Truncation SELEX by Hybridization" is a variation on the Truncation SELEX Method whereby amplifiable molecules are obtained by hybridizing the selected nucleic acid (containing minimal or no fixed sequences) to the original candidate mixture. An example of Truncation SELEX by Hybridization is illustrated in FIG. 9. Other examples of the method are also contemplated.

"Target" means any compound or molecule of interest for which a ligand is desired. A Target can be a protein (such as PDGF, thrombin, and selectin), peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation.

The SELEX process provides a class of products which are Nucleic Acid molecules, each having a unique sequence, and each of which has the property of binding specifically to a desired Target compound or molecule. Target molecules are preferably proteins, but can also include among others carbohydrates, peptidoglycans and a variety of small molecules. SELEX methodology can also be used to Target biological structures, such as cell surfaces or viruses, through specific interaction with a molecule that is an integral part of that biological structure.

In its most basic form, the SELEX process may be defined by the following series of steps:

1) A Candidate Mixture of Nucleic Acids of differing sequence is prepared. The Candidate Mixture generally includes regions of fixed sequences (i.e., each of the members of the Candidate Mixture contains the same sequences in the same location) and regions of randomized sequences. The fixed sequence regions are selected either: (a) to assist in the amplification steps described below, (b) to mimic a sequence known to bind to the Target, or (c) to enhance the concentration of a given structural arrangement of the Nucleic Acids in the Candidate Mixture. The randomized sequences can be totally randomized (i.e., the probability of finding a base at any position being one in four) or only partially randomized (e.g., the probability of finding a base at any location can be selected at any level between 0 and 100 percent).

2) The Candidate Mixture is contacted with the selected Target under conditions favorable for binding between the Target and members of the Candidate Mixture. Under these circumstances, the interaction between the Target and the Nucleic Acids of the Candidate Mixture can be considered as forming Nucleic Acid-target pairs between the Target and those Nucleic Acids having the strongest affinity for the Target.

3) The Nucleic Acids with the highest affinity for the target are partitioned from those Nucleic Acids with lesser affinity to the target. Because only an extremely small number of sequences (and possibly only one molecule of Nucleic Acid) corresponding to the highest affinity Nucleic Acids exist in the Candidate Mixture, it is generally desirable to set the partitioning criteria so that a significant amount of the Nucleic Acids in the Candidate Mixture (approximately 5–50%) are retained during partitioning.

4) Those Nucleic Acids selected during partitioning as having the relatively higher affinity for the target are then amplified to create a new Candidate Mixture that is enriched in Nucleic Acids having a relatively higher affinity for the target.

5) By repeating the partitioning and amplifying steps above, the newly formed Candidate Mixture contains fewer and fewer unique sequences, and the average degree of affinity of the Nucleic Acids to the target will generally increase. Taken to its extreme, the SELEX process will yield a Candidate Mixture containing one or a small number of unique Nucleic Acids representing those Nucleic Acids from the original Candidate Mixture having the highest affinity to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," now abandoned (see U.S. Pat. No. 5,707,796), describes the use of SELEX in conjunction with gel electrophoresis to select Nucleic Acid molecules with specific structural characteristics, such as bent DNA. U.S. patent application Ser. No. 08/123,935, filed Sep. 17, 1993, entitled "Photoselection of Nucleic Acid Ligands," now abandoned (see U.S. Pat. No. 5,763,177), describes a SELEX based method for selecting Nucleic Acid Ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," now U.S. Pat. No. 5,580,737, describes a method for identifying highly specific Nucleic Acid Ligands able to discriminate between closely related molecules, termed Counter-SELEX. U.S. patent application Ser. No. 08/143,564, filed Oct. 25, 1993, entitled "Systematic Evolution of Ligands by Exponential Enrichment: Solution SELEX," now U.S. Pat. No. 5,567,588, describes a SELEX-based method which achieves highly efficient partitioning between oligonucleotides having high and low affinity for a target molecule. U.S. patent application Ser. No. 07/964,624, filed Oct. 21, 1992, entitled "Nucleic Acid Ligands to HIV-RT and HIV-1 Rev," now U.S. Pat. No. 5,496,938, describes methods for obtaining improved Nucleic Acid Ligands after SELEX has been performed. U.S. patent application Ser. No. 08/400,440, filed Mar. 8, 1995, entitled "Systematic Evolution of Ligands by Exponential Enrichment: Chemi-SELEX," now U.S. Pat. No. 5,705,337, describes methods for covalently linking a ligand to its target.

The SELEX method encompasses the identification of high-affinity Nucleic Acid Ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified Nucleic Acid Ligands containing modified nucleotides are described in U.S. patent application Ser. No. 08/117,991, filed Sep. 8, 1993, entitled "High Affinity Nucleic Acid Ligands Containing Modified Nucleotides," now U.S. Pat. No. 5,660,985, that describes oligonucleotides containing nucleotide derivatives chemically modified at the 5- and 2'-positions of pyrimidines. U.S. patent application Ser. No. 08/134,028, supra, describes highly specific Nucleic Acid Ligands containing one or more nucleotides modified with 2'-amino (2'-$NH_2$), 2'-fluoro (2'-F), and/or 2'-O-methyl (2'-OMe). U.S. patent application Ser. No. 08/264,029, filed June 22, 1994, entitled "Novel Method of Preparation of Known and Novel 2' Modified Nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX," now U.S. Pat. No. 5,637,459, and U.S. patent application Ser. No. 08/234,997, filed Apr. 28, 1994, entitled "Systematic Evolution of Ligands by Exponential Enrichment: Blended SELEX," now U.S. Pat. No. 5,683,867, respectively. These applications allow the combination of the broad array of shapes and other properties, and the efficient amplification and replication properties, of oligonucleotides with the desirable properties of other molecules.

The SELEX method further encompasses combining selected Nucleic Acid Ligands with Lipophilic Compounds or Non-Immunogenic, High Molecular Weight Compounds in a diagnostic or therapeutic Complex as described in U.S. patent application Ser. No. 08/434,465, filed May 4, 1995, entitled "Nucleic Acid Ligand Complexes." The SELEX method further encompasses combining selected VEGF Nucleic Acid Ligands with lipophilic compounds, such as diacyl glycerol or dialkyl glycerol, as described in U.S. patent application Ser. No. 08/739,109, filed Oct. 25, 1996, entitled "Vascular Endothelial Growth Factor (VEGF) Nucleic Acid Ligand Complexes," now U.S. Pat. No. 5,859,229. VEGF Nucleic Acid Ligands that are associated with a High Molecular Weight, Non-Immunogenic Compound, such as Polyethylene glycol, or a Lipophilic Compound, such as Glycerolipid, phospholipid, or glycerol amide lipid, in a diagnostic or therapeutic complex are described in U.S. patent application Ser. No. 08/897,351, filed Jul. 21, 1997, entitled "Vascular Endothelial Growth Factor (VEGF) Nucleic Acid Ligand Complexes." Each of the above described patent applications that describe modifications of the basic SELEX procedure are specifically incorporated by reference herein in their entirety.

SELEX identifies Nucleic Acid Ligands that are able to bind targets with high affinity and with outstanding specificity, which represents a singular achievement that is unprecedented in the field of Nucleic Acids research. These characteristics are, of course, the desired properties one skilled in the art would seek in a therapeutic or diagnostic ligand.

In order to produce Nucleic Acid Ligands desirable for use as a pharmaceutical, it is preferred that the Nucleic Acid Ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the Nucleic Acid Ligand has the highest possible affinity to the target. Additionally, Nucleic Acid Ligands can have facilitating properties.

In commonly assigned U.S. patent application Ser. No. 07/964,624, filed Oct. 21, 1992, now U.S. Pat. No. 5,496,938 ('938), methods are described for obtaining improved Nucleic Acid Ligands after SELEX has been performed. The '938 patent, entitled "Nucleic Acid Ligands to HIV-RT and HIV-1 Rev," is specifically incorporated herein by reference.

As discussed above, generally the candidate mixture in the SELEX process includes regions of fixed sequences and randomized sequences. The fixed sequences are usually present for assisting in the amplification steps of the SELEX process and may participate in binding to the target or contribute to structures that bind to the target. In some circumstances, the participation of the fixed sequences in binding to the target may not be desirable. Generation of nucleic acid ligands in which the participation of fixed sequences in binding to the target is minimized or eliminated can be accomplished is several ways:

1) The participation of fixed regions in the binding of the target could be reduced or eliminated by annealing complementary oligonucleotides to the fixed regions prior to contacting the candidate mixture with the target. The double-stranded region is then bound together through Watson/Crick base pairing, and, therefore, is not available for binding to the target.

2) The fixed regions can also be changed at different rounds. As these sequences are changed, their participation of any one fixed region in binding is reduced.

3) Reduce the size of the fixed regions.

4) Eliminate the fixed sequences before interaction with the target.

Figure 30:
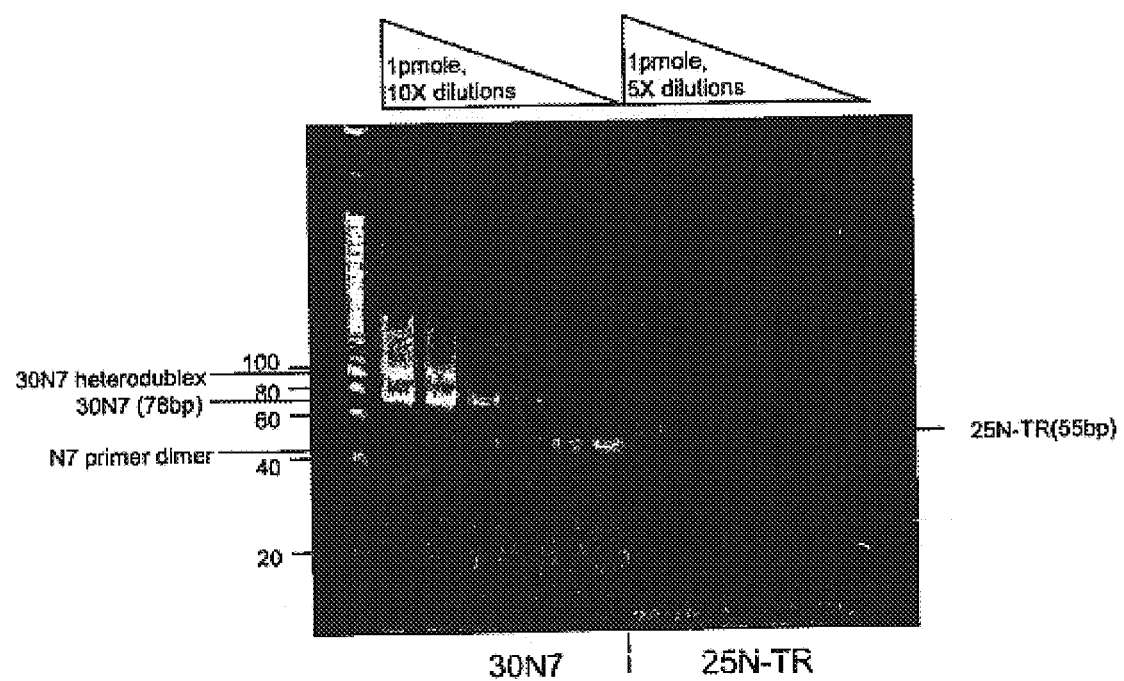
FIG. 30 shows the electrophoretic analysis of RT/PCR products using the 30N7 and the 25NTR template-primer set. 1 pmole of starting RNA was diluted 10-fold or 5-fold as shown and was subject to RT/PCR in the presence of appropriate primers as described. The products following 15 PCR cycles were analyzed on a 10% polyacrylamide TBE gel. The identity and size of the products are as indicated. Heterodublex represents annealed products having nonhomologous random regions. The size in bases of the markers used are as shown.

As described above, in some circumstances it is desirable to have short ligands following the SELEX process. The reduction in the fixed region of the template will accomplish reduction in the overall size of the individual molecules. Reduction of the fixed regions is limited in order to maintain PCR amplification. The shortest primer binding site reported for specific amplification is 7-bases long (Vincent et al. (1994) DNA and Cell Biology 13:75–82). Based on this approach, templates were designed to allow amplification of RNA that has 5' and 3' fixed regions of 5- and 8-bases long (FIG. 29). RT/PCR efficiency of such abbreviated template is about two logs lower than the N7 template series but nevertheless, sub-picomole amounts of RNA can be amplified within a reasonable number of PCR cycles (FIG. 30).

Reduction of the random region of the template will also accomplish reduction in the overall size of the individual molecules. Random region of a certain length however might be crucial in the isolation of high affinity and bioactivity ligands as evident by experiments where libraries with random regions of different length were applied to the same target in parallel. In one such experiment where TGFβ1 was the SELEX target, it was determined that the length of the random region affected the recovery of bioactive ligands with only the 40N libraries yielded high affinity bioactive ligands, as described in U.S. patent application Ser. No. 09/046,247, filed Mar. 23, 1998.

To further illustrate the approach for elimination of fixed sequences, the primer binding sites are removed from the molecules of the library, before the interaction with the target. After selection, primer binding sites are re-introduced for amplification and generation of the pool for the next round. Primer-binding-site-removal requires nucleolytic digestion either before or after generation of the population of single stranded molecules. In SELEX experiments requiring transcription, removal of at least the 5' fixed region must occur after transcription because digestion before transcription will remove the promoter site and will eliminate transcription.

Figure 32:
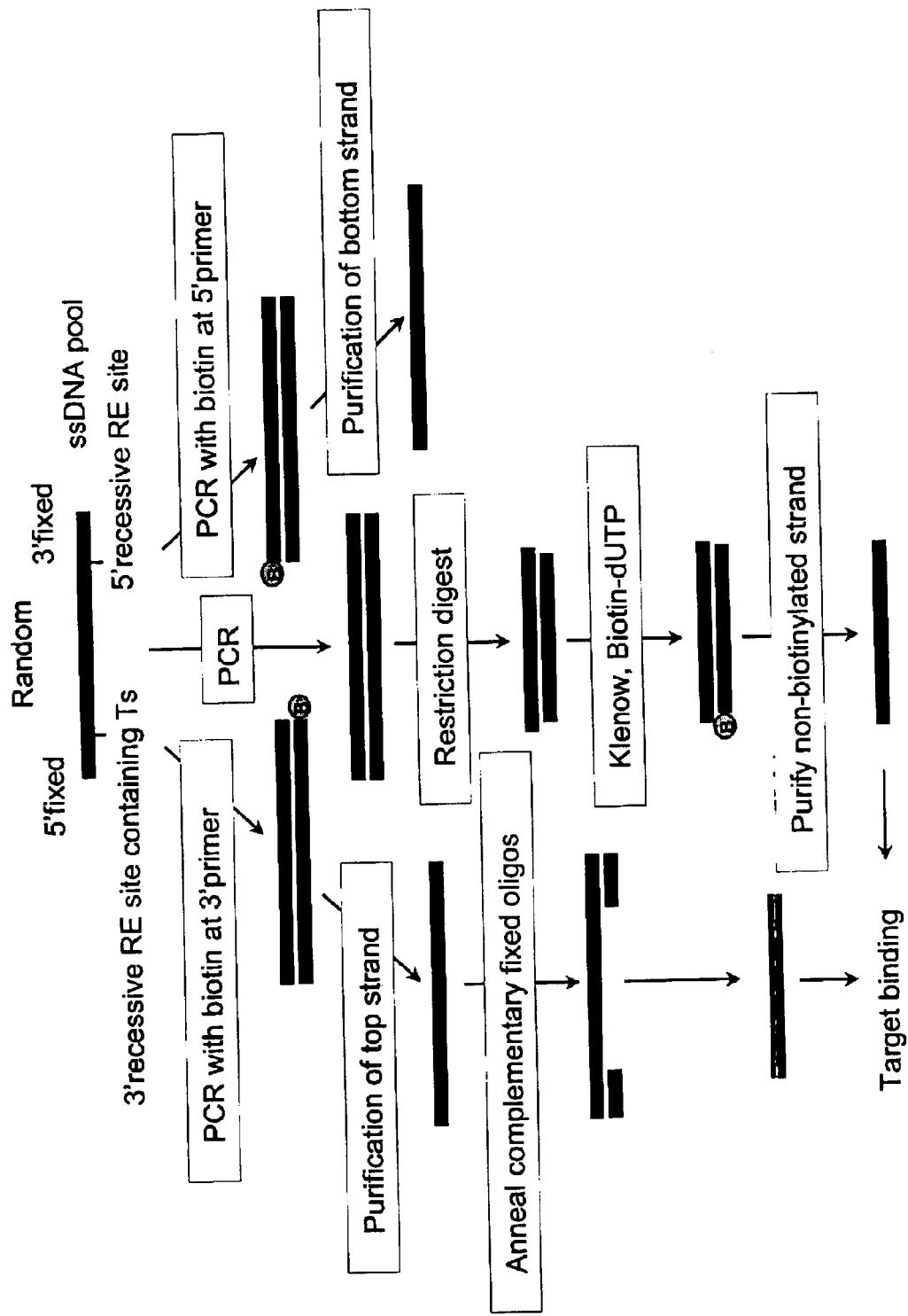
FIG. 32 shows the generation of ssDNA for truncation SELEX with DNA libraries. The left and middle branch show processes to generate sense strands of the library lacking the fixed sequences. The right branch shows the process to generate the antisense full length strand of the library for the hybridization SELEX process.

For SELEX experiments using DNA based libraries, removal of primer binding sites can be done as described in FIG. 32. The original synthetic oligonucleotide library utilized for this approach can be engineered to include restriction endonuclease digestion sites that generated 3' or 5' recessive ends as shown in FIG. 32. For digestion after generation of single stranded molecules, oligonucleotides complementary to the fixed regions are annealed and the complexes are digested by appropriate restriction endonucleases. Alternatively, digestion can occur at the dsDNA level and digested single strands can be purified by incorporation of biotin at the 3' recessive restriction site by using the Klenow fragment of $E.$ $coli$ DNA polymerase-I and biotin-dUTP. For biotinylation at one end, restriction digestion at that end can be followed by a fill-in reaction with the Klenow DNA polymerase-I when a restriction enzyme that generates 3' recessive sites is used, or by a terminal transferase reaction in the presence of biotin-dUTP. Biotinylation reactions are then followed by restriction digestion at the other end. If the digestion occurs at the ssDNA level the use of 3' versus 5' recessive restriction sites is not important and any restriction site can be used.

For SELEX experiments using RNA based libraries, removal of primer binding sites can be done by site specific digestion by RNaseH as described below, where DNA-2'OMeRNA oligonucleotides are annealed to RNA molecules and the hybridization products are digested by RNaseH.

Following digestion and selection the fixed sequences need to be added back to the library in order to allow amplification and carry the pool forward to the next round. Generation of amplifiable pools following nuclease digestion and affinity selection can be achieved as described below in two ways (FIGS. 6B and 6C), namely either enzymatically (Truncation-SELEX-by-Ligation or Truncation-SELEX-by-Tailing) or by hybrid selection of purified complementary strands from the pool in use (Truncation-SELEX-by-Hybrid-Selection).

Overview of Truncation-SELEX-by-Ligation

This is an enzymatic method of Truncation SELEX. The steps of Truncation-SELEX-by-ligation are summarized in FIG. 7. This approach can be applied either at the beginning of a SELEX experiment or following several regular rounds of the SELEX process.

Figure 41A:
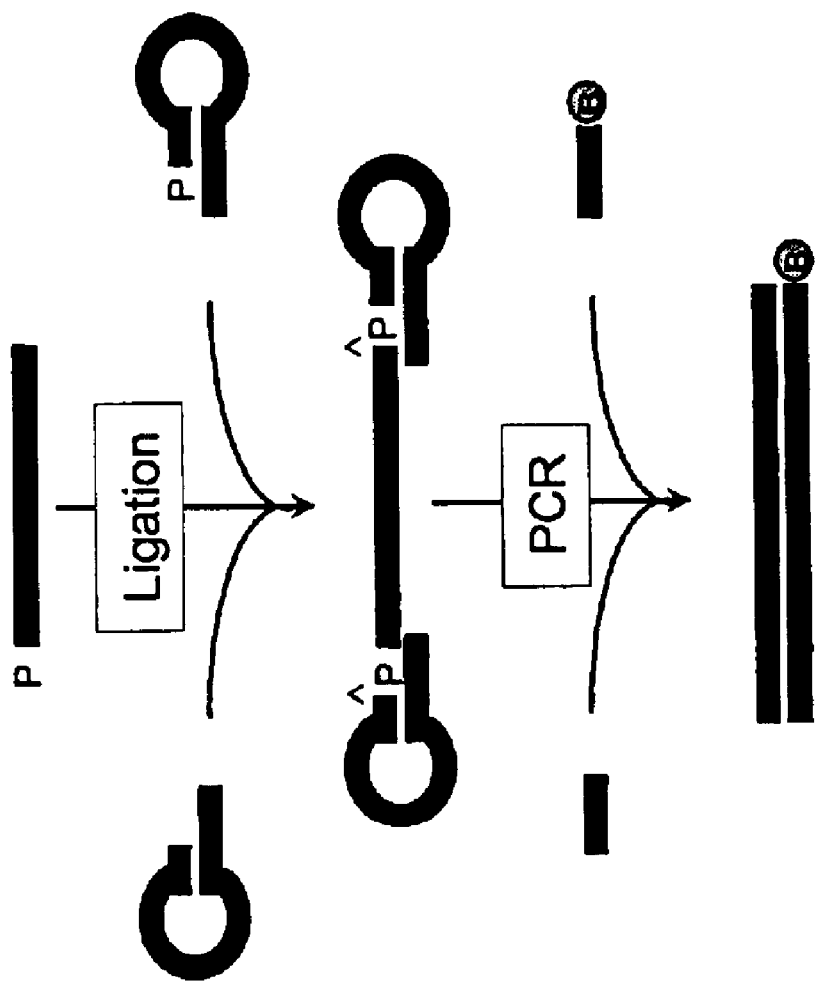
FIGS. 41A and B show the enzymatic addition of the fixed sequences to selected truncated ssDNA from truncation SELEX with DNA libraries.
Figure 41B:
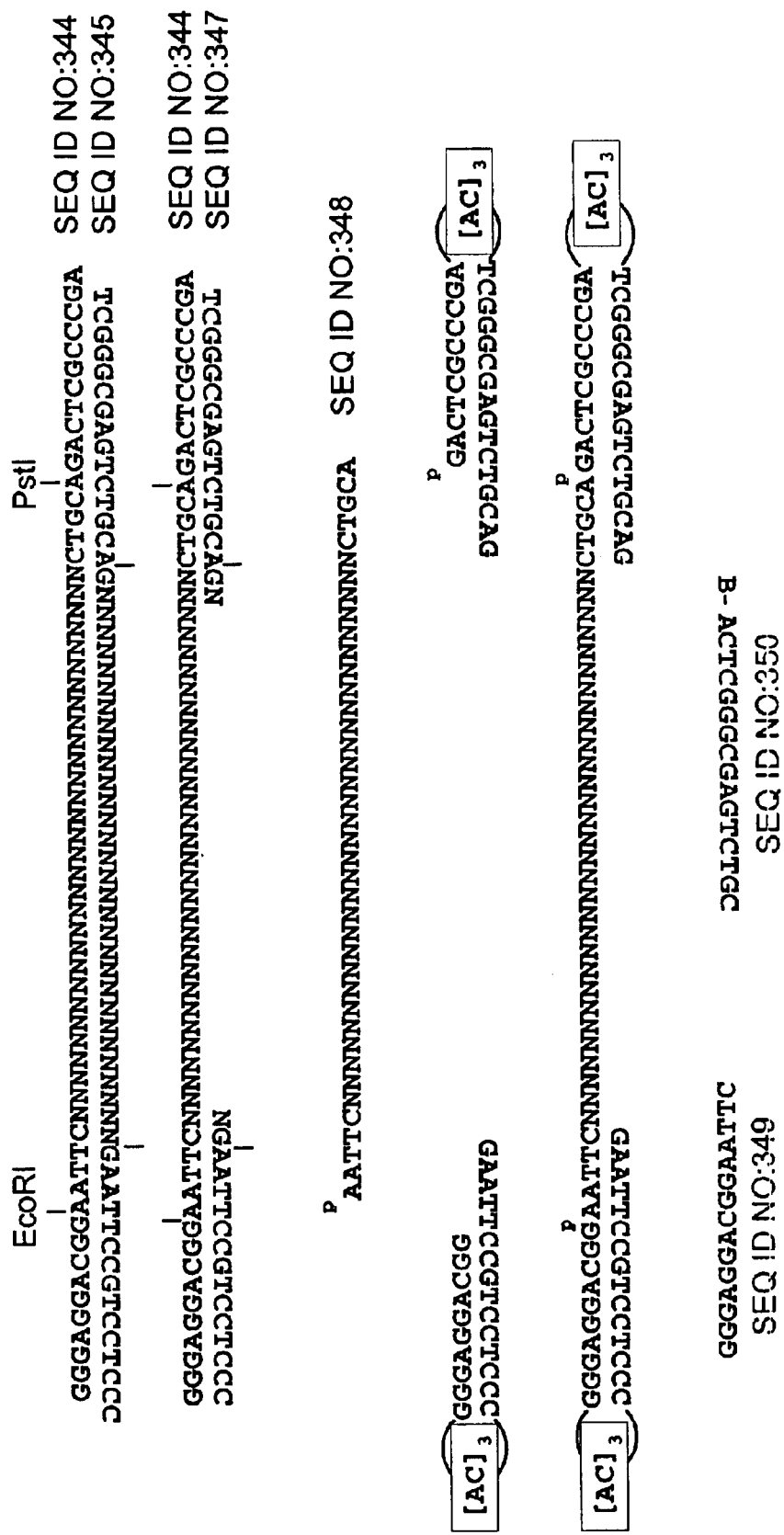
FIG. 41B shows the proposed sequences for the process shown in FIG. 41A. P indicates the addition of 5' phosphates during phosphoramidite synthesis.

For de novo Truncation-SELEX-by-ligation, the starting synthetic oligonucleotide pools can be designed to include just the random region. In order to avoid potential counterselection pressure due to transcription efficiency, especially if modified nucleotides are used as polymerase substrates, it might be beneficial to include a transcription initiation sequence immediately downstream of the T7 promoter such as 5'GGGAG followed by the random region. The starting pool may include a 3' primer binding site or it may not. If no 3' primer binding site is used at the starting pool, then single stranded oligonucleotides can be converted to double stranded templates by including the T7 promoter-initiator complement at the 3' end of the random region, for example 5'[N]$_{30}$CTCCCTATAGTGAGTCGTA TTA (SEQ ID NO:325), and performing primer extension using a primer such as 5'TAATACGACT CACTATAGGGAG (SEQ ID NO:46). If there is a 3' primer binding site, then RNaseH digestion can be used, as described below, to remove that fixed sequence before binding to the target. Alternatively, a starting pool of DNA templates can be used where appropriate restriction sites were incorporated downstream of the T7 promoter and random region as shown in FIG. 41. The pool of RNA is then generated by transcription of templated digested by the appropriate restriction enzyme.

For application of truncation SELEX on pools evolved by conventional SELEX experiments, the primer binding sites are removed by digestion and then they are reintroduced following affinity selection by ligation. These steps will be done at each truncation SELEX round. Alternatively, a 5' truncated library can be generated before affinity selection starts. This is a preferential alternative to avoid the use of a random bridge sequence for the 5' end ligation since such ligation condition is inefficient. The generation of the 5' truncated library will allow introduction of the transcription initiation sequence 5'GGGAG adjacent to the 5' end of the random region of the template. This initiation sequence in addition of relieving potential transcription selection bias, it can also provide a specific sequence for the ligation bridge used in the introduction of the 5' primer binding site. Therefore, a conventional SELEX pool (FIG. 7-1) is converted into dsDNA template by extension with the 3' primer; the ds template is then transcribed to generate the full length RNA transcripts (FIG. 7-2); these transcripts are then digested with RNaseH to remove either both or just the 5' primer binding site FIG. 7-3); the digested RNA is then reverse transcribed (FIG. 7-5) using the 3' primer after ligation of the 3' primer binding site by T4 RNA ligase (if necessary (FIG. 7-4)) to generate appropriate cDNA (FIG. 7-6); the generated cDNA is then ligated using T4 DNA ligase (FIG. 7-7) to the DNA oligonucleotide encoding the T7 promoter-initiator (5'TAATACGACTCACTATAGG GAGNNNNN (SEQ ID NO:37)) which has been preannealed to the bridge DNA oligonucleotide 5'CTCCCTAT-AGTGAGTCGTATTA (SEQ ID NO:36) (Table 4, set two); the ligation product (FIG. 7-8) is PCR amplified to generate a new dsDNA template (FIG. 7-9) lacking the bulk of the 5' primer binding site; this new template is transcribed to generate a 5' truncated transcript (FIG. 7-10); the 5' truncated RNA is then digested with RNaseH at the 3' end (FIG. 7-11) to generate the truncated RNA for selection (FIG. 7-12).

For each truncation-SELEX-by-ligation round, truncated RNA (FIG. 7-13) generated by either method described above is bound to the target, and bound molecules are partitioned with an appropriate partition method and ligated to the 3' primer binding site (FIG. 7-14) using RNA ligase and an appropriate DNA oligo complementary to the 3' primer. The resulting ligation product is reverse transcribed using the 3' primer (FIG. 7-15) to generate cDNA (FIG. 7-16). The cDNA is then ligated (FIG. 7-17) to the DNA oligonucleotide encoding the T7 promoter (5'TAATACGACTCA CTATAG GGA (SEQ ID NO:35)) which has been preannealed to the bridge DNA oligonucleotide 5'TATAGTGAGTCGTATTA (SEQ ID NO:34) (Table 4, set one), and PCR amplified (FIG. 7-18) to generate a new dsDNA template (FIG. 7-19); this new template pool is then transcribed to generate a new RNA pool which is carried to the next round following removal of the 3' primer binding site by RNaseH digestion (FIG. 7-20).

Overview of Truncation SELEX by Tailing

Figure 8:
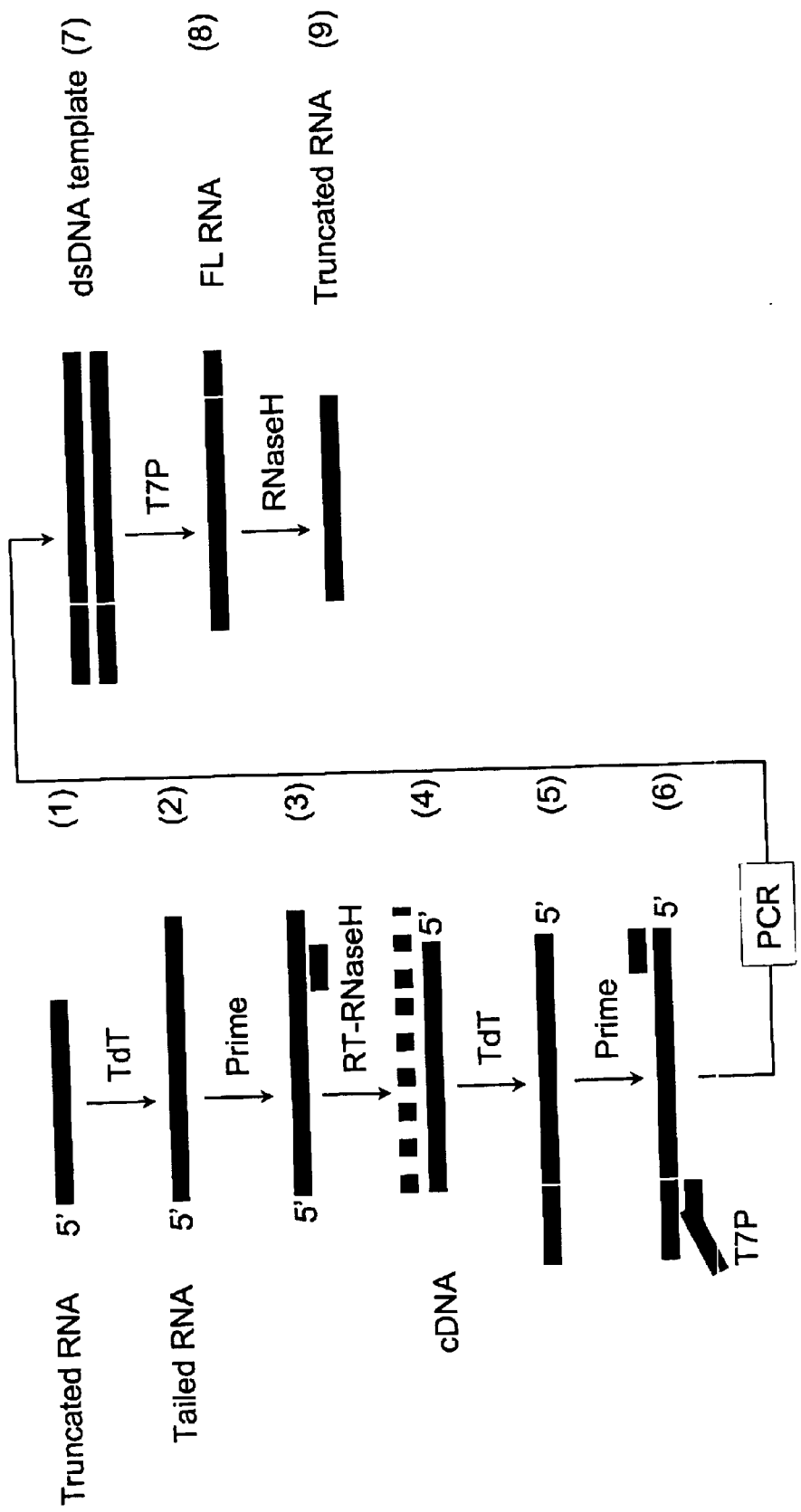
FIG. 8 shows truncation SELEX by tailing. Schematic representation of the truncation process by tailing is described. Symbols TdT, RT-RNaseH, T7P and FL, indicate terminal deoxyribonucleotide transferase, RNaseH activity of reverse transcriptase, T7 promoter, and full length, respectively.

This is an alternative enzymatic method of Truncation SELEX. The steps of Truncation-SELEX-by-tailing are summarized in FIG. 8. This approach is similar to the truncation SELEX by ligation protocol where the fixed sequences are the result of a tailing reaction by the terminal deoxy transferase instead of ligase. Like the ligation approach, it can be applied either at the beginning of a SELEX experiment or following several rounds of the regular SELEX process. According to this scheme, selected truncated RNA (generated as described in the ligation protocol), (FIG. 8-1) is incubated with terminal deoxy transferase (TdT) and a single dNTP to add homopolymeric tail at its 3' end FIG. 8-2). The length of the tail can be adjusted by including either ddNTP or NTPs at different ratios to the dNTPs to slow down the tailing reaction (Schmidt et al. (1996) Nucleic Acids Research 24:1789–1791). Tailed RNA is then reverse transcribed with reverse transcriptase (RT) and a complementary oligonucleotide to the added tail (FIG. 8-3). The complementary to the tail oligonucleotide could be engineered to contain a couple of fixed positions to its 3' end complementary to fixed positions of the 3' end of the truncated RNA so it can be anchored adjacent to the 3' end of the selected RNA. The generated cDNA (FIG. 8-4) is then tailed with TdT and a different dNTP (FIG. 8-5) preferably with pyrimidines to generate templates with appropriate T7 transcription initiation sites. The generated tailed cDNA can be amplified by PCR (FIG. 8-6) using the 3' primer used in the RT reaction and a 5' primer engineered to be complementary to the 3' tail of the cDNA and to contain the T7 promoter sequence to allow in vitro transcription of the selected and PCR amplified pool (FIG. 8-7) for the next SELEX cycle. The in vitro transcribed transcript (FIG. 8-8) can then be digested at both ends with RNaseH and appropriate targeting 2-OMe-deoxy oligonucleotide chimeras to generated the new truncated RNA pool (FIG. 8-9) for the next round of selection.

Overview of Truncation-SELEX-by-Hybrid-Selection

The steps of RNA Truncation-SELEX-by-hybrid-selection are summarized in FIG. 9. This approach relies in the ability of selected RNA to function as a capture probe of its complementary sequence found in the same pool that generated the RNA used in this particular round. Complementary sequences are generated by either strand separation and purification from the dsDNA PCR product (Pagratis (1996) Nucleic Acids Research 24:3645–6) or by in vitro T3 or SP6 transcription from templates designed to contain appropriate promoter sequences at the 5' end of the negative strands as part of the 3' fixed sequence. Such complementary strands are still full length, containing their primer binding sites and therefore PCR amplifiable. This method can be applied to both RNA and DNA SELEX differing only by the method of generation of single stranded pool and the digestion of such single stranded pool. For DNA SELEX, the single stranded molecules are generated by strand separation (Pagratis (1996) Nucleic Acids Research 24:3645–6) and are digested as described above. For RNA SELEX, the single stranded molecules are generated by in vitro transcription followed by RNaseH digestion.

Each RNA truncation-SELEX-by-hybrid-selection round, starts with a dsDNA template (FIG. 9-1) generated by PCR in the presence of 5' primer biotinylated at its 5' end. A portion of the dsDNA template is used to purify the template (negative) strand as described above, while another portion is used to generate the single stranded selection pool, for example RNA (FIG. 9-2); the single stranded selection pool is then digested, for example with RNaseH (FIG. 9-3); digested molecules (FIG. 9-4) are partitioned based on their binding to the target (FIG. 9-5); partitioned molecules are biotinylated, for example with terminal deoxynucleotidyl transferase (FIG. 9-6); biotinylated selected molecules are then hybridized to prepurified template strands from the same starting pool and hybrids are partitioned by streptavidin capture (FIG. 9-7); captured template strands are then PCR amplified (FIG. 9-8) to generate the new pool for the next truncation-SELEX-by-hybrid-selection round.

When the hybrid selection method is used, the hybridization rate of complex nucleic acids must be taken into consideration, so enough hybridization time is given at early rounds to allow capture of selected sequences. There is a practical limit on the complexity of pools that can be utilized in the hybrid selection method. This practical limit needs to be determined experimentally in the presence of compounds that enhance hybridization rate such as CTAB (Pontius and Berg (1991) Proc. Natl. Acad. Sci. U.S.A. 88:8237–8241; Nedbal et al. (1997) Biochemistry 36:13552–57).

Size Selection

This approach is a variation of the scheme, which involves removal of fixed sequence and subsequent reintroduction of the same or different fixed sequences either enzymatically, or by hybrid selection. It involves the random fragmentation of an advanced or semiadvanced SELEX pool at either the DNA or RNA level followed by size selection (for example using gel electrophoresis), and finally by introduction of fixed sequences either enzymatically or by hybrid selection.

Digestion at the DNA level (FIG. 10) can be done with DNaseI and fragments of specified length are extracted from a sizing gel slice (or by any other method i.e. density gradient sedimentation, gel filtration etc.) and ligated to a circular vector (for example PCR-Script, Stratagene, Inc., La Jolla, Calif.). Ligation reactions are then served as templates for PCR amplification using a new set of fixed sequences, which include the T7 RNA polymerase promoter with the 5', fixed sequence. PCR amplification of the pool can follow *E. coli* transformation but this step could be limiting in sequence space due to the *E. coli* transformation efficiency ($10^8$–$10^{10}$). The PCR generated pool is the starting library of the truncation SELEX where the pool is transcribed by T7 RNA polymerase, digested by RNaseH to remove the new fixed sequences, and affinity selected by binding to the target. Selected RNA is then amplified by reintroducing fixed sequences by either the truncation SELEX-by-Ligation, -Tailing or -Hybrid Selection methods as described above.

Digestion at the RNA level can be done with a nuclease and digested RNA can be size selected by gel electrophoresis (or any other method). Size selected RNA can either be used for affinity selection directly or can be used to generate a starting pool for subsequent truncation SELEX rounds. When RNA is used directly following affinity selection, the next pool is generated by either the truncation SELEX-by-Ligation, -Tailing or -Hybrid Selection methods as described above. When RNA is used to generate the starting pool for truncation SELEX, fixed sequences can be introduced enzymatically by either the truncation SELEX-by-Ligation, or -Tailing methods as described above. The new pools are then used as described above.

Screening for Ligands of a Certain Size

There is a desire for obtaining short ligands following application of the SELEX process for economical reasons. Therefore an efficient way to screen for ligands that can be truncated to an appropriate length could be very useful. Screening can be done by procedures that allow boundary determination. Currently boundary determination (Fitzwater and Polisky (1996) Methods Enzymol 267:275–301) is done in two separate experiments where each boundary is first determined separately followed by experiments where both boundaries are tested together in one molecule for binding activity (FIG. 11). This procedure is tedious and it can be done in a small set of ligands. Furthermore, there are examples that combination of the two boundaries, determined independently in the same molecule, results in inactive ligands (data not shown).

Presented here is an alternative way of screening for ligands that can tolerate truncation to a given length. This approach is based on random cleavage of internally labeled RNA ligands and then partition of those fragments that retain binding to the target followed by gel electrophoresis (FIG. 11). Random cleavage of oligonucleotides on n length generates (n(n+1))/2 fragments (FIG. 11). Among these fragments only those that contain the minimum necessary fragment will retain binding to the target. Electrophoretic analysis on sequencing gels of all randomly generated fragments that have been partitioned for target binding will generate a pattern containing a continuous range of partial length fragments greater or equal of a minimum length (FIG. 11). This method can be used to screen ligands for their possible minimal length.

Therefore, the size of the minimal fragment necessary for binding can be determined in a large number of ligands at once as follows. Each ligand is randomly cleaved to generate a ladder of molecules. These molecules are radioactively labeled by either using body labeled starting material or end labeling the resulting fragments, following fragmentation. End labeling can be done with either kinase or RNA ligase or terminal transferase with $\gamma$-$^{32}$P-ATP or $^{32}$P-pCp or $\alpha$-$^{32}$P-ddNTP, respectively. The resulting radiolabeled ladder is allowed to bind to the target and the target bound molecules are then partitioned and analyzed on a sequencing gel along with size markers. Following auto-radiography, minimum retained fragment for each ligand can be observed and ligands with minimum fragments of desired length can be identified.

In addition to screening, minimum fragment methodology can be used for truncation SELEX where the minimum fragments are excised from the gel and used in the truncation SELEX schemes described above.

EXAMPLE 1

Experimental Procedures for Performing the SELEX Process by Annealing of the Complementary Oligonucleotides to the Fixed Sequence Region or by Changing the Fixed Sequences This example provides general procedures followed by and incorporated into Example 2.

Materials and Methods

Genomic Library

The library from *E. coli* B genomic DNA was constructed as described previously (Singer et al. (1997) Nuc. Acids Res. 25:781–786). Briefly, genomic DNA was denatured and annealed to a primer with a fixed 5' end and 9 randomized nucleotides at the 3' end. After annealing at 2° C., the primer was extended with Klenow on ice, followed by room temperature, and 50° C. Another primer with a different fixed sequence was added, and the denaturation/annealing/extension was repeated. The molecules were separated by size on a denaturing polyacrylamide gel, and amplified by PCR using the above two primers minus the randomized sequences, plus the T7 promoter.

Genomic SELEX

A non-aggregating MS2 CP variant V75E; A81G with RNA-binding properties identical to wild type was purified as described previously (LeCuyer et al. (1995) Biochemistry 34:10600–6). Any endogenous *E. coli* RNA was removed in the purification process, as indicated by the binding stoichiometry and the UV absorbance spectra (LeCuyer et al. (1995) Biochemistry 34:10600–6).

SELEX was initiated with 1 nmole of RNA, transcribed from the *E. coli* genomic DNA library. This amount is theoretically equivalent to more than $10^7$ copies of every possible genomic insert, assuming the inserts start with equal probability at any position within the *E. coli* genome.

In each round of selection, 1 nmole of gel-purified RNA (a mixture of unlabeled RNA and a trace amount of RNA labeled during transcription with [$\alpha$-$^{32}$P]GTP) was denatured in TE at 95° C. for 1 minute, quickly chilled on ice and incubated on ice for 10 more minutes. Binding buffer was added to give a final concentration of 100 mM HEPES-KOH, pH 7.5, 80 mM KCl, 10 mM MgCl$_2$. The mixture was pre-filtered through nitrocellulose (0.45 micron pore, 25 mm diameter filter unit, Micro Filtration Systems (Dublin, Calif.), connected to a 3 ml disposable syringe and pre-wetted with 0.5 ml of the binding buffer) to reduce the fraction of the nitrocellulose-binding RNA. The volume was adjusted with the binding buffer to make up for the loss on the filter. MS2 CP was added to the final concentration of 100 nM of the dimer in a 0.1 ml reaction. Binding proceeded for 45 minutes at room temperature (22–24° C.).

The binding reaction was vacuum manifold-filtered through nitrocellulose (0.45 micron pore, 25 mm diameter, Micron Separations, Westborough, Mass.) and washed with 5 ml of the binding buffer. The fraction of the bound RNA, that is retained on nitrocellulose, was estimated by Cerenkov counting. The protein and RNA concentrations were chosen so that in every round this fraction was as low as possible, usually less than 1–2% of the total (to speed up the selection), but higher than in the control reaction without MS2 CP (to reduce the "background" selection of nitrocellulose binders).

The bound RNA was eluted from the cut filters by denaturation at 95° C. for 2 minutes in a suspension of 0.5 ml of 8 M urea in TBE and 0.5 ml of phenol, and then amplified for the next round of SELEX essentially as in Tuerk ((1997) Methods Mol. Biol. 67:219–230) with the following changes. RNA and primer B (5'-tcccgctcgtcgtctg-3' (SEQ ID NO:3)) were denatured at 95° C. for 1 minute, annealed at 70° C. for 10 minutes, and reverse transcribed at 48° C. for 30 minutes with SuperScript (Gibco BRL) reverse transcriptase (these temperatures were chosen to melt RNA secondary structures). The cDNA was amplified in PCR with Taq DNA polymerase as in Singer et al. ((1997) Nuc. Acids Res. 25:781–786) with primers B and A (5'-gaaa ttaatacgactcactataggg aggacgatgcgg-3' (SEQ ID NO:326); T7 promoter underlined). In this PCR, as well as in all others in this study, the relatively low concentrations of $MgCl_2$ (3 mM) and dNTPs (50 $\mu$M each) served to decrease the error rate. RNA was transcribed, labeled and gel-purified as in Schneider et al. ((1992) J. Mol. Bio. 228:862–9) and Tuerk ((1997) Methods Mol. Biol. 67:219–230). After the completion of SELEX, DNA was cloned and sequenced as in Singer et al. ((1997) Nuc. Acids Res. 25:781–786).

SELEX with Annealing of the Complementary Oligonucleotides

Instead of 1 nmole of RNA, 0.1 nmoles of RNA and 0.4 nmoles of each of the two complementary oligonucleotides were used (Table 1). An extra 10 minute incubation at room temperature was introduced directly after the addition of the binding buffer to allow oligonucleotides to anneal. The annealed oligonucleotides decreased the yield of the full-length reverse transcription product only by 10%. Otherwise, this SELEX was identical to the conventional SELEX.

SELEX with Changing the Fixed Sequences

Step 1. Changing the 3' fixed sequence: DNA purification and PCR. Conventional SELEX was carried out for 3 rounds using the old fixed sequence primers A and B described above. Since the old fixed sequences did not contain FokI restriction sites, the sites had to be introduced by PCR (alternatively, the sites can be introduced during the library construction). DNA product from either the reverse transcription reaction, or from PCR after round 3, was purified from primer B. Primer B interferes with the subsequent steps if not completely removed. Reverse transcription product was purified on a Microcon-30 filter (Amicon, Mass.), by centrifugation 3 times with 0.2 ml of TE buffer for 10 minutes at 16,000×g. PCR product, since it contains more primer B, had to be purified, instead of Microcon-30, by native polyacrylamide gel electrophoresis (PAGE) with ethidium bromide staining, followed by crush-and-soak elution for 30 minutes at 37° C.

Purified DNA was amplified by PCR (FIG. 1) using primer A and primer B+FokI (5'-tcccgctcgtGgATGg-3' (SEQ ID NO:327)). Primer B+FokI introduces the FokI recognition site (GgATG, shown in boldface) into the old 3' fixed sequence, and differs from primer B at the uppercase nucleotides (G, ATG).

The amplified DNA was extracted with chloroform, phenol, and 2 more times with chloroform, then ethanol precipitated and resuspended in water (unpurified PCR product inhibits subsequent FokI digestion).

Step 2. FokI digestion. Purified DNA product of 0.1 ml PCR was incubated with FokI (New England Biolabs) at a ratio of >1.5 units per microgram of DNA (the DNA mass was estimated assuming that <100% of the primers were converted into the full-length PCR product). This ratio had to be optimized with every new DNA preparation. FokI digestion was carried out in 40 $\mu$l at 37° C. for 1 hour in the manufacturer's buffer with 0.1% of Tween-20 detergent to decrease the exonuclease activity.

Step 3. Klenow extension. dNTPs (final concentration of 0.5 mM each) and the Klenow fragment of E. coli DNA polymerase I (from US Biochemicals, final concentration 370 units/ml) were added directly to the FokI digest. Extension proceeded for 15 minutes at 37° C. The digested and blunt-ended library DNA was then purified from the other digestion fragments by native PAGE as in step 1. PAGE showed that 60% of the input DNA was cut as expected, 40% was degraded nonspecifically, and a negligible fraction was left uncut.

Step 4. Ligation. The purified library DNA was resuspended in water and blunt-end ligated to the new fixed sequence. The new fixed sequence was a duplex of two DNA oligonucleotides: C (5'-ggtgcggcagttcggt-3' (SEQ ID NO:328)) and its complement, cC (5'-accgaactgccgcacct-3' (SEQ ID NO:329)). The duplex was formed by incubation of the mixture of 200 pmoles of each oligo in 4 $\mu$l of TE at 95° C. for 1 minute, followed by 60° C. for 10 minutes and room temperature for 10 minutes. The duplex was added to the purified DNA, and incubated with 2 units of T4 DNA ligase (Roche Molecular Biochemicals) in the manufacturer's buffer in 20 $\mu$l for 1 hour at 30° C. The ligation yield was 50%, estimated by Molecular Dynamics phosphorimager quantification of $^{32}$P-labeled DNA separated by PAGE. The overall yield of all steps was 10% relative to the input DNA at the beginning of step 2. The relatively high blunt-end ligation yield was achieved by keeping all DNAs as concentrated as possible (more than a few $\mu$M), since the $K_m$ of ligase for blunt ends is 50 $\mu$M (Sugino et al. (1997) J. Biol. Chem. 252:3987–94). The oligonucleotides, lacking a phosphate, cannot be ligated to anything except the digested library DNA. To reduce ligation of the library DNA molecules to each other, an excess of oligonucleotides over the library DNA was used (>2-fold excess, estimated by assuming that <100% of the primers were converted into the full-length PCR product, and that <100% of it was recovered after gel purification). The length of the ligation products was verified by PAGE.

Step 5. PCR. One-third of the ligation product was amplified by PCR with the new 3' fixed sequence primer C (sequence shown above) and primer A+FokI (which introduces the FokI site into the old 5' fixed sequence, and relates to primer A as B+FokI relates to B). Higher concentrations of the primers were used in this PCR (10 $\mu$M each, instead of 1 $\mu$M, as in all other PCRs in this study). This served to provide an excess of primer C over cC (cC is complementary to C, and was carried over from the ligation in step 4).

Only one of the two major ligation products can be amplified in PCR with primers C and A+FokI, namely, the product in which the duplex of oligonucleotides C and cC has been ligated in one of the 2 possible orientations with respect to the FokI-digested library DNA molecule. A single T was added to the 3' end of oligonucleotide cC, as shown above, in order to create a single base overhang in the C-cC duplex. Under the experimental conditions, adding a single overhanging T directs ligation more toward the desired orientation: blunt end to blunt end, as opposed to the undesired orientation of overhanging end to blunt end (data not shown).

Step 6. Changing the 5' fixed sequence. DNA was purified as in the third paragraph of step 1, and then steps 2–5 for 3' fixed sequence were essentially repeated for the 5' fixed sequence. For the PCR in step 5, primers for the new fixed sequences were used: C (step 4, above) and D (5'-gaaattaatacgactcactatagggaaagcccacgcc-3' (SEQ ID NO:330)). The resulting molecules had both fixed sequences replaced with the new ones, with both tails removed entirely. One such molecule is shown in FIG. 2D. After changing the fixed sequences, SELEX proceeded as in "Conventional SELEX," with 1 μM RNA and 100 nM MS2 CP. In the SELEX experiment where the new fixed sequences were chosen without the help of the STOGEN computer program (see below), the primers that correspond to C and D were, respectively, 5'-atgtcgggccgccgaa-3' (SEQ ID NO:331) and 5'-gaaattaatacgactcactatagggcccggc gcataa-3' (SEQ ID NO:332).

rffG End-Point Analysis

To find the sequences of the library molecules that share the rffG site, the method described previously (Singer et al., 1997, supra) was used. Briefly, the starting library DNA was amplified by PCR with the library primer B, and the genomic primer from rffG gene (5'-bbbcactgagcatcagccag-3' (SEQ ID NO:333); b stands for biotin). The products that contained the genomic primer were purified on immobilized streptavidin. Their complementary strands were eluted, and amplified using primer B and a nested genomic rffG primer (5'-bbbatcagccagactgtgtca-3' (SEQ ID NO:334); the sequence in common is in boldface). The PCR products were purified on immobilized streptavidin again, eluted, and amplified with uracil-primers for subsequent cloning and sequencing.

Binding Analysis

Figure 4:
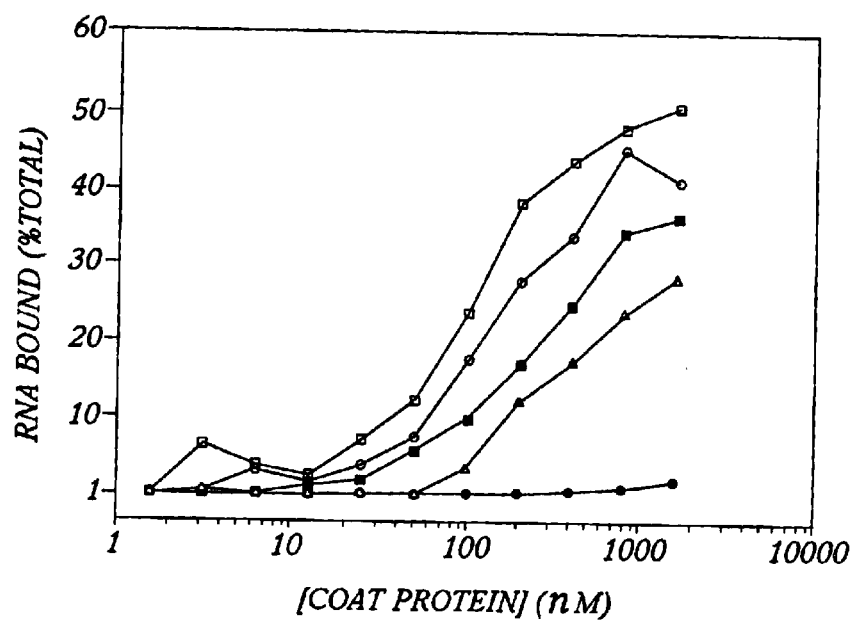
FIG. 4 shows binding of RNA to MS2 CP. SELEX isolates with the consensus binding site, rffG and ebgR, bind well. To test whether the fixed sequences contribute to binding of the rffG isolate, the RNA fragment that corresponds exactly to its insert was obtained from *E. coli* genomic DNA using PCR and in vitro transcription. This RNA fragment (rffG minus fixed sequences) binds only marginally worse than the original rffG SELEX isolate. For comparison, the natural MS2 CP binding site (bacteriophage MS2 replicase fragment) binds more weakly than all of the SELEX isolates with the consensus binding site (Table 2), except secY isolate (data not shown). A typical SELEX isolate without the consensus binding site does not appreciably bind MS2 CP, and neither does the starting library (data not shown).

The MS2 replicase fragment (the natural MS2 CP binding site; FIG. 4) was chemically synthesized, amplified by PCR and labeled by in vitro transcription as above. The resulting RNA molecule contained the fragment of the original MS2 sequence (as published in the GenBank) with the same fixed sequences (for primers C and D) attached to it as in the real SELEX isolates. The molecule also matched the SELEX isolates in length (70 nucleotides, with most isolates being 60–80 nucleotides). The MS2 CP binding site was positioned approximately in the middle of the molecule.

The RNAMOT site Nos. 8, 12 and 14 (Table 3) were amplified from *E. coli* genomic DNA template by PCR. The transcribed RNA molecules had the MS2 CP binding sites positioned approximately in the middle (just as they were positioned for simplicity when their predicted secondary structures were examined). The molecules also had the same fixed sequences, and were 70 nucleotides long.

Labeled RNA (0.1 nM) was bound to MS2 CP in variable excess concentrations as above, but without pre-filtering, at 24–25° C. Each binding reaction was filtered through nitrocellulose (0.45 micron pore, from Bio-Rad) using a Bio-Dot apparatus (Bio-Rad) and washed with 0.5 ml of the binding buffer.

STOGEN: A Computer Program to Choose New Fixed Sequences

To reduce the possible influence of the fixed sequences on the outcome of the SELEX experiments, a computer program to design new fixed sequences was developed. The program (available by anonymous ftp from /usr/local/ftp/pub/STOGEN at beagle.colorado.edu or by e-mailing to timur@colorado.edu or javornik@nexstar.com) takes as input the old fixed sequences. It generates possible candidates for the new fixed sequences, using 4 heuristic rules with user-adjustable parameters (see below). For computational efficiency, the program does not generate and test all possible sequences of a given length, but rather randomly generates a subset of sequences, tests them, and repeats the process again, until it arrives at sequences that conform to all of the rules (hence the name of the program—STOGEN, short for stochastic generator). The STOGEN rules are:

1. The new fixed sequences should have approximately the same annealing temperatures to the primers as the old fixed sequences, in order to facilitate amplification. Therefore, the new fixed sequences have the same length and the same number of G+C as the old ones (Wu et al. (1991) Prog Nucleic Acid Res. Mol. Biol. 40:185–220).

2. The new fixed sequences should form among themselves as little secondary structure as possible. In addition to potentially influencing SELEX, the structure may hinder either PCR or reverse transcription. The longest allowed continuous stem was usually limited to 3 base pairs.

3. The new fixed sequences should share as little similarity as possible to the old ones. Thus, all the molecules that used the old fixed sequences for binding, will be lost in subsequent rounds of SELEX. Two criteria were used to this end: shared sequence size and position-by-position identity. The maximum allowed size of any sequence in common between the old and the new fixed sequences was usually set to 2 nucleotides. That is, if the old fixed sequence contains AUG, the new one may contain AU or UG, but not AUG. The only exception is the invariant starting GGG, required for optimal transcription yield (Milligan et al. (1987) Nucleic Acids Res. 15:8783–98).

Also, position-by-position identity between the old and the new fixed sequences is limited. Since the parts of the fixed sequences closest to the insert participate in binding more often, identity is weighted by position, assigning greater penalty to positions closest to the insert. The weight function was derived by evaluating the fixed sequence participation data from 11 different SELEX experiments. Seven experiments were randomized sequence SELEXes for protein binders (Brown et al (1997) J. Biol. Chem. 272:14969–74; Brown and Gold (1995) Biochemistry 34:14765–74; Burke et al. (1996) J. Mol. Biol. 264:650–66; Jellinek et al. (1994) Biochemistry 33:10450–6; Kubik et al. (1994) Nucleic Acids Res. 22:2619–26; Tuerk et al. (1992) Proc. Natl. Acad. Sci. USA 89:6988–92; Tuerk & MacDougal-Waugh (1993) Gene 137(1):33–9), two were genomic SELEX experiments (experiments 1 and 2, FIG. 3) described in the present paper, one was SELEX for small-molecule binders (Burke et al. (1997) Chem. Biol. 4:833–43), and one was SELEX for RNA best cleaved with an endonuclease (Jayasena et al. (1996) Biochemistry 35:2349–56). In every SELEX experiment, the data generated for the individual isolates by boundary experiments or by any other similarly reliable method, were used. Although each SELEX experiment yielded very different results, the cumulative data from all of these SELEX experiments is approximated well by the formula:

$$f=0.027+2.0\times10^{-8}\times(n-20)^6, \text{ for } n\leq 10, \text{ and}$$

$$f=0.022, \text{ for } n>10.$$

Here f is the relative frequency of participation of each position within the fixed sequence, and n is the position (counting from the insert, n=1 is the first fixed nucleotide). The program assigns the identity score for each position to be f, if the new fixed sequence and the old one both have the same nucleotide at this position, and to 0—otherwise. New fixed sequences with a particularly high total identity score (=the sum of the identity scores over all positions) are avoided.

4. The new fixed sequences should have minimal potential to form secondary structure with the genomic insert. In most cases, the sequence of the genomic insert is not known in advance. Hence, the generalized potential to form secondary structure is evaluated in the following way.

For each of the candidates for the new fixed sequences, the free energy of annealing to its complement is calculated (the complement used here includes A:U, G:C and G:U base pairs). For example, the sequence AC thus has one possible perfect complement, GU. The sequence GU has 4 possible perfect complements: AC, AU, GC and GU, since U can base pair with either A or G, and G—with either C or U.

The sum of free energies of all possible complements annealing to the fixed sequence is calculated using the Turner rules (Serra & Turner (1995) Methods Enzymol. 259:242–61). The more negative the sum, the larger the potential to form secondary structure. Sequences with a particularly negative sum of free energies (typically, G, U-rich) are avoided.

EXAMPLE 2

Binding Sites from the MS2 CP SELEX Agree with the Known Consensus Structure

A library of genomic DNA was prepared from *E. coli* B by random primer extension (Singer et al. (1997) Nucleic Acids Research 25:781–786). The library contained approximately 65 nucleotide genomic inserts flanked by fixed sequences, which serve as primer annealing sites for amplification. Insert refers to the genomic sequence located in the library molecule between the two fixed sequences. In each round of SELEX, the transcribed library was allowed to bind MS2 CP, and then the bound RNA was amplified. In SELEX experiment 1, the DNA was cloned and sequenced after 5 rounds, when the optimal binding was observed.

Out of 25 isolates sequenced, 12 had the predicted consensus (Witherell et al. (1991) Prog Nucleic Acid Res. Mol. Biol. 40:185–220) binding site (FIG. 2A), which could be identified either by folding by hand, or by computerized Zuker-Turner folding (Genetics Computer Group, *Program Manual for the Wisconsin Package,* 8$^{th}$ edition, Madison, Wis., 1994; Serra and Turner (1995) Methods Enzymol. 259:242–61; Zuker (1989) Science 244:48–52). Of the 12 isolates, 10 were found in the GenBank, which included the complete *E. coli* sequence, by the BLAST search (Altschul et al. (1990) J. Mol. Biol. 215:403–410) using the network service at the NCBI (Genetics Computer Group, *Program Manual for the Wisconsin Package,* 8$^{th}$ edition, Madison, Wis., 1994). The remaining 2 isolates did not have significant similarities to any sequences in GenBank, and probably resulted from contamination of the starting genomic library DNA.

Surprisingly, the genomic sequences, obtained from the GenBank, that corresponded to 9 out of the 10 isolates with the consensus binding site, did not contain this site. Thus, they were not predicted to bind MS2 CP. In other words, 9 out of the 10 isolates were experimentally induced artifacts.

Figure 2A:
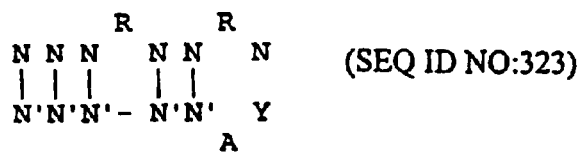
FIGS. 2A–E show MS2 CP binding sites.
Figure 2B:
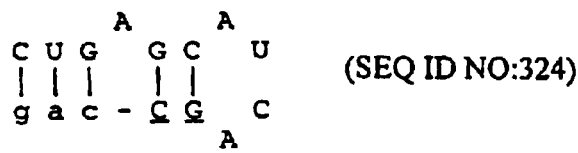
Figure 2C:
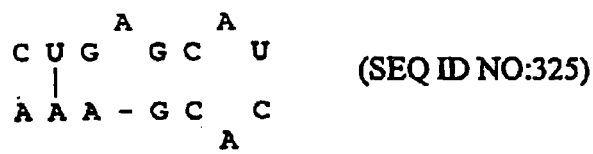
Figure 2D:
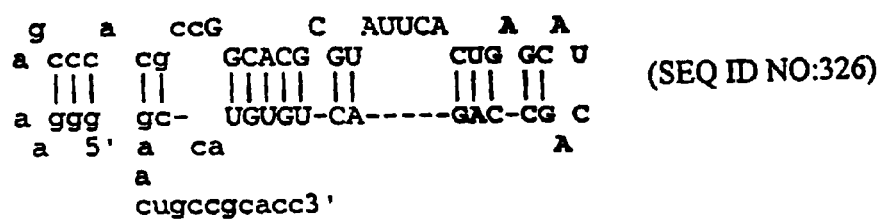
Figure 3:
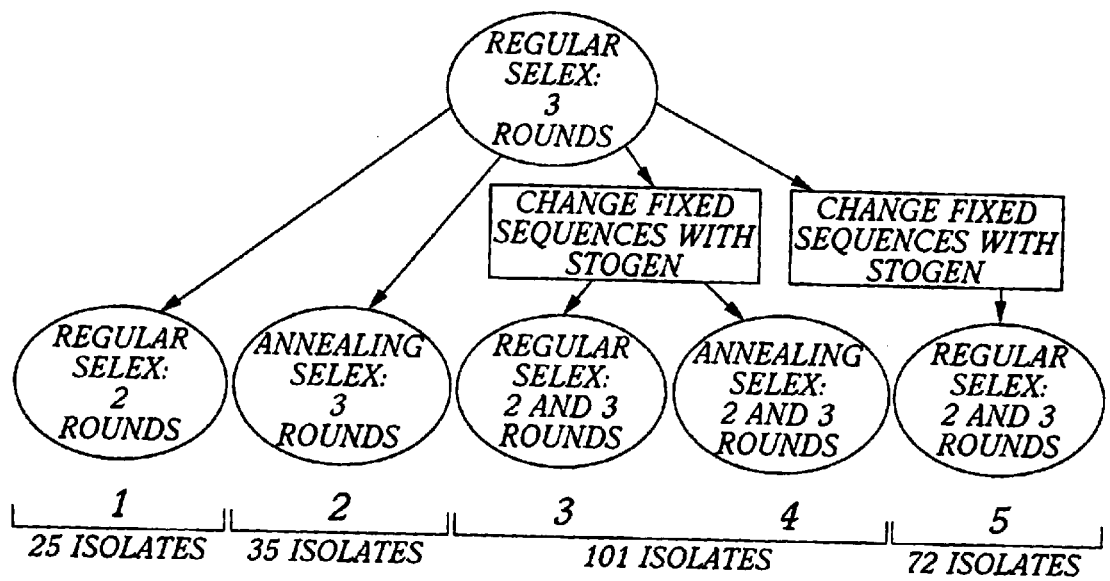
FIG. 3 shows an outline of the genomic SELEX experiments 1–5, with the number of isolates sequenced at the end of each SELEX.

One of the frequent artifacts is shown in FIGS. 2B and 2C. In this isolate, the fixed sequence participates in forming the binding site. This isolate also has several mutations in the insert that participate in forming the binding site. All of the mutations are at the junction with the fixed sequence. This junction is much more prone to mutations than the rest of the genomic insert because of the random sequence introduced when the randomized primer misannealed during library construction (Singer et al. (1997) Nucleic Acids Research 25:781–786). The mutated region of the genomic insert at its junction with the fixed sequence is termed the tail.

In the isolate shown in FIGS. 2B and 2C, as well as in most other isolates, the tail and the fixed sequence both participate in forming the binding site. The corresponding genomic sequences from the GenBank were very different from the tails and, obviously, from the fixed sequences, and thus were unable to form the binding site.

Note that the binding of the genomic sequences was not actually measured, but rather inferred from the sequence. The sequence alone should predict the binding fairly well, as confirmed in this paper (see below), and as shown earlier by others (Schneider et al. (1992) J. Mol. Biol. 228:862–9; Stockley et al. (1995) Nucleic Acids Res. 23:2512–8; Uhlenbeck et al. (1983) J. Biomol. Struct. Dyn. 1:539–52; Witherell et al. (1991) Prog Nucleic Acid Res. Mol. Biol. 40:185–220).

Annealing of the Complementary Oligonucleotides Reduces the Fraction of SELEX Artifacts It was desirable to reduce the fraction of isolates in which the fixed sequences, or tail, or both, participate in binding. The first method to solve this problem was designed to reduce the participation in binding of only the fixed sequences, but not the tails. The genomic SELEX described in Example 1 above (termed conventional genomic SELEX) was carried out for 3 rounds. In each subsequent round, two DNA oligonucleotides complementary to the two fixed sequences were annealed prior to binding of RNA to MS2 CP (Table 1). SELEX with annealing was carried out for 3 rounds (FIG. 3, SELEX experiment 2). Switching from "no annealing" to "annealing," rather than doing all 6 rounds "annealing," should reduce the fraction of isolates that require annealing for binding to MS2 CP.

Out of 35 sequenced isolates from "annealing" SELEX, 26 had the consensus binding site, and 17 of those 26 were found in the GenBank. Of these 17 isolates, 7 (40%) had a consensus binding site present in the corresponding genomic sequence from the GenBank, and the rest were artifacts as described above. The fraction of artifacts in which fixed sequences, but not tails, participated in binding, decreased only by approximately twofold.

Changing Fixed Sequences Eliminates Most of the SELEX Artifacts

The second, and more efficient, method of reducing the artifacts consists of changing the fixed sequences sometime through the course of SELEX, replacing them with entirely new fixed sequences, and at the same time eliminating the "tails" altogether (FIG. 1).

FokI endonuclease was used to cut the 3' fixed sequence and the tail of the library DNA after round 3 of conventional genomic SELEX. FokI cuts at a specific distance (9–13 nucleotides, regardless of their sequence) away from its recognition site, which was introduced in the fixed sequence near its junction with the genomic insert. After digestion with FokI, the overhang at the cut end of the library DNA was extended with Klenow, and blunt-end ligated to the new 3' fixed sequence, which was a duplex of synthetic oligonucleotides. The ligation product was amplified by PCR, and the whole procedure was repeated again—this time to change the 5' fixed sequence. The new fixed sequences were chosen using a specially developed computer program termed STOGEN (see Example 1). The sequences may also be chosen manually, with the careful consideration of all the important factors involved (discussed in Example 1).

After changing the 5' and 3' fixed sequences, SELEX was preformed in 2 different ways in parallel: (1) with annealing of the DNA oligonucleotides complementary to the new fixed sequences, and (2) without any complementary oligonucleotides, as in conventional genomic SELEX (FIG. 3, SELEX experiments 3 and 4). Both SELEX experiments gave virtually identical results. After 2 and 3 rounds of SELEX with the new fixed sequences, 101 isolates were sequenced. Out of 101 isolates, 76 had the consensus binding site, and 75 out of these 76 were found in the GenBank.

The fixed sequences never made any part of the consensus binding site. Neither did the tails, except for 1 artifact. Practically all tails had been successfully removed by FokI. Internal, rather than tail, mutations caused 2 artifacts. This is comparable to the frequency of any mutations in genomic SELEX (1.7 mutations per 100 nucleotides after 5–6 SELEX rounds, data not shown).

Five isolates closely resembled the consensus binding site, but had mutations in those parts that do not contact the coat protein directly (Valegard et al. (1994) Nature 371:623–6; Valegard et al. (1997) J. Mol. Biol. 270:724–38). None of the F6-like, 3 nucleotide loop variants, which binds more weakly than the consensus binding site (Convery et al. (1998) Nat. Struct. Biol. 5:133–9), has been found in the genomic SELEX experiments.

All of the SELEX isolates with the MS2 CP consensus binding site (Table 2) had the higher-affinity RNCA tetraloop instead of the lower-affinity RNUA tetraloop of the natural MS2 CP binding site on MS2 mRNA (Johansson (1998) Proc. Natl. Acad. Sci. USA 95:9244–9; Lowary and Uhlenbeck (1987) Nucleic Acids Res. 15:10483–93). As expected, these SELEX isolates bound better than the natural binding site, as measured by the nitrocellulose filter-binding assay (FIG. 4). Four most frequent isolates without the consensus binding site were also tested. Three isolates did not bind MS2 CP (a typical one is shown in FIG. 4), and one bound nitrocellulose and also, weakly, MS2 CP (data not shown).

Figure 2E:
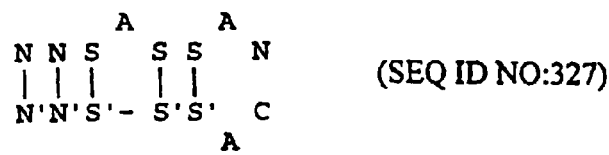

The consensus of the isolates in Table 2, with consideration of their frequencies in the selected pool, is shown in FIG. 2e. Most of the differences between the SELEX consensus site and the consensus site in FIG. 2A, should make the binding tighter, or the binding structure more stable (Uhlenbeck et al. (1983) J. Biomol. Struct. Dyn. 2:539–52; Witherell et al. (1991) Prog Nucleic Acid Res. Mol. Biol. 40:185–220). This SELEX consensus also agrees with the data from the randomized sequence SELEX (Schneider et al. (1992) J. Mol. Biol. 228:862–9).

The isolates that bind MS2 CP were located in 8 distinct genomic sites. Locations of the MS2 CP binding sites within the corresponding genes did not follow any obvious pattern, with some sites being on the sense, and some on the antisense strand.

Fifty-six isolates were from the sense strand of mRNA of the rffG gene (FIG. 2D). These molecules were not only the most frequent, but also the tightest binders among the SELEX isolates. The corresponding genomic fragment (without the fixed sequences) also bound MS2 CP well (FIG. 4). The rffG open reading frame, o355, was mistakenly labeled rffE in the GenBank version 90.0 (Marolda and Valvano (1995) J. Bacteriol. 177:5539–46). Encoded by rffG is the enzyme dTDP-D-glucose 4,6 dehydratase. This enzyme participates in formation of O-specific polysaccharide, or O antigen, which, joined together with lipid A via core oligosaccharide, forms lipopolysaccharide in the bacterial outer membrane (Raetz, *Escherichia Coli and Salmonella: Cellular and Molecular Biology*, $2^{nd}$ edition, 1996, pp. 1035–1063). The enzyme also participates in formation of the polysaccharide part of the enterobacterial common antigen, a cell surface glycolipid (Rick & Silver, *Escherichia Coli and Salmonella: Cellular and Molecular Biology*, $2^{nd}$ edition, 1996, pp. 104–122).

Library Composition Partially Explains SELEX Results

It is worth noting that 93% of all the rffG isolates were virtually copies of each other, with the 15 nucleotide consensus binding site always starting at any of only 4 adjacent positions (or adjacent "registers") within the 40 nucleotide insert. The site was predicted ideally to shift everywhere within the 40−15+1=26 available registers within the insert. The fact that it did not, was possibly due to a bias in the starting library. The end-point analysis (Singer et al. (1997) Nucleic Acids Research 25:781–786) showed that more than half of the molecules of the starting library have end-points that correspond to the registers of the majority (93%) of all rffG SELEX isolates (FIG. 5A). Such clustering of end-points might have been caused by annealing of the fixed part of the library primer to the E. coli DNA during the library construction (FIG. 5B).

Comparison of the MS2 CP Binding Sites Predicted by the Computer Search with the Sites Found by SELEX Other sites in the E. coli genome that bind to MS2 CP were much less frequent than rffG, in these (Table 2) and prior rounds of SELEX (data not shown). This raised the question about the efficiency of finding all potentially biologically important binding sites. To check if any other binding sites were missed by the SELEX process, a search was performed for the MS2 CP consensus binding site (FIG. 2A) in the complete E. coli genome, using the RNAMOT program (Gautheret et al. (1990) Comput. Appl. Biosci. 6:325–31). The search revealed 412 matches to the consensus binding site, each of which theoretically binds the coat protein as well as, or better than, the wild-type MS2 mRNA. Only 280 sites were expected by chance.

To narrow this list to only the tightest binding sites, the SELEX consensus binding site (FIG. 2E) was searched for. It is based on the genomic SELEX isolates, and is more restrictive than the consensus binding site, which is based on the studies of mutants. RNAMOT found 21 such "SELEX consensus" binding sites (Table 3). Only 3 sites were expected to be found at random.

Three binding sites were found both by SELEX and by RNAMOT program, including the major (rffG) SELEX isolate. Most of the minor SELEX isolates were not found by RNAMOT. Some of these did not fit the SELEX consensus used for searching the database. For example, had G:U pairs been allowed in the consensus, these sites would have been found, too. Others, like isolate Nos. 7 and 9 from Table 2, were not in the database.

Most of the RNAMOT sites were not found by the SELEX process. It is possible that some of them were under-represented in the starting library, or that they were poorly amplifiable in the SELEX process, or that they bound MS2 CP weakly because the RNA folds into alternate, non-binding, structures within the context of a larger molecule. It is unlikely that these sites were entirely absent from the library. In a previous experiment, all of the 13 other independently tested genomic fragments were successfully amplified by PCR from the same E. coli genomic library (Singer et al. (1997) Nucleic Acids Research 25:781–786).

To find out why the RNAMOT sites were not isolated in SELEX, 20–40 most stable predicted secondary structures of some RNAMOT sites were compared to those of the actual SELEX isolates. In addition, structures of the rffG binding site present in all possible registers within the insert were examined. There appeared only a weak correlation between structures and the frequency of isolation in SELEX. The absolute free energy of the binding site structure, or of the whole molecule, was not correlated with its isolation in SELEX. However, the major rffg isolate had a fairly long stem that supported the binding site (FIG. 2D), relative to other SELEX isolates, and to many other rffG registers.

Perhaps a longer stem provides extra stability to the correct binding site structure and thus reduces the fraction of molecules folded into other, non-binding, structures. In the randomized sequence SELEX for R17 coat protein binders, Schneider and coworkers also found mostly long (7 base pairs) and stable (mostly G:C or C:G base pairs) stems (Schneider et al. (1992) J. Mol. Biol. 228:862–9). Also, in the regular MS2 CP genomic SELEX experiment (without changing the fixed sequences or annealing of oligonucleotides; FIG. 3, experiment 1), many isolates used fixed sequences not only to form the consensus binding site, but also to extend its stem past the minimum 5 base pairs. In SELEX experiments 3 and 4, the fixed sequences, while not forming the consensus binding site, sometimes extended the stem to longer than the minimal 5 base pairs. In SELEX experiment 5, the new fixed sequences were chosen without STOGEN, and their potential to base-pair to each other and to the insert was accidentally overlooked. In most of the isolates from this SELEX experiment, the fixed sequences extended the minimal stem by additional 12 base pairs.

However, when RNAMOT sites were considered as well, longer stems did not correlate with the frequency of isolation in SELEX. For example, site Nos. 8, 12 and 14 (Table 3), which were found by RNAMOT, are also predicted to have long stems, just like the most frequent genomic SELEX isolates (Nos. 1, 2 and 3, Table 2), and yet they were not found in the SELEX process. They fit the randomized sequence SELEX consensus stems (Schneider et al. (1992) J. Mol. Biol. 228:862–9) as well or better than the most frequent genomic SELEX isolates. They also bind MS2 CP rather well. Site Nos. 8 and 14 bind to MS2 CP with affinities between those of SELEX isolate Nos. 1 and 2 (data not shown). Site No. 12 binds MS2 CP with affinity only slightly weaker than SELEX isolate No. 6.

In short, the only parameters that apparently affect isolation of any particular molecule in the SELEX process are the molecule's affinity and its frequency in the starting library. Perhaps the sites predicted by RNAMOT, but not found in SELEX, were less frequent in the library.

Examples 1 and 2 demonstrate methods for generating nucleic acid ligands in which the participation of the fixed region in binding to the target is minimized or eliminated by changing fixed region sequences or by annealing of complementary nucleotides to the fixed regions. These methods were demonstrated using the Genomic SELEX methodology; however, it would be known by one of skill in the art that these methods are not specific to the Genomic SELEX methodology, but can by applied to the more broad SELEX methodology.

EXAMPLE 3

This Example provides general procedures followed by and incorporated into Examples 4–12.

Materials

Recombinant human Transforming Growth Factor Beta 1 (hTGFβ1) and human Vascular Endothelial Growth Factor (VEGF) were from R&D Systems (Minneapolis, Minn.). DNA and RNA modifying enzymes were from Roche Molecular Biochemicals (Indianapolis, Ind.), BRL (Gaithersburg, Md.), or NEB (Beverly, Mass.) or PE (Foster City, Calif.). Biotin-21-dUTP was from Clontech (Palo Alto, Calif.), terminal deoxynucleotidyl transferase was from Clontech (Palo Alto, Calif.) or Roche Molecular Biochemicals (Indianapolis, Ind.). T7 RNA polymerase, 2'F-modified CTP and UTP were prepared in house. Taq DNA polymerase was from Perkin Elmer (Foster City, Calif.). DNA oligonucleotides were obtained from Operon Technologies, Inc. (Alameda, Calif.). All other reagents and chemicals were from commercial sources.

Affinity Selection (SELEX)

The SELEX procedure has been described in detail in the SELEX Patent Applications. The DNA templates contained either 40 or 30 random nucleotides, flanked by 5' and 3' constant regions for primer annealing sites for PCR and cDNA synthesis (Table 5). Truncation SELEX started with VEGF round 12 VT30 or TGFβ1 round 13 40N7 or 30N7 pools. These pools were described previously (see Ruckman et al. (1998) J. Biol. Chem. 273:20556–67 and U.S. Ser. No. 09/046,247, filed Mar. 23, 1998). Selection conditions for truncation SELEX are summarized in Tables 6A–D. RNA pools were prepared by transcription with about 5 µM DNA template, 5 units/µl T7 RNA polymerase, 40 mM Tris-HCl (pH8), 12 mM MgCl$_2$, 5 mM DTT, 1 mM spermidine, 0.002% Triton X-100, 4% PEG 8000, 2–4 mM each 2'OH ATP, 2'OH GTP, 2'F CTP, 2'F UTP, and 0.25 µM α$^{32}$P-ATP (800 Ci/mmole). When necessary, RNA pools were prefiltered and/or preadsorbed with multiple layers of same nitrocellulose filter type used in the SELEX process in order to reduce the frequency of molecules selected for nitrocellulose binding. To prepare binding reactions, the RNA molecules were incubated with recombinant h TGFβ1 in Dulbecco's Phosphate-Buffered Saline (DPBS) (Life Technologies, Gaithersburg, Md.) containing 1 mM MgCl$_2$ and 0.01% human serum albumin or with recombinant VEGF in TBS (Sambrook et al., *Molecular Cloning: A Laboratory Manual*, 2$^{nd}$ Edition, Cold Spring Harbor, N.Y., 1989) containing 1 mM MgCl$_2$, 1 mM CaCl$_2$ and 0.01% human serum albumin. Following incubation at 37° C. (about 30 minutes) the protein-RNA complexes were partitioned from unbound RNA by capture on nitrocellulose. Nitrocellulose filter bound RNA was recovered by phenol/urea extraction. Pools were amplified by RT/PCR or PCR. Reverse transcriptions were done by AMV reverse transcriptase at 48° C. for 60 minutes in 50 mM Tris-HCl pH 8.3, 60 mM NaCl, 6 mM Mg(OAc)$_2$, 10 mM DTT, 50 pmol DNA 3' primer (3G7) (Table 5), 0.4 mM each of dATP, dCTP, dGTP, and dTTP, and 1 unit/µl AMV RT. PCR amplifications were done with 2 µM each 3G7 and 5G7 primers (FIG. 1), 50 mM KCl, 10 mM Tris-HCl, pH 9, 0.1% Triton X-100, 3 mM MgCl$_2$, 0.5 mM of each dATP, dCTP, dGTP, and dTTP, 0.1 units/µl Taq DNA polymerase. Typically 15 cycles were used of 30 seconds denaturation at 95° C., 30 seconds annealing at 60° C., and 1 minute elongation at 72° C.

Nitrocellulose Filter Partitioning

To partition the protein-RNA complexes away from uncomplexed RNA, the binding reactions were filtered through nitrocellulose/cellulose acetated mixed matrix, 0.45 µm pore size filter disks, type HA, (Millipore, Co., Bedford, Mass.). For filtration, the filters were placed onto a vacuum manifold and wetted by aspirating 5 ml of binding buffer. The binding reactions were aspirated through the filters, then filters were washed with 5–50 ml of binding buffer (without BSA) and counted in a scintillation counter (Beckmann). When necessary, nitrocellulose filters were preblocked with 2 ml of PBS+0.01% BSA to reduce background binding of RNA.

Nitrocellulose partitioning was also used for determining the equilibrium dissociation constants of RNA ligands to hVEGF or hTGFβ1. High specific activity transcripts for affinity determination were prepared in 20 µl reactions containing 5 µl crude PCR product and 15 µl transcription mix (3.9 µl 5×transcription buffer, 0.1 µl 1 mM ATP, 0.2 µl 100 mM GTP, 0.6 µl 100 mM 2'F-CTP, 0.6 µl 100 mM 2'F-UTP, 2.5 µl α-$^{32}$P-ATP (800 Ci/mmol, NEN, Boston, Mass.), 0.5 µl T7 RNA polymerase (at 14.7 µM)). Following incubation (1 hour—overnight), transcripts were gel purified from denaturing polyacrylamide TBE gels (for example 10% or 15%, Novex, San Diego, Calif.) and were used at about 25,000–50,000 cpm per 8–12 point binding curve. Binding curves obtained by nitrocellulose filtration indicated that RNA pools and some RNA ligands bind monophasically while others bind biphasically. Biphasic binding can be described as the binding of two affinity species derived from the same ligand sequence that can fold into alternate structures that are kinetically trapped and are not in equilibrium.

To obtain the monophasic equilibrium dissociation constants of RNA ligands to hTGFβ1 the binding reaction:

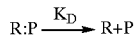

R=RNA

P=Protein $K_D$=dissociation constant is converted into an equation for the fraction of RNA bound at equilibrium:

$$q=(f/2R_T)(P_T+R_T+K_D-((P_T+R_T+K_D)^2-4P_TR_T)^{1/2})$$

q=fraction of RNA bound $P_T$=total protein concentration $R_T$=total RNA concentration f=retention efficiency of RNA-protein complexes The average retention efficiency for RNA-TGFβ1 complexes on nitrocellulose filters is 0.4–0.8. Biphasic binding data were evaluated with the equation:

$$q=2P_T+R_T+K_{D1}+K_{D2}-[(P_T+X_1R_1+K_{D1})^2-4P_TX_1R_T]^{1/2}-[(P_T+X_2R_T+K_{D2})^2-4P_TX_2R_T]^{1/2},$$

where $X_1$ and $X_2$ are the mole fractions of the affinity species $R_1$ and $R_2$ and $K_{D1}$ and $K_{D2}$ are the corresponding dissociation constants.

The $K_D$s were determined by least square fitting of the data points using the software Kaleidagraph (Synergy Software, Reading, Pa.).

RNaseH Digestion

Primer binding sites of RNA transcripts were removed by RNaseH digestion as follows. Gel purified 2'fluoropyrimidine modified RNA (about 200 pmoles) was incubated with 0.1 mM each final concentration of 3H7 and 5H7 oligonucleotides (Table 7) in 50 µl volume. The transcript oligonucleotide mix was heated at 95° C. for 4 minutes, incubated at 50° C. for 10 minutes and at 37° C. for 2 minutes and was supplemented with 5 µl of 10×RNaseH buffer (200 mM Hepes-KOH, pH 9.0, 500 mM KCl, 100 mM MgCl$_2$) and 25 µl of RNaseH (1 U/µl, Roche Molecular Biochemicals, Indianapolis, Ind.). The transcripts were digested at 37° C. for 30–60 minutes and then were ethanol precipitated in 2 M ammonium acetate in the presence of 20 µg of glycogen carrier (Roche Molecular Biochemicals, Indianapolis, Ind.) and resuspended in appropriate volume of H$_2$O. RNaseH digestion of small amounts (0.03–0.5 pmoles) of high specific activity RNA was done in a smaller volume (usually 20 µl) in the presence of 1 unit of RNaseH and 250 nM each 3H7 and 5H7.

Mapping of RNaseH Digestion Sites

To map RNaseH digestion sites, 2'F RNA transcripts of ligands VT30-07 and VT30-44 (Ruckman et al. (1998) J. Biol. Chem. 273:20556–67) were $^{32}$P labeled at their 5' or 3' ends. For 5' end labeling, 2.5 pmols of each transcript were phosphatased in 25 µl reactions containing 2.5 units shrimp alkaline phosphatase (Roche Molecular Biochemicals cat#1758250) in manufacturer's specified buffer, for 60 minutes at 37° C. Following heat inactivation at 70° C. for 20 minutes, the phosphatased RNA was kinased with T4 polynucleotide kinase (Roche Molecular Biochemicals cat#709557) per manufacturer's instruction and 2 µCi γ$^{32}$P-ATP (10 Ci/mmole, New England Nuclear, cat#NEG502) at 37° C. for 30 minutes. For 3' end labeling, 10 pmols of each transcript were incubated with T4 RNA ligase (Roche Molecular Biochemicals cat#1449478) and 10 pmols of Cytidine 3', 5'-bis(phosphate), [5'-$^{32}$P] (3000 Ci/mmol, New England Nuclear, cat# NEG019A) in 30 µl (total) of reaction buffer containing 10% DMSO. Ligation reactions were incubated at 4° C. overnight. Labeled RNA was recovered by ethanol precipitation in the presence of glycogen as carrier (Roche Molecular Biochemicals, cat# 901393) and gel purified from a denaturing 10% polyacrylamide 8M urea gel. About 10$^5$ cpm equivalents of labeled RNA was then digested by RNaseH as described before using such oligonucleotides to digest the 5' end labeled RNA at its 3' primer binding site while the 3' end labeled RNA at its 5' primer binding site. Following RNaseH digestion, the RNAs were recovered by ethanol precipitation with glycogen as above. To prepare size markers, RNA equivalent to 2.5×10$^5$ cpm were subject to alkaline hydrolysis as follows. RNAs were incubated in 50 mM NaCO$_3$ pH 9.75 at 92° C. for 12 minutes and was then neutralized with 2 µl (a tenth volume) 3M Na(CH$_3$COO) pH 5.5. Hydrolyzed RNAs were recovered by ethanol precipitation as above. RNaseH digested and alkaline hydrolyzed RNAs were then analyzed on a 15% acrylamide, 8M urea gel.

Mapping of 5' RNaseH Digestion Sites by Primer Extension

To map the RNaseH digestion sites by primer extension, 200 pmol 2'F RNA transcripts of ligands VT30-07 and VT30-44 (Ruckman et al. (1998) J. Biol. Chem. 273:20556–67) were RNaseH digested and gel purified as above. Primer 3G7 was 5' end labeled with T4 polynucleotide kinase (Roche Molecular Biochemicals cat# 709557) per manufacturer's instructions and 4 µCi γ$^{32}$P-ATP (10 Ci/mmole, New England Nuclear, cat#NEG502) at 37° C. for 30 minutes followed by heat inactivation at 70° C. for 10 minutes. For sequencing reactions, 0.5 pmoles of template (RNaseH digested VT30-07 or VT30-44) were mixed with 5 pmoles of kinased 3G7 primer in 10 µl 1×RT-no-Mg buffer (50 mM Tris-HCl, pH 8.6, 60 mM NaCl, 10 mM DTT), incubated at 70° C. for 5 minutes and chilled on ice. Extension reactions were set in 5 µl volumes, utilizing 2 µl of the annealing mix, and 0.2 mM (final concentration) dideoxy mix (A or C or G or T) in 1×RT buffer (50 mM Tris-HCl, pH 8.6, 60 mM NaCl, 10 mM DTT, 6 mM Mg(CH$_3$COO)$_2$) and 5 U AMV RT (Boheringer Mannhein cat #1495062). Dideoxy mixes were prepared in 5×concentration containing one dideoxy nucleotide at 1 mM and each dNTP at 1.87 mM, in 1×RT buffer (50 mM Tris-HCl, pH 8.6, 60 mM NaCl, 10 mM DTT, 6 mM Mg(CH$_3$COO)$_2$) supplemented to 24 mM Mg(CH$_3$COO)$_2$). Extension reactions were incubated at 37° C. for 15 minutes, supplemented with formamide dye, denatured at 95° C. for five minutes and analyzed on an 8% polyacrylamide, 8 M urea gel.

Short Primer RT/PCR

Primers and templates are as shown in Table 8. RT reactions were set in 50 µl volume 1×reaction buffer (manufacturer supplied), containing 1 µM primer 3GTR, 0.4 mM each dNTP and 25 Us AMV RT (Boheringer Mannhein cat# 1495062). Prior to adding the RT, reaction mixes were denatured at 95° C. for 3 minutes, annealed at 40° C. for 10 minutes and following the addition of RT, they were incubated at 40° C. for 45 minutes. RT reactions were then supplemented to 100 µl PCR reactions containing 1×buffer (manufacturer supplied) 3 mM MgCl$_2$, 0.5 mM each dNTP, 1 µM each 3GTR and 5GTR primers, 10% DMSO and, 5 Us Taq DNA polymerase (Perkin Elmer, cat#1248). PCR reactions were denatured at 93° C. for 3 minutes and then cycled (20–25 cycles) at 93° C. 2 minutes, 40° C. 1 minute, 72° C. 1 minute. PCR products were analyzed on 10% polyacrylamide TBE gels and used for transcription without purification.

RNA Ligation

Primer binding sites at the 3' end were introduced to RNA using RNA ligations by mixing 16 µl (about 1 pmole) RNA, 3 µl 10×buffer (500 mM HEPES pH 7.8, 200 mM MgCl$_2$, 35 mM DTT, 100 µg/ml BSA), 1 µl 3' oligo (5'-CAGACGACTCGCCCGA (SEQ ID NO:174) or 5'-GACGACTCGCCCGA (SEQ ID NO:175)) at 20 µM, 6 µl DMSO, and 1 µl RNA ligase (10 U/µl, Roche Molecular Biochemicals, Indianapolis, Ind.). Reactions were incubated at 4° C. for 12–16 hours and ligated RNA was purified by ethanol precipitation in the presence of 10 µg glycogen. Purified RNA usually was resuspended in water.

DNA Ligation

Primer binding sites at the 5' end were introduced by ligation at the 3' end of cDNA synthesized on selected RNA. For reverse transcription, to 18 µl of 3' end ligated RNA we added 2 µl of 3G7 primer (Table 5) at 100 µM, and the mix was annealed by heating at 95° C. for 5 minutes, then at 55° C. for 10 minutes, followed at 37° C. for 15 minutes and 25° C. for 5 minutes. Following annealing, the reaction was supplemented with 8 µl 5×superscript buffer (Roche Molecular Biochemicals, Indianapolis, Ind.), 5 µl H$_2$O, 4 µl DTT at 100 mM, 2 µl dNTPs at 10 mM each, and 1 µl superscript (200 U/µl, Roche Molecular Biochemicals, Indianapolis, Ind.). The reaction was then incubated at 45° C. for 45 minutes, the enzyme was heat inactivated at 95° C. for 5 minutes, and the cDNA was ethanol precipitated in 2M ammonium acetate, resuspended in 14 µl water and carried into a ligation reaction where it was supplemented with 2 µl preannealed bridge/linker (Table 4, Set One or Two) at 10 µM, heated at 42° C. for 10 minutes and 25° C. for 10 minutes, supplemented with 2 µl ligase storage buffer (Roche Molecular Biochemicals, Indianapolis, Ind.), 2 µl 10×ligation buffer (Roche Molecular Biochemicals, Indianapolis, Ind.), and 1 µl of T4 DNA ligase (5 U/µl, Roche Molecular Biochemicals, Indianapolis, Ind.), and incubated at 16° C. overnight. Half of the ligated cDNA was PCR amplified as follows. In PCR tubes we mixed 14 µl H$_2$O, 2.5 µl 10×amplitaq buffer (Perkin Elmer, Foster City, Calif.), 2.5 µl MgCl$_2$ at 25 mM, 2 µl each 5' (5'N7) and 3'(3G7) primer (Table 4 and Table 5, respectively), and 2 µl of dNTPs at 10 mM each. The mix was then sealed with wax (ampliwax, Perkin Elmer, Foster City, Calif.), and supplemented above the wax layer with 53 µl H$_2$O, 7.5 µl 10×amplitaq buffer, 3.5 µl MgCl$_2$ at 25 mM, 10 µl ligated cDNA, and 1 µl Taq polymerase (Perkin Elmer, Foster City, Calif.). The mix was cycled 25 times at 54° C. (annealing) for 30 seconds, 72° C. (extension) for 1 minute, and 95° C. (denaturation) for 30 seconds. Amplified products were ethanol precipitated and gel purified on a 6% polyacrylamide TBE gel and reamplified for an additional 10 cycles as above. Final amplified DNA was used as template for transcription.

Truncation SELEX by Ligation

SELEX pools were in vitro transcribed and the generated RNA was digested with RNaseH to remove either both (VEGF) or just the 5' primer binding site (TGFβ1). Digested RNA was reverse transcribed following (if appropriate) ligation of 3' primer binding site at its 3' end. Generated cDNA was ligated with preannealed oligonucleotides 5N7 Linker (5'pCTCCCT ATAGTGAGTCGTATTA (SEQ ID NO:36)), and 5N7 bridge (TAATACGACTCACTATAGGGAGNNNNN (SEQ ID NO:37)) as described above (Table 4). These oligos introduce the T7 promoter and a transcription initiation site GGGAG at the 5' end of the library's sense strand while removing the bulk of the 5' primer binding site (5'Trunc-Library). Resulting cDNA is PCR amplified to generate the starting library as described above. For affinity selection, the 5'Trunc-Library is transcribed with about 5 µM DNA template, 5 units/µl T7 RNA polymerase, 40 mM Tris-HCl (pH 8), 12 mM MgCl$_2$, 5 mM DTT, 1 mM spermidine, 0.002% Triton X-100, 4% PEG 8000, 2–4 mM each 2'OH ATP, 2'OH GTP, 2'F CTP, 2'F UTP, and 0.25 µM α$^{32}$P-ATP (800 Ci/mmole). The 3' primer binding site is then removed by RNaseH digestion. Resulting truncate RNA is then incubated with recombinant h TGFβ1 in Dulbecco's Phosphate-Buffered Saline (DPBS) (Life Technologies, Gaithersburg, Md.) containing I mM MgCl$_2$ and 0.01% human serum albumin or with recombinant VEGF in TBS (Sambrook et al., *Molecular Cloning: A Laboratory Manual*, 2$^{nd}$ Edition, Cold Spring Harbor, N.Y., 1989) containing 1 mM MgCl$_2$, 1 mM CaCl$_2$ and 0.01% human serum albumin. Following incubation at 37° C. (about 30 minutes) the protein-RNA complexes were partitioned from unbound RNA by capture on nitrocellulose. Nitrocellulose filter bound RNA was recovered by phenol/urea extraction. When necessary, RNA pools were prefiltered and/or preadsorbed with multiple layers of same nitrocellulose filter type used in the SELEX process in order to reduce the frequency of molecules selected for nitrocellulose binding. Affinity selected RNA was ligated to the 3' primer binding site, and was reverse transcribed into cDNA as described above. Resulting cDNA was ligated with preannealed oligonucleotides 5G7 RC Linker (5'pTATAGTGAGTCGTATTA (SEQ ID NO:34)) (Table 4), and 5'N7 (TAATACGACTCACTATA GGGAG (SEQ ID NO:46)) (Table 8) and PCR amplified as described above to generate the next Truncate SELEX pool.

Streptavidin Gel Shift on Denaturing Gels

Streptavidin gel shifts on denaturing gels (Pagratis (1996) Nucleic Acids Research 24:3645–6) was used to either analyze the presence of biotin on oligonucleotides or to purify ssDNA following PCR. Briefly, biotinylated nucleic acid was mixed with 0.5 mg/ml (final) streptavidin (Pierce, Rockford, Ill.) in buffer (PBS, TBS, or PCR), incubated at room temperature for 10 min and mixed with equal volume of 2×formamide dye (Sambrook et al., *Molecular Cloning: A Laboratory Manual*, 2$^{nd}$ Edition, Cold Spring Harbor, N.Y., 1989). Following denaturation at 95° C. for 5 minutes, the mix was resolved on a 10% polyacrylamide 7M denaturing TBE gel (Novex, San Diego, Calif.). To purify end-labeled ssDNA template strand from SELEX pools, 3' primer was first end labeled by mixing 1 µl of primer at 1 mM, 2 µl of 10×T4 polynucleotide kinase (PNK) buffer (Boheringer Mannhein, Indianapolis, Ind.), 1 µl PNK (Boheringer Mannhein, Indianapolis, Ind.) at 10 u/µl, and 16

μl of γ-$^{32}$P-ATP (3000 Ci/mmole, NEN, Boston, Mass.), and incubating at 37° C. for 30 minutes. The labeled primer (in 20 μl) was then heat treated at 65° C. for 10 minutes and mixed with 5 μl crude PCR template (SELEX pool), 40 μl 10×PCR buffer (Perkin Elmer, Foster City, Calif.), 48 μl 25 mM MgCl$_2$, 20 μl 10 mM each dNTP, 1 μl 1 mM 5' primer which contains 3 biotin molecules at its 5' end (incorporated as phosphoramidites, Operon Technologies, Alameda, Calif.), and 4 μl Taq polymerase (Perkin Elmer, Foster City, Calif.), in 400 μl final volume and was PCR amplified for 15 cycles as described before. The volume of the amplified DNA was then reduced to 50 μl using microcon 30 cartridges (Amicon, Beverly, Mass.), mixed with 5 μl of streptavidin (Pierce, Rockford, Ill.) at 5 mg/ml, incubated at room temperature for 10 minutes, mixed with equal volume of 2×formamide dye, and denatured and electrophoresed as described above. Following electrophoresis the radioactive band was purified by crushing-soaking and ethanol precipitation.

RNA 3' Biotinylation Using RNA Ligase

Acceptor RNA (0.1–10 pmole) was incubated with 20–200-fold excess donor dinucleotide (FIG. 15), 1 mM ATP, 20% DMSO, and 50 units of T4-RNA ligase (BMB) in 30 μl of 1×reaction buffer (50 mM HEPES pH 7.8, 3.5 mM DTT, 20 mM MgCl$_2$, 10 μg/ml BSA) for 16 hours at 4° C. Labeled RNA was used as is or after ethanol precipitation.

RNA 3' Biotinylation Using Terminal Deoxynucleotidyl Transferase

Selected RNA was biotinylated by terminal deoxynucleotidyl transferase by mixing 3 μl RNA (about 1 pmole), 2 μl 5× (Clontech, Palo Alto, Calif.) buffer, 0.5 μl 25 mM CoCl$_2$, 2 μl 0.5 mM Biotin-21dUTP (Clontech, Palo Alto, Calif. or Roche Molecular Biochemicals, Indianapolis, Ind.), and 2 μl terminal deoxynucleotidyl transferase (25 U/μl, Clontech, Palo Alto, Calif. or Roche Molecular Biochemicals, Indianapolis, Ind.), in total of 10 μl reaction volume. Reactions were incubated at 37° C. for 3 hours and labeled RNA was used as is or after ethanol precipitation.

Hybrid Formation

Selected RNA was biotinylated and then was mixed with ssDNA templated strands purified (as described) at 10×excess DNA over RNA, 1000×excess synthetic 40-mer oligonucleotide DNA randomized at each position, 2 μl 10×renature buffer (100 mM Tris, pH 7.5, 10 mM EDTA), 2 μl 500 mM NaCl in a total volume of 18 μl. The mix was heated at 95° C. for 4 minutes, transferred on ice for 10 minutes, supplemented with 2 μl of 10 mM cetyltrimethylammonium bromide (CTAB), and annealed overnight at 72° C. Following overnight hybridization the reaction was stopped by adding 30 μl of 1×renature buffer containing 0.2% SDS, and ethanol precipitated in 2 M ammonium acetate and 10 μg glycogen (Roche Molecular Biochemicals, Indianapolis, Ind.). The pellet was resuspended in 1×renature buffer and hybridized ssDNA strands were capture by streptavidin gel shift on native gels or by streptavidin agarose beads (cat# 20349, Immunopure immobilized streptavidin, Pierce, Rockford, Ill.).

Hybrid Selection by Streptavidin Beads

Following hybridization and ethanol precipitation, the reactions were resuspended in 100 μl 1×renature buffer-50 mM NaCl. Streptavidin-agarose beads (50 μl) were washed in 0.45 μm spin-X filter units (costar, Cambridge, Mass.), 2 times with 250 μl 1×renature buffer-50 mM NaCl and incubated with the 100 μl of hybridization mix for 10 minutes at room temperature. Noncaptured nucleic acid was removed and the beads were washed 3 times with 250 μl 1×renature buffer-50 mM NaCl (or until counts are no longer in the wash) and captured ssDNA was eluted by adding 100 μl H$_2$O incubated at 95° C. for 5 minutes. Collected ssDNA was supplemented with 20 μl 10×Taq buffer, 24 μl 25 mM MgCl$_2$, 10 μl 10 mM each dNTPs, 0.5 μl each 1 mM 3G7 and 5G7, 2 μl Taq polymerase in total volume of 200 μl and PCR amplified taking 30 μl samples after 3, 6, 9, 12, and 15 cycles for electrophoretic analysis (8 μl). The PCR aliquot with the best signal to noise ratio was amplified further in 400 μl PCR reactions for additional 15 cycles.

Hybrid Selection by Gel Shift

Following hybridization and ethanol precipitation, the reactions (usually 15 μl total) were supplemented with streptavidin at 2.5 mg/ml (final concentration), incubated at room temperature for 10 minutes supplemented with 6×glycerol dye to final 1× and electrophoresed on a 6%, 0.5×TBE gel, at 150 volts, for 30 minutes at room temperature. Streptavidin shifted bands were visualized following auto-radiography and excised to recover ssDNA following crush-soaking and ethanol precipitation. Eluted ssDNA was then PCR amplified as in the hybrid selection by streptavidin beads.

Truncation SELEX by Hybrid Selection

SELEX pools were in vitro transcribed and the generated RNA was digested with RNaseH to remove both primer binding sites. Resulting truncate RNA was then incubated with recombinant h TGFβ1 in Dulbecco's Phosphate-Buffered Saline (DPBS) (Life Technologies, Gaithersburg, Md.) containing 1 mM MgCl$_2$ and 0.01% human serum albumin or with recombinant VEGF in TBS (Sambrook et al., *Molecular Cloning: A Laboratory Manual*, 2$^{nd}$ Edition, Cold Spring Harbor, N.Y. 1989) containing 1 mM MgCl$_2$, 1 mM CaCl$_2$ and 0.01% human serum albumin. Following incubation at 37° C. (about 30 minutes) the protein-RNA complexes were partitioned from unbound RNA by capture on nitrocellulose. Nitrocellulose filter bound RNA was recovered by phenol/urea extraction. When necessary, RNA pools were prefiltered and/or preadsorbed with multiple layers of same nitrocellulose filter type used in SELEX in order to reduce the frequency of molecules selected for nitrocellulose binding. Affinity selected RNA was biotinylated with either terminal deoxynucleotidyl transferase or RNA ligase as described above, and was hybridized to purified ssDNA from the same pool as described. Hybridized molecules were then captured by either streptavidin beads (TGFβ1) or streptavidin gel shifts (VEGF) and were PCR amplified to generate the next Truncation SELEX pool.

Cloning and Sequencing

RNA recovered from the final-round filters was reverse transcribed and PCR amplified as in every round. The PCR products were purified by PAG electrophoresis and cloned into the SrfI restriction site of pCR-Script Direct SK(+) plasmid using the pCR-Script Amp SK(+) cloning kit (STRATAGENE CLONING SYSTEMS, La Jolla, Calif.). Clones were sequenced with ABI Prism sequencing kit (Applied Biosystems, Perkin-Elmer, Foster City, Calif.).

TGFβ1 Bioassay

The bioactivity of TGFβ1 nucleic acid ligands was measured with mink lung epithelial cells as described in U.S. patent application Ser. No. 09/046,247, filed Mar. 23, 1998. Briefly, proliferation of these cells is inhibited by TGFβ1. Human TGFβ1 was titrated on the cells and $^3$H-thymidine incorporation was measured. The point at which $^3$H-thymidine incorporation by the cells was inhibited by 90–100% was determined (typically 1–4 pM). This inhibitory amount of TGFβ1 along with varying amounts of nucleic acid ligand (typically 0.3 or 1 nM to 1 or 3 μM, in 3 fold increments) was used. Cells were plated at 1×10$^5$/ml in 96-well plates in 100 μl MEM, 10 mM HEPES pH 7.5, 0.2% FBS. Following 4 hours of incubation at 37° C., when cells were well attached to the well surface, TGFβ1 was added at 1–4 pM with or without nucleic acid ligands as follows: the ligands were diluted across the 96 well plate in 3-fold dilution steps and then TGFβ1 was added at 1–4 pM to all wells except controls. The cells were incubated for 16–18 hours prior to addition of $^3$H-thymidine, and continued incubation for 20 additional hours following $^3$H-thymidine addition at 0.25 μCi per well. After incubation, the cells were lysed with 1% Triton X-100 and harvested onto GF/B filter plates by the Packard 96 well plate harvester, and $^3$H-thymidine incorporation in cellular DNA was quantitated by scintillation counting in microscint at the Packard Top-Count. Data were plotted as % of max $^3$H-thymidine incorporation vs RNA concentration and were fitted by the software Kaleidagraph (Synergy Software, Reading, Pa.) to the equation m3*(m0+m1+(m2)–((m0+m1+(m2))*(m0+m1+(m2))–4*(m0)*((m2)))^0.5)/(2*(m2)); where m0 is the concentration of competitor RNA; m1 is the IC50, m2 is the concentration of TGFβ1, and m3 is the plateau value of the fraction of max $^3$H-thymidine incorporation. Ki values were determined from $IC_{50}$ values according to the equation $K_i=IC_{50}/(1+([T]/K_{dT}))$, where [T] is the molar concentration of TGFβ1 present in the assay and $K_{dT}$ is the concentration of TGFβ1 causing 50% inhibition of MLEC proliferation as determined by TGFβ1 titration experiments.

EXAMPLE 4

RNaseH Digestion

For application of RNaseH site specific cleavage of RNA to truncation SELEX where 2'F modified nucleotides are present, it is necessary that RNaseH is able to digest 2'F-deoxyribopyrimidine substituted RNA. In addition, in order to eliminate the bulk of the 3' primer binding site, it would be desirable for the RNaseH to accept targeting oligonucleotides that include the 2'deoxyribonucleotide gap at its 3' end.

RNaseH is an enzyme that recognizes RNA-DNA hybrids and digests the RNA strand through an endonucleolytic mechanism (Hostomsky et al., Cold Spring Harbor Laboratory Press, New York, pp. viii, 499, 1993). RNaseH is a ubiquitous enzyme found in procaryotes and eukaryotes mechanism (Hostomsky et al., Cold Spring Harbor Laboratory Press, New York, pp. viii, 499, 1993). E. coli encodes at least two RNaseH isotypes on separate genes (Itaya (1990) Proc. Natl. Acad. Sci. U.S.A. 87:8587–91). The E. coli RNaseH1 is most extensively studied. The digestive mechanism of E. coli RNaseH1 is similar to DNases where the 2'OH group does not participate in the nucleophilic attack of the phosphodiester bond and the product ends are 3'OH and 5'P (Crooke et al. (1995) J. Biochemistry 312:599–608). It has been shown that E. coli RNaseH1 could be used for site directed digestion of RNA using DNA molecules complementary to the site of digestion (Inoue et al. (1987) FEBS Letters 215:327–330). The digestion site could be targeted to a single position using chimeric targeting oligonucleotides containing regions of 2'deoxyribonucleotides flanked by regions of 2'OMe nucleotides (Inoue et al. (1987) FEBS Letters 215:327–330) taking advantage of the inability of the enzyme to digest RNA-2'OMeRNA hybrids (Inoue et al. (1987) FEBS Letters 215:327–330; Lima and Crooke (1997) Biochemistry 36:390–398). The length of the 2'deoxyribonucleotide region influences the function of the E. coli RNaseH1 where the cleavage rate is decreased with diminishing number of contiguous 2'deoxyribonucleotides, where no cleavage occurring with less than four contiguous 2'deoxyribonucleotides (Monia et al. (1993) J. Biol. Chem. 268:14514–22; Crooke et al. (1995) J. Biochemistry 312:599–608). The site of cleavage by E. coli RNaseH1 of RNA bound to chimeric oligonucleotide containing a 2'deoxyribonucleotide region flanked by 2'OMe-ribonucleotide regions, has been demonstrated to occur at the 3' site of the RNA base found opposite to the most 5' nucleotide of the 2'deoxyribonucleotide region (Inoue et al. (1987) FEBS Letters 215:327–330; Crooke et al. (1995) J. Biochemistry 312:599–608; Lapham and Crothers (1996) RNA 2:289–296). Cleavage by E. coli RNaseH1 can occur when the targeting chimeric oligonucleotide contains at least 4 contiguous 2'deoxyribonucleotides in the middle or at the 5' end (Inoue et al. (1987) FEBS Letters 215:327–330; Lapham and Crothers (1996) RNA 2:289–296), but not at the 3' end (Inoue et al. (1990) Proc. Natl. Acad. Sci. U.S.A. 87:8587–91) of the targeting chimeric oligonucleotide. Recently, different digestion specificities were found depending on the commercial source of RNaseH used, where RNaseH from Pharmacia (cat.#27-0894), Sigma (cat. R-6501) or Takarashuzo digest like the E. coli RNaseH1, while RNaseH from Roche Molecular Biochemicals (cat.#786-349) cleaves at one base upstream of the expected site (Lapham et al. (1997) RNA3:950–951). The effect of 2'F modifications was determined with E. coli RNaseH1 in examples where the modified bases were at the targeting oligonucleotide. Full 2'F modified targeting oligonucleotides reduced the overall affinity of RNaseH1 for the hybrid complex with RNA (Crooke et al. (1995) J. Biochemistry 312:599–608). Replacing 2'OMe-deoxyribonucleotide positions of the chimeric targeting oligonucleotide (which include a gap of 2'deoxyribonucleotides in the middle) with 2'F-2'deoxynucleotides reduced the initial cleavage rate by about 5 fold. The effect of 2'F modification of the RNA substrate, instead of the targeting oligonucleotide, was determined only at a single site, namely at the site of cleavage and found to reduce the reaction rate by 1000-fold (Uchiyama et al. (1994) J. Mol. Biol. 243:782–791).

Figure 18:
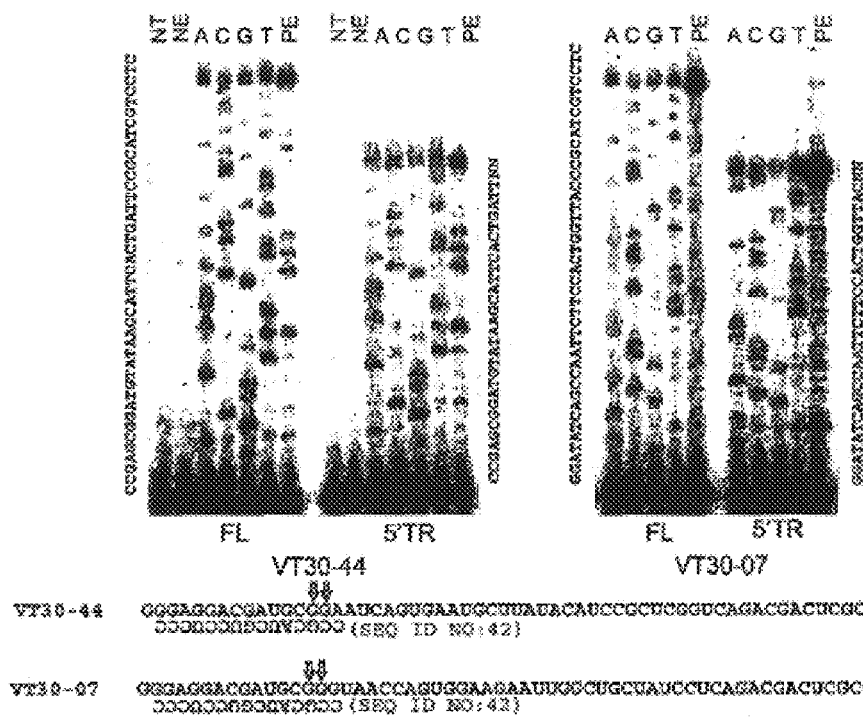
FIG. 18 shows the mapping of RNaseH of the 5' digestion site using primer extension. Two different Nucleic Acid Ligands were used as full length (FL) or 5' truncates (5'TR) in reverse transcriptase reactions in the presence of 3G7 5' end labeled primer. RT reactions were done in the presence or all 4 dNTPs (PE) or with one of ddATP (A), ddCTP (C), ddGTP (G), and ddTTP (T). Chain termination products were used to align the gel pattern to the sequence of the RNA used. The sequence of the RNA molecules and the digestion sites (arrowheads) are also shown under the gel patterns.
Figure 19:
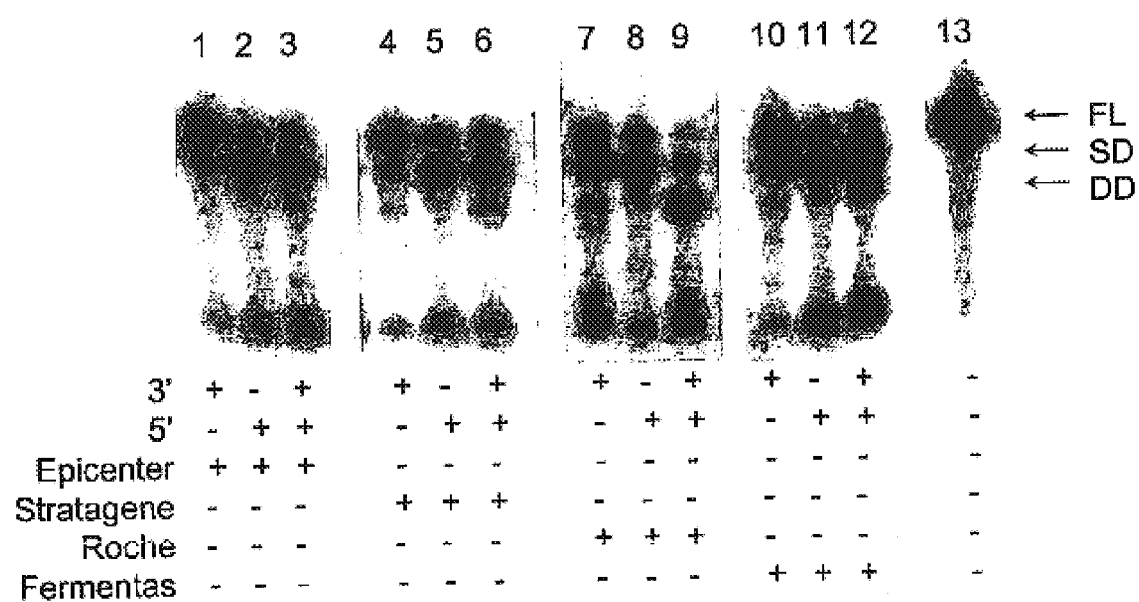
FIG. 19 shows the digestion activity of various enzyme preparations on body labeled 2'F pyrimidine modified RNA using the targeting oligonucleotides described. Enzymatic reactions were set as described. The presence or absence of the targeting oligonucleotides or the enzyme sample is indicated by + or – respectively. Symbol FL, SD and DD, indicate full length, single digestion product, and double digestion product, respectively.

The ability of E. coli RNaseH obtained from Pharmacia and Roche Molecular Biochemicals to cleave 2'F-deoxyribopyrimidine substituted RNA with chimeric oligonucleotides containing 11 or 12 2'OMe-deoxyribonucleotides and a gap of 4 contiguous 2'deoxyribonucleotides at either their 5' or 3' end (FIG. 16) was determined. The data show that only the enzyme from Roche Molecular Biochemicals had significant activity against the tested substrate. This enzyme can cleave with either the 5', the 3', or both targeting oligonucleotides and it requires the presence of the targeting oligonucleotide for activity. The enzyme from Pharmacia is largely inactive against the 2'F-deoxyribopyrimidine substituted RNA showing only slight activity with only the 5' primer consistent with RNaseH1 type activity. We determined the digestion specificity of the enzyme from Roche Molecular Biochemicals. We used two defined templates (VT30-07, and VT30-44) to generate in vitro 2'F-deoxyribopyrimidine substituted RNA transcripts. Such transcripts were end labeled at either the 5' or the 3' end, and then treated with RNaseH (from Boheringer Mannhein) and the appropriate targeting oligonucleotide so that the 5' and 3' end labeled RNA was cleaved at its 3' primer, or 5' primer binding site, respectively. Digested RNA was then gel purified and analyzed on a sequencing gel along with full length RNA and size markers generated by alkaline partial hydrolysis of the corresponding end labeled RNA. Alkaline hydrolysis attacks only the unmodified positions in the RNA transcripts (2'OH), thus these markers show the positions of purines within the transcript. The results are summarized in FIG. 17. The data show that digestion at the 3' position occurs at a single phosphodiester bond namely at the 5' side of the base across the second base (from the 5') of the 2'dexyribonucleotide gap in the 3' targeting oligonucleotide. Digestion at the 5' occurs at two positions, namely at the 5' sides of the bases across the first and second base (from the 5') of the 2'dexyribonucleotide gap in the 5' targeting oligonucleotide. The digestion specificity at the 5' end was confirmed by primer extension results (FIG. 18). Full length, and RNaseH digested RNA transcripts, as above, were used as extension templates of 5' end labeled primers complementary to the 3' primer binding site by AMV RT. All extension reactions were done in the presence of all four 2'-deoxyribonucleotide-triphosphates. To facilitate mapping of the 3' end to the template used, additional four extension reactions were done, each containing one of the four chain terminating 2'dideoxyribonucleotide-triphosphates, ddATP, ddCTP, ddGTP, and ddTTP. Extended products were then analyzed on sequencing gels as shown in FIG. 18. Extension products with all four 2'deoxyribonucleotide-triphosphates show not only bands corresponding to the 5' end of the template, but also bands corresponding to pause sites of RT. The pattern of pause sites is identical for the corresponding regions of the full length and truncated templates. In agreement with the previous experiment (FIG. 17), there are two bands corresponding to the 5' end of the digested RNA, and the shorter bands it does not appear to be a pausing site since there is no corresponding band in the full length template. As expected, this second 5' end is also present in all four chain termination reactions. Using the banding pattern of the chain termination reactions, the 5' ends of the RNaseH digested RNAs could be mapped to the same positions mapped with the previous experiment. The results from the mapping experiments at the 5' digestion site show that the *E. coli* RNase H from Boheringer Mannhein in able to digest at the 3' phosphodiester bond of a 2'F-modified pyrimidine, consistent with the DNase type of reaction mechanism reported for *E. coli* RNaseH1 (Crooke et al. (1995) J Biochemistry 312:599–608). Since the commercial source of RNaseH was shown to be important in cleavage specificity (Lapham et al. (1997) RNA 3:950–951), a panel of 4 RNaseH preparations were tested from different commercial suppliers (Epicenter cat#06100; Stratagene cat#600215; Roche Molecular Biochemicals cat#786357; and MBI Fermentas cat#EN0201) for their ability to digest 2'F-deoxyribopyrimidine substituted RNA in the presence of either the 5', 3', or both targeting oligonucleotides described above. The results in FIG. 19 show that only the enzyme from Roche Molecular Biochemicals was able to digest efficiently at both positions while the rest could digest efficiently only at the 5' position, consistent with RNasH1 type of specificity. All enzymes showed some trace activity at the 3' position with the MBI Fermentas lot being slightly more active.

The data presented here clearly show for the first time, that RNase H can digest 2'F-deoxyribopyrimidine substituted RNA at a specific site, directed by an appropriate targeting oligonucleotide. They also show, for the first time, that the Roche Molecular Biochemicals enzyme can use targeting oligonucleotides containing a gap of four contiguous 2'deoxyribonucleotide bases at its 3' end.

EXAMPLE 5
Biotinylation of RNA

The truncation-SELEX-by-hybridization protocol requires the ability to biotinylate RNA following RNaseH digestion and affinity selection. There are several procedures that allow such RNA modification of which two were tested with RNaseH digested RNA, namely photo biotinylation and tailing by Terminal Deoxynucleotidyl Transferase (TdT). In addition, biotinylation scheme was developed using RNA ligase. Extent of biotinylation was determined by measuring streptavidin complexing of body labeled RNA by either gel shift, or capture to streptavidin loaded-beads (Pierce) or membranes (Promega).

Figure 20:
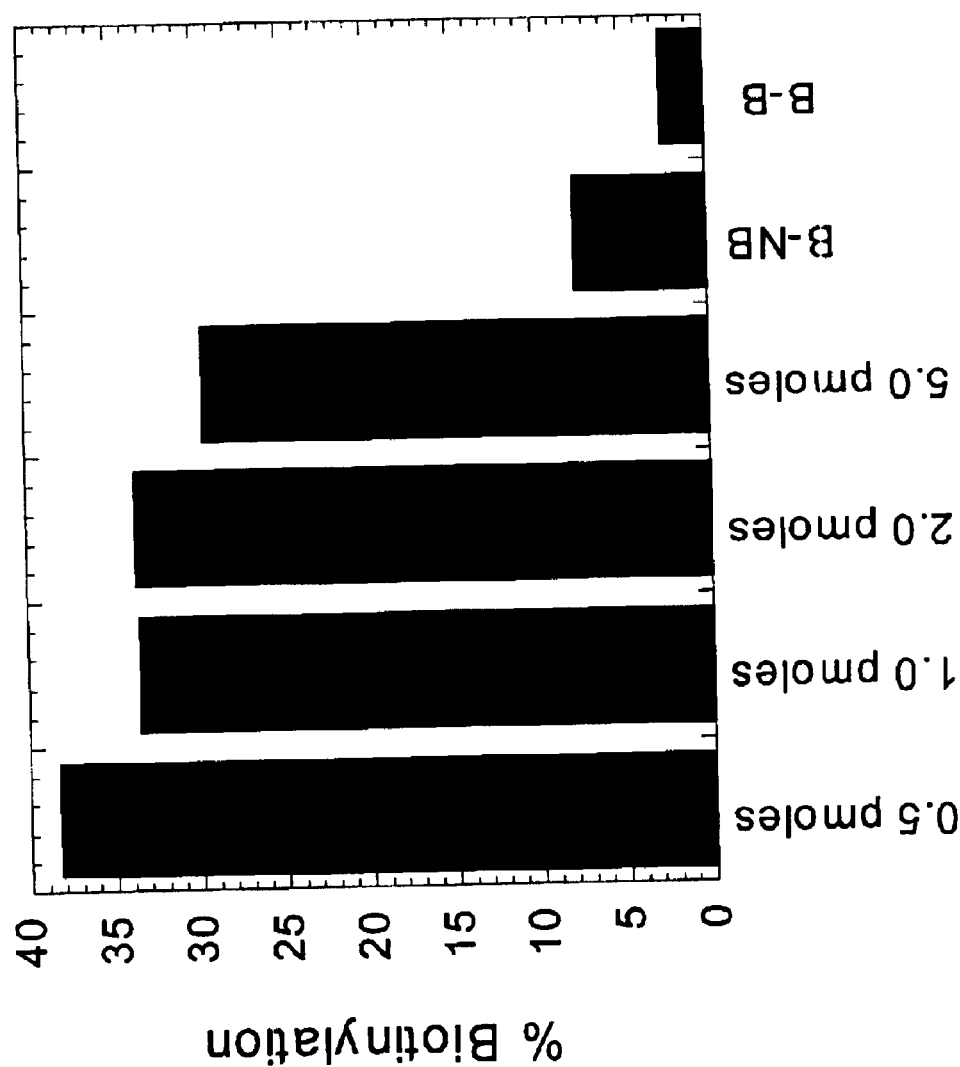
FIG. 20 shows the biotinylation efficiency of 2'F pyrimidine modified RNA by terminal transferase. Biotinylation reactions were set with 0.1 mM biotin-dUTP and various amounts of body labeled RNA as shown, in 10 μl reactions. Following incubation at 37° C. for 1 hour the reactions were spotted on SAM filters (streptavidin loaded nitrocellulose filters, Promega, Madison, Wis.), washed 5 times with 2 ml of 50 mM NaCl, 10 mM Tris-HCl pH 7.5, 1 mM EDTA and quantitated on an instant imager. Filter retained radioactivity was normalized to radioactivity loaded on filters without washing. Symbols B-NB and B—B indicate background on filters without or with preblocking, respectively. Background is defined as the amount of RNA from terminal transferase reactions lacking biotin-dUTP retained on the filters after washing.

For photobiotinylation and tailing reactions, commercially available kits (Clontech) were used per manufacturer's instructions. From these two methods only the tailing reaction was successful. By using the enzyme and reaction buffer from Roche Molecular Biochemicals (Indianapolis, Ind.) it was observed that biotinylation efficiencies could be improved. FIG. 20 shows typical biotinylation efficiencies by the tailing reaction, suggesting that under these experimental conditions the enzyme is saturated and biotinylates about 30% of the available truncated RNA at concentrations as low as 50 nM (0.5 pmoles in 10 µl binding reaction). A little higher efficiencies can be obtained (up to ~45%) by using Biotin-$N^6$-ddATP (cat#NEL508, NEN, Boston, Mass.).

As stated above, we developed a new RNA biotinylation method based on T4 RNA ligase. In analogy to the RNA labeling reaction utilizing $^{32}$PCP (Cytidine 3',5'-bis (phosphate), [5'-$^{32}$P]), two biotinylation substrates were used as shown in FIG. 15 obtained by phosphoramidite chemistry (Operon Technologies, Alameda, Calif.). Biotinylation results with two different transcripts (40N7 and TGFβ1 ligand 4003) at two temperatures (4° C. and 0° C.) are shown in FIG. 33. These results show clear biotinylation reactions only with the longer biotinylation substrate used. To follow the reaction, the biotinylated short oligonucleotides were kinased using T4 polynucleotide kinase and $γ^{32}$P-ATP as described above. The presence of biotin was confirmed using streptavidin induced electroporetic mobility shifts of gel purified ligation products as described before. Estimated yields of this biotinylation reaction were about 80–90%.

EXAMPLE 6
Specificity of Hybridization

Figure 21:
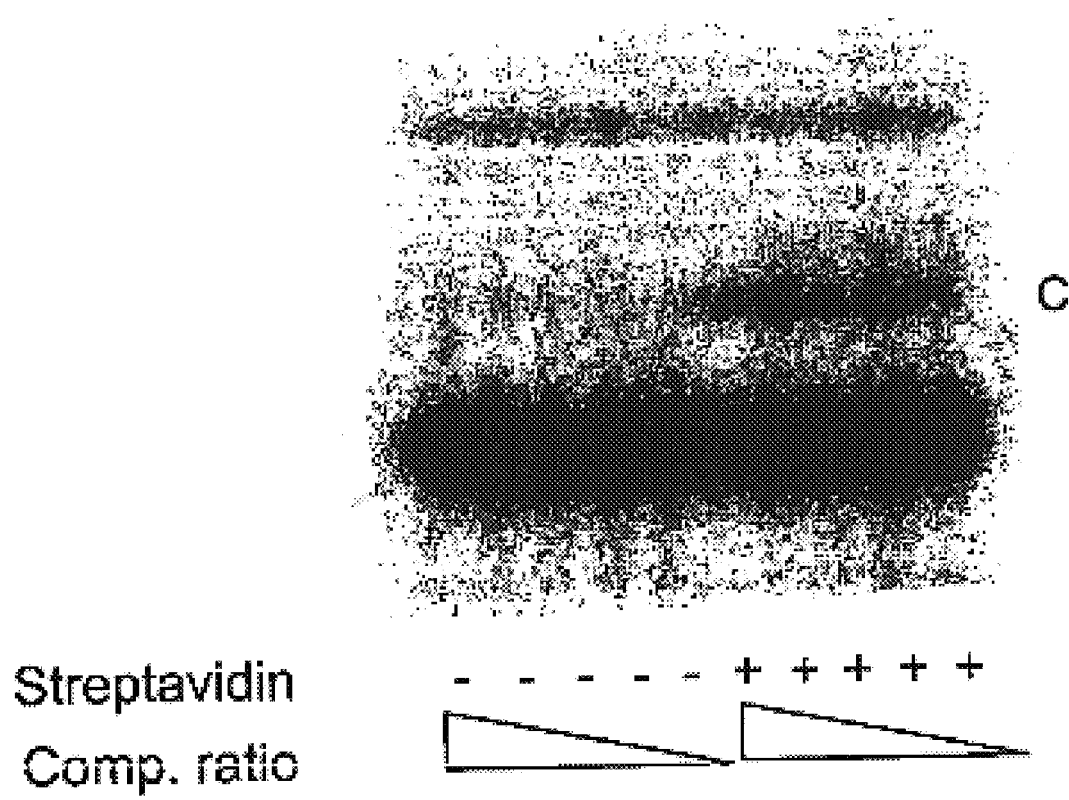
FIG. 21 shows specificity of the hybrid selection step of the truncation SELEX by hybridization process. Hybrid selection of purified ssDNA complementary strands using terminal transferase biotinylated truncate RNA. VEGF VT30 Rd 12 RNA was RNaseH digested to remove 5' and 3' fixed regions and biotinylated using terminal transferase and biotin-dUTP. Biotinylated truncate RNA (0.3 pmoles) was mixed with 10 fold excess, 5'-end-labeled ssDNA complementary strands from the same pool and was hybridized overnight at 72° C. in the presence of 0.1 mM C-TAB in 10 mM Tris, pH 7.5, 50 mM NaCl, 1 mM EDTA. Reactions with competitor salmon sperm DNA at 1-, 10-, 100-, and 1000-x over biotinylated RNA were also included. The RNA, ssDNA, and salmon sperm DNA were denatured at 95° C. and fast cooled prior to incubation at 72° C. Following hybridization, the reaction products were treated with streptavidin (+) or not (–) and analyzed on a 10% acrylamide TBE gel. C indicates the position of the streptavidin/hybridization reaction complex.

The success of the truncation SELEX by hybridization depends on the ability of the selected biotinylated truncated RNA to specifically hybridized to its complementary sequence. The hybridization specificity of an evolved pool (VEGF Rd2), (Ruckman et al. (1998) J. Biol. Chem. 273:20556–67) in the presence of different amounts of excess salmon sperm DNA (FIG. 21) was determined. Briefly, VEGF VT30 Rd 12 RNA was RNaseH digested to remove 5' and 3' fixed regions and biotinylated using terminal transferase and biotin-dUTP. Biotinylated truncate RNA (0.3 pmoles) was mixed with 10 fold excess, 5'-end-labelled ssDNA complementary strands and was hybridized overnight at 72° C. in the presence of 0.1 mM C-TAB in 10 mM Tris, pH 7.5, 50 mM NaCl, 1 mM EDTA. Reactions with competitor salmon sperm DNA at 1-, 10-, 100-, and 1000-x over biotinylated RNA were also included. The RNA, ssDNA, and salmon sperm DNA were denatured at 95° C. and fast cooled prior to addition to hybridization reaction and incubation at 72° C. Following hybridization, the nucleic acid was recovered by ethanol precipitation, mixed with streptavidin and analyzed on a native 1XTBE polyacrylamide gel. Hybrid formation is apparent in this gel system by a slower electrophoretic mobility of the labeled ssDNA due to complexing streptavidin through the hybridized biotinylated input RNA. The results clearly show that biotinylated RNA was able to hybridize to its complement even the presence of 1000 fold excess nonlabeled competitor DNA.

EXAMPLE 7
Truncation-SELEX-by-Hybrid-Selection

Figure 22A:
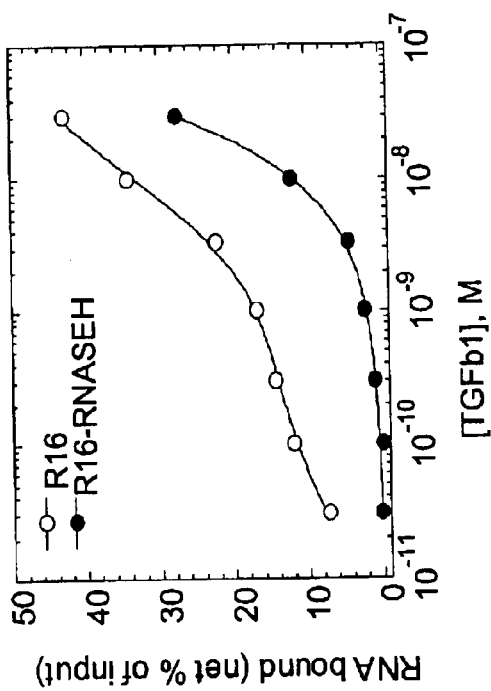
FIGS. 22A–C show binding properties of TGFβ1 pools with and without their fixed sequences. Body labeled 2'F pyrimidine modified transcripts from TGFβ1 40N7 round 12 (R12) (FIG. 22A), round 13 (R13) (FIG. 22B), and round 16 (R16) (FIG. 22C) were used as fall length or were previously treated with RNaseH to remove the 5' and 3' fixed sequences as described. The RNA was used to determine the fraction of RNA bound at various concentrations of TGFβ1 using nitrocellulose filter binding. Symbols ○ and ● indicate full length and truncated RNA, respectively.
Figure 22B:
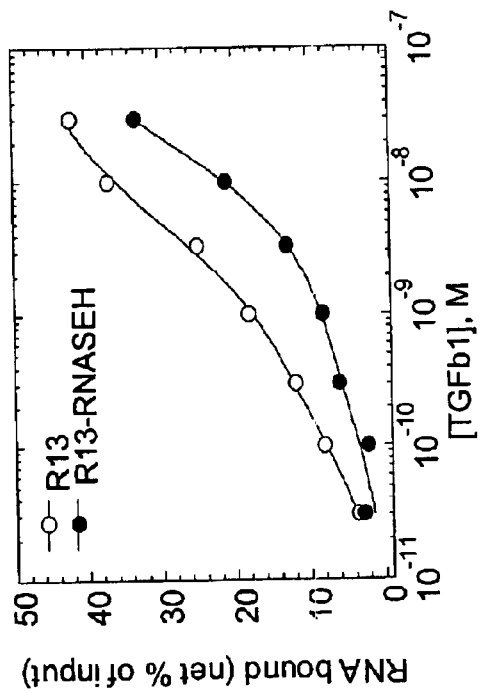
Figure 22C:
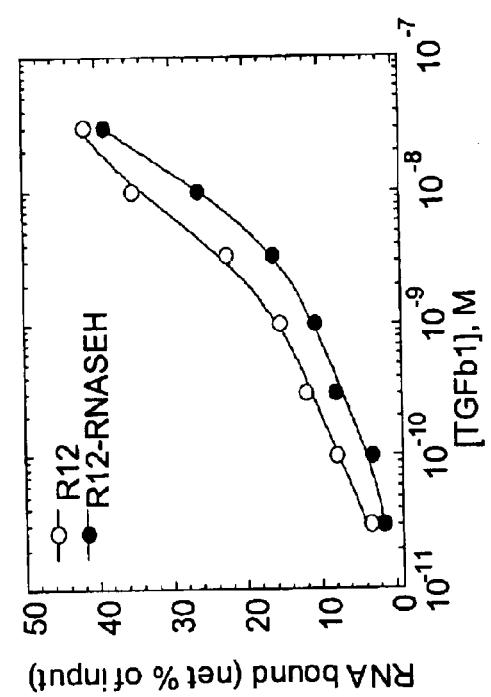
Figure 23:
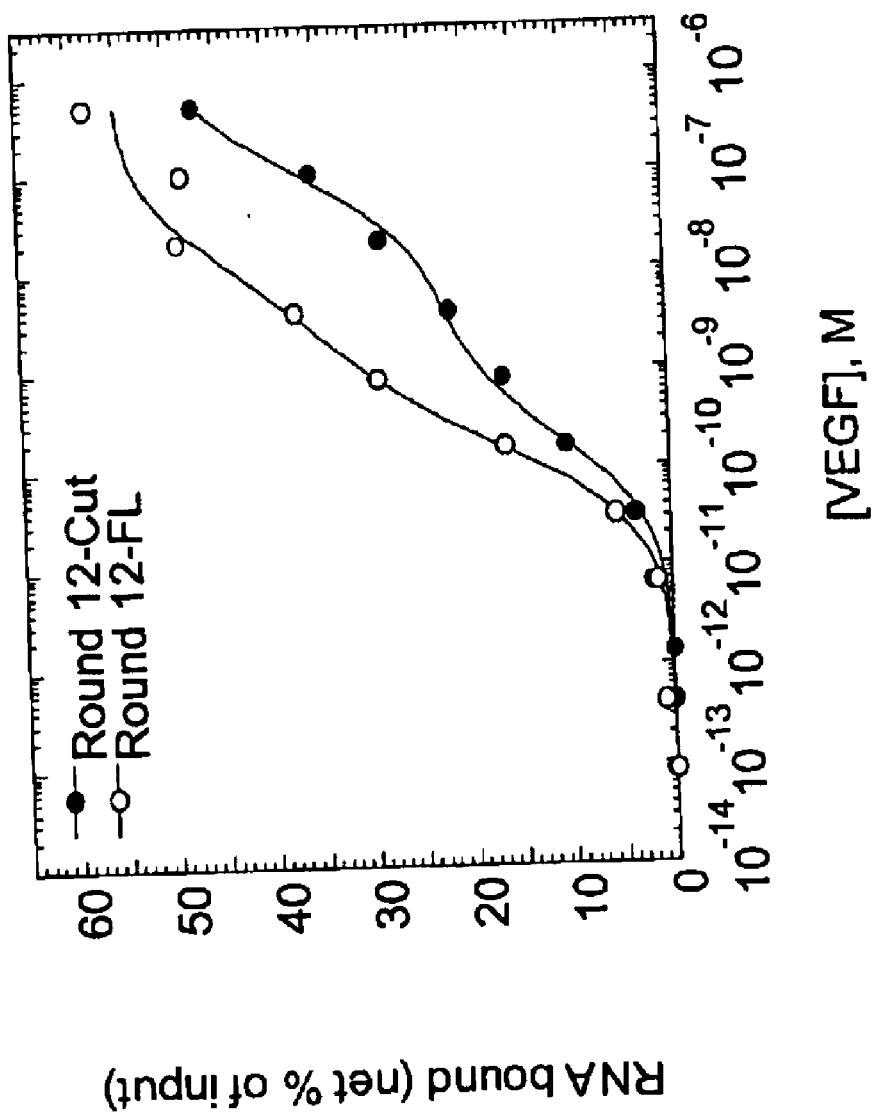
FIG. 23 shows binding properties of the Rd12 VEGF VT30 pool with and without its fixed sequences. Body labeled 2'F pyrimidine modified transcripts were used as full length or were previously treated with RNaseH to remove the 5' and 3' fixed sequences as described. The RNA was used to determine the fraction of RNA bound at various concentrations of VEGF using nitrocellulose filter binding. Symbols ○ and ● indicate fall length and truncated RNA, respectively.

The truncation SELEX by hybrid selection protocol was applied to two pools. The first pool, Round 12 VT30, was derived from the 30N7 random library, and was selected for binding to VEGF for 12 rounds (Ruckman et al. (1998) J. Biol. Chem. 273:20556–67). The second pool, Round 12 40N-TGFβ1, was derived from the 40N7 random library, and was selected to bind TGFβ1 for 12 rounds as described in U.S. patent application Ser. No. 09/046,247, filed Mar. 23, 1998. These pools were selected because removal of fixed regions did not completely eliminate binding to their respective targets. FIGS. 22 and 23. Determining the ability of the starting pools to retain binding after removal of the primer binding sites might be important because during the SELEX rounds truncatable ligands might be eliminated from the population by nontruncatable ligands that have better affinities for the target. This was found to be true with the TGFβ1 pool (FIG. 22) where more advanced pools retained almost no binding following removal of their primer binding sites. As shown in FIG. 22 there is little difference in the binding of the full length and truncated Rd12 pool. There is >1000 fold better binding of the full length Rd16 pool compared to truncated Rd16 pool, while the Rd13 pool showed an intermediate binding.

Affinity selections were done as described in Example 3. The conditions of affinity selections are summarized in Tables 6A and 6B. The RNA used at each round was generated by RNaseH digestion as described in Example 3. We used two different methods to partition the hybrids following hybridization. For the VEGF pool, a gel shift method was used on native gels while for the TGFβ1 pool streptavidin-agarose beads were used as described in Example 3.

Figure 24A:
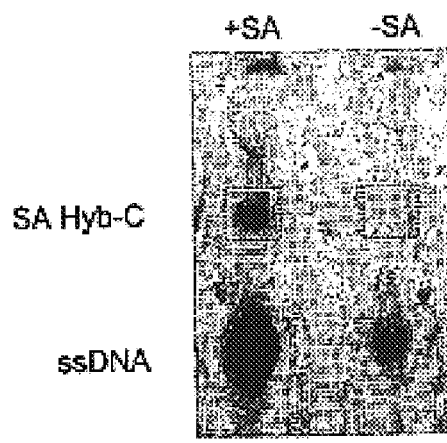
FIGS. 24A–C show the application of gel shifts to partition the hybridization products during the truncation SELEX by hybridization process.
Figure 24B:
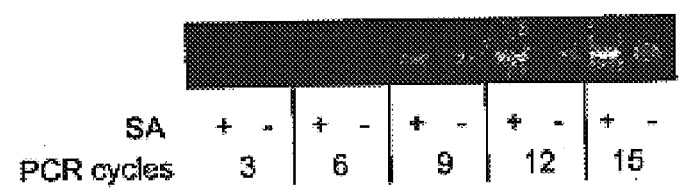
Figure 24C:
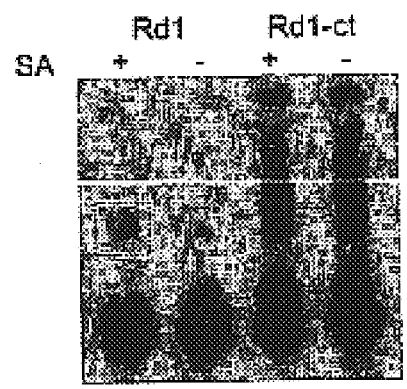

FIG. 24 shows typical results with the native gel shift partition method. As seen in FIG. 24A there is a clear streptavidin induced shift of labeled complementary ssDNA only when streptavidin is used. We excised the shifted material from +SA lane, (designated Rd1) and the corresponding region from the lane where streptavidin was omitted (from −SA lane, designated Rd1-ct). Both gel slices were crushed to recover any nucleic acid present and eluted material was subject to PCR amplification using the 5P7 and 3P7 primers as described in Example 3. Amplification results, at various numbers of cycles, as shown in FIG. 24B indicate that as expected the +SA lane contained more amplifiable nucleic acid since there is a significant amount of product generated after 9 PCR cycles. PCR results also show that the native gel partition method has some background since we were able to amplify gel shifted material from the −SA lane. Both of these amplified pools (Rd1 and Rd1-ct) were transcribed and generated RNA was RNaseH digested and used for a second round of affinity selection and gel shift partition of hybridized molecules. As seen in FIG. 24C the +SA lane of the Rd1 pool contained streptavidin shifted material as expected. However, the −SA lane also contained shifted material suggesting that within one round molecules with altered mobility on native gels were selected. We designated such molecules as background. The evolution of "background" was more severe in the Rd1-ct pool presumably due to the sole presence of such molecules in the −SA lane from the first round of this truncation SELEX experiment.

Figure 25:
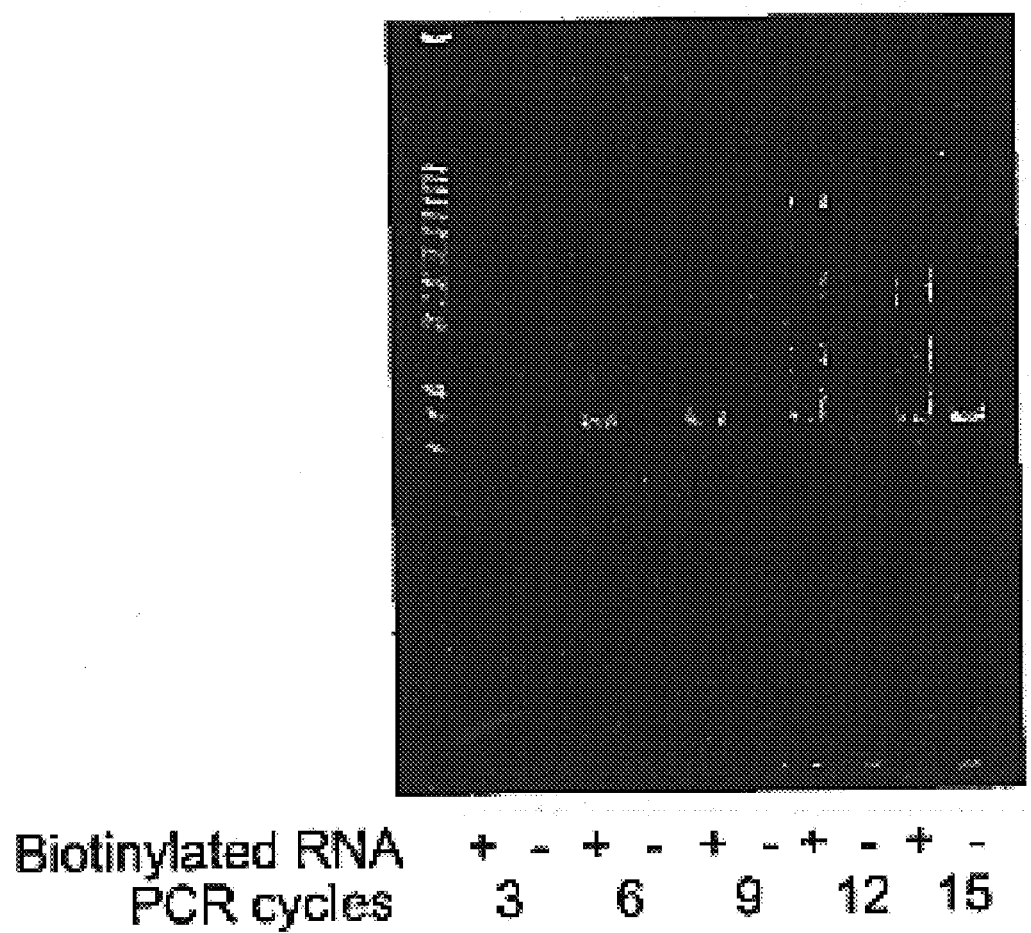
FIG. 25 shows the effectiveness of hybrid selection using streptavidin beads. Hybridization reactions between biotinylated truncated RNA transcripts and full length antisense ssDNA were set as described. Control reactions were also set in the absence of biotinylated RNA. Hybrids were captured and recovered with streptavidin beads as described. Captured ssDNA was PCR amplified and the product was analyzed by gel electrophoresis at different PCR cycles as shown. The gel was calibrated using a 20 bp ladder.

FIG. 25 shows typical PCR amplification profiles observed with the streptavidin-agarose beads partition method. These results suggest good signal to noise ratios and during truncation SELEX rounds nonspecific binding of labeled ssDNA to the streptavidin beads were not observed.

As seen in Tables 6A and 6B improving signal to noise ratios and an increase of the amount of RNA binding to the target were observed suggesting the selection process was successful. Pools Rd1-VEGF, Rd1-ct-VEGF and Rd2-TGFβ1 truncation by a hybridization SELEX experiment were cloned and sequenced.

RNA Sequences from the Truncation SELEX by Hybrid Selection

Twenty four clones from the Rd1-VEGF and Rd1-ct-VEGF were sequenced, and 70 clones from the Rd2-TGFβ1 truncation by hybridization SELEX pools were sequenced. The sequences obtained, and their alignment, suggested family classification, and binding properties are summarized in Tables 9–11.

Greater than half of the sequences from the two VEGF experiments could be classified into Family 1 and Family 3 identified in the previous SELEX experiment with VEGF (Ruckman et al. (1998) J. Biol. Chem. 273:20556–67). The remaining ligands represent orphan sequences although some have some limited homology to ligands from Family 2 of the original SELEX experiment. Family 2 from the Rd1-VEGF pool contained isolates of frequent ligands from the original SELEX experiment, namely VT30.3 and VT30.1. Interestingly their relative frequencies is opposite from the relative frequency seen in the original SELEX experiment but consistent in their binding phenotype in the presence or absence of their fixed sequences.

Sequences from the Rd2- TGFβ1 truncation by hybridization SELEX pool can be assigned into ten groups, namely 9 families and a group of orphans. The largest family contains ligands that have been identified as nitrocellulose binding molecules in previous experiments (TGFβ1 patent). The remaining families are rather small and they could be clonal derivatives of unique sequences by PCR mutations. Families 1 and 5 resemble families 3 and 1, respectively, from the TGFβ1 SELEX described in U.S. patent application Ser. No. 09/046,247, filed Mar. 23, 1998.

Binding Properties of Ligands from the Truncation SELEX by Hybrid Selection

The binding activity of several ligands was determined by nitrocellulose filter binding, and data are summarized in Tables 9–11.

Figure 27:
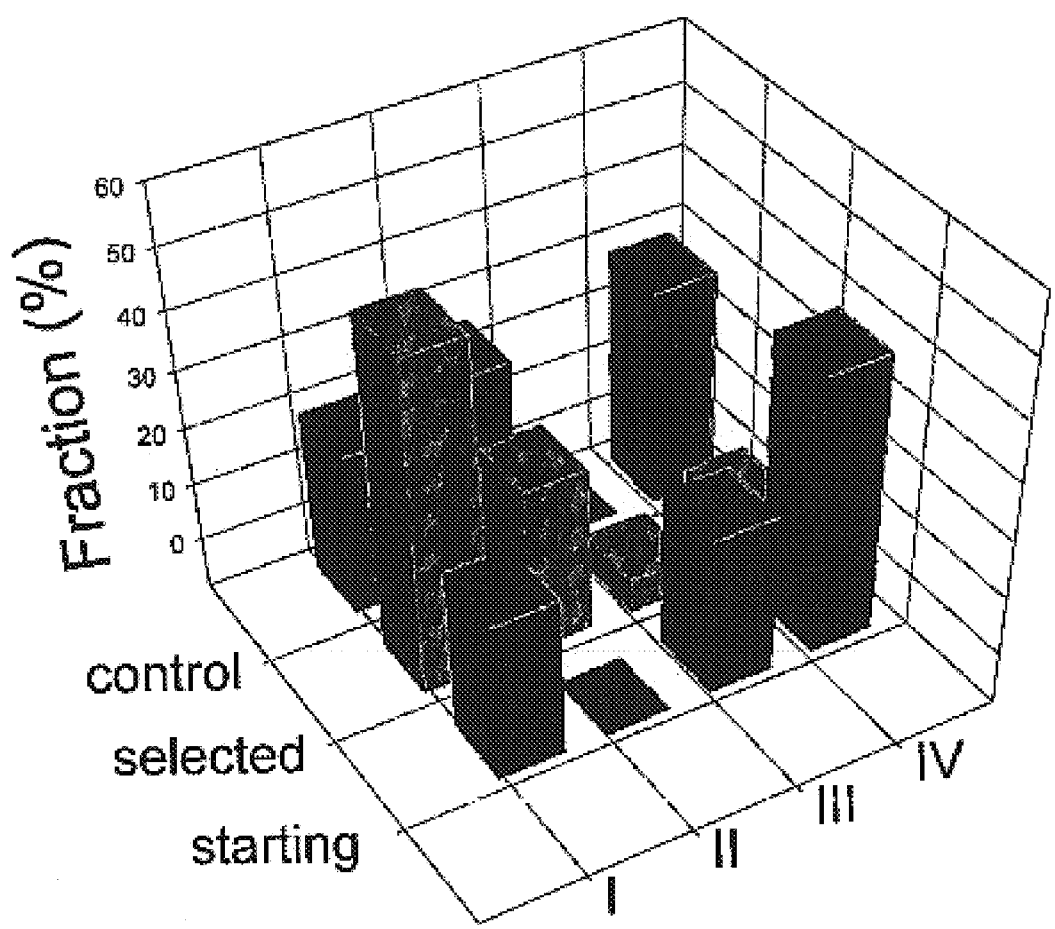
FIG. 27 shows the frequency of affinity points in the four affinity quadrants from the VEGF truncation SELEX by hybridization experiment.

Binding activities of ligands from the VEGF experiments were compared in the presence or absence of fixed sequences. Several ligands were also analyzed in the same way from the starting pool (Rd12 VT30) as shown in Table 12. Ligands from all pools included example of both monophasic and biphasic binding. Each ligand was then scored and classified into five groups as follows: (1) ligands that lose significant affinity for VEGF upon removal of their fixed sequences; (2) molecules with affinities for VEGF somewhat affected (positively or negatively) upon removal of their fixed sequences; (3) molecules that gain significant affinity for VEGF upon removal of their fixed sequences; (4) molecules with affinities for VEGF not affected upon removal of their fixed sequences; and (5) non-binding ligands either with or without fixed sequences. For quantitative comparison, the data were analyzed in % plateau vs Kd values (FIG. 26). For biphasic curves, values of the major affinity component were used. The data points from the full-length ligands define an area representing the average affinity of the full length population. The graphs are divided into four quadrants (I, II, III, and IV) according to this average affinity where quadrant I represents low Kds and high plateaus (optimum affinities). The remaining three quadrants represent sub-optimal affinities with quadrant IV being the worst. If the analyzed population includes ligands that lose affinity upon removal of the fixed sequences, then affinity points will migrate suboptimal quadrants if affinity measurements were done in the absence of the fixed sequences. The data (FIG. 26) show that the majority of affinity points of the starting population occupy the suboptimum affinity quadrants while the majority of affinity points of the selected population occupy the optimum affinity quadrants. As expected the control population shows a distribution similar to the starting population. Comparison of the frequencies of ligands in each quadrant is shown in FIG. 27. These data clearly show that Truncation SELEX by hybrid selections, within one round, shifted the population frequencies so truncatable ligands become more abundant.

Figure 28:
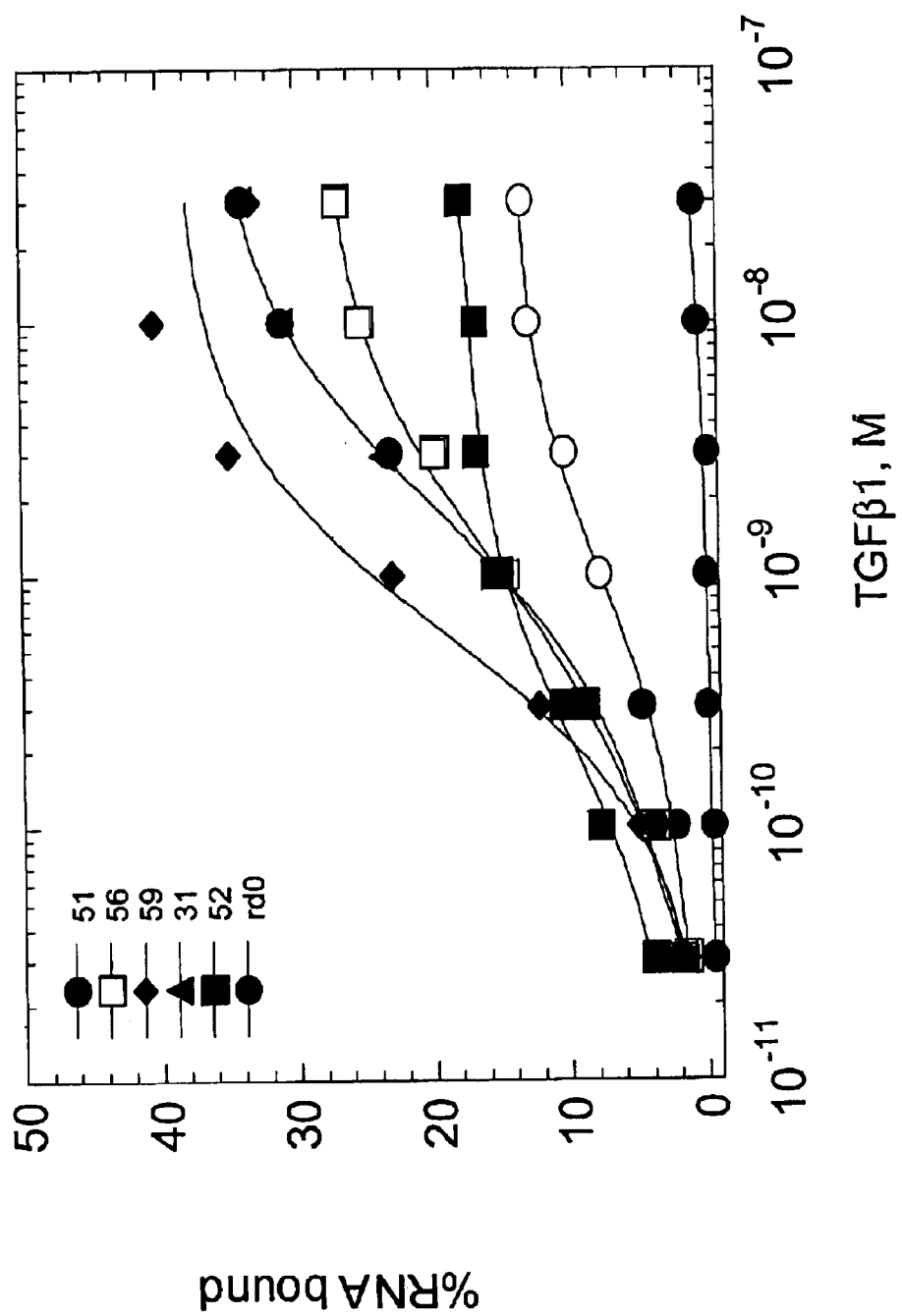
FIG. 28 shows nitrocellulose filter binding curves with a set of ligands from the TGFβ1 40N truncation SELEX by the hybridization experiment. All RNAs were high specific activity body labeled and were digested to remove their fixed regions. RNA was incubated with various concentrations of TGFβ1 and bound RNA was partitioned by nitrocellulose filtration and quantitated. Ligands tested are as shown. The binding of truncated random RNA (rd0) is also shown.
Figure 31:
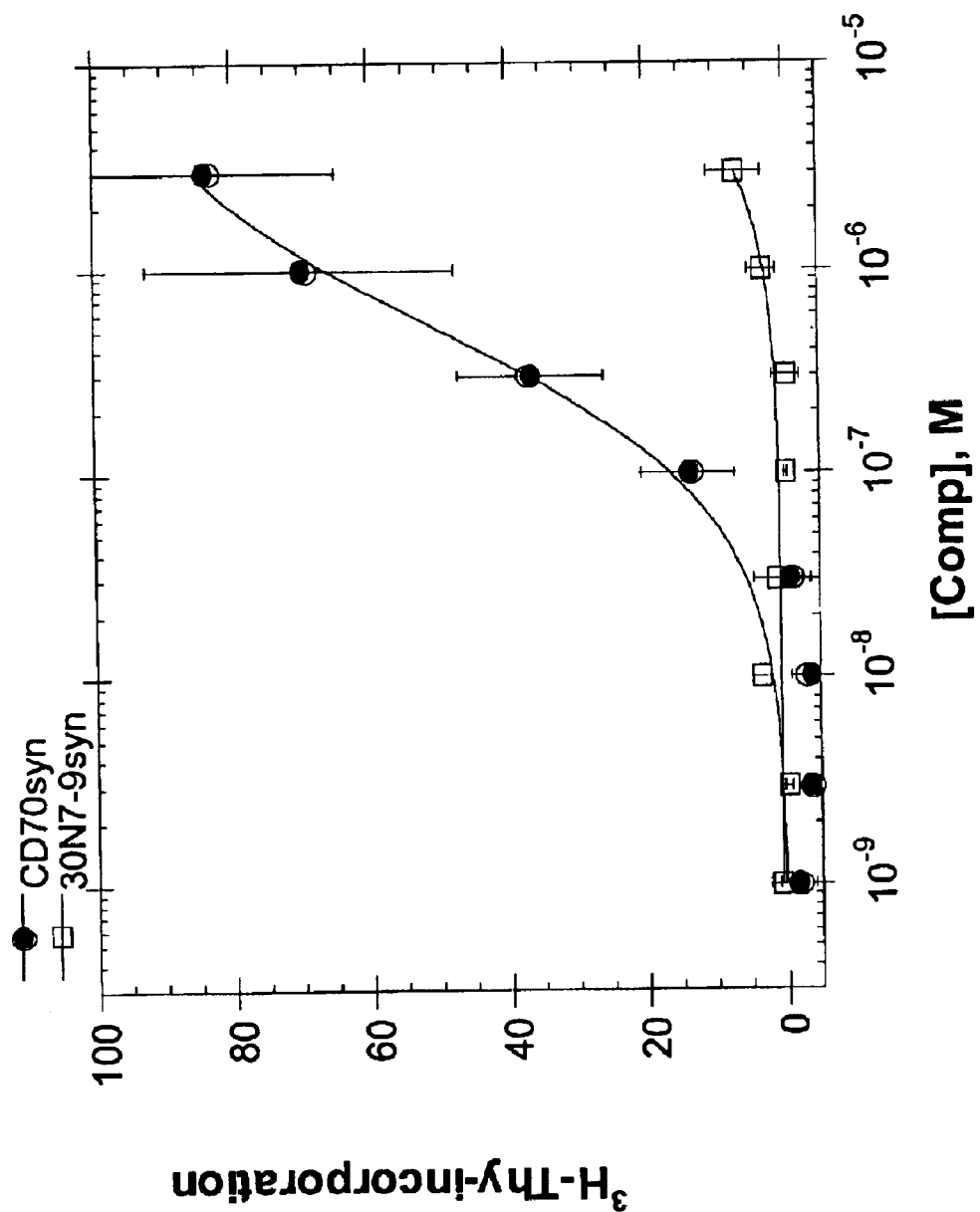
FIG. 31 shows the bioactivity of TGFβ1 Nucleic Acid Ligands isolated from the truncation SELEX by hybridization. RNA was synthesized by phosphoramidite chemistry. Indicator cells (mink lung epithelial cells) were incubated with TGFβ1 and dilutions of RNA as described. The extent of cell proliferation was measured by $^3$H-thymidine incorporation and the data were analyzed as described. The points represent an average of n=2 and error bars are standard errors. The sequence of CD70syn and 30N7-9syn are 5'GGGUGCCUUUUGCCUAGGUUGUGAUUU-GUAACCUUCUGCCCA (SEQ ID NO:323) and 5'AGGGGUCUGGAAUUUUUGGUUUAC-CCGUACGCU (SEQ ID NO:324), respectively.

Since in the original TGFβ1 SELEX we did not isolate any truncatable ligands, finding any truncatable ligand in the truncation SELEX pools would be an indication of the successful application of the methods described here. The binding of the ligands from the TGFβ1 truncation SELEX was determined only after RNaseH digestions and the data are summarized in Table 11. More than half (52%) of ligands tested bound the target with high affinity in the absence of fixed sequences. Sample binding curves are shown in FIG. 28. Truncation SELEX did not only identified truncatable nucleic acid ligands that can bind TGFβ1 but also nucleic acid ligands that could be TGFβ1 inhibitors. FIG. 31 shows the inhibition of TGFβ1 by ligand 70 from the TGFβ1 Rd2 truncation SELEX by hybridization. This ligand causes full inhibition with an approximate Ki of 74.6 nM while a control sequence show no inhibition with an estimated Ki of worse than 1000 fold compared to ligand 70.

EXAMPLE 8

Ligation of 3' Primer Binding Sequence

One of the essential steps of the truncation SELEX by ligation process is the introduction of the 3' fixed sequence at the 3' end of the selected RNA by ligation. The ability of T4 RNA ligase to catalyze such a reaction utilizing RNA transcripts generated by two different templates (35N-Nae and 35N-Bsm) was determined as shown in FIG. 34. Before transcription, the templates were digested by the corresponding restriction enzyme (BsmI or NaeI). Transcription was done with α-$^{32}$P-ATP and 2'F-pyrimidine-triphosphates to generate body labeled 2'F modified transcripts. In addition, the ability of bridging complementary oligonucleotides to improve reaction yields was tested. Oligonucleotides used in this ligation experiment are shown in Table 13. Ligation oligonucleotides were designed to include three biotin residues at their 3' end to allow the measurement of the ligation efficiency by gel shift and were also synthesized with phosphates at their 5' end. Bridging oligonucleotides were designed to be complementary to the 5' end of the ligation oligonucleotide and to include a 6N random region at their 3' ends to allow hybridization at the RNA template thus helping in aligning and holding the two participating templates (the RNA and the 3' fixed sequence oligonucleotide) in juxtaposition to facilitate their ligation. Oligonucleotides 3G7RC and 3G7R6 were used with the 35N-Nae RNA while 3LBsmC and 3LBsm with the 3N-Bsm RNA. Ligation reactions were set as described in the materials and methods and ligation efficiency was determined by quantitation of the residual transcript (TR) and the ligated product (LP) as shown in FIG. 34. Control lanes showing streptavidin induced gel shift also confirmed correct ligation products. In these control lanes, the only way that streptavidin could cause gel retardation of the body labeled transcripts would be by the action of T4 RNA ligase causing the covalent attachment of the biotinylated oligodeoxynucleotide to the labeled RNA. 66% and 55% ligation efficiency was observed for the 35N Nae RNA in the absence and presence of the bridge oligonucleotide, respectively. Similarly, the ligation efficiency for the 35N Bsm RNA was 78% and 41% in the absence and presence of the bridge oligonucleotide, respectively. These results clearly demonstrate that T4 RNA ligase can very efficiently add 3' fixed sequences to 2'F modified RNA in the absence of a bridging oligonucleotide. This method was routinely used in the truncation SELEX by ligation scheme.

Ligation of 5' Primer Binding Sequence

A second essential step of the truncation SELEX by ligation process is the introduction of the 5' fixed sequence to the selected RNA. There are two ways that this can be accomplished. One way is to attach the 5' fixed sequence to the 5' end of the selected RNA using T4 DNA ligase and a bridge oligonucleotide. The second way relies on the same type of reaction where the complement of the 5' fixed sequence is attached to the 3' end of the cDNA copy of the selected RNA. This cDNA copy is generated following ligation of the 3' fixed sequence as described above and RT reaction using a primer complementary to the introduced 3' fixed sequence. Both of these approaches were tested (FIG. 35).

For ligation at the 5' end of 2'F modified RNA, lightly body labeled transcript generated as above on the 35N Bsm template was used. This transcript was then phosphatased by calf intestinal alkaline phosphatase (Roche Molecular Biochemicals, cat#1097075) as described above to remove the phosphate structures generated by transcription initiation (usually a tri- or di-phosphate). The phosphatased RNA was then kinased with T4 polynucleotide kinase and γ$^{32}$P-ATP as described above and then used as a substrate in ligation reactions with T4 DNA ligase from two vendors (Roche Molecular Biochemicals, cat#0481220 and New England Biolabs, cat#202S) containing the oligonucleotide 5G7NOT7 and the bridge oligonucleotide 5G7RC at 20 and 50 fold excess over the RNA, respectively (sequences of DNA oligonucleotides used are shown in FIG. 35. Ligation reactions were set at different concentrations of 2'F modified RNA (two of which are shown in FIG. 35 and were incubated at 4° C. for 16 hours. Following ligation, the reaction products were analyzed on denaturing (7 M urea) 10% polyacrylamide gels. The data clearly show that under these reaction conditions ligation occurs with at least 50% efficiency at RNA concentrations 25–50 nM and both enzyme lots were equivalent.

For ligation at the 3' end of the cDNA, 2'F RNA transcripts from VT30 round 12 pool were reverse transcribed using appropriate primer in the presence of α-$^{32}$P-dCTP (NEN, 800 Ci/mmol cat#BLU013A). Labeled cDNA was ligated to preannealed 5G7RC Linker/5'N7 or 5N7 Linker/5N7 bridge as described in Example 3 and ligation products were analyzed on denaturing (7M urea) 10% polyacrylamide gels. The linker oligonucleotides were in 2- or 5-fold excess over the cDNA while the bridge oligos were at 3- or 7.5 fold excess. The data shown in FIG. 35 show that ligation reactions occurred with varied efficiencies. The set that included a fixed sequence bridge had better yields of about 42% and 46% for the 1:2 and 1:5 ratio of cDNA to linker oligonucleotide, respectively. The ligation efficiencies with the bridge sequence containing 5 random positions were about 15% at the 1:5 ratio of cDNA to linker oligonucleotide. During truncation by ligation SELEX rounds we used the ligation to the cDNA method to introduce the 5' fixed sequence to the truncated RNA since the ligation at the 5' end of the RNA would require additional enzymatic manipulations at each step, namely phosphatase treatment and kination.

Truncation SELEX by Ligation

We applied the truncation SELEX by ligation protocol to three pools namely, the same two pools used for the truncation SELEX by hybrid selection protocol and in addition the round 12 30N-TGFβ1 pool.

Figure 36A:
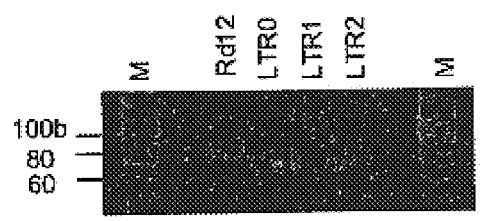
FIGS. 36A and B show properties of pools from the VEGF truncation SELEX by ligation experiment.
Figure 36B:
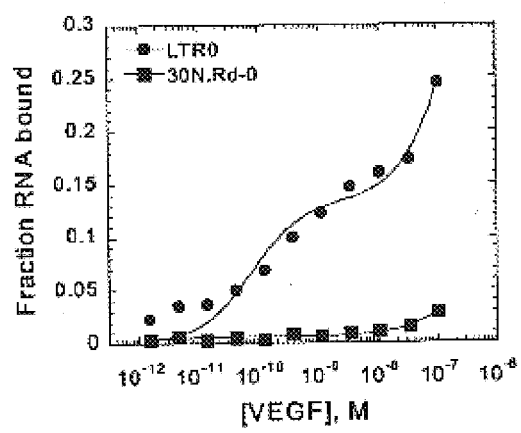
FIG. 36B depicts properties of the 5' truncated starting pool. Body labeled 2'F pyrimidine modified transcript was digested with RNaseH to remove the 3' fixed sequence. Digested 5' truncated starting pool (LTR0) and digested at both ends random RNA (30N.Rd0) were used to determine the fraction of RNA bound at various concentrations of VEGF using nitrocellulose filter binding. Circles and squares indicate LTR0 and 30N.Rd-0, respectively.
Figure 37A:
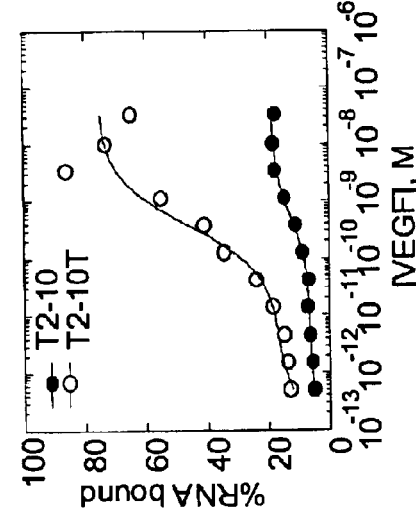
FIGS. 37A–F show nitrocellulose filter binding curves with an example set of ligands from the VEGF round 1 truncation SELEX by ligation experiment. All RNAs were high specific activity body labeled. Binding was measured with undigested and RNaseH truncated (designated by T after the ligand designation) RNA lacking both the bulk of 5' and the 3' fixed sequences. RNA was incubated with various concentrations of VEGF and bound RNA was partitioned by nitrocellulose filtration and quantitated. Ligands tested are as shown.
Figure 37B:
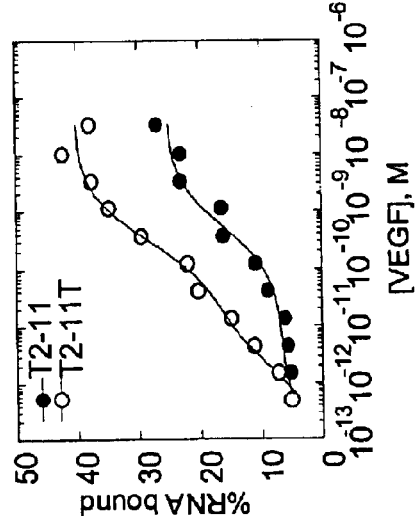
Figure 37C:
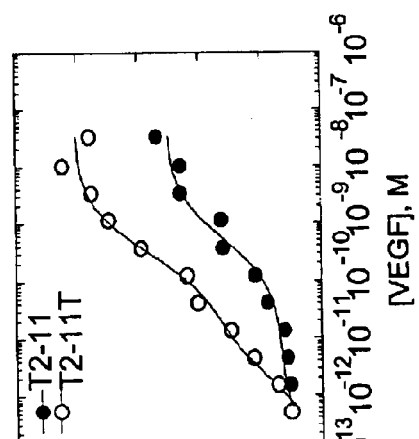
Figure 37D:
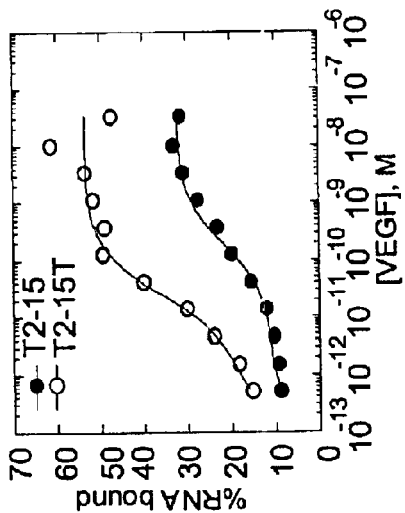
Figure 37E:
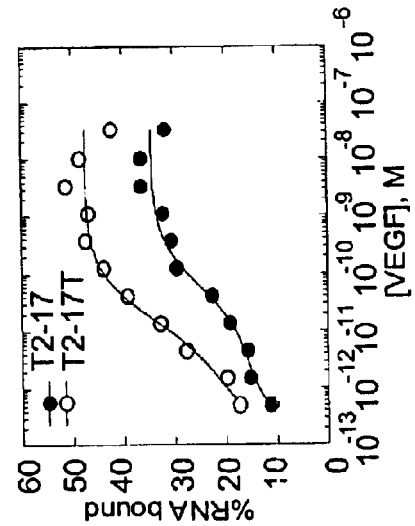
Figure 37F:
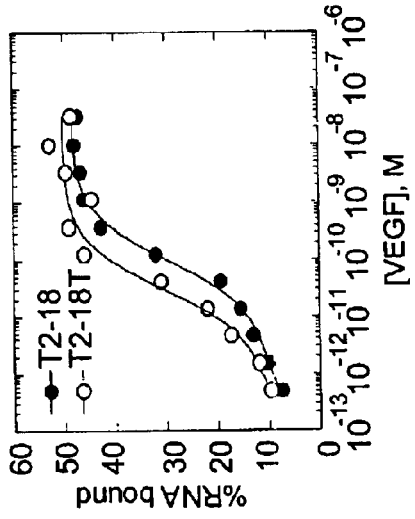

For generating the 3' fixed sequence we used oligo 3G7RC (Table 13) for the VEGF pool while 3G7RCD was used for the TGFβ1 pools. The reason for using 3G7RCD was to avoid repetitions of the sequence 5'CA at the end of the library with each SELEX round due to the RNaseH digestion leaving behind the CA sequence from the fixed sequence. To ensure better efficiency at each round, the starting library was modified by removing a significant portion of 5' fixed sequence leaving behind the 5'GGGAG transcription initiation site as follows. RNA transcripts from each of the starting pools were RNaseH digested at their 5' ends, reverse transcribed using a primer complementary to the 3' fixed sequence, and resulting cDNAs were ligated to the 5N7-Linker/5N7-Bridge set of oligos (FIG. 35) as described above. This ligation (even though inefficient) generates molecules that have their 5' fixed sequence replaced with the T7 promoter-5'GGGAG sequence fused to the RNaseH digestion site. These new templates generate RNA containing just 5'GGGAG as fixed sequence. These RNA molecules do not require RNaseH digestion at the 5' end prior to selection and the 5' primer binding sequence can be introduced (following selection, 3' ligation and reverse transcription) using the 5G7RC-Linker/5'N7 oligonucleotide set (FIG. 35) which showed better ligation efficiencies compared to the 5N7-Linker/5N7-Bridge set. FIG. 36 shows that as expected, PCR products of the 5' truncated VEGF pools are shorter than the starting round 12 pool. In addition, the 5' truncated starting pool retain some binding to VEGF compared to random RNA (FIG. 36).

At each round, affinity selections were done as described in Example 3. The conditions of affinity selections are summarized in Tables 6C and 6D. The RNA used at each round was generated by RNaseH digestion at the 3' fixed sequence as described in Example 3.

As seen in Tables 6C and 6D improving signal to noise ratios and an increase of the amount of RNA binding to the target was observed suggesting the selection process was successful. The starting 5' truncated starting VEGF pool (designated T1), VEGF round 1 (designated T2), VEGF round 2 (designated T3), TGFβ1-30N round 2, and TGFβ2-40N round 2 pools were cloned and sequenced. The pools from these rounds were chosen for cloning and sequencing based on their binding properties.

EXAMPLE 9
RNA Sequences from the Truncation SELEX by Ligation

With the Truncation SELEX by Hybridization protocol it was easy to determine the effect of the selection process on the ligand frequency with respect to the effect of the fixed sequences on their binding activity. This was feasible since the cloned ligands contained both fixed sequences. With the Truncation SELEX by Ligation protocol as it was applied here, this was not feasible because the starting pool was truncated at the 5' end removing the bulk of the 5' fixed sequence. To determine the effect of the ligation protocol on the phenotype frequency of selected VEGF ligands, the starting 5' truncated pool as well as the pools from round 1 and round 2 were cloned and sequenced. 43, 22, and 21 ligands were sequenced from the starting 5' truncated, round 1 and round 2 VEGF pools, respectively. With the TGFβ1 experiment, the ability to identify truncatable molecules was of interest and not in the comparison of phenotype frequencies. Therefore, only the final pools, namely round 2 from both the 30N and 40N experiment were sequenced.

The obtained sequences, their alignment, suggested family classification, and binding properties are summarized in Tables 14–18.

The starting 5' truncated VEGF pools contained ligands that could be assigned into the three families identified previously (Ruckman et al. (1998) J. Biol. Chem. 273:20556–67) and into a fourth family and a group of orphan sequences pyrimidine rich at their 3' ends. The conserved sequence found at the 5' end of members of family 4 is identical to the sequence of the 3' fixed sequence and most likely this family might represent an artifact of the ligation reactions. As with the unmodified VT30 pool, members of family 2 are rare with only one example found. The majority of sequences in this starting pool contain the 3' fixed sequence 5'CA probably a remnant of the 3' terminal sequence removed during the process of construction of this pool. In both of the selected VEGF pools, the frequency of the first three families is increased compared to the starting pool especially for family 2 while the frequency of the orphan sequences was decreased. The selected pools also contained versions of ligand VT30.3 with additional sequences at both ends. Ligand VT30.3 was found in high frequency in the first SELEX experiment (Ruckman et al. (1998) J. Biol. Chem. 273:20556–67). The majority of ligands from the round 2 pool contain multiple copies of the sequence 5'CA at their 3' ends, presumably a remnant of the RNaseH digested 3' fixed sequence, which was added with each ligation step and left behind after each RNaseH digestion.

Sequences from the Rd2-30N TGFβ1 truncation by ligation SELEX pool can be assigned into three groups, namely 2 families and a group of orphans. The orphan group contains ligands that have been identified as nitrocellulose binding molecules in previous experiments described in U.S. patent application Ser. No. 09/046,247, filed Mar. 23, 1998. The remaining two families contain several highly homologous members that could be clonal derivatives of one or a few unique sequences by PCR mutations. Family 2 contains ligands that were identified at very low frequency in the first TGFβ1 SELEX experiment described in U.S. patent application Ser. No. 09/046,247, filed Mar. 23, 1998. Namely, there is a group of sequences (20, 27, 19, 12, 34, and 3) that share a large block of common sequence in the majority of the molecule differing only by two bases (5'CA) at their 3' end and 1–8 bases at their 5' end possibly due to ligation artifacts. Their common sequence is identical to the sequence of ligand 30–32 isolated in our first SELEX experiment with TGFβ1 described in U.S. patent application Ser. No. 09/046,247, filed Mar. 23, 1998. Ligands from family one are highly conserved (and could be derivatives of a single sequence found in the starting random RNA pool) and were not isolated before. Since we use DNA oligo without the CA sequence at its 5' end for ligation at the 3' end of TGFβ1 selected RNA, the isolated ligands from the Rd2-30N TGFβ1 truncation by Ligation SELEX pool do not contain the sequence 5'CA at their 3' ends.

Sequences from the Rd2-40N TGFβ1 truncation by ligation SELEX pool can be assigned into seven families. These families are rather small and they could be clonal derivatives of one or a few unique sequences by PCR mutations. The last family contains ligands with sequences characteristic of nitrocellulose binders. All the ligands from family 1 contain the 3' fixed sequence of the N7 series at their 5' end and the majority of them contain at their 3' ends a large portion of the T7 promoter. Thus, these ligands must represent artifacts of the ligation reactions. Family two contains ligands of the same class as ligands from family 2 of the Rd2-30N TGFβ1 truncation by ligation SELEX pool but the majority of them contain the 3' fixed sequence at their 5' ends. Therefore they could be contaminants from the 30N pool that were modified due to undesirable ligation side reactions. Family 2, however, contains three ligands that could be true isolates from the 40N pool. The other families contain ligands that were not identified in U.S. patent application Ser. No. 09/046,247, filed Mar. 23, 1998. Family four contains members that are longer than expected by ten bases. As with the ligands from the 30N pool, the ligands from the 40N pool do not contain the sequence 5'CA at their 3' end, but unlike the 30N ligands the 40N ligands have a somewhat heterogeneous 5' initiator sequence.

EXAMPLE 10
Binding Properties of Ligands from the Truncation SELEX by Ligation

The binding activity of several ligands from the Truncation SELEX by Ligation experiments was determined by nitrocellulose filter binding and data are summarized in Tables 14–18.

Figures 38A, 38B, 38C:
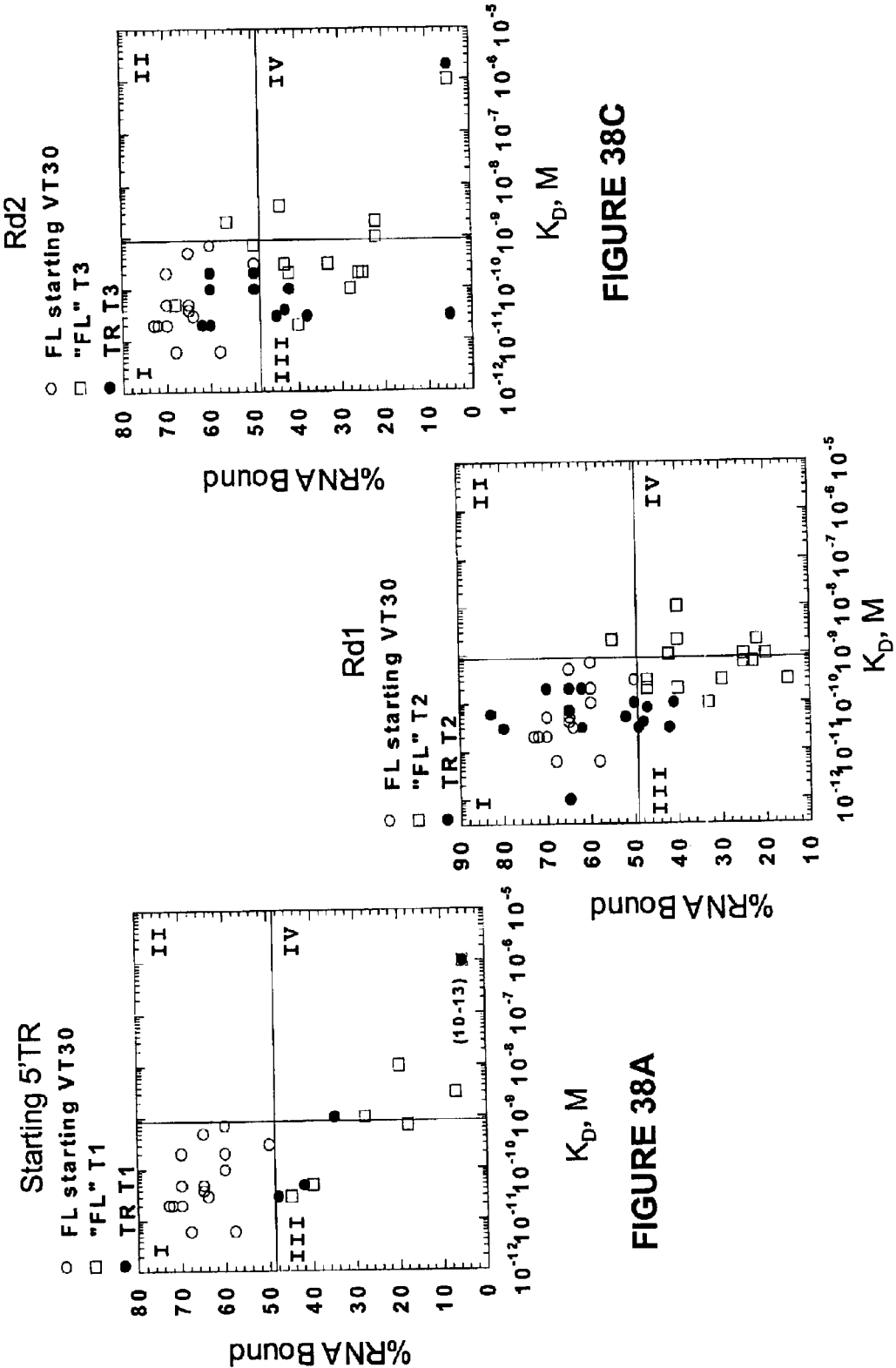
FIGS. 38A–C show the effect of removal of fixed sequences on the affinities of ligands from the starting 5' truncated (5'TR) (FIG. 38A), round 1 (Rd1) (FIG. 38B), and round 2 (Rd2) (FIG. 38C) libraries obtained in the VEGF truncation SELEX by ligation experiment. Full length and truncated RNA transcripts from individual ligands were used to determine Kd and plateau values using nitrocellulose filter binding curves. Each graph point is defined by the Kd and plateau for an RNA. Open circles are affinity values obtained with starting full length round 12 VT30 RNA. Closed circles are affinity values from truncated RNA (lacking both the bulk of 5' and the 3' fixed sequences). Open squares are affinity values from ligands containing their 3' fixed sequences but lacking the bulk of their 5' fixed sequence. The closed circles and open squares come from the same set of ligands within each library shown, while the open circles are a different set, coming from the round 12 VT30 pool. This different set of VT30 ligands was used to define quadrant I. Quadrant IV of the starting 5'TR pool contained 10–13 points with Kd>1×10$^{-6}$ M and plateaus <5%. These points were set as Kd=1×10$^{-6}$ and plateau=5.
Figure 39:
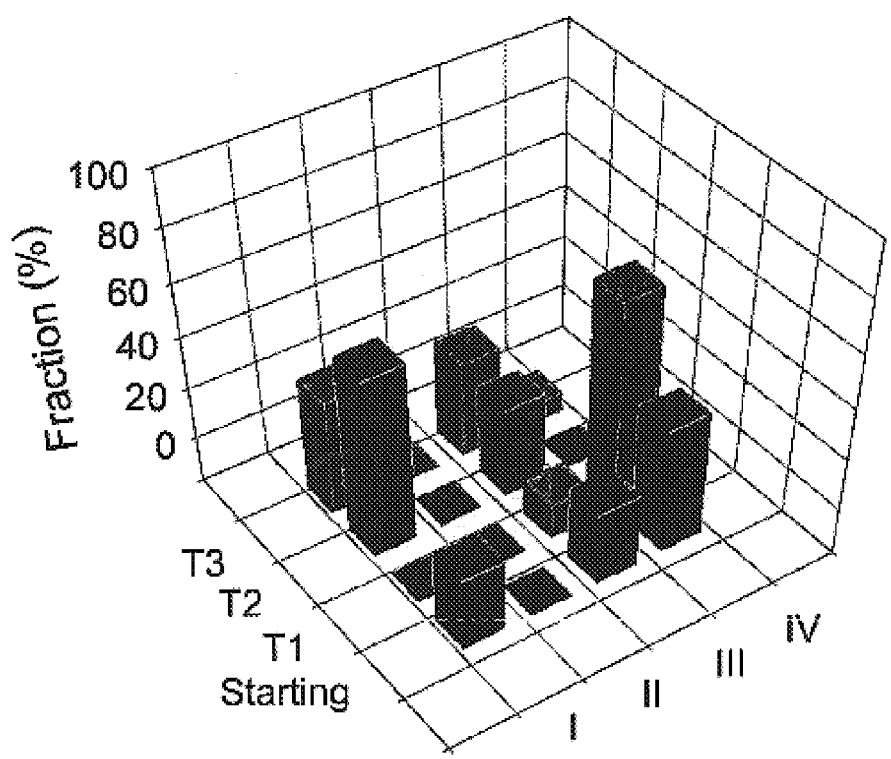
FIG. 39 shows the frequency of affinity points in the four affinity quadrants from the VEGF truncation SELEX by ligation experiment.

Binding activities of ligands from the VEGF experiments were determined with or without the 3' fixed sequence. Ligands from all pools included examples of both monophasic and biphasic binding. Example binding curves are as shown in FIG. 37. Like the truncation SELEX by hybridization experiment, each ligand was scored and classified into five groups as follows: (1) ligands that lose significant affinity for VEGF upon removal of their 3' fixed sequences; (2) molecules with affinities for VEGF somewhat affected (positively or negatively) upon removal of their 3' fixed sequences; (3) molecules that gain significant affinity for VEGF upon removal of their 3' fixed sequences; (4) molecules with affinities for VEGF not affected upon removal of their 3' fixed sequences; and (5) non-binding ligands either with or without the 3' fixed sequences. For quantitative comparison, the data were analyzed as above in % plateau vs Kd values (FIG. 38). For biphasic curves, values of the major affinity component were used. Because the members of the starting pool for this SELEX experiment were truncated at their 5' ends, the phenotype of ligands as full-length molecules containing both the 5' and 3' fixed sequences could not be compared. In order to define the affinity quadrants, the affinity points of full-length ligands from the Rd12 VT30 pool were used. Therefore, based on the affinity values of the Rd12 VT30 ligands, the graphs are divided into four quadrants (I, II, III, and IV) where quadrant I represents low Kds and high plateaus (optimum affinities). The remaining three quadrants represent sub-optimal affinities with quadrant IV being the worst. In all pools from this truncation SELEX by ligation experiment, the ligands containing the 3' fixed sequence occupied sub-optimal affinity quadrants (FIG. 38). Upon removal of the 3' fixed sequence, the majority of the affinity points of the selected pools (but not of the 5' truncated starting pool) occupied the optimum affinity quadrant. Comparison of the frequencies of ligands in each quadrant is shown in FIG. 39. These data clearly show that truncation SELEX by ligation, within one round, shifted the population frequencies so truncatable ligands become more abundant. Of interest is the observation that in the presence of the 3' fixed sequence the majority of ligands tested showed worse affinities suggesting that the 3' fixed sequence probably influences the folding of these ligands towards incorrect conformations.

Figure 40B:
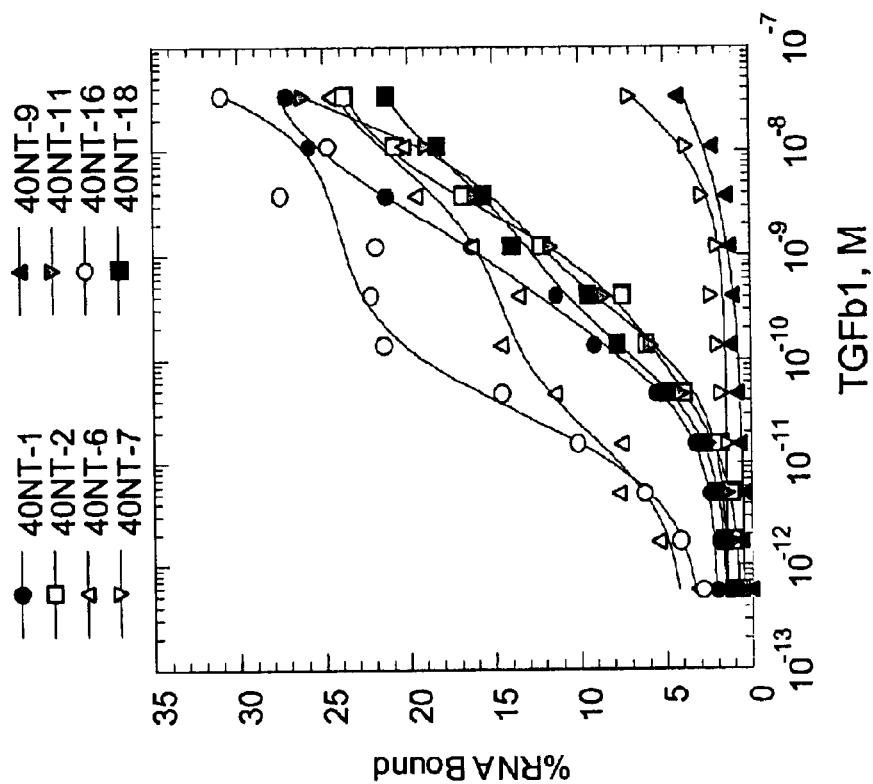
FIGS. 40A and B show nitrocellulose filter binding curves with a set of ligands from the TGFβ1 30N and 40N truncation SELEX by ligation experiment. All RNAs were high specific activity body labeled and were digested to remove their fixed regions. RNA was incubated with various concentrations of TGFβ1 and bound RNA was partitioned by nitrocellulose filtration and quantitated. Ligands tested are as shown. The binding of truncated 40-03 ligand (described in U.S. patent application Ser. No. 09/046,247, filed Mar. 23, 1998) is also shown.
Figure 40A:
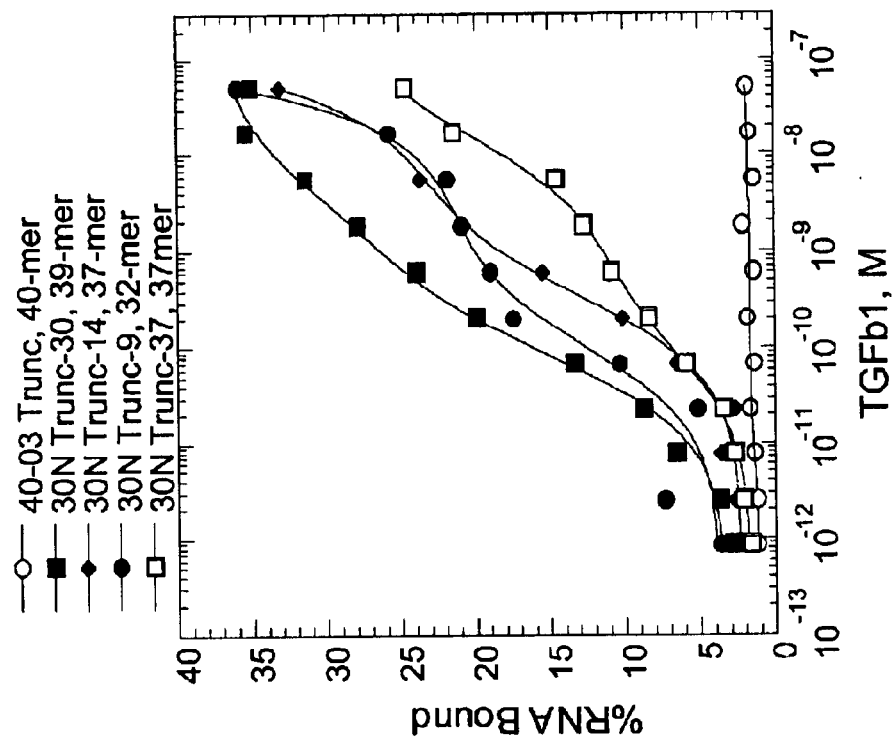

As with the truncation SELEX by hybridization experiment, the binding of the ligands from the TGFβ1 truncation by ligation SELEX was determined only after RNaseH digestions to remove the 3' fixed sequence and the data are summarized in Tables 17 and 18. The majority of selected ligands tested bound the target with high affinity in the absence of the 3' fixed sequence. Sample binding curves are shown in FIG. 40.

EXAMPLE 11
Truncation SELEX with DNA Libraries

The truncation SELEX process described herein is designed for use with RNA (native or modified) libraries. With slight modification, this approach can be applied to ssDNA libraries. These modifications could be applied to templates engineered to include restriction enzyme recognition sites at the junction of the random region with the 5' and 3' fixed sequences (FIGS. 32 and 41). The ssDNA library lacking the 5' and 3' fixed sequences can be generated in at least three ways (FIG. 32). First, sense strands can be purified using a biotinylated 3' primer and streptavidin induced gel shift on denaturing gels (FIG. 32, left branch) (Pagratis (1996) Nucleic Acids Research 24:3645–6). Purified sense strands can then be annealed to single stranded oligos complementary to the 5' and 3' fixed sequences containing the restriction sites (sequences could be as shown in FIG. 41. Annealed oligonucleotides are then digested with the appropriate restriction endonuclease and the fragment containing the random region is purified by denaturing gel electrophoresis. Second, double stranded PCR templates can be digested with appropriate restriction endonuclease to remove the 5' and 3' fixed sequences (FIG. 32, middle branch). In this case, restriction sites are chosen to generate a 3' recessive and a 5' recessive end at the 5' and 3' fixed sequences, respectively. Following digestion the 3'recessive end is filled-in with the Klenow fragment of E. coli DNA polymerase-I and biotin-dUTP. The non-biotinylated sense strand is then purified by streptavidin induced gel shift on denaturing gels (Pagratis (1996) Nucleic Acids Research 24:3645–6). Third, in a variation of the second method, the double stranded PCR templates can be digested with appropriate restriction endonuclease to remove first the 5' fixed sequence. In this case restriction sites that generate a 3' recessive end can be used at the 3' fixed sequence. Following digestion at the 5' fixed sequence, the products are biotinylated as above with the Klenow fragment of E. coli DNA polymerase-I and biotin-dUTP. Following biotinylation, the 3' fixed sequence is digested away using the appropriate restriction enzyme and the nonbiotinylated sense strand is purified as above (Pagratis (1996) Nucleic Acids Research 24:3645–6). Following target partition, selected ssDNA molecules can be amplified by either following the hybrid selection approach or the ligation approach. For the hybrid selection approach, a portion of the selected pool from the previous round is amplified using a biotinylated 5' primer and the nonbiotinylated antisense strands are purified as above (Pagratis (1996) Nucleic Acids Research 24:3645–6). The selected RNA is then biotinylated as in the case of RNA (for example with terminal transferase and Biotin-dUTP) and hybridized in excess of purified full length antisense strand in the presence of nonspecific competitor (as described above with the RNA truncation SELEX by hybridization method). Hybridized molecules are then captured as before (for example streptavidin beads) and PCR amplified to generate the pools for the next round. For the ligation approach, the selected ssDNA is ligated to primers in the presence of appropriate bridging oligonucleotides or alternative using appropriately designed stem-loop structures (FIG. 41).

Figure 42:
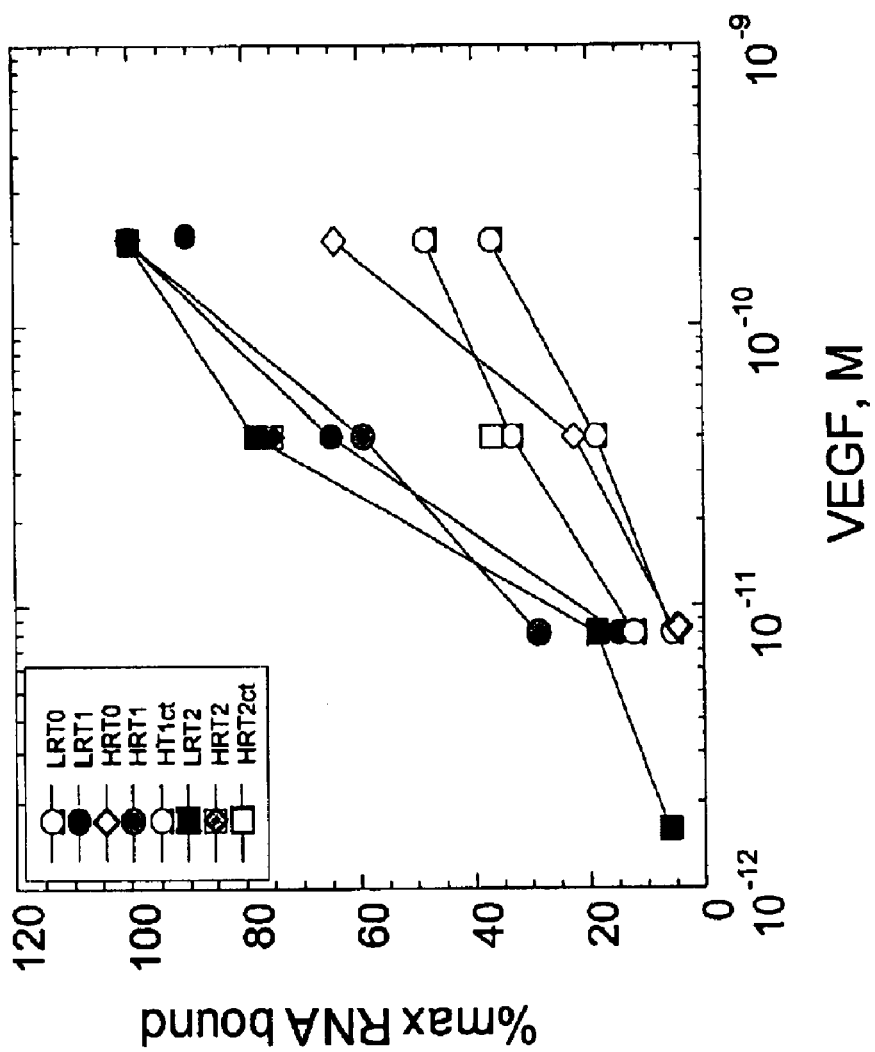
FIG. 42 shows the comparison of the progress of the VEGF truncation SELEX by hybridization and ligation experiments. During the SELEX rounds, the amount of RNA bound to the target was quantitated and expressed as % fraction of expected max binding and was plotted as a function of target concentration as shown. Pools shown are: ligation 5' truncated starting pool (LRT0), ligation round 1 (LRT1), ligation round 2 (LRT2), VT30 round 12 (HRT0), hybridization round 1 (HRT1), hybridization round 1 control (HRT1-ct), hybridization round 2 (HRT2), and hybridization round 2 control (HRT2-ct).
Figure 43A:
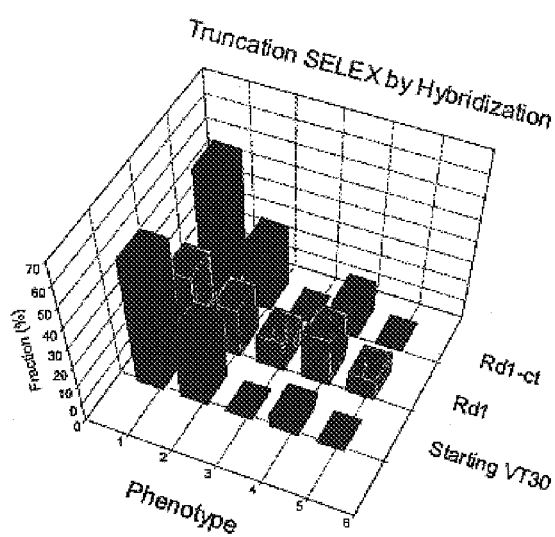
FIGS. 43A and B show the comparison of phenotype frequencies from ligands obtained in the truncation SELEX by hybridization and ligation as shown. For phenotype determination, the binding of each ligand was determined with and without its fixed sequence and then each ligand was evaluated if it retained binding following removal of its fixed sequence. Phenotypes were determined by filter binding and were classified according to five groups as follows: (1) molecules that lose significant affinity for VEGF upon removal of their fixed sequences; (2) molecules with affinities for VEGF somewhat affected (positively or negatively) upon removal of their fixed sequences; (3) molecules that gain significant affinity for VEGF upon removal of their fixed sequences; (4) molecules with affinities for VEGF not affected upon removal of their fixed sequences; and (5) non-binding ligands either with or without fixed sequences.
Figure 43B:
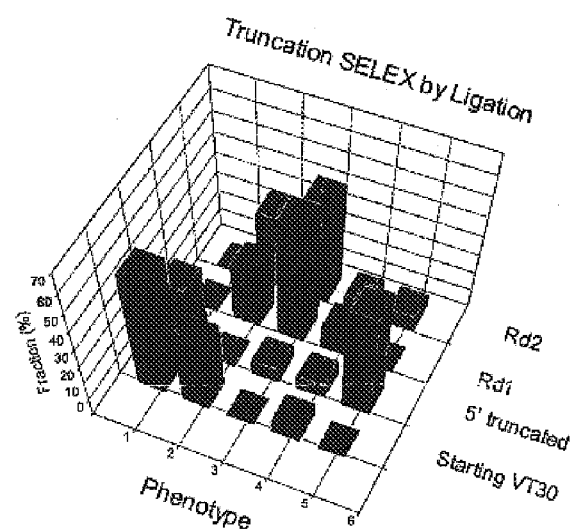

The data presented in Examples 3–11 clearly demonstrate the feasibility of isolating nucleic acid ligands that utilize just the random region for high affinity binding to their target. To isolate such nucleic acid ligands it is not necessary to start with unselected pools. When starting with evolved pools, selection could happen relatively fast within 1–2 rounds. Two different approaches were described, one based on hybrid selection of complementary full-length molecules and the other based on enzymatic generation of primer binding sites to allow PCR amplification. Both methods gave similar results. FIG. 42 shows the progress of both selection processes showing almost superimposible results. FIG. 43 compares the binding phenotype of individual ligands with or without their fixed sequences. Within one round of selection the two processes described here dramatically increase the frequency of ligands that bind the same or better to the target if their fixed sequences are removed. The shift in frequencies with the ligation method is more pronounced suggesting a more efficient selection. Although the ligation method gave more striking results, it was found that this method yielded artifact ligands that resulted from the shuffling of fixed sequences by the enzymatic steps used. Such sequence rearrangements were not found with the hybrid selection method.

EXAMPLE 12
Screening for Ligands of a Certain Size

Figure 12A:
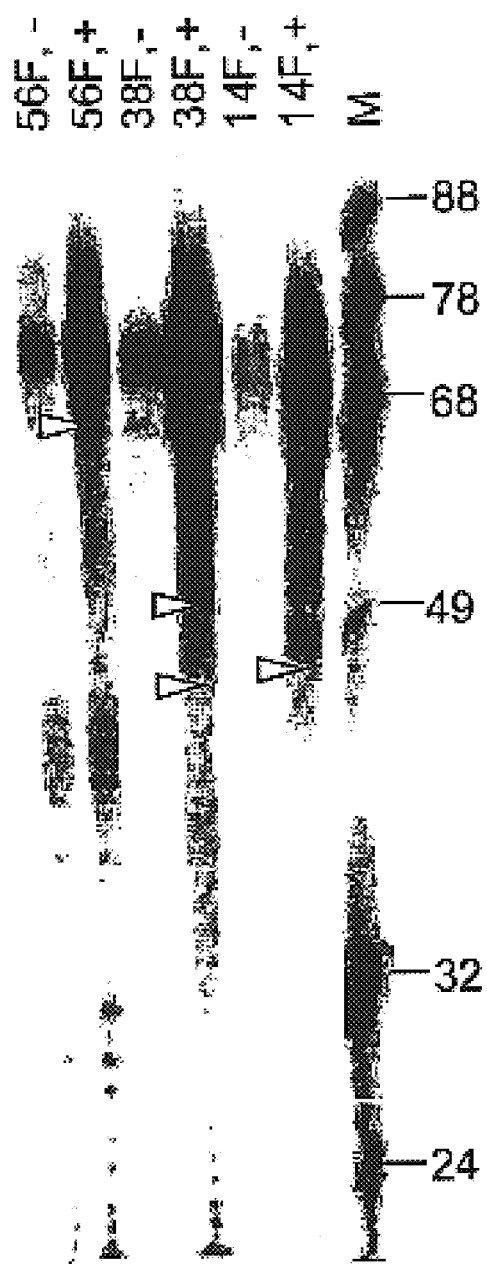
FIGS. 12A and B show the determination of minimum binding fragments of several KGF ligand. Body labeled 2'F pyrimidine modified transcripts were alkaline hydrolyzed in 50 mM $Na_2CO_3$, pH 9.0, 1 mM EDTA, at 90° C. for 10 minutes. Alkaline hydrolyzed RNA was recovered by ethanol precipitation and was incubated with KGF in PBS, 0.01% HAS for 15 min at 25° C. and bound RNA was partitioned by nitrocellulose filtration. The amount of KGF used for each ligand was determined by the ligand's Kd and ranged from 2–0.1 nM. Bound RNA was extracted from the nitrocellulose filter with phenol urea and was analyzed on a sequencing gel. RNA from control reactions lacking KGF was also run for some ligands. Symbols 56F, 38F, 14F, 53F, 26F, and 15F are designations for KGF ligands (KGF patent); + or – indicate the use of KGF or not, respectively; M are molecular markers with the indicated sizes. Minimum fragments are shown by arrowheads.
Figure 12B:
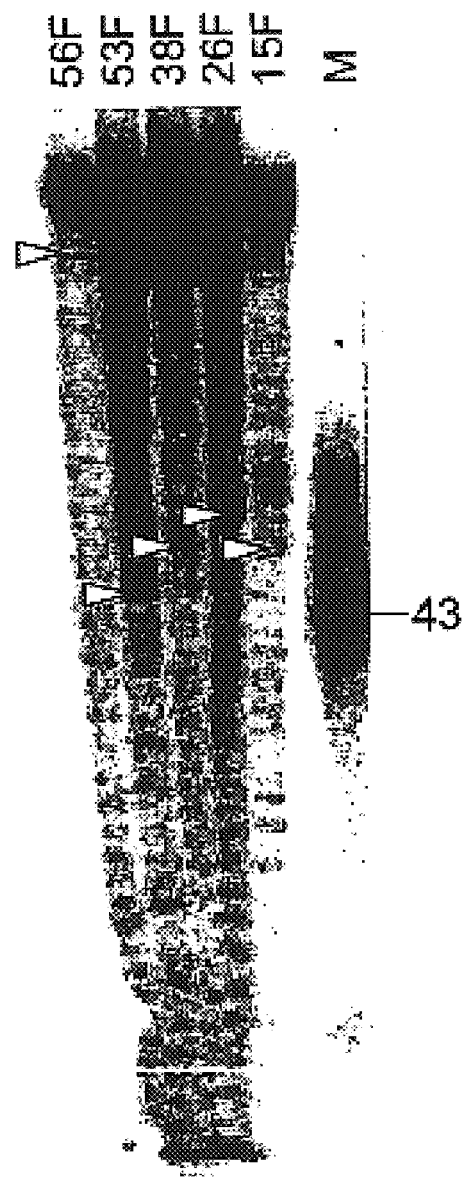
Figure 13:
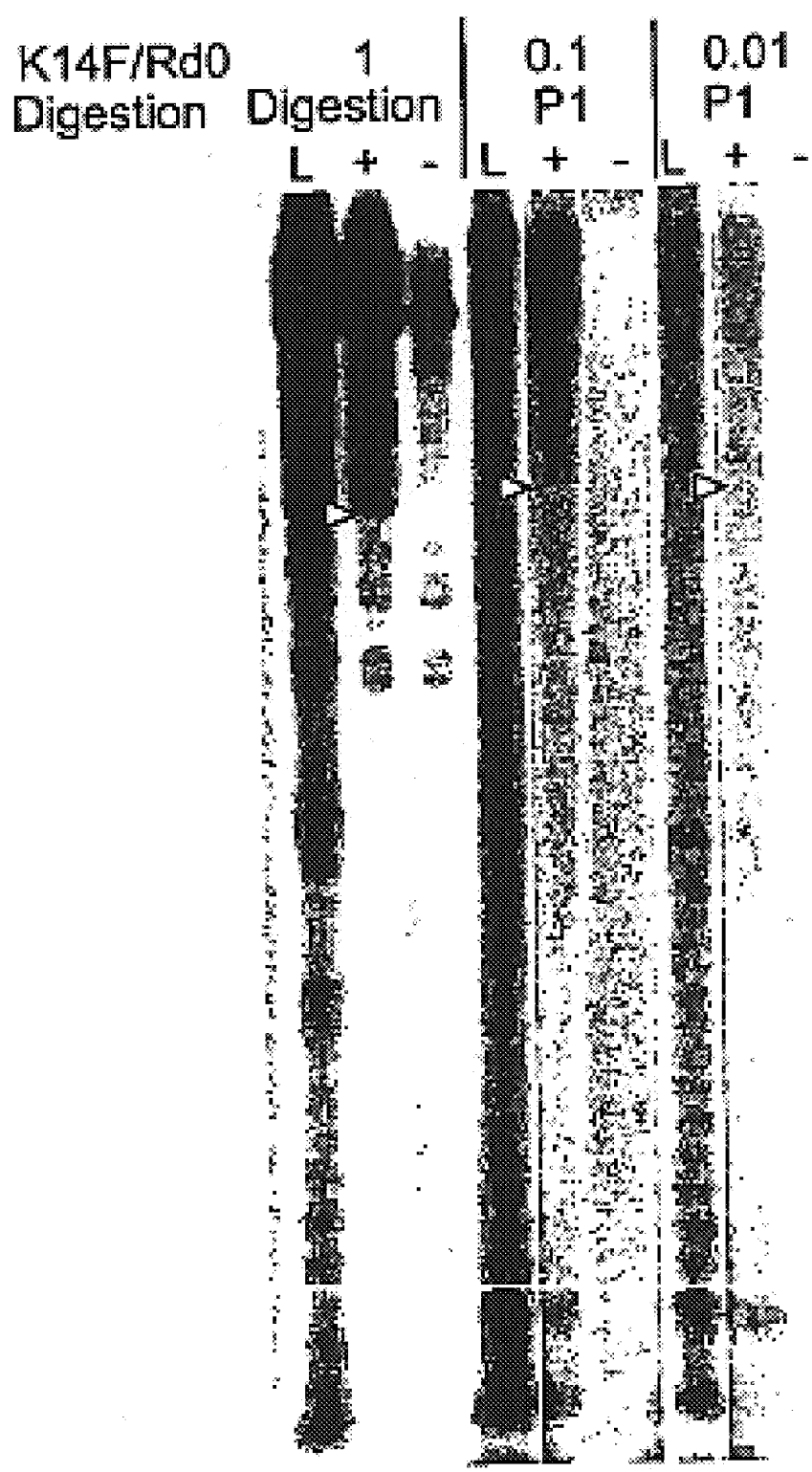
FIG. 13 shows the reconstruction experiment for determining the average minimum fragments of pools. KGF ligand K14F 2'F transcript was mixed with 40N7 at the indicated ratios. RNA mixes were digested with RNaseP1 at 0.0024 U/pmole of RNA in manufacturers buffer at 65° C. for 5 minutes. Prior to digestion the RNA were denatured in digestion buffer containing 6.8 M urea (final). Digestion was done in the presence of urea. Following digestion the RNA was recovered by ethanol precipitation and was phosphatased and 5' end labeled by kinase as described. Kinased RNA was recovered by ethanol precipitation, then it was incubated with KGF at 200 pM and RNA:protein ratio of 100 at 25° C. for 15 minutes in PBS, 0.01% HSA and target bound RNA was recovered by nitrocellulose filtration followed by urea/phenol recovery and ethanol precipitation. Nitrocellulose recovered RNA was analyzed on a sequencing gel. As a control, ligand K14F was partially alkaline hydrolyzed as described, and bound fragments were recovered and analyzed on the same gel. Minimum fragments are shown by arrowheads. Symbols AH, P1, L, +, – indicate alkaline hydrolysis, RNaseP1 digestion, starting RNA digest (ladder), incubation with KGF and incubation without KGF, respectively.

The experimental demonstration of the method shown in FIG. 5 is described in this example. Body labeled KGF ligands 56F, 53F, 38F, 26F, 15F and 14F were cleaved by alkaline hydrolysis, bound to KGF and the bound fragments were partitioned by nitrocellulose filtration and analyzed on a sequencing gel (FIG. 12). The potential minimal fragments are marked on the gel suggesting that ligands 53F, 38F, 26, 15F, and 14F show minimal possible sizes in the 45 base range.

Minimum size fragments can also be identified in pools of molecules containing truncatable ligands to reasonable frequencies. As shown the reconstruction experiment in FIG. 13, alkaline hydrolysis followed by affinity selection, allows the identification of the minimum fragment as predicted by conventional truncation experiments with approximate size of 59 bases. Mixing of K14 ligand with random RNA at rations of p to 1:100, random fragmentation and affinity selection allows the identification of the expected K14 minimum fragment.

Figure 14:
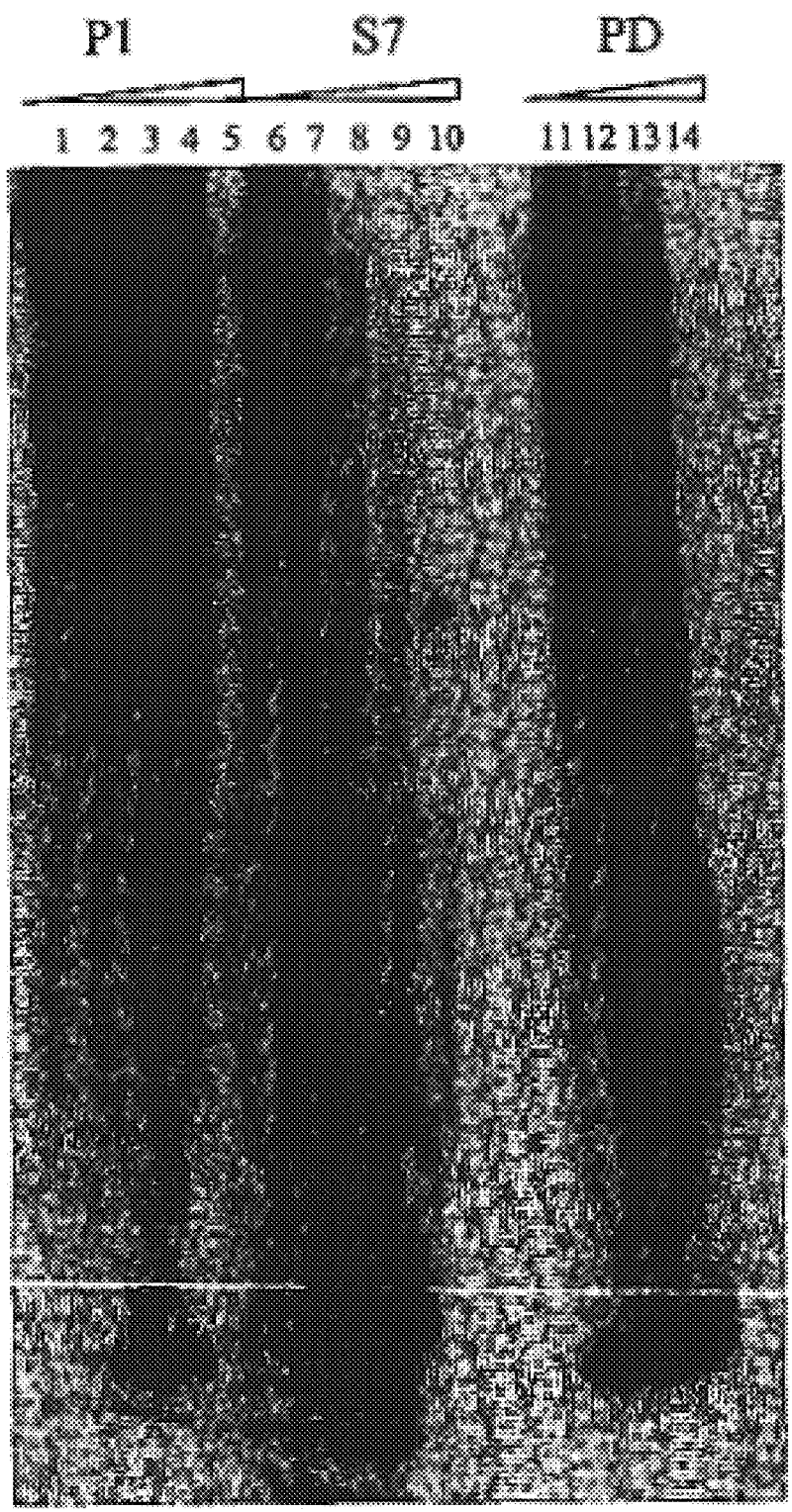
FIG. 14 shows partial digestion of 2'F pyrimidine modified RNA. Body labeled 30N7 2'F pyrimidine modified RNA was digested with RNaseP1 (P1), nuclease S7 (S7) or phosphodiesterase (PD). Digestions were done in manufacturers specified buffers containing 7 M urea at 65° C. for 15 minutes. RNA was present at 0.9 μM. Digests were analyzed on a sequencing gel. Phosphodiesterase was used at 20, 2, 1, and 0.5 ng. Nuclease S7 was used at 3, 0.3, 0.03, and 0.003 units. RNaseP1 was used at 0.1, 0.01, 0.001, and 0.0001 units. Lanes 1, 6, and 11 were incubation reactions lacking enzyme.
Figure 16:
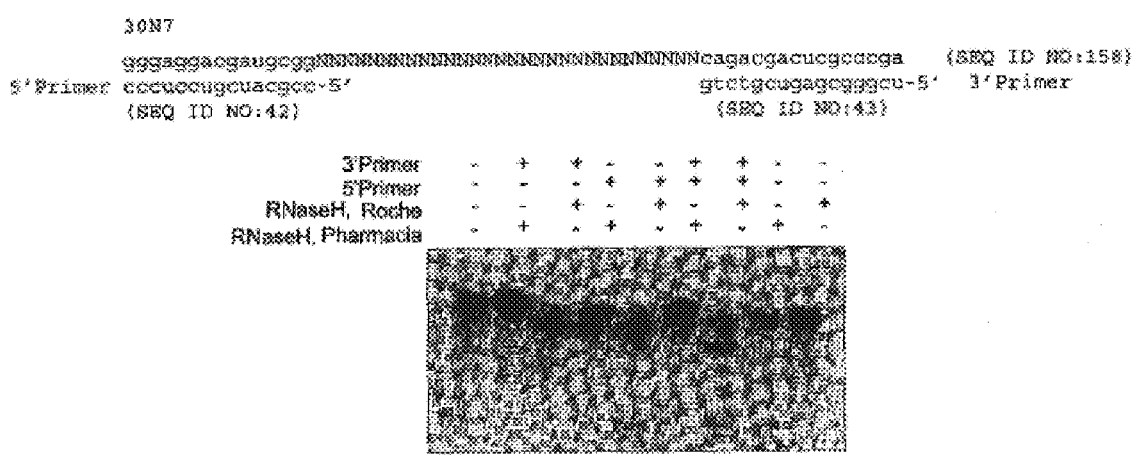
FIG. 16 shows the digestion of 2'F pyrimidine modified transcripts by RNase H. Two enzymes were used as shown. The presence or absence of the 5' or 3' targeting oligonucleotides are indicated by + and –, respectively. The sequence of the RNA and the targeting oligonucleotides used are also shown.
Figure 17:
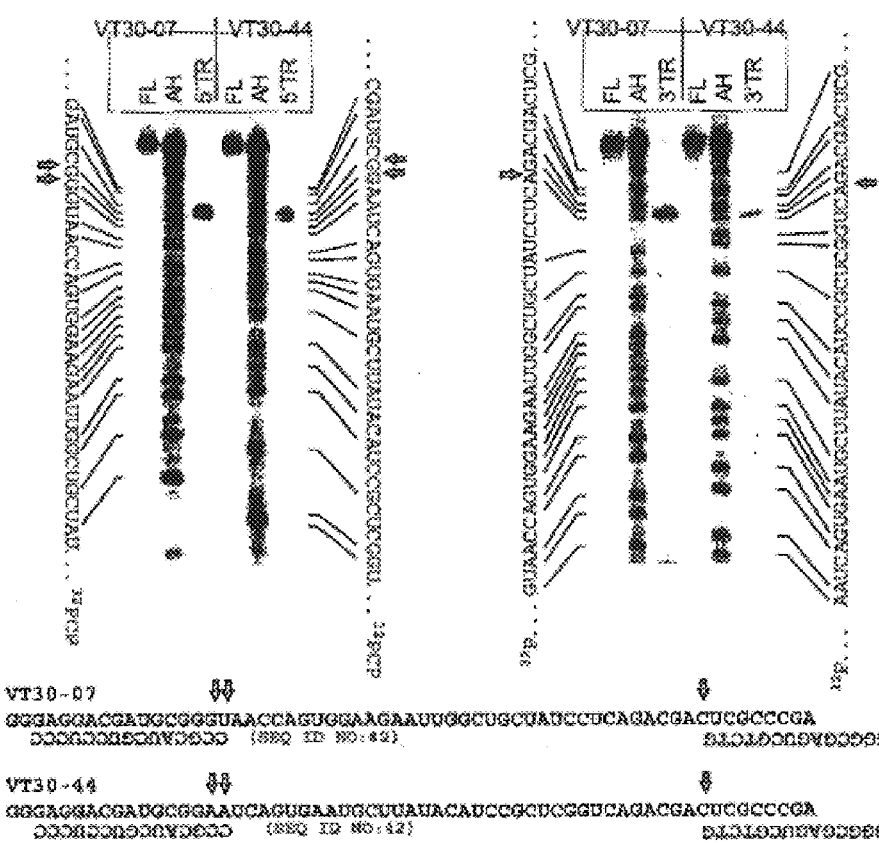
FIG. 17 shows the mapping of RNaseH digestion sites using end labeled substrates. Two different Nucleic Acid Ligands were used in this experiment as described. Digestion sites are indicated by arrowheads. The alignment of the alkaline hydrolysis pattern with the RNA sequence is as shown. The sequence of the RNA molecules and the digestion sites are also shown under the gel patterns. Symbols FL, AH, 5'TR, and 3'TR indicate fall length, alkaline hydrolysis, 5' truncate and 3' truncate.

Alkaline hydrolysis is routinely used to create the random cleavage ladders, but it creates homogeneous ladders only with RNA. Modified RNA at the 2' position of pyrimidines gives sequence specific incomplete ladders while DNA is not susceptible to alkaline hydrolysis. We tested a group of nucleases for their ability to generate random complete ladders with 2'F-pyrimidine modified RNA. Enzymes tested were mung bean nuclease, nuclease S1, snake venom phosphodiesterase, nuclease S7, and nuclease P1. Only snake venom phosphodiesterase, nuclease S7, and nuclease P1 resulted in homogeneous laddering of the oligonucleotide used (FIG. 14). Since snake venom phosphodiesterase is an active 3' to 5' exonuclease with some endonuclease activity only the nuclease P1 and S7 can be used in minimum fragment determination experiments.

TABLE 1

```
(SEQ ID NO:1)
5'-gggaggacgaugcgg-GENOMIC INSERT-cagacgacgagcggga-3'
   |||||||||||||||                ||||||||||||||||
3'-ccctcctgctacgcc-5'            3'-gtctgctgctcgccct-5'
(SEQ ID NO:2)                    (SEQ ID NO:3)
```

TABLE 2

Isolates with the consensus binding site from SELEXes with changing fixed sequences.

| Isolate | SEQ ID NO: | Sequence of the isolate's insert Location in E.coli genome | # Copies 3 + 4 | 5 |
|---------|------------|------------------------------------------------------------|----------------|---|
| 1 | 4 | GGCACGCGUAUUCA<u>CUG</u> $ <u>GC</u> AUCA <u>GC</u> <u>CAG</u><br>ACUGUGU<br>sense of *rffG* (dTDP-D-glucose 4,6 dehydratase; participates in formation of lipopolysaccharide in the bacterial outer membrane) 210 nt from start codon | 58 | 4<br>2 |
| 2 | 5 | CUUCGCUUCAGUACCGUCG <u>AGC</u> $ <u>GC</u> ACCA <u>GC</u><br><u>GUU</u> UCGCC<br>antisense of *pheT* (phenylalanyl-tRNA synthetase), 250 nt from start codon | 5 | — |
| 3 | 6 | AAUGU <u>UCC</u> $ CC AGCA <u>GG</u> <u>GGA</u><br>AAUGAUGUUGUUCUGGCU<br>antisense of o356 (similarity to *lpfD* from *S. typhimurium* fimbrial operon), 140 nt from stop codon;<br>antisense upstream of o180 (similarity to *fimI* from *S. typhimurium*, which is a fimbriate-related, fibrin-like protein), | 7 | 7 |
| 4 | 7 | UAGGAGAGCGUUAAC <u>AAC</u> $ <u>GC</u> AUCA <u>GC</u> <u>GUU</u><br>GAAGUGACGGAGGU<br>antisense of *ygiI* (hypothetical transmembrane protein), 470 nt from start codon | 1 | — |
| 5 | 8 | UGAUU <u>UGC</u> $ <u>GC</u> AACA <u>GC</u> <u>GCA</u><br>AUGAGGAAAGAGAGCCAGAUUACCC<br>antisense of *mreD* (responsible for formation of the rod shape of *E. coli* cells, integral membrane protein, 50 nt from start codon | 1 | — |

TABLE 2-continued

Isolates with the consensus binding site from SELEXes with changing fixed sequences.

| Isolate | SEQ ID NO: | Sequence of the isolate's insert Location in E.coli genome | # Copies 3 + 4 | 5 |
|---|---|---|---|---|
| 6 | 9 | UGACUG GAC $ UC AUCA GA GUU UGCACUUGAG<br>antisense of *secY* (membrane protein essential for protein export), 60 nt from stop codon | 1 | — |
| 7 | 10 | AGUAAUUAC GCC $ UG AACA CA GGC<br>AUAAAGAAGUACAUAUGGU<br>not in GenBank | 1 | — |
| 8 | 11 | UAUUCUGGCUAUCUACA GCU $ CC AGCA GG AGC<br>UGGAGAUCAACGAUCCU<br>sense of *ebgR* (*ebg* (beta-galactosidase) repressor), 210 nt from start codon | 1 | — |
| 9 | 12 | UGAGUGCCGAAGAUCGUGAG CAG $ GG AACA CC<br>CUG AUUAUCC<br>not in GenBank | — | 1 |

The consensus binding site elements (FIG. 1A) are separate by spaces. The RNYA loop is in boldface, the buldged $ is VKDGRZ HG, the 2 nucleotide stem is double-underlined, and the 3 nucleotide stem is underlined. Isolate no. 1 is shown folded in FIG. 1d. "# copies" indicates in how many copies a particular isolate was found, out of the total 101 isolates sequenced in SELEX experiments 3 and 4, and out of 72 isolates in SELEX experiment 5 (FIG. 3).

TABLE 3

Matches found in *E. coli* genome to the structure of SELEX consensus MS2 CP binding site, using RNAMOT program.

| No. | SEQ ID NO: | Binding Site Location in E. coli genome |
|---|---|---|
| 1 | 13 | CCG $ CG ACCA CG CGG<br>antisense of *ybdH* (some similarity to glycerol dehydrogenates), 20 nt from start codon;<br>sense upstream of o386 (similarity to YJG0_YEAST, which is a hypothetical aminotrasferase), 130 nt from start codon |
| 2 | 14 | ACG $ CC AUCA GG CGU<br>antisense of *jltJ* (glutamate/aspartame transport system (membrane-bound) permeate protein GltJ), 90 nt from start codon;<br>antisense downstream of *ybeJ* 60 nt from stop codon |
| 3 | 15 | CUG $ CG AGCA CG CAG<br>antisense of ORF F486 (similarity to YC39_CYAPA), 400 nt from start codon |
| 4 | 16 | ACC $ GC ACCA GC GGU<br>antisense of *bglX* (periplasmic beta-glucosidase precursor), 660 nt from stop codon |
| 5 | 17 | GCC $ GC AACA GC GGC<br>antisense of *nuoN* (putative membrane protein, chain N of NADH dehydrogenate I (multisubunit membrane protein)), 740 nt from stop codon |
| 6 | 18 | UGC $ GC AGCA GC GCA<br>antisense of *nuoK* (putative membrane protein, chain K of NADH dehydrogenate I (multisubunit membrane protein)), 60 nt from stop codon, 230 nt from start codon |
| 7 | 19 | CCC $ GC AACA GC GGG<br>antisense of *yfcA* (potential integral membrane protein), 30 nt from start codon |
| 8 | 20 | CAC $ GCAUCA GC GUG<br>antisense of ORF f848 (similarity to PBPA_HAEIN, which is penicillin-binding protein 1A, potential inner membrane protein), 220 nt from stop codon |
| 9 | 21 | UGC $ GC AACA GCGCA<br>antisense of *mreD* (responsible for formation of the rod shape of *E. coli* cells, integral membrane protein), 50 nt from start codon |
| 10 | 22 | CUG $ GC AUCA GC CAG<br>sense of *rffG* ((dTDP-D-glucose 4,6 dehydratase; participates in formation of lipopolysaccharide in the bacterial outer membrane), 210 nt from start codon |
| 11 | 23 | GCC $ GC AACA GC GGC<br>antisense of *yigR*, 350 nt from start codon |
| 12 | 24 | GUG $ CC AACA GG CAC<br>antisense of *yhiN*, 250 nt from stop codon |
| 13 | 25 | GCC $ GC AGCA GC GGC<br>sense of *fic* (involved in cell division; filamentation and induction of a membrane protein in presence of cyclic AMP in mutant), 80 nt from start codon;<br>sense downstream of *yhfG*, 70 nt from stop codon |

TABLE 3-continued

Matches found in *E. coli* genome to the structure of SELEX consensus MS2 CP binding site, using RNAMOT program.

| SEQ ID NO: | Binding Site Location in E. coli genome |
|---|---|
| 14 | 26 <u>UGC</u> $ <u>CC</u> AUCA <u>GG</u> <u>GCA</u><br>antisense of *dacB* (penicillin-binding protein 4, DD-carboxypepidase 1B, cytoplasmic membrane protein), 110 nt from stop codon |
| 15 | 27 <u>UCC</u> $ <u>GC</u> ACCA <u>GC</u> <u>GGA</u><br>antisense of *agaZ* (putative tagatose 6-phosphate kinase), 80 nt from stop codon; sense upstream of *agaR* (putative transcriptional repressor of *aga* operon for N-acetylgalactosamine transport and metabolism), 330 nt from start codon |
| 16 | 28 <u>ACC</u> $ <u>GC</u> AUCA <u>GC</u> <u>GGU</u><br>antisense of *ygjT* (probable integral membrane protein), 340 nt from stop codon |
| 17 | 29 <u>GGC</u> $ <u>GG</u> AACA <u>CC</u> <u>GCC</u><br>antisense of o1025 (similarity to *acrF*, which is an integral membrane protein involved in cell division (cell envelope formation and multidrug resistance), 1330 nt from strat codon |
| 18 | 30 <u>UCG</u> $ <u>CC</u> ACCA <u>GG</u> <u>CGA</u><br>antisense of *topA* (alternate name *supX* DNA topoisomerase I, omega protein I), 600 nt from stop codon |
| 19 | 31 <u>UCC</u> $ <u>CC</u> AGCA <u>GG</u> <u>GGA</u><br>antisense of o356 (similarity to *lpfD* from the *S. typhimurium* fimbrial operon), 140 nt from stop codon;<br>antisense upstream of o180 (similarity to *fimI* from *S. typhimurium*, which is a fimbriate-related fibrin-like protein), 150 nt from start codon |
| 20 | 32 <u>GCC</u> $ <u>GC</u> AUCA <u>GC</u> <u>GGC</u><br>sense of *tesA* (alternate gene name *apeA*, acyl-CoA thioesterase I, periplasmic enzyme, involved in membrane lipid biosynthesis), 200 nt from start codon, 420 nt from stop codon;<br>antisense upstream of *ybbA* (hypothetical ABC transporter), 160 nt from start codon |
| 21 | 33 <u>GGC</u> $ <u>GC</u> AUCA <u>GC</u> <u>GCC</u><br>sense of *yagX* (similarity to *cfaC*, which is colonization factor antigen I fimbrial subunit C precursor, may serve as anchor for the fimbriate in the outer membrane), 1170 nt from stop codon |

The sites shown double-underlined and in boldface (9. 10 and 19) correspond to SELEX isolates 5, 1 and 3 in Table 1. The consensus binding site elements (FIG. 1E) are separated by spaces. The ANCA is in boldface, the bulged $ □ is VKDGRZHG the <u>2 nucleotide stem</u> is double-underlined, and the <u>3 nucleotide stem</u> is underlined.

TABLE 4

| | | SEQ ID NO: |
|---|---|---|
| Set One | | |
| 3'-ApTpTpApTpGpCpTpGpApGpTpGpApTpApTp<br>\|\|\|\|\|\|\|\|\|\|\|\|\|\|\|\|\|<br>5'-TpApApTpApCpGpApCpTpCpApCpTpApApGpGpA | 5G7 RC Linker<br><br>5'N7 | 34<br><br>35 |
| Set Two | | |
| 3'-ApTpTpApTpGpCpTpGpApGpTpGpApTpApTpCpCpCpTpCp<br>\|\|\|\|\|\|\|\|\|\|\|\|\|\|\|\|\|\|\|\|\|<br>5'-TpApApTpApCpGpApCpTpCpApCpTpApApGpGpGpApGpNpNpNpNpN-3'<br>5N7 Bridge | 5N7 Linker | 36<br><br>37 |

Bridge/Linker sequences used to ligate at the 3' end of truncated cDNA. Set two was used to constract the starting library only while set one

TABLE 5

| Starting DNA templates: | SEQ ID NO: |
|---|---|
| 40N7:<br>5'GGGAGGACGATGCGG[-40N-]CAGACGACTCGCCCGA 3' | 38 |
| 30N7:<br>5'GGGAGGACGATGCGG[-30N-]CAGACGACTCGCCCGA 3' | 39 |

SELEX PCR Primers:

TABLE 5-continued

| Starting DNA templates: | SEQ ID NO: |
|---|---|
| 5G7:<br>5'TAATACGACTCACTATAGGGAGGACGATGCGG 3' | 40 |
| 3G7:<br>5'TCGGGCGAGTCGTCTG 3' | 41 |

TABLE 6A

VEGF Truncation-by-hybridization SELEX

| SELEX-Rd | [P]¹, nM | [R]², nM | %B³ | S/N⁴ | PF⁵ | PB⁶ | Bf.Wsh⁷ | U.Wsh⁸ | Used⁹ |
|---|---|---|---|---|---|---|---|---|---|
| Rd1 | 0.200 | 1.00 | 64.0 | 85.0 | + | – | 20 ml | – | comb. |
|  | 0.040 | 0.20 | 22.5 | 25.0 | + | – | 20 ml | – |  |
|  | 0.008 | 0.04 | 5.0 | 5.50 | + | – | 20 ml | – |  |
| Rd2 | 0.040 | 0.20 | 77.0 | 37.50 | + | – | 20 ml | – | comb. |
|  | 0.008 | 0.04 | 75.0 | 18.00 | + | – | 20 ml | – |  |

¹Protein concentration in nanomolar
²RNA concentration in nanomolar
³Bound RNA expressed as % of max
⁴Signal to noise
⁵Use of nitrocellulose prefiltered RNA
⁶Use of preblocked nitrocellulose with BSA
⁷Volume in ml of buffer wash
⁸Volume in ml of 0.5 M urea wash (– indicates no urea wash)
⁹Pool carried forward to the next round (comb. means that the pools were combined before taken to the next round)

TABLE 6B

TGFβ1 Truncation-by-hybridization SELEX

| SELEX-Rd | [P]¹, nM | [R]², nM | %B³ | S/N⁴ | PF⁵ | PB⁶ | Bf.Wsh⁷ | U.Wsh⁸ | Used⁹ |
|---|---|---|---|---|---|---|---|---|---|
| 40N-Rd1 | 1.0 | 5.0 | 1.9 | 18.70 | + | + | 5 ml | 10 ml | comb. |
|  | 0.3 | 1.5 | 1.5 | 9.00 | + | + | 5 ml | 10 ml |  |
| 40N-Rd2 | 1.0 | 5.0 | 4.8 | 14.73 | + | + | 10 ml | 5 ml | comb. |
|  | 0.3 | 1.5 | 4.4 | 34.75 | + | + | 10 ml | 5 ml |  |
| 40N-Rd3 | 0.3 | 1.5 | 4.0 | 8.00 | + | + | 10 ml | 5 ml |  |
| 40N-Rd4 | 0.3 | 1.5 | 3.0 | 1.50 | + | + | 10 ml | 5 ml | stopped |
|  | 0.1 | 0.5 | 2.0 | 3.30 | + | + | 10 ml | 5 ml |  |

¹Protein concentration in nanomolar
²RNA concentration in nanomolar
³Bound RNA expressed as % of max
⁴Signal to noise
⁵Use of nitrocellulose prefiltered RNA
⁶Use of preblocked nitrocellulose with BSA
⁷Volume in ml of buffer wash
⁸Volume in ml of 0.5 M urea wash
⁹Pool carried forward to the next round (comb. means that the pools were combined before taken to the next round)

TABLE 6C

VEGF Truncation-by-ligation SELEX

| SELEX-Rd | [P]¹, nM | [R]², nM | %B³ | S/N⁴ | PF⁵ | PB⁶ | Bf.Wsh⁷ | U.Wsh⁸ | Used⁹ |
|---|---|---|---|---|---|---|---|---|---|
| Rd1 | 0.2000 | 1.000 | 37.0 | 32 | – | + | 8 ml | – | yes |
|  | 0.0400 | 0.200 | 18.5 | 26 | – | + | 8 ml | – | yes |
|  | 0.0080 | 0.040 | 4.0 | 80 | – | + | 8 ml | – | no |
| Rd2 | 0.2000 | 1.000 | 108.5 | 166 | – | + | 25 ml | – | no |
|  | 0.0400 | 0.200 | 65.5 | 98 | – | + | 25 ml | – | yes |
|  | 0.0080 | 0.040 | 15.5 | ND¹⁰ | – | + | 25 ml | – | no |
| Rd3 | 0.2000 | 1.000 | 103.5 | 192 | – | + | 25 ml | – | – |
|  | 0.0400 | 0.200 | 92.0 | 204 | – | + | 25 ml | – | – |
|  | 0.0080 | 0.040 | 21.0 | 51 | – | + | 25 ml | – | – |
|  | 0.0016 | 0.008 | 6.0 | 10 | – | + | 25 ml | – | – |

¹Protein concentration in nanomolar
²RNA concentration in nanomolar

TABLE 6C-continued

VEGF Truncation-by-ligation SELEX

| SELEX-Rd | [P]¹, nM | [R]², nM | %B³ | S/N⁴ | PF⁵ | PB⁶ | Bf.Wsh⁷ | U.Wsh⁸ | Used⁹ |
|---|---|---|---|---|---|---|---|---|---|

³Bound RNA expressed as % of max
⁴Signal to noise
⁵Use of nitrocellulose prefiltered RNA
⁶Use of preblocked nitrocellulose with BSA
⁷Volume in ml of buffer wash
⁸Volume in ml of 0.5 M urea wash
⁹Pool carried forward to the next round (comb. means that the pools were combined before taken to the next round)
¹⁰Not determined

TABLE 6D

TGFβ1 Truncation-by-ligation SELEX

| SELEX-Rd | [P]¹, nM | [R]², nM | %B³ | S/N⁴ | PF⁵ | PB⁶ | Bf.Wsh⁷ | U.Wsh⁸ | Used⁹ |
|---|---|---|---|---|---|---|---|---|---|
| 40N-Rd1 | 1.000 | 5.000 | 3.75 | 2.1 | − | 10 ml | 10 ml | − | yes |
|  | 0.330 | 1.650 | 2.30 | 1.2 | − | 10 ml | 10 ml | − | no |
|  | 0.110 | 0.550 | 0.30 | <1.0 | − | 10 ml | 10 ml | − | no |
| 40N-Rd2 | 1.000 | 5.000 | 10.40 | 3.3 | + | 2 ml | 10 ml | − | yes |
|  | 0.330 | 1.650 | 4.20 | 1.4 | + | 2 ml | 10 ml | − | no |
|  | 0.110 | 0.550 | 0.25 | 1.0 | + | 2 ml | 10 ml | − | no |
| 40N-Rd3 | 0.330 | 1.650 | 4.50 | 2.2 | + | 2 ml | 10 ml | − | yes |
|  | 0.110 | 0.550 | 1.80 | 1.4 | + | 2 ml | 10 ml | − | no |
|  | 0.033 | 0.165 | 0.30 | 1.1 | + | 2 ml | 10 ml | − | no |
| 40N-Rd4 | 0.330 | 1.000 | 11.20 | 29.1 | + | 2 ml | 10 ml | − |  |
|  | 0.110 | 0.330 | 5.50 | 13.5 | + | 2 ml | 10 ml | − |  |
|  | 0.033 | 0.100 | 1.80 | 5.5 | + | 2 ml | 10 ml | − |  |
| 30N-Rd1 | 1.000 | 5.000 | 2.00 | 6.8 | − | 10 ml | 10 ml | − | yes |
|  | 0.330 | 1.650 | 1.00 | 3.5 | − | 10 ml | 10 ml | − | yes |
|  | 0.110 | 0.550 | 0.30 | 1.1 | − | 10 ml | 10 ml | − | no |
| 30N-Rd2 | 1.000 | 5.000 | 32.50 | -### | + | 2 ml | 10 ml | − | yes |
|  | 0.330 | 1.650 | 22.00 | 3.7 | + | 2 ml | 10 ml | − | no |
|  | 0.110 | 0.550 | 9.00 | 3.1 | + | 2 ml | 10 ml | − | no |
| 30N-Rd3 | 0.330 | 1.650 | 34.00 | 13 | + | 2 ml | 10 ml | − | no |
|  | 0.110 | 0.550 | 15.00 | 4.5 | + | 2 ml | 10 ml | − | yes |
|  | 0.033 | 0.165 | 6.20 | 3.5 | + | 2 ml | 10 ml | − | yes |
| 30N-Rd4 | 0.330 | 1.650 | 15.25 | 25.0 | + | 2 ml | 10 ml | − | − |
|  | 0.110 | 0.550 | 7.00 | 11.0 | + | 2 ml | 10 ml | − | − |
|  | 0.033 | 0.165 | 2.00 | 3.0 | + | 2 ml | 10 ml | − | − |

¹Protein concentration in nanomolar
²RNA concentration in nanomolar
³Bound RNA expressed as % of max
⁴Signal to noise
⁵Use of nitrocellulose prefiltered RNA
⁶Use of preblocked nitrocellulose with BSA
⁷Volume in ml of buffer wash
⁸Volume in ml of 0.5 M urea wash
⁹Pool carried forward to the next round (comb. means that the pools were combined before taken to the next round)
¹⁰Not determined

TABLE 7

|  | SEQ ID NO: |
|---|---|
| 5H7: |  |
| 5'BBBccgcAUCGUCCUCCC 3' | 42 |
| 3H7: |  |
| 5'BBBUCGGGCGAGUCGtctg 3' | 43 |

B is biotin. A, G, C, and U are 2'-O-methyl-2'deoxy-ribo-adenosine, -guanosine, -cytidine, or -uridine, respectively, while a, g, c, and t are 2-deoxy-ribo- adenosine, -guanosine, -cytidine, or -thymidine, respectively.

TABLE 8

Short PCR Templates and Primers

| Starting DNA templates: | SEQ ID NO: |
|---|---|
| 30NTR: |  |
| 5'GGGAG[-30N-] CGGGCGGG 3' | 44 |
| 30NTR: |  |
| 5'GGGAG[-27N-] CGGGCGGG 3' | 45 |
| SELEX PCR Primers: |  |
| 5GTR: |  |
| 5'TAATACGACTCACTATAGGGAG'3' | 46 |
| 3GTR: |  |
| 5'CCCGCCCG 3' | 47 |

TABLE 9

Sequence of isolated ligands from VEGF Rd1 Truncation SELEX by hybridization

| Ligand | Sequence | Phenotype | SEQ ID NO: |
|---|---|---|---|
| Family 1 | | | |
| 13a | UUGAAGAAUUGGGCGCAUGUUCUCCGUCCU | 1 | 48 |
| 18 | AAACGGAAGUAUUGGAUACAUAAGCACCCCU | | 49 |
| 9 | CAGGAUUUUGGAAGAAUUGGAUAUUGGCCU | 2 | 50 |
| 20 | CUUAAGUUUUGGAAGAAUUGGAAUACUGGGU | 4 | 51 |
| 10,16b | UGAAACGGAAGAAUUGGAAACAUUGCUCGU | 4 | 52 |
| 14a | GAAACGGAAGAAUUGGAUACUCGCUGUGGU | | 53 |
| 4b | AGACUUUGGAAGAAUUGAAUUUGUCCGUGU | 2 | 54 |
| 15b,19 | ACAUGUAGGAAGAAUUGGAAGAUGCCGCGU | 2 | 55 |
| 5a | UAGGAAGUAUUGUAAGUGUGUUGUCCUCGU | 1 | 56 |
| 2b | ggAAGAAUUGAUACGAUCGUCCAUCUACUCCU | 1 | 57 |
| Family 3 | | | |
| 2a,23 (VT30.3) | AGAAUCAGUGAAUGCUUAUAAAUCUCGUGU | 4 | 58 |
| 3a (VT30.1) | AACUAGUGAAUGCUUAUACGACCGUGUUGU | 2 | 59 |
| 5b | AAUCAGUGAACGCUUAUAGCUCUGCAUGGU | 1 | 60 |
| 7 | AUCAGUGAAUGCUUACAAACCGUGUGUCCC | 1 | 61 |
| 22 | CUUUUUCUGAAUCAGUGAAUGCUUAGUGCU | 1 | 62 |
| Orphans | | | |
| 1 | AGCUAGGUGAAUGCCGAUAUUCUCUUCCGU | 4 | 63 |
| 21b | UACUAGGUGAAUGCCGAUAAUCUUAUCCGU | 3 | 64 |
| 11 | AUGGAAGUAUUGAGCCGAUUGUCAUCUCCC | 1 | 65 |
| 15a | UCUUUGGGUUUUUGCCAACGGUUUUCGCC | | 66 |
| 14b | UCGAUCGCUUAUUUUCUCGGUCAUCUCCC | | 67 |
| 4a | AAACGGAACUUCUUGGAUACAUCUGCUCGU | 3 | 68 |
| 3b | UUGAAUAUUUCUCGGUCGUGAUUCCCGCCU | 5 | 69 |
| 6 | AUUUGGAUGCAUGUCAAGGCGUUUUGCCCU | 4 | 70 |
| 13b,21a | UGUUGAUCGAGAUUUAAUCUAUUUCCACGU | 3 | 71 |
| 16a | UGAUCGAUUUCCUGGUCUGUUCUCCCUCCU | 5 | 73 |
| 12 | AUCAGUAUUGGCUGCUUCUAUUCCUCUGGU | | 74 |
| 24 | AAGGCGACUUGUAUGUGAUUCAGUAUUGGU | 2 | 75 |

Sequence shown is only from the random region of the molecules. Identical sequences are indicate by additional designation numbers. Ligands that were also found in the first SELEX experiment (Ruckman et al., J. Biol. Chem. 273:20556-67, 1998) are shown by paraenthases with their designation from the first SELEX experiment. Phenotypes were classified according to five groups as follows: (1) Molecules that lose significant affinity for VEGF upon removal of their fixed sequences; (2) Molecules with affinities for VEGF somewhat affected (positively or negatively) upon removal of their fixed sequences; (3) Molecules that gain significant affinity for VEGF upon removal of their fixed sequences; (4) Molecules with affinites for VEGF not affected upon removal of their fixed sequences;and (5) Non-binding ligands either with or without fixed sequences.

TABLE 10

Sequence of isolated ligands from VEGF Rd1-ct Truncation SELEX by hybridization

| Ligand | Sequence | Phenotype | SEQ ID NO: |
|---|---|---|---|
| Family 1 | | | |
| 34,36a | UGAAACGGAAGAAUUGGAAACAUUGCUCGU | 1 | 52 |
| 31a | AUUUGGAAGAAUUGGAUUUAGCACGUCCCU | | 75 |
| 36b | GAACGGAAGAAUUGGAUACGCUAGCAUGGU | | 76 |
| 38 | UAAACGGAAGAAUUGGAACAUUGCUCGU | 4 | 77 |
| 44 | CUUAAGUUUUGGAAGAAUUGAAUACUGGGU | 2 | 51 |
| Family 3 | | | |
| 26 | AAACCAGUGAAUGCUUAUCGGAUCCGUUGU | 4 | 78 |
| 27,33 | AAAUCAGUGAAUGCUUAUAGUUUCUCGCGU | 2 | 79 |
| 32 | AAUCAGUGAAUGCUUAGAAAUCCACACCGU | 2 | 80 |
| 39 | AUCAGUGAAUGCUUACAAACCGUGUGUCCU | 1 | 81 |

TABLE 10-continued

Sequence of isolated ligands from VEGF Rd1-ct Truncation SELEX by hybridization

| Ligand | Sequence | Phenotype | SEQ ID NO: |
|---|---|---|---|
| 41a | AAUCAGUGAAUGCUUAGAAAUCCACACCGU | | 82 |
| 45 | GGAAAUCAGUGAAUGCUUAUACCUUCGCCU | 1 | 83 |
| Orphans | | | |
| 25 | AUAACAGAAUUUUUGGAGAACAAGUGUCGU | 1 | 84 |
| 35 | AAAUUGACUAGUUUCGGUCUUCUACCCCCU | 1 | 85 |
| 28 | UUGAAAUUUCUCGGUCUUUCUCUCCCUCCU | 1 | 86 |
| 29 | UGUAGAGGUUUUGACUUUUCCCUUUUCCGU | 2 | 87 |
| 31b,41b,42b | UUGCACUUCUCGAUUGUUCUCCUGUCCU | | 88 |
| 48 | UUGAUCGGACGUUAGUCAUUUCCCGAUCGU | | 89 |
| 42a | UUGAUCGACUUUCCUGAUCUUCUCCUCCU | | 90 |
| 43 | GAUCACGAACAUUUUGACGAUUUUCCUCCC | 1 | 91 |
| 46 | ACACUGGUUCCGAAGUAUUGUCUUUGUCCU | 1 | 92 |
| 47 | GGGUUAUUGGGCGUCAACAUUCUUUUCACGUC | | 93 |

Sequence shown is only from the random region of the molecules. Identical sequences are indicate by additional designation numbers. Phenotypes were classified according to five groups as follows: (1) Molecules that lose significant affinity for VEGF upon removal of their fixed sequences; (2) Molecules with affinities for VEGF somewhat affected (positively or negatively) upon removal of their fixed sequences; (3) Molecules that gain significant affinity for VEGF upon removal of their fixed sequences; (4) Molecules with affinites for VEGF not affected upon removal of their fixed sequences; and (5) Non-binding ligands either with or without fixed sequences.

TABLE 11

Sequence of isolated ligands from TGFβ1 Rd2 Truncation SELEX by hybridization

| Ligand | Sequence | Kd (Nm) | Plateau | SEQ ID NO: |
|---|---|---|---|---|
| Family 1 | | | | |
| *2,7,44 | GGUGCCUGUAGUCUUUGCAUCUUAUAAAUGCAAUCUGCCC | 4.0 | 10% | 94 |
| *18 | GGUGCCUUUAGUCUUUGCAUCUUAUAAAUGCAAUCUGCCC | 0.2 | 5% | 95 |
| Family 2 | | | | |
| 62 | UAGUGAUGAAUUUUUGCUGGAUCUGGUUUUGAACCGUCCC | NB | | 96 |
| 20 | UAGUGACGAAUUUUUGCUGGAUCUGGUUUUGAACCGUCCC | NB | | 97 |
| 3 | UAGUGAUGAACUUUUGCUGGAUCUGGUUUUGAGCCGUCCC | NB | | 98 |
| 16 | UAGUGAUGAACUUUUGCUGGAU UGGUUUUGAACCGUCCC | NB | | 99 |
| Family 3 | | | | |
| 51 | AUCUGAAUUUAUUCGUCUACAGUUAC GCUGGGCCUUCCG | 0.3 | 10% | 100 |
| 41 | AUCUGAAUUUAUUCGUCUACAGUUACGGCUGGGCCUUCCG | 0.6 | 10% | 101 |
| *1,12 | AUCUGAAUUUAUUCGUCUACAGUUACAGCUGGGCCUUCCG | 1.0 | 10% | 102 |
| Family 4 | | | | |
| 14,43a,71 | AUGCCUUUUGCCUUCAGGGUGUGAUUCCUUGAUCUGUCCG | 0.6 | 5% | 103 |
| *70 | GUGCCUUUUGCCUAGGUUGUGAUUUGUAACCUUCUGCC | 0.2 | 25% | 104 |
| Family 5 | | | | |
| 33 | UUAGUUCGGGCUCAACACCGCUAAUAUUCUUCGUUCCCC | NB | | 105 |
| 22,28 | UUAGUUCGGGCUCAACACCGCUAAGAUUCUUCGUUCCCC | NB | | 106 |
| 49 | UUAGGUCGGGCUCAACACCGCUAAAAAAUUCUUCGUUCCCC | NB | | 107 |
| Family 6 | | | | |
| *29 | UGCCUUUAGUCUGAAUCUUACCAUGAUUCUCUGCCG | 0.8 | 10% | 108 |
| 39 | UGCCUU AGCAUGAAUAUACUGAUGUAUAUUCUCUGCCC | NB | | 109 |
| 60 | UGCCUUUAGCCUG AUAUGCGUUUCGUGUAUAUCUCUGCCG | | | 110 |
| Family 7 | | | | |
| 50 | GACGUAGCGGGAUGCUUUAACUUUGAUCGUCCAUCAUGUG | NB | | 111 |
| 53 | GAUGUAGCGGGAUGCUUUAACUUUGAUCGUCCACCAUGUG | NB | | 112 |

TABLE 11-continued

Sequence of isolated ligands from TGFβ1 Rd2 Truncation SELEX by hybridization

| Ligand | Sequence | Kd (Nm) | Plateau | SEQ ID NO: |
|---|---|---|---|---|
| Family 8 | | | | |
| 66 | AGUUUCAGGAUAUGUUGUGUGGUCGUUCUUUUUCCUCCC | NB | | 113 |
| 32 | AUCUGGGUGACCUCUGUGUACGUUUAUUUUUACCGACCC | NB | | 114 |
| *56 | AAGGCAAGAAGCUUUAUGUGUCGCGUAACACAACUGUCCG | 4.0 | 30% | 115 |
| 40 | AGUUUUGGGAUCGCCACAGAUCUUACUGUGAGCUACUGUG | 3.0 | 5% | 116 |
| *59 | UCUUUCGAACUCGGAAUUUUUGGUGUAGCCGUAUGCC | 0.5 | 40% | 117 |
| *31 | AAGACCGUUCCGAGUGGUACAAGUAAACCCCUGUGUUCCG | 2.0 | 60% | 118 |
| Family 9 | (nitrocellulose binders) | | | |
| 46 | GUUUCUCUUUCACAUUUUUUUUUUUUUUUCACUUCCC | | | 119 |
| 54 | GAUAGGUUUUUUUCUAGGUUUUUUUUUUCAGUGUCCC | | | 120 |
| 65 | CGUUGUUUUUCUUUAUUUUUUGUUCUUUUGGUUGGC | | | 121 |
| 61 | UGACCACAUUUAUUUUUUCUUCUUACCUCCUUUGGUCCC | | | 122 |
| 63 | UCUUCAUCUGUGUUUUUAUCUCUCUCUUCUCACGCUCCC | | | 123 |
| 48 | CCUAAGCUUCCUUUUAUUUUUUUCUUCUUUAAUUUCCUGGGC | | | 124 |
| 6 | CUCUUUUCUUUAUGUUUUUUUCUUUUUUUCUUGUCCCCC | | | 125 |
| 13 | UCCCAUCAUCCAAGCGUGAUACUUUUUUUUUCCCCUCCC | | | 126 |
| 69 | GACCUUUUUUUCUUGCUUUUCUUUUUGCCUUUCCGUCCC | | | 127 |
| 19 | UUUCGUUUUCUUUAUCUUUUUUCUCGUUUUUUGCCCC | | | 128 |
| 30 | UUAAUUUCAUAUUUUUUUUUUUCUUUUUCCCUAACGUGGC | | | 129 |
| 36 | UCCCUAUCACAACUUUGUUUUCUUUUAUUUUUCUCUUCGC | | | 130 |
| 38 | GNNCUGGGUUCNACUUUNCAUAUUUGUNUUUUUU | | | 131 |
| 24 | GACGUUGUGUUUACUGAUUUCUUUUUCUUUUUUCCGCCUG | | | 132 |
| 37 | CACUAGUCAUUUUCUAUCUUUCUUUUUCUCCCUUGUGCCC | | | 133 |
| 25 | ACUGGGUUUAUUCUUCUUUUUUCUUGUUCCUACCACCCCC | | | 134 |
| 45 | AUCCUCUUGUCAUAGAUCGUUUGUUUUGUUUUUGUACCG | | | 135 |
| 10 | UCUUUUCUCUGUUCCUUUUGUUUUUUCCCUGUACUCCC | | | 136 |
| 58 | UCCUUUGGUUUUAGUUGUUAUUGUUUUUUCCUUUUGUGUCGC | | | 137 |
| 57 | CGACCAUUUAUUUCUCUUAUCAUUCUUUUUCUCCCUAUCGC | | | 138 |
| 15 | UCGUCGGAUUCUCUAUGUUUUUGUUUUCAUUUCUUCCCCC | | | 139 |
| 73 | UCGAACUAUUACUCUUUUAUUAUUCCUUAAUUUUUGCCGC | | | 140 |
| 4 | AUUGAGGGUUUCUUUUUCGUCUUUUUCCUUUCCCUCUCCC | | | 141 |
| 47 | UUCCGGUCUUUUCUUGUGUUUAUGUUUCUUUCUGUUGCC | | | 142 |
| 5 | GGACAUAUUUCUUCUUCUUCCUCUGCUUUUUGUUGUCCC | | | 143 |
| 55 | GUACUUGCUUCUCUACUAUUUUCUCCUCAUUCCCCUGUG | | | 144 |
| 72 | UUCUUCGUUUCUUUCUCUCUCUUUCUAGCCGUCCUUCGCCCC | | | 145 |
| 64 | CUCAGUUUAUAUGACACUUCACUUCUUUUCGUUUUACCG | | | 146 |
| 42 | UGCGACAUUAUUUAAUUUUCUCCCUUCCUUUCAUCGUGCC | | | 147 |
| Orphans | | | | |
| 34 | CAGCUCACUUAUAUUUCCGUCCAAUUCCUUCUUUACUGCC | NB | | 148 |
| *52 | UGUCUUUAGCCUACAGUUGACUGUUCAAUUGUUCUGCC | 1.0 | 30% | 149 |
| 23 | UGUUUGUGCUACGACCUACAUUCGUUGGAAUGUUCUGCC | 0.4 | 10% | 150 |
| *67 | AUCACUAGGCUCAUUUGUGAGCCGUUAUUCCUUGACUC | 0.1 | 8% | 151 |
| 11 | AGUGAAUUGCAUCCUUCGAUUACCUACUCUUUUGUGCCC | NB | | 152 |
| 43b | GGAGGGAAAUGAAAUGACAAGAACGAGACUAAGAUGGGA | | | 153 |
| 27 | UUGUUCCG | | | 154 |
| 35 | NUCUUNUUCCCUCNANUGUCCC | | | 155 |
| 26 | CNUAA | | | 156 |
| 68 | GGUGUNUUU | | | 157 |

Sequence shown is only from the random region of the molecules. Identical sequences are indicate by additional designation numbers. Ligand affinities were determined by nitrocellulose filter binding following removal of fixed sequences and are indicated by Kd and plateaue values obtained. NB indincate ligands unable to bind the target under the experimental conditions used. Stars (*) indicates repeats of binding experiments where we are showing the best determined values for Kds and plateaues.

TABLE 12

Sequence of Rd12 VT30 ligands tested for binding without fixed sequences

| Ligand | Sequence of Random Region 5'gggaggacgaugcgg [Random Region] cagacgacucgcccga | Phenotype | SEQ ID NO: 158 |
|---|---|---|---|
| Family 1 | | | |
| VT30.20 | AAACGGAAGAAUUGGAUACCGCUACGUGUU | 1 | 159 |
| VT30.7 | UAACCAGUGGAAGAAUUGGCUGCUAUCCU | 2 | 160 |
| VT30.4 | CUUAAGUUUUGGAAGAAUUGAAUACUGGGU | 1 | 161 |
| VT30.53 | AGCUAACGGAAGAAUUGGAAACAACCGCGU | 2 | 162 |
| Family 2 | | | |
| VT30.9,14,34, 37,48,50 | UCAACCGGUUGAAUAUUUGGUCGCUGACCU | 4 | 163 |
| Family 3 | | | |
| VT30.1,25 | AACUAGUGAAUGCUUAUACGACCGUGUUGU | 1 | 164 |
| VT30.21 | AUCAGUGAAUGCUUAUAGACCGUAUUGCGU | 1 | 165 |
| VT30.3,5,16, 31,36,43 | AGAAUCAGUGAAUGCUUAUAAAUCUCGUGU | 2 | 166 |
| VT30.44 | cggAAUCAGUGAAUGCUUAUACAUCCGCUCGGU | 1 | 167 |
| VT30.15 | AACCAGUGAAUGCUUAUAAGACUGCUCGU | 1 | 168 |
| VT30.29 | AAUCAGUGAAUGCUUAUAGCUCCGCGUGGU | 1 | 169 |
| VT30.35 | ACCAGUGAAUGCUUAUAAGCCCAUCGACCU | 1 | 170 |
| VT30.45 | AAUCAGUGAAUGCUUAUAGCUCCGNGUCCU | 1 | 171 |
| Orphans | | | |
| VT30.12,30,39,46 | UCUUUGGGUUUUUGCCAACGGUUUUUCGCU | 2 | 172 |
| VT30.40 | AUUUGGAUGCAUGUCAAGGCGUUUUGCCCU | 2 | 173 |

Sequence information shown is from published work (Ruckman et al., J. Biol. Chem. 273:20556–67, 1998). Sequence shown is only from the random region of the molecules except for VT30.44 where the required for binding portion of the 5' fixed sequence is also shown in lower case. Identical sequences are indicated by additional designation numbers. Phenotypes were determined by filter binding and were classified according to five groups as follows: (1) molecules that lose significant affinity for VEGF upon removal of their fixed sequences; (2) molecules with affinities for VEGF somewhat affected (positively or negatively) upon removal of their fixed sequences; (3) molecules that gain significant affinity for VEGF upon removal of their fixed sequences; (4) molecules with affinities for VEGF not affected upon removal of their fixed sequences; and (5) Non-binding ligands either with or without fixed sequences.

TABLE 13

| | | | SEQ ID NO: |
|---|---|---|---|
| 3G7RC | 5' | pCAGACGACTCGCCCGABBB | 174 |
| 3G7RCD | 5' | pGACGACTCGCCCGABBB | 175 |
| 3G7R6 | 5' | TCGGGCGAGTCGTCTGNNNNNN | 176 |
| 3LBsmC | 5' | pCGCATTCTCCCTTTABBB | 177 |
| 3LBsm | 5' | GGAGAATGCGNNNNNN | 178 |

TABLE 14

Sequence of isolated ligands from VEGF 5' Truncated Starting Pool

| Ligand | Sequence of Random Region 5'gggag [Random Region] cagacgacucgcccga | Phenotype | SEQ ID NO: 179 |
|---|---|---|---|
| Family 1 | | | |
| T1-26 | UGUGAAACGGAAGAAUUGGAAACAUUGCUCGUCA | | 180 |
| T1-19 | CUGGCUUAAGUUUUGGAAGAAUUGAAUACUGGGUCA | 4 | 181 |
| T1-47 | UGGAAGAAUUGGAUAUAUCGUUCGUUUUCCGGUCA | | 182 |
| T1-21 | UUGGAAGAAUUGAUACGAUCGUCCAUCUACUCUUCAG | 1 | 183 |
| T1-11 | GAAGAAUUGGAAACAUUGCUCGU | 5 | 184 |
| Family 2 | | | |
| T1-22 | UGGUCAACCGGUUGAAUAUUUGGUCGCUGACCUA | 1 | 185 |
| Family 3 | | | |
| T1-49 | CGGAAAUUAGUGAAUGCUUAUAACUUCCACGGUCA | | 186 |

TABLE 14-continued

Sequence of isolated ligands from VEGF 5' Truncated Starting Pool

| Ligand | Sequence of Random Region 5'gggag [Random Region] cagacgacucgcccga | Phenotype | SEQ ID NO: 179 |
|---|---|---|---|
| T1-7 | GGACUAGGUGAAUGCCGUUAUUCUUCCUGUCA | 3 | 187 |
| T1-30 | GGGGACUAGGUGAAUGCCAAUAUUCUUCUCCGUC | | 188 |
| T1-39-1 | GGGGACUAGGUGAAUGCCAAUAUUCUUCUCCGUCA | | 189 |
| T1-50 | CUAGGGACUAGGUGAAUGCCAAUAUUCUUCUCCGUCA* | | 190 |
| T1-1 | CGGACGACCUGGUGAAUGCCAAUAUACUUUUCGCGUCA | 5 | 191 |
| T1-38 | GCCCUCAGGUACUCGGUGAAUGCCAUUAUGCUUGCCCU | | 192 |
| T1-15 | GGGGGGGGAGUGAAUGCUUAUUAGAUCUGCCGUCA | 5 | 193 |
| T1-5 | GGUGAAUGCCAACGAUUUUAUCGCCUAUCGUCA | 5 | 194 |
| T1-42-1 | CUGGUGAAUGCCAACGAUUUUAUCGCCUAUC | | 195 |

Family 4

| T1-13 | CAGACGACUCGCCCGACAGACCACUCGCCCGA* | 5 | 196 |
| T1-3 | CAGACGACUCGCCCGAGGAGGAGGGGGG* | 5 | 197 |
| T1-2 | ACCACCAGACGACUCGCCCGAACGCUUAUCCUCUGGU* | 5 | 198 |
| T1-4 | GCCAGACGACUCGCCCGAGGAUACACAUCGUGUGGU* | 5 | 199 |
| T1-29 | AUAGGCAGACGACUCGCCCGAGGAAACAUUGCUCGU* | | 200 |
| T1-41 | CAGACGACUCGCCCGACAGACAACUCGCCC* | | 201 |
| T1-53 | GCCAGACGACUCGCCCGAUUGAAUUUGUCCGUGU* | | 202 |
| T1-54 | CAGACGACUCGCCCGACAGACGACUC* | | 203 |
| T1-44 | UGCAUCAGACGACUCGCCCGACAACACUCGCCCGA* | | 204 |
| T1-55 | GGGGCCAGACGACUCGCCCGACAGACGACUC* | | 205 |
| T1-42-2 | NGCAGCAGACGACUCGCCCGACAGACGAUCGCCCGA | | 206 |

Orphans

| T1-9 | GUCUUCGAAUCAGUAAAUGCUUAGCGCUCGU* | 1 | 207 |
| T1-17 | AGAGGUUUCAGUAUUGGCAUCGCGUUUGUCCUCA* | 1 | 208 |
| T1-18 | CUAGUUGAUCGAUUUCCUGAUGUCCUUUCCUCCUCA* | 1 | 209 |
| T1-23 | GAAUGGAUACUCGCUGUGGUUCUUCCCCCU* | | 210 |
| T1-37 | GCAUUGACUAGGCUAGGCUUCUCUUUUCCCCA* | | 211 |
| T1-25 | UGAUCAAAAGUGGAUUCUUCGUUUUUCCCCCCCA* | | 212 |
| T1-28, 31 | UAGUUGACUUUUCCCGAUUAUCCUCUCGUGCCUCA* | | 213 |
| T1-36 | GUGGACACUGGUUCCGAAGUAUUGUCUUUGUCCU* | | 214 |
| T1-39-2 | CGUGACAUUUCUCGAUCGUAAUACCUCCCCCU | | 215 |
| T1-43 | UUCCGGUUUGGCAUUCUUCGUCUCCCUCA* | | 216 |
| T1-48 | UGGUUGGCACUUCUCGAUUGUUCUCCUGUCCUCA* | | 217 |
| T1-35 | CAGGUGUNGCACAUGGUGCUG* | | 218 |
| T1-40 | GGGGAGGACGAUGCG | | 219 |
| T1-16 | GUCUC* | 5 | 220 |
| T1-34 | CGCUG* | | 221 |

Sequence shown is only from the random region of the molecules. All ligands start with 5'GGGAG except T1-37 and T1-35 which start with 5'GGGAT and 5'GGGA, respectively. Identical sequences are indicate by additional designation numbers. Phenotypes were classified according to five groups as follows: (1) Molecules that lose significant affinity for VEGF upon removal of their fixed sequences; (2) Molecules with affinities for VEGF somewhat affected (positively or negatively) upon removal of their fixed sequences; (3) Molecules that gain significant affinity for VEGF upon removal of their fixed sequences; (4) Molecules with affinities for VEGF not affected upon removal of their fixed sequences; and (5) Non-binding ligands either with or without fixed sequences. Stars (*) indicate repeats of binding experiments.

TABLE 15

Sequence of isolated ligands from VEGF Rd1 Truncation SELEX by Ligation.

| Ligand | Sequence of Random Region 5'gggag [Random Region] cagacgacucgcccga | Phenotype | SEQ ID NO: 179 |
|---|---|---|---|
| Family 1 | | | |
| T2-2 | CUGGAAACGGAAGUAUUGGAUACAUAAGCAUCCCCACA | 2 | 222 |
| T2-6 | GGAGACUUUGGAAGAAUUGAAUUUGUCCGUGUCACA | 3 | 223 |
| T2-7 | GAAACGGAAGAAUUGGAAAACACCCGUC | 2 | 224 |
| T2-14 | GGAGACUUUGGAAGAAUUGAAUUUGUCCGCGUCA | | 225 |
| T2-20 | GGGAGGAAACGGAAGAAUUGGAAAACACCCGUCAGCA | 2 | 226 |
| T2-21 | GGUGAUGCAGUGGAAGAAUUGGUUGCAGCCGUCACA | 3 | 227 |
| T2-24-1 | UGGUGAAACGGAAGAAUUGGAAACAUUGCUCGUCCA | | 228 |
| T2-24-3 | GGCUAGUAGGAAGAAUUGUAAGCUGCCUCGUGCA | | 229 |

TABLE 15-continued

Sequence of isolated ligands from VEGF Rd1 Truncation SELEX by Ligation.

| Ligand | Sequence of Random Region<br>5'gggag [Random Region] cagacgacucgcccga | Phenotype | SEQ ID NO: 179 |
|---|---|---|---|
| Family 2 | | | |
| T2-9 | CGGGGAUAACAGAAUUCUUGGUGAACAACCGGUCACA | 3 | 230 |
| T2-5 | UGGUCAACCGGUUGAAUAUUUGGUCGCUGACCUCA | 3 | 231 |
| T2-24-2 | UGGUCAACCGGUUGAAUAUUUGGUCGCAGAC | | 232 |
| T2-16 | GGGUCAACCGGUUGAAUAUUUGGUCGCUGACCUCACA | 233 | |
| Family 3 | | | |
| T2-1 | GGCGAAUCAGUGAAUGCUUAAUGCUCGUCGGUCACA | 3 | 234 |
| T2-4 (VT30.3) | UCUGGAGAAUCAGUGAAUGCUUAUAAAUCUGUGUCCA | 3 | 235 |
| T2-10 | GGGACCGGGUGAAUGCCAAUGUACUUUUCGCGUCCA | 3 | 236 |
| T2-15 | GGUACCUAGGUGAAUGCCGUUAUUCUGUUGCCCACA | 3 | 237 |
| T2-17 (VT30.3) | AGGAGAAUCAGUGAAUGCUUAUAAAUCUCGUGUCACA | 2 | 238 |
| T2-18 | UGGAAAUCAGUGAAUGCUUAUAGUUUCUCGCGUCACA | 4 | 239 |
| T2-23 | GGACGAAUGAAUGUUGACGGUUACGCUUUCCCCA | 4 | 240 |
| Orphans | | | |
| T2-11 | GGACACUGGUUCCGAAGUAUUGUCUUUGUCCUCACAG | 2 | 241 |
| T2-12 | GGGACACUGGUUCCGAAGUAUUGUCUUUGUCCUCACA | 3 | 242 |
| T2-22 | GGACACUGGUUCCGAAGUAUUGUCUUUGUCCUCACA | 3 | 243 |

Sequence shown is only from the random region of the molecules. Identical sequences are indicate by additional designation numbers. Ligands that were also found in the first SELEX experiment (Ruckman et al., J. Biol. Chem. 273:20556–67, 1998) are shown by parentheses with their designation from the first SELEX experiment. Phenotypes were determined by filter binding and were classified according to five groups as follows: (1) Molecules that lose significant affinity for VEGF upon removal of their fixed sequences; (2) Molecules with affinities for VEGF somewhat affected (positively or negatively) upon removal of their fixed sequences; (3) Molecules that gain significant affinity for VEGF upon removal of their fixed sequences; (4) Molecules with affinities for VEGF not affected upon removal of their fixed sequences; and (5) Non-binding ligands either with or without fixed sequences. Stars (*) indicate repeats of binding experiments.

TABLE 16

Sequence of isolated ligands from VEGF Rd2 Truncation SELEX by Ligation

| Ligand | Sequence of Random Region<br>5'gggag [Random Region] cagacgacucgcccga | Phenotype | SEQ ID NO: 179 |
|---|---|---|---|
| Family 1 | | | |
| T3-5 | GGUUUGGAACGGAAGAAUUGGAUACGCACCUCACACA | 3 | 244 |
| T3-13 | AGGAUGUAGGAAGAAUUGGAAGAUCCGUGUGCGUA | 3 | 245 |
| T3-15-2 | UGGCAGGAUUUUGGAAGAAUUGGAUAUUGGCCUCA | | 246 |
| T3-17-1 | GGACCUUUUGGAAGUUAUUGGAUAGGCCGUGUCACGCA | | 247 |
| T3-18 | GGACAUGUAGGAAGAAUUGGAAGAUGCGCCACAG | 2 | 248 |
| Family 2 | | | |
| T3-2 | GGUAACCGGUUGAAGUUAUUGGUCGCUAUGCU | 3 | 249 |
| T3-6 | GGAGGUCAACCGGUUGAAUAUUUGGUCGCUGACCUCACACA | | 250 |
| T3-8 | GGUCAACCGGUUGAAUAUUUGGUCGCUGAUCUCGCCACA | 3 | 251 |
| T3-9 | UGGUCAACCGGUUGAAUAUUUGGUCGCUGACCUCACA | 3 | 252 |
| T3-11 | AGCGUAACCGUCAACAUUCAUUCAGUCCCCUCCC | 5 | 253 |
| FAMILY 3 | | | |
| T3-7 | GGAGAAUCAGUGAAUGCUUAUUGCUUCUCGUCACACA | 3 | 254 |
| T3-10 | GGCACUAGGUGAAUGCCGUUAUUCUUGCUGCUCUCUCU | 2 | 255 |
| T3-12-1 | GGGAGAAAUCAGUGAAUGCUUAUCGUUUCUCGUCACACA | | 256 |
| T3-12-2 | GGGGACUAGGUGAAUGCCAAUAUUCUUCUCCGUCACCACA | | 257 |
| T3-14 | GGCGGAUCAGUGAAUGCUUACAAACCGUGUGUCCC | 2 | 258 |
| T3-15-1 | GCAAAAUCAGUGAAUGCUUAUUGCUUUGGCUCACCA | | 259 |
| T3-16 | GGCGGAACUAGUGAAUGCUUAUACGACCGUGUUGUCACA | 4 | 260 |
| T3-19 | UUAGGAAUCAGUGAAUGCUUAUACAUCCGCUCGGUC | 3 | 261 |
| Orphans | | | |
| T3-1 | UGGACACUGGUUCCGAAGUAACGUUGAAGUAAAAUUCGUUCUCUCGGCGUUUGGC | 2 | 262 |

TABLE 16-continued

Sequence of isolated ligands from VEGF Rd2 Truncation SELEX by Ligation

| Ligand | Sequence of Random Region 5'gggag [Random Region] cagacgacucgcccga | Phenotype | SEQ ID NO: 179 |
|---|---|---|---|
| T3-3 | GGACACUAGGUGCAUGCCAAAAUUCUUGUCCUCAGCA | 2 | 263 |
| T3-17-2 | GGGACAUUGGUUCCGAAGUAUUGACUUUGUCCUCACACA | | 264 |

Sequence shown is only from the random region of the molecules. All ligands start with 5'GGGAG except T3-11 which starts with 5'GGGAA. Identical sequences are indicate by additional designation numbers. Ligands that were also found in the first SELEX experiment (Ruckman et al., J. Biol. Chem. 273:20556–67, 1998) are shown by parentheses with their designation from the first SELEX experiment. Phenotypes were determined by filter binding and were classified according to five groups as follows: (1) Molecules that lose significant affinity for VEGF upon removal of their fixed sequences; (2) Molecules with affinities for VEGF somewhat affected (positively or negatively) upon removal of their fixed sequences; (3) Molecules that gain significant affinity for VEGF upon removal of their fixed sequences; (4) Molecules with affinities for VEGF not affected upon removal of their fixed sequences; and (5) Non-binding ligands either with or without fixed sequences. Stars (*) indicate repeats of binding experiments.

TABLE 17

Sequence of isolated ligands from 30N TGFβ1 Rd2 Truncation SELEX by Ligation

| Ligand | Sequence of Random Region 5'gggag [Random Region] cagacgacucgcccga | Kd (Nm) | Plateau | SEQ ID NO: 179 |
|---|---|---|---|---|
| Class 1 | | | | |
| 30NtruNc 1,11, 22,26,29, 30,31,33 | GGUUAACCGUUAAGACGGCGUCAUUUUGUCCC | 0.081 | 30% | 265 |
| 30NtruNc 8,40 | GGUUAACCGUUAAGACGGCUUCAUUUUGUCCC | NB | | 266 |
| 30NtruNc 24,25 | GGUUAACCGUUAAGACGGCGUUAUUUUGUCCC | 2.5 | 30% | 267 |
| 30NtruNc 10 | GGUUAACCGUUAAGACGGCNUCAUUUUGUCCC | NB | | 268 |
| 30NtruNc 13 | GGUUAACCGUUAAGACGGCUUUAUUUUGUCCC | 1.4 | 20% | 269 |
| 30NtruNc 7 | GGUUAACCGUUAAGACGGCGUNAUUUUGUCCC | 2.0 | 25% | 270 |
| 30NtruNc 36 | GGUUAACCGUAAAGACGGCAUUAUGUAGUCCC | 31.0 | 40% | 271 |
| Class 2 | | | | |
| 30NtruNc 20,14 | GGGAAUUUUUGGUAAAGCCGUAUGCCUCGC | 0.34 | 25% | 272 |
| 30NtruNc 27 | GGGAAUUUUUGGUAAAGCCAUAUGCCUCGCCA | >30.0 | | 273 |
| 30NtruNc 19 | CGGGAAUUUUUGGUAAAGCCGUAUGCCUCGCCA | 0.56 | 35% | 274 |
| 30NtruNc 12 | UGGGAAUUUUUGGUAAAGCCGUAUGCCUCGC | 0.88 | 35% | 275 |
| 30NtruNc 34 | CGGGGAAUUUUUGGUAAAGCCGUAUGCCUCGC | | | 276 |
| 30NtruNc 3 | GGUUUCAUGGAAUUUUUGGUAAAGCCGUAUGCCUCGCCA | 30.0 | 70% | 277 |
| 30NtruNc 18 | AUUUUUGGUAAAGC | NB | | 278 |
| 30NtruNc 38 | GGAAUUUUUGAUUUAGUCGUACGCCGCAUCCC | 0.2 | 17% | 279 |
| 30NtruNc 6 | GGUUUCAUGGAAUUUUUGGUUUAGCCGUAUGC | 2.0 | 35% | 280 |
| 30NtruNc 2 | GGUUCUGGAAUUUUUGGUUUAGCCGUACGC | 1.2 | 37% | 281 |
| 30NtruNc 4 | AGGGAUCUGGAAUUUUUGGUUUAGCCGUACGC | 0.088 | 20% | 282 |
| 30NtruNc 32 | ANCUGGUAAUUUUGGUUUANCCGUAUNCC | 22.0 | 15% | 283 |
| 30NtruNc 9 | AGGGGUCUGGAAUUUUUGGNUUACCCGUACGC | 0.1 | 20% | 284 |
| 30NtruNc 23 | GGAAUUUUUGUGUAGACGUAUGCCCUUUGCC | 0.93 | 35% | 285 |
| 30NtruNc 37 | CGGAAUUUUUGUGUAGACGUAUGCCGCUUUGNC | 0.083 | 15% | 286 |
| Class 3 (nitrocellulose binders) | | | | |
| 30NtruNc 15 | GGGCUCAACUUUUCUCUUCUUCUUUUUCCGCCC | | | 287 |
| 30NtruNc 5 | GGCCCCAUUCUUUUUUAUUUCUUUUUUGCCCCA | | | 288 |
| 30NtruNc 2 | GGCCCGGUUUUUCUUUUUCUUUUCUUUUUCCC | | | 289 |
| 30NtruNc 39 | GGCCUUCUUUCUUUCUUUUCUUUUUUCCGUCCC | | | 290 |

Sequence shown is only from the random region of the molecules. All ligands start with 5'GGGAG except 30NtruncNc-9 and 30NtruncNc-18 which start with 5'GGGTC and GGGA, respectively. Identical sequences are indicate by additional designation numbers. Ligand affinities were determined by nitrocellulose filter binding following removal of fixed sequences and are indicated by Kd and plateau values obtained. NB indicate ligands unable to bind the target under the experimental conditions used.

TABLE 18

Sequence of isolated ligands from 40N TGFβ1 Rd2 Truncation SELEX by Ligation

| Ligand | Sequence of 5'Fixed-Random Region 5' gggag [Random Region] cagacgacucgcccga | | Kd (nM) | Plateau | SEQ ID NO: 291 |
|---|---|---|---|---|---|
| Family 1 | | | | | |
| AG34 | GGGA                CAGACGACUCGCCCGA | UAAUACGACUCACUAUAGGGAGGN | | | 292 |
| AG30 | GGGAG         GGCAGACGACUCGCCCGA | UAAUACGACUCACUAUA | | | 293 |
| AG22 | GGGA                 CACGACGACUCGCCCGA | UAAUACGACUCACUAUAGGNAGUUG | | | 294 |
| AG8 | GGGA    CUCACUAUACAGACGACUCGCCCGA | CCGCUAUUACAAUCUUCGCCUCCC | | | 295 |
| AG15 | GGGA             CCAGACGACUCGCCCGA | GGGAACGUUCUCCCACCUUCCUGCC | | | 296 |
| AG7 | GGGA                CAGACGACUCGCCCGA | GGGAUUUUACGUUCGUCUCGCGUCUCCC NB | | | 297 |
| Family 2 | | | | | |
| AG6 | GGGAG            CAGACGACUCGCCCGA | ACUGGGAAUUUUUGGUUGAGCCGUAUGCC | 0.004 (0.2) | 12% (25%) | 298 |
| AG24 | GGGAG            CAGACGACUCGCCCGA | GCUGGGAAUUUUUGGCUGAGCCGUAUGCC | | | 299 |
| AG48 | GGGAG        GGUCCAGACGACUCGCCCGA | GGGGGAAUUUUUGGUUGAGCCGUAUGCC | | | 300 |
| AG4 | GGGAG            CAGACGACUCGCCCGA | GGGGAAUUUUUGGUUGAGCCGUAUGCC | | | 301 |
| AG31 | GGGA             CAGACGACUCGCCCGA | GACGGGAAUUUUUGGUUGAGCCGUAUGCC | | | 302 |
| AG40 | GGGA             CAGACGAACUCGCC CGAACUGGGAAUUUU GGUUGAGCNGUAUGCC | | | | 303 |
| AG16 | GGGAG                   GGUGUUUCGAACUGGGAAUUUUUGGUUUAGCCGUAUGCC | | 0.02 | 23% | 304 |
| AG13,27,33 | GGGAG                 GGUGUUUCGAACUGGGAAUUUUUGGUUGAGCCGUAUGCC | | | | 305 |
| AG35 | GGGAG                 GGUGUUUCGAACUGGGAAUUUUUGGUUGAGCCGUAUCCC | | | | 306 |
| Family 3 | | | | | |
| AG11 | GGGAG GGAUUCUGCCGAGUUAAUUUCGGUGUCUGUAGCUUAUCCC | | 1.0 | 22% | 307 |
| AG2 | GGGAG GGAUUCUGCCGAGUUAACGUCGGUGUCUGUAGCUUAUCCC | | 1.0 | 25% | 308 |
| Family 4 | | | | | |
| AG32 | GGGAG GACGAUGCGGGGGUUAUUGGGNGUCAACAUCCCCGAUUCUUUUCACGUC | | | | 309 |
| AG36 | GGGAG GACGAUGCGGGGGUUAUUGGGCGUCAACAUCCCCGAUUCUUUUCACGUC | | | | 310 |
| AG9 | GGGAG GACGAUGCGGGGGUUAUUGGGCGUCAACAUCCCCGAUUCUUUUCACCUC | | | | 311 |
| Family 5 | | | | | |
| AG21 | GGGAG GACGAUGCGGAGCGGAUUAAUUAGUCUGACUUCUUGUCCC | | | | 312 |
| AG25 | GGGAG GACGAUGCGGUAAAGUAGCAUUAUCCUCUAACAUCCUGCC | | | | 313 |
| Family 6 | | | | | |
| AG18 | GGGAG GGGUGCCUUUAGCUUGGUCUGUUUAGUACAUUCCUCUGCCC | | 1.0 | 22% | 314 |
| AG1 | GGGAG GGGUGCCUGUAGUCUUUGCAUCUUAUAAAUGCAAUCUGCCC | | 0.1 (0.5) | 14% (25%) | 315 |
| Family 7 (Nitrocellulose binders) | | | | | |
| AG5 | GGGAGG | | | | 316 |
| AG29 | GGGAG GGUGUUACGAGCGUCGGACCCUGUUUCCAACAUCCUCCC | | | | 317 |
| AG14 | GGGA  CUUCCUCCGGCUAUCAUUUUCUUCUCUUUCUCUCUCCC | | | | 318 |
| AG12 | GGGAG GGAGUGGUCGACCAUGAUUCUUUUUAUUUCUCCUUCCUCCC | | | | 319 |
| AG19, 20 | GGGAG GGACCUUUCUACUUCAUCAUUUUUCUUCACUCUCUCCGUCCC | | | | 320 |
| AG37 | GGUAG GGAGGUUUCUGACUCUUAGCUUUCCUUUCCUCCUGCCUCCC | | | | 321 |
| AG38 | GGGA  CAGACGACUNGCCCGACGUAUGCC | | | | 322 |

Sequence shown is from the initiator sequence (usually 5'GGGAG) and random region of the molecules. Identical sequences are indicate by additional designation numbers. Ligand affinities were determined by nitrocellulose filter binding following removal of fixed sequences and are indicated by Kd and plateau values obtained. For biphasic binding, low affinity Kd and plateau values are in parentheses. NB indicate ligands unable to bind the target under the experimental conditions used.

What is claimed is:

1. A method of identifying a single stranded RNA ligand of a target molecule from a candidate mixture of single-stranded RNA molecules each comprising a region of randomized sequence, said method comprising:
   a) contacting said candidate mixture with said target molecule;
   b) partitioning the RNA molecules having an increased affinity to the target molecule relative to the candidate mixture from the remainder of the candidate mixture;
   c) adding a first tail sequence to said RNA molecules partitioned in step b) using terminal transferase;
   d) reverse transcribing said tailed RNA molecules to cDNA using a primer complementary to said first tail sequence;
   e) adding a second tail sequence to said cDNA molecule using terminal transferase, wherein said first and said second tail sequences have different sequences;
   f) amplifying said tailed cDNA molecules of e) using said primer of step d) and a primer comprising sequence complementary to said second tail sequence and further comprising an RNA polymerase promoter sequence, whereby double stranded DNA template is produced;
   g) transcribing said double stranded DNA template off) to yield single-stranded RNA molecules; and
   h) removing said tail sequences from said single-stranded RNA molecules of g) whereby a single-stranded RNA ligand of said target molecule is identified.

2. The method of claim 1 further comprising repeating steps a) through h).

3. A method of identifying a single stranded RNA ligand of a target molecule from a candidate mixture of single-stranded RNA molecules each comprising a region of randomized sequence, said method comprising:
   a) contacting said candidate mixture with said target molecule;
   b) partitioning the RNA molecules having an increased affinity to the target molecule relative to the candidate mixture from the remainder of the candidate mixture;
   c) attaching a first oligonucleotide to the 3' end of said RNA molecules partitioned in step b);
   d) reverse transcribing said RNA molecules of c) to form cDNA using a primer complementary to said first oligonucleotide;
   e) attaching a double-stranded deoxy oligonucleotide to said cDNA, said double-stranded deoxy oligonucleotide comprising a RNA polymerase promoter;
   f) amplifying the cDNA of step e) to form a double-stranded DNA template;
   g) transcribing said amplified double-stranded DNA template to yield single-stranded RNA molecules; and
   h) removing said first oligonucleotide sequence from said single-stranded RNA molecules of g) whereby a single-stranded RNA ligand of said target molecule is identified.

4. The method of claim 3 further comprising repeating steps a) through h).

5. A method for identifying nucleic acid ligands of a target molecule from a candidate mixture comprised of single stranded nucleic acids each having a region of randomized sequence, said method comprising:
   a) contacting the candidate mixture with the target, wherein nucleic acids having an increased affinity to the target relative to the candidate mixture may be partitioned from the remainder of the candidate mixture;
   b) partitioning the increased affinity nucleic acids from the remainder of the candidate mixture;
   c) amplifying the increased affinity nucleic acids, in vitro, to yield a ligand-enriched mixture of nucleic acids;
   d) optionally repeating steps a)–c) using the ligand enriched mixture of each successive repeat as many times as required to yield a desired level of ligand enrichment;
   e) randomly fragmenting the amplified increased affinity nucleic acids;
   f) inserting fragments of a predetermined length into a circular vector; and
   g) amplifying the inserted fragments using primers complementary to sequences in said circular vector that flank said inserted fragments, whereby nucleic acid ligands of said target having said predetermined length are identified.

6. The method of claim 5 wherein said candidate mixture is comprised of RNA.

7. The method of claim 5 wherein said candidate mixture is comprised of DNA.

8. The method of claim 6 wherein said ribonucleic acids are modified ribonucleic acids.

9. The method of claim 7 wherein said deoxyribonucleic acids are modified deoxyribonucleic acids.

* * * * *